(12) United States Patent
Alvarez et al.

(10) Patent No.: US 10,709,724 B2
(45) Date of Patent: Jul. 14, 2020

(54) METHODS OF TREATING MITOCHONDRIAL DYSFUNCTION

(71) Applicant: Ecole Polytechnique Federale de Lausanne (EPFL), Lausanne (CH)

(72) Inventors: Carlos Canto Alvarez, Ecublens (CH); Peter Bai, Basel-Debrecen (HU); Riekelt Houtkooper, Amsterdam (NL); Johan Auwerx, Buchillon (CH); Laurent Mouchiroud, Lausanne (CH)

(73) Assignee: Ecole Polytechnique Federale de Lausanne (EPFL), Lausanne (CH)

(*) Notice: Subject to any disclaimer, the term of this patent is extended or adjusted under 35 U.S.C. 154(b) by 0 days.

(21) Appl. No.: 15/923,542

(22) Filed: Mar. 16, 2018

(65) Prior Publication Data
US 2019/0328758 A1 Oct. 31, 2019

Related U.S. Application Data

(63) Continuation of application No. 15/293,640, filed on Oct. 14, 2016, now abandoned, which is a continuation of application No. 13/984,157, filed as application No. PCT/IB2012/001146 on Feb. 15, 2012, now abandoned.

(60) Provisional application No. 61/443,052, filed on Feb. 15, 2011, provisional application No. 61/446,303, filed on Feb. 24, 2011.

(51) Int. Cl.
| | | |
|---|---|---|
| A61K 31/706 | (2006.01) | |
| A61K 31/05 | (2006.01) | |
| A61K 31/405 | (2006.01) | |
| A61K 31/7064 | (2006.01) | |
| A61K 31/502 | (2006.01) | |
| A61K 45/06 | (2006.01) | |
| A61K 31/473 | (2006.01) | |
| A61K 31/7088 | (2006.01) | |
| C12N 15/113 | (2010.01) | |

(52) U.S. Cl.
CPC ............ *A61K 31/706* (2013.01); *A61K 31/05* (2013.01); *A61K 31/405* (2013.01); *A61K 31/473* (2013.01); *A61K 31/502* (2013.01); *A61K 31/7064* (2013.01); *A61K 31/7088* (2013.01); *A61K 45/06* (2013.01); *C12N 15/1137* (2013.01); *C12N 2310/14* (2013.01)

(58) Field of Classification Search
CPC .. A61K 31/706; A61K 31/105; A61K 31/405; A61K 31/7064; A61K 31/502; A61K 45/06; A61K 31/473
See application file for complete search history.

(56) References Cited

U.S. PATENT DOCUMENTS

| | | | |
|---|---|---|---|
| 7,776,326 B2 | 8/2010 | Milbrandt et al. | |
| 2007/0117765 A1 | 5/2007 | Sauve et al. | |
| 2007/0244202 A1 | 10/2007 | Murase et al. | |
| 2007/0292883 A1* | 12/2007 | Ossovskaya ......... | C12Q 1/6886 435/6.14 |
| 2008/0234364 A1 | 9/2008 | Ahrens et al. | |
| 2014/0065099 A1 | 3/2014 | Alvarez et al. | |
| 2017/0182076 A1 | 6/2017 | Alvarez et al. | |

FOREIGN PATENT DOCUMENTS

| | | |
|---|---|---|
| WO | WO 2000/32179 A2 | 6/2000 |
| WO | WO 2001/93874 A1 | 12/2001 |
| WO | WO 2006/105440 A2 | 10/2006 |
| WO | WO 2007/008548 A2 | 1/2007 |
| WO | WO 2007/109024 A2 | 9/2007 |
| WO | WO 2008/030891 A2 | 3/2008 |
| WO | WO 2009/019600 A2 | 2/2009 |
| WO | WO 2009/051609 A1 | 4/2009 |
| WO | WO 2009/054994 A2 | 4/2009 |
| WO | WO 2009/080033 A1 | 7/2009 |
| WO | WO 2009/089011 A2 | 7/2009 |
| WO | WO 2009/140265 A2 | 11/2009 |

OTHER PUBLICATIONS

Weston et al. (Blood 2010 116:4578-45).*
Ahn, B.H. et al. (2008). "A role for the mitochondrial deacetylase Sirt3 in regulating energy homeostasis." *Proc Natl Acad Sci USA* 105, 14447-14452.
Aksoy, P. et al. (2006). "Regulation of SIRT 1 mediated NAD dependent deacetylation: a novel role for the multifunctional enzyme CD38." *Biochem Biophys Res Commun* 349, 353-359.
Ame, J.C. et al. (1999). "PARP-2, a novel mammalian DNA damage-dependent poly(ADP-ribose) polymerase." *J Biol Chem* 274, 17860-17868.
Ame, J.C. et al. (2004). "The PARP superfamily." *Bioessays* 26, 882-893.
Asher G. et al. (2010). "Poly(ADP-ribose) polymerase 1 participates in the phase entrainment of circadian clocks to feeding." *Cell* 142, 943-953.
Bai, P. et al. (2001). "Partial protection by poly(ADP-ribose) polymerase inhibitors from nitroxyl-induced cytotoxicity in thymocytes." *Free Radic Biol Med* 31, 1616-1623.
Bai, P. et al. (2007). Poly(ADP-ribose) polymerase-2 controls adipocyte differentiation and adipose tissue function through the regulation of the activity of the retinoid X receptor/peroxisome proliferator-activated receptor-gamma heterodimer. *JBiolChem* 282, 37738-37746.

(Continued)

*Primary Examiner* — Shirley V Gembeh
(74) *Attorney, Agent, or Firm* — Cooley LLP; Ivor R. Elrifi; Cynthia A. Kozakiewicz

(57) ABSTRACT

The present invention provides methods of treating various disorders associated with mitochondrial dysfunction, including but not limited to metabolic disorders, neurodegenerative diseases, chronic inflammatory diseases, and diseases of aging.

7 Claims, 47 Drawing Sheets
Specification includes a Sequence Listing.

(56) References Cited

OTHER PUBLICATIONS

Ballinger, S. W. (2005). "Mitochondrial dysfunction in cardiovascular disease," *Free Radical Biology & Medicine* 38, 1278-1295.
Banks, A.S. et al. (2008). "SirT1 gain of function increases energy efficiency and prevents diabetes in mice." *Cell Metab* 8, 333-341.
Barbosa, M.T. et al. (2007). "The enzyme CD38 (a NAD glycohydrolase, EC 3.2.2.5) is necessary for the development of diet-induced obesity." *Faseb J* 21, 3629-3639.
Baur, J.A. et al. (2006). "Resveratrol improves health and survival of mice on a high-calorie diet." *Nature* 444, 337-342.
Bitterman, K.J. et al. (2002). "Inhibition of silencing and accelerated aging by nicotinamide, a putative negative regulator of yeast sir2 and human SIRT1." *J Biol Chem* 277, 45099-45107.
Borra, M.T. et al. (2005). "Mechanism of human SIRT1 activation by resveratrol." *J Biol Chem* 280, 17187-17195.
Brunet, A. et al. (2004). "Stress-dependent regulation of FOXO transcription factors by the SIRTI deacetylase." *Science*, 303, 2011-2015.
Burkle, A. (2005). "Poly(ADP-ribose). The most elaborate metabolite of NAD+." *FEBS J* 272, 4576-4589.
Buteau, J., and Accili, D. (2007). Regulation of pancreatic beta-cell function by the forkhead protein FoxO1. *Diabetes Obes Metab* 9 Suppl 2, 140-146.
Canto, C., and Auwerx, J. (2009). "Caloric restriction, SIRT1 and longevity." *Trends Endocrinol Metab* 20, 325-331.
Canto, C. et al. (2009). "AMPK regulates energy expenditure by modulating NAD+ metabolism and SIRT1 activity." Nature 458, 1056-1060.
Canto, C. et al. (2010). "Interdependence of AMPK and SIRT1 and longevity." *Cell Metabolism* 11:213-9.
Chen, D. et al. (2008). "Tissue-specific regulation of SIRT1 by calorie restriction." *Genes Dev* 22, 1753-1757.
Chen, D. et al. (2005). "Increase in activity during calorie restriction requires Sirt1." *Science*310, 1641.
Chua, K.F. et al. (2005). "Mammalian SIRT1 limits replicative life span in response to chronic genotoxic stress." *Cell Metab* 2, 67-76.
Dai, H. et al. (2010). "SIRT1 activation by small molecules: kinetic and biophysical evidence for direct interaction of enzyme and activator." *J Biol Chem* 285, 32695-32703.
Dali-Youcef, N. et al. (2007). "Adipose tissue-specific inactivation of the retinoblastoma protein protects against diabesity because of increased energy expenditure." *Proc Natl Acad Sci USA* 104, 10703-10708.
Devalaraja-Narashimha, K., and Padanilam, B.J. (2010). PARP1 deficiency exacerbates diet-induced obesity in mice. *J Endocrinol* 205, 243-252.
El Ramy, R. (2009). "Functional interplay between Parp-1 and SirT1 in genome integrity and chromatin-based processes." *Cell Mol Life Sci* 66, 3219-3234.
Erdelyi, K. et al. (2009). "Dual role of poly(ADP-ribose) glycohydrolase in the regulation of cell death in oxidatively stressed A549 cells." *Faseb J* 23, 3553-3563.
Feige, J.N. et al. (2008). "Specific SIRT1 activation mimics low energy levels and protects against diet-induced metabolic disorders by enhancing fat oxidation." *Cell Metab* 8, 347-358.
Fong, P.C. et al. (2009). "Inhibition of Poly(ADP-Ribose) Polymerase in Tumors from BRCA Mutation Carriers." *N Engl J Med* 24, 123-134.
Frescas, D. et al. (2005). "Nuclear trapping of the forkhead transcription factor FoxO1 via Sirt-dependent deacetylation promotes expression of glucogenetic genes." *J Biol Chem* 280, 20589-20595.
Garcia Soriano, F. et al. (2001). "Diabetic endothelial dysfunction: the role of poly(ADP-ribose) polymerase activation." *Nat Med* 7, 108-113.
Gerhart-Hines, Z. et al. (2007). "Metabolic control of muscle mitochondrial function and fatty acid oxidation through SIRT1/PGC-1alpha." *Embo* 126, 1913-1923.
Gross, D.N. et al. (2008). "The role of FoxO in the regulation of metabolism." *Oncogene* 27, 2320-2336.

Haigis, M.C., and Guarente, L.P. (2006). "Mammalian sirtuins—emerging roles in physiology, aging, and calorie restriction." *Genes Dev* 20, 2913-2921.
Haigis, M.C., and Sinclair, D.A. (2010). "Mammalian sirtuins: biological insights and disease relevance." *Annu Rev Pathol* 5, 253-295.
Hall, A. M., and Unwin, R. J. (2007). "The Not So 'Mighty Chondrion': Emergence of Renal Diseases due to Mitochondrial Dysfunction," *Nephron Physiol* 105, 1-10.
Houtkooper, R.H. et al. (2010). "The secret life of NAD+: an old metabolite controlling new metabolic signaling pathways." *Endocr Rev* 31, 194-223.
Howitz, K.T. et al. (2003). "Small molecule activators of sirtuins extend *Saccharomyces cerevisiae* lifespan." *Nature* 425, 191-196.
Jagtap, P., and Szabo, C. (2005). "Poly(ADP-ribose) polymerase and the therapeutic effects of its inhibitors." *Nat Rev Drug Discov* 4, 421-440.
Kaeberlein, M. et al. (2005). "Substrate-specific activation of sirtuins by resveratrol." *J Biol Chem* 280, 17038-17045.
Kawamori, D. et al. (2006). "The forkhead transcription factor Foxo1 bridges the JNK pathway and the transcription factor PDX-1 through its intracellular translocation." *J Biol Chem* 281, 1091-1098.
Kitamura, T. et al. (2002). "The forkhead transcription factor Foxo 1 links insulin signaling to Pdx I regulation of pancreatic beta cell growth." *J Clin Invest* 110, 1839-184.
Kolthur-Seetharam, U. et al. (2006). "Control of A1P-mediated cell death by the functional interplay of SIRTI and PARP-1 in response to DNA damage." *Cell Cycle* 5, 873-877.
Krishnakumar, R. et al. (2008). "Reciprocal binding of PARP-1 and histone H1 at promoters specifies transcriptional outcomes." *Science* 319, 819-821.
Kun, E., et al. (2002). "Coenzymatic activity of randomly broken or intact double-stranded DNAs in auto and histone HI trans-poly(ADP-ribosylation), catalyzed by poly(ADP-ribose) polymerase (PARP I)." *J Biol Chem* 277, 39066-39069.
Lagouge, M. et al. (2006). "Resveratrol Improves Mitochondrial Function and Protects against Metabolic Disease by Activating SIRTI and PGC-1alpha." *Cell* 127, 1109-1122.
Lin, S.J. et al. (2000). "Requirement of NAD and SIR2 for life-span extension by calorie restriction in *Saccharomyces cerevisiae.*" *Science* 289, 2126-2128.
Lopez-Lluch, G. et al. (2006). "Calorie restriction induces mitochondrial biogenesis and bioenergetic efficiency." *Proc Natl Acad Sci USA* 103, 1768-1773.
Malik, R. et al. (2009). "Comparative deacetylase activity of wild type and mutants of SIRT1." *Biochem Biophys Res Commun* 391,739-743.
Menissier-De Murcia, J. et al. (1997). "Requirement of poly(ADP-ribose) polymerase in recovery from DNA damage in mice and in cells." *Proc Natl Acad Sci USA* 94, 7303-7307.
Menissier-De Murcia, J. et al. (2003). "Functional interaction between PARP-1 and PARP-2 in chromosome stability and embryonic development in mouse." *EMBO J.* 22, 2255-2263.
Milne, J.C., et al. (2007). "Small molecule activators of SIRT1 as therapeutics for the treatment of type 2 diabetes." *Nature* 450, 712-716.
Moynihan, K.A. et al. (2005). "Increased dosage of mammalian Sir2 in pancreatic beta cells enhances glucose-stimulated insulin secretion in mice." *Cell Metab.* 2, 105-117.
Mukhopadhyay et al. (2011). "PARP inhibitors and epithelial ovarian cancer: an approach to targeted chemotherapy and personalised medicine", *BJOG*, Jan. 8, 2011;118:429-432.
Narkar, V.A. et al. (2008). "AMPK and PPARdelta agonists are exercise mimetics." *Cell*134, 405-415.
Nemoto, S. et al. (2004). "Nutrient availability regulates SIRT1 through a forkhead-dependent pathway." *Science* 306, 2105-2108.
North, B.J. et al. (2003). "The human Sir2 ortholog, SIRT2, is an NAD+-dependent tubulin deacetylase." *Mol Cell* 11, 437-444.
Pacholec, M. et al. (2010). "SRT1720, SRT2183, SRT1460, and resveratrol are not direct activators of SIRT1." *J Biol Chem* 285, 8340-8351.

(56) References Cited

OTHER PUBLICATIONS

Peralta-Leal A et al: "PARP inhibitors: New partners in the therapy of cancer and inflammatory diseases", Free Radical Biology and Medicine, Jul. 1, 2009, vol. 47, No. 1, pp. 13-26.
Pfluger, P.T. et al. (2008). "Sirt1 protects against high-fat diet-induced metabolic damage." *Proc Natl Acad Sci USA* 105, 9793-9798.
Picard, F. et al. (2004). "Sirt1 promotes fat mobilization in white adipocytes by repressing PPAR-gamma." *Nature* 429, 771-776.
Rajamohan, S.B. et al. (2009). "SIRT1 promotes cell survival under stress by deacetylation-dependent deactivation of poly (ADP-ribose) polymerase 1." *Mol Cell Biol* 29(15), 4116-4129.
Rodgers, J.T. et al. (2005). "Nutrient control of glucose homeostasis through a complex of PGC-1alpha and SIRT1." *Nature* 434, 113-118.
Sakamaki, J. et al. (2009). "Regulation of FOXO1-mediated transcription and cell proliferation by PARP-1." *Biochem Biophys Res Commun* 382, 497-502.
Sauve, A.A. (2009). "Pharmaceutical strategies for activating sirtuins." *Curr Pharm Des*, 15, 45-56.
Sauve, A.A. et al. (2005). "Chemical activation of Sir2-dependent silencing by relief of nicotinamide inhibition." *Mol Cell* 17, 595-601.
Schwer, B. et al. (2002). "The human silent information regulator (Sir)2 homologue hSIRT3 is a mitochondrial nicotinamide adenine dinucleotide-dependent deacetylase." *J Cell Biol* 158, 647-657.
Shah, R.G. et al. (2005). "DNA vector-based RNAi approach for stable depletion of poly(ADP-ribose) polymerase-1 ." *Biochem Biophys Res Commun* 331, 167-174.

Shieh, W.M. et al. (1998). "Poly(ADP-ribose) polymerase null mouse cells synthesize ADP-ribose polymers." *J Biol Chem* 273, 30069-30072.
Um, H.J. et al. (2010). "Differential effects of resveratrol and novel resveratrol derivative, HS-1793, on endoplasmic reticulum stress-mediated apoptosis and Akt inactivation." *Int J Oncol* 36, 1007-1013.
Um, J.H. et al. (2009). "AMP-activated protein kinase-deficient mice are resistant to the metabolic effects of resveratrol." *Diabetes* 59, 554-563.
Vousden, K.H. and Ryan, K.M. (2009). "p53 and metabolism." *Nat Rev Cancer* 9, 691-700.
Watanabe, M. et al. (2006). "Bile acids induce energy expenditure by promoting intracellular thyroid hormone activation." *Nature* 439,484-489.
Yang, H. et al. (2007). "Nutrient-sensitive mitochondrial NAD+ levels dictate cell survival." *Cell* 130, 1095-1107.
Yelamos, J. et al. (2008). "Toward specific functions of poly(ADP-ribose) polymerase-2." *Trends Mol. Med.* 14, 169-178.
Yu, J., and Auwerx, J. (2009). "Protein deacetylation by SIRT1: An emerging key post-translational modification in metabolic regulation." *Pharmacol Res* 62(1), 35.
Mouchiroud, L. et al., "The NAD+/sirtuin pathway modulates longevity through activation of mitochondrial UPR and FOXO signaling," Cell, 154(2):430-441 (2013), and Supplemental Information (25 pages).
Sorrentino, V. et al., "Enhancing mitochondrial proteostasis reduces amyloid-β proteotoxicity," Nature, 552(7684):187-193 (2017), and Supplementary Information (18 pages).

* cited by examiner

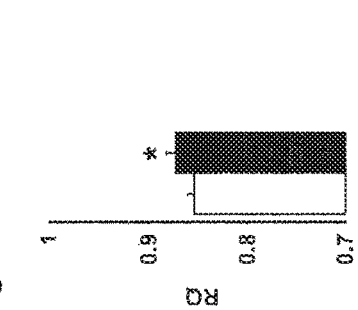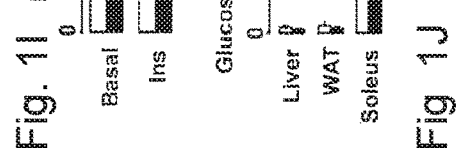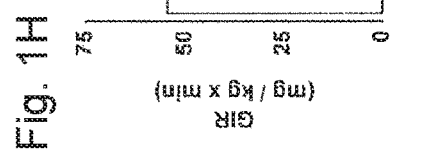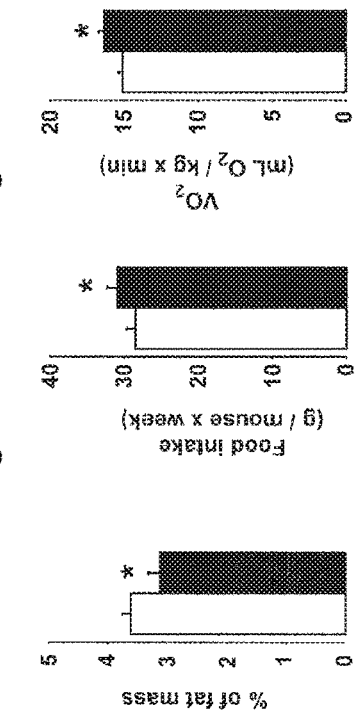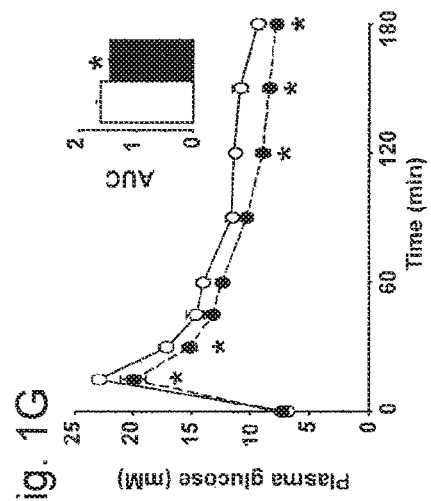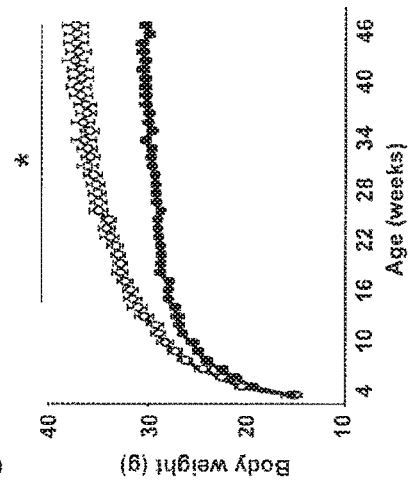

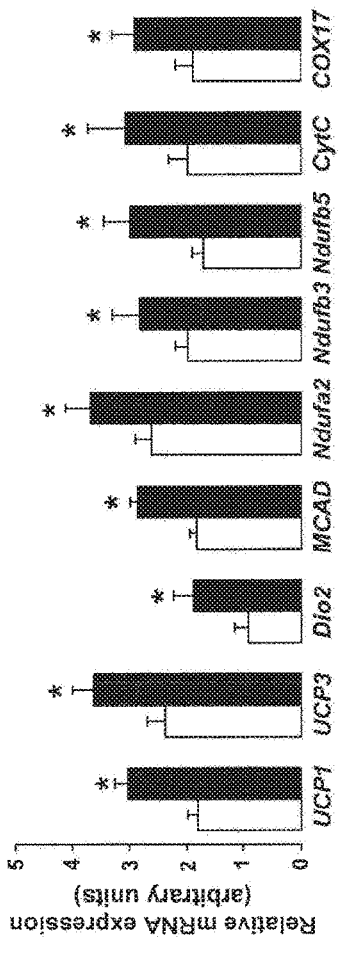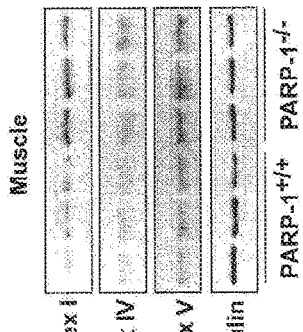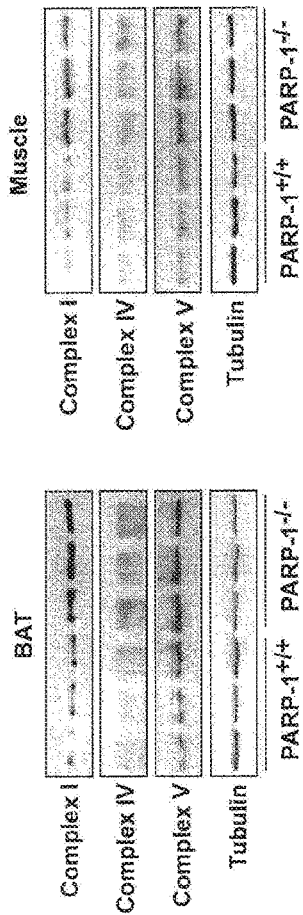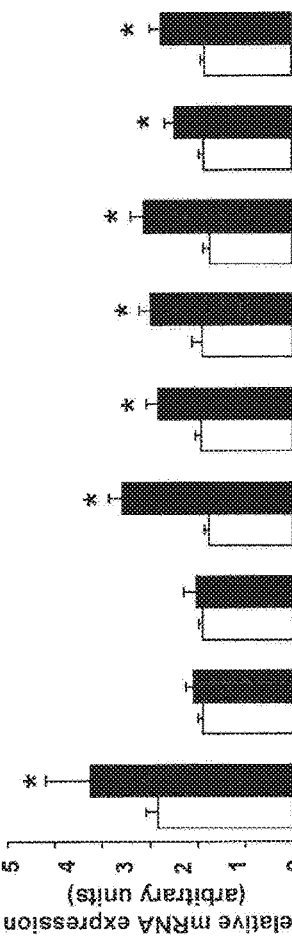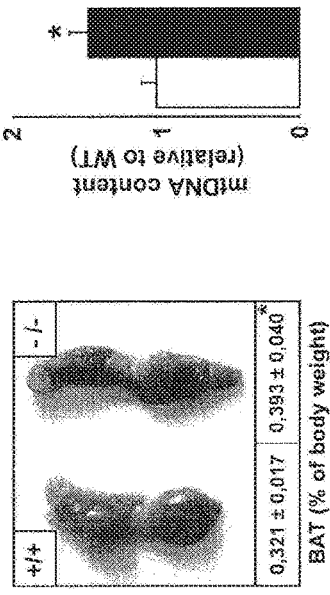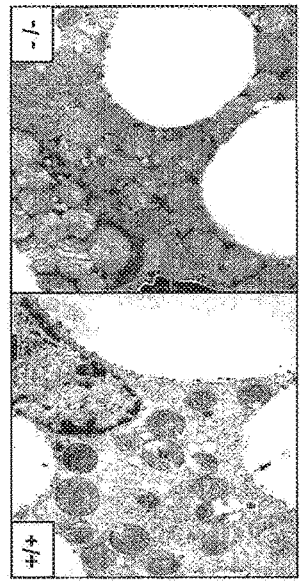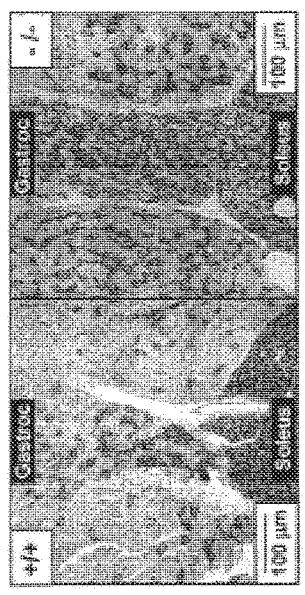

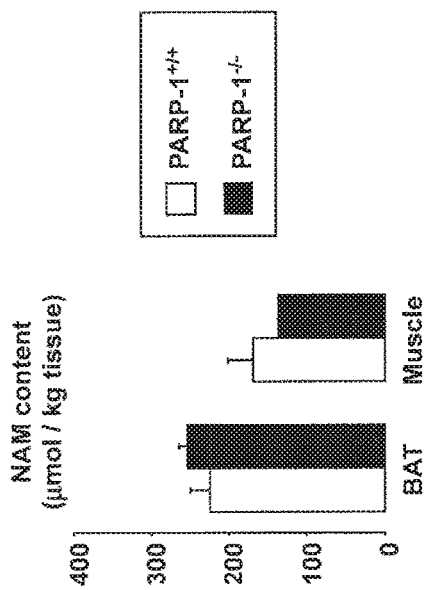
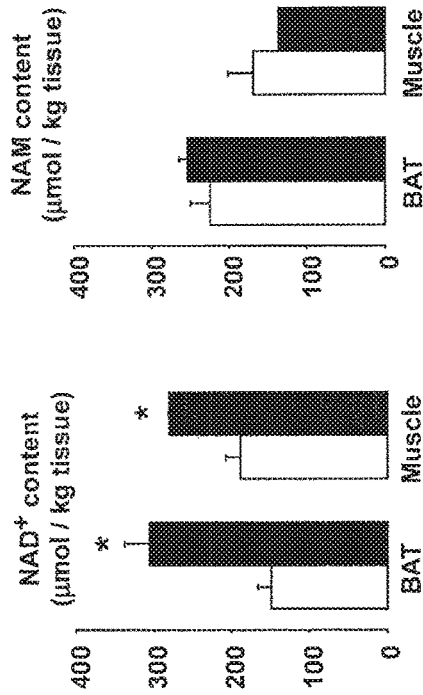
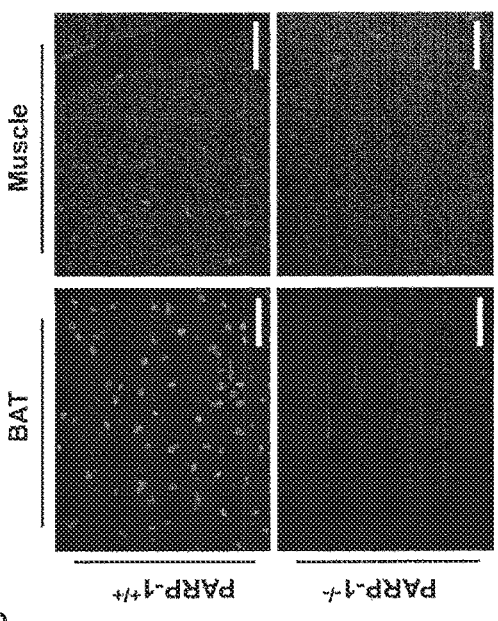
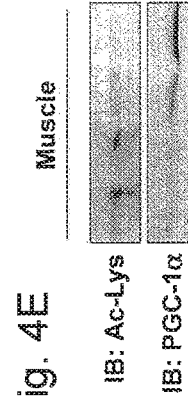
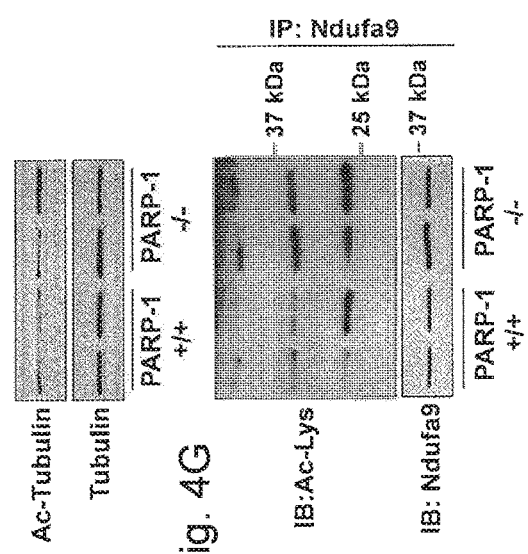
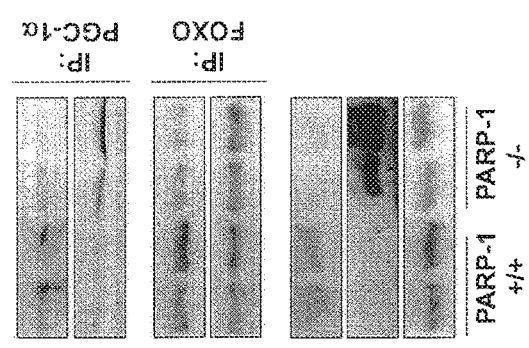
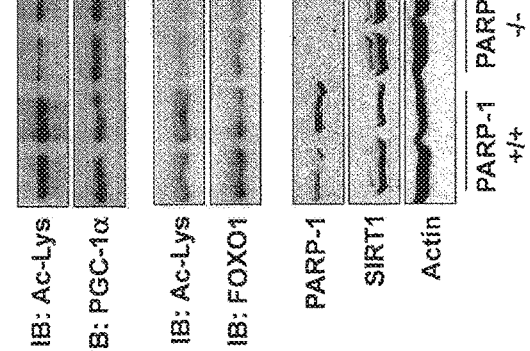
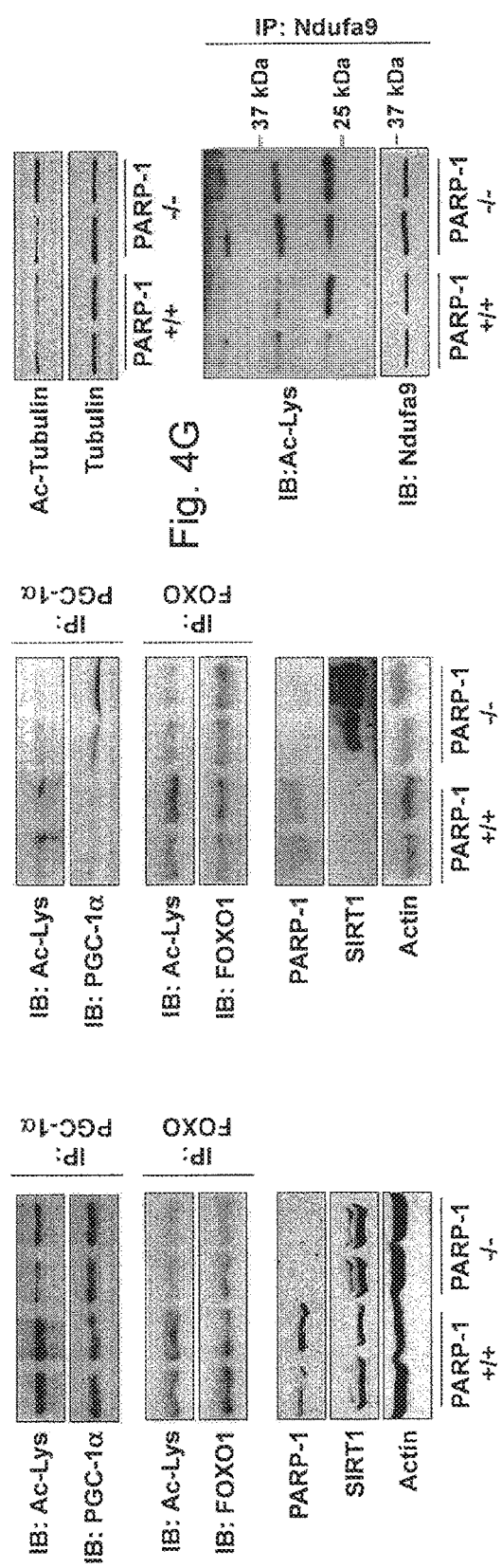

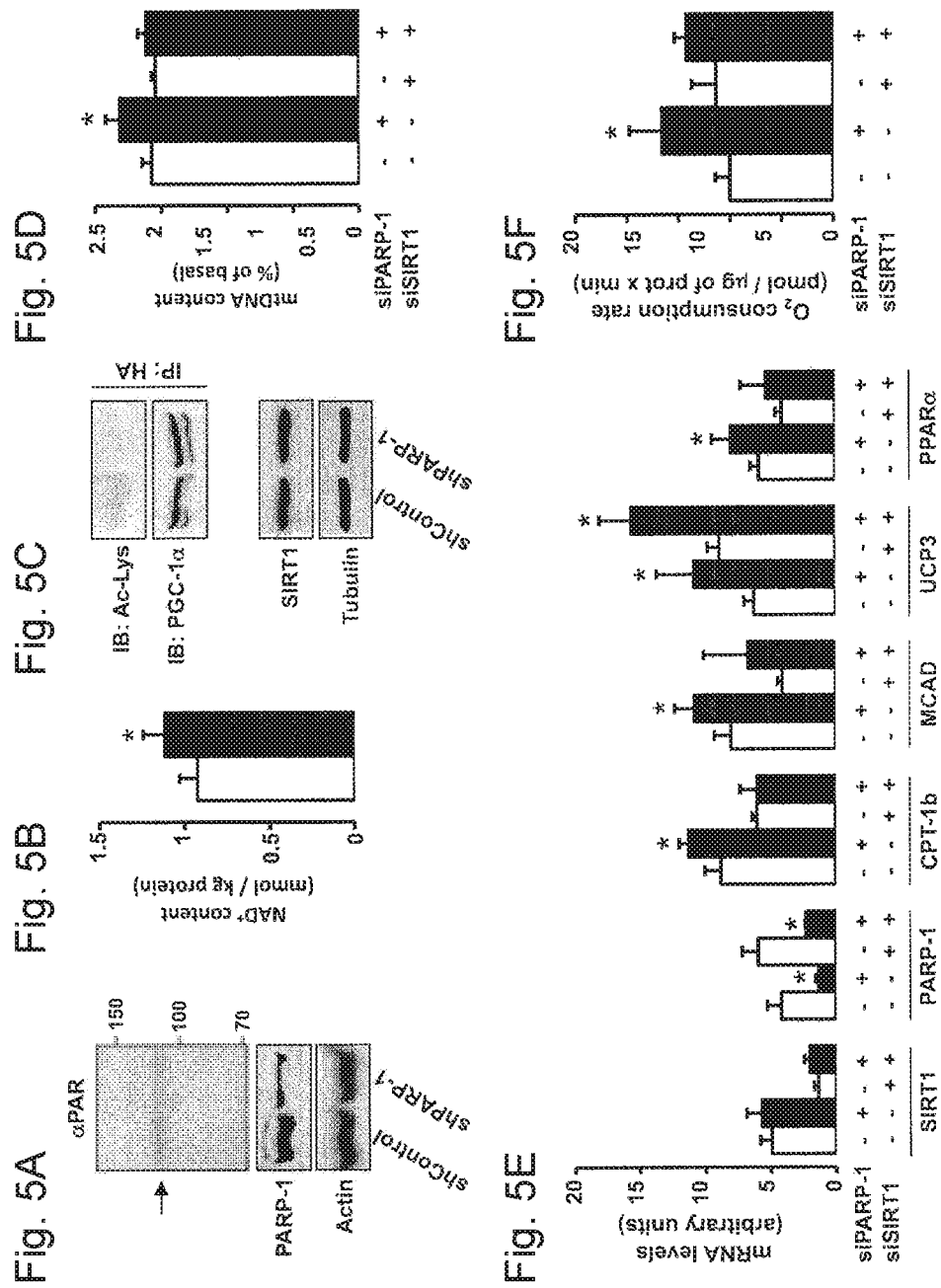

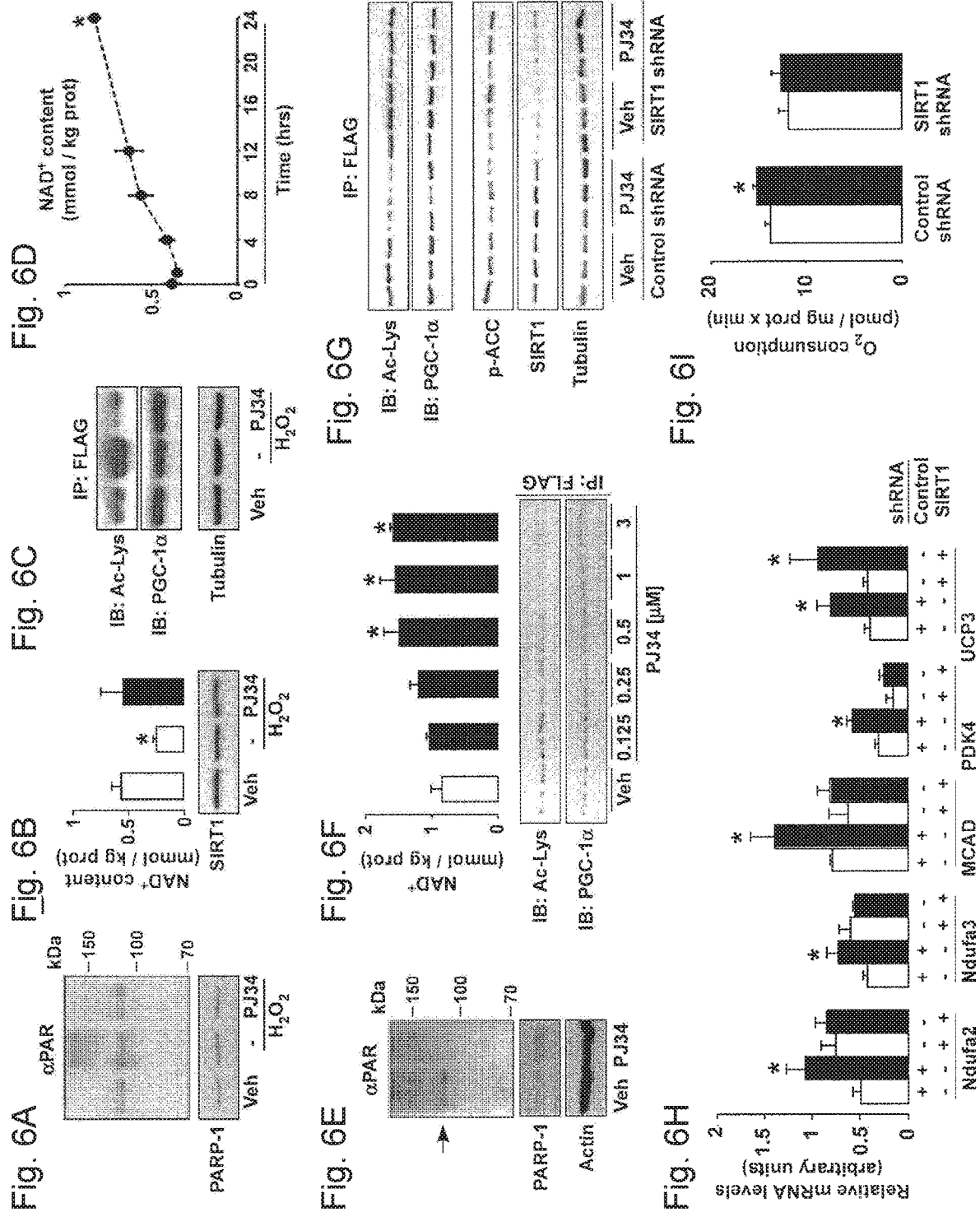

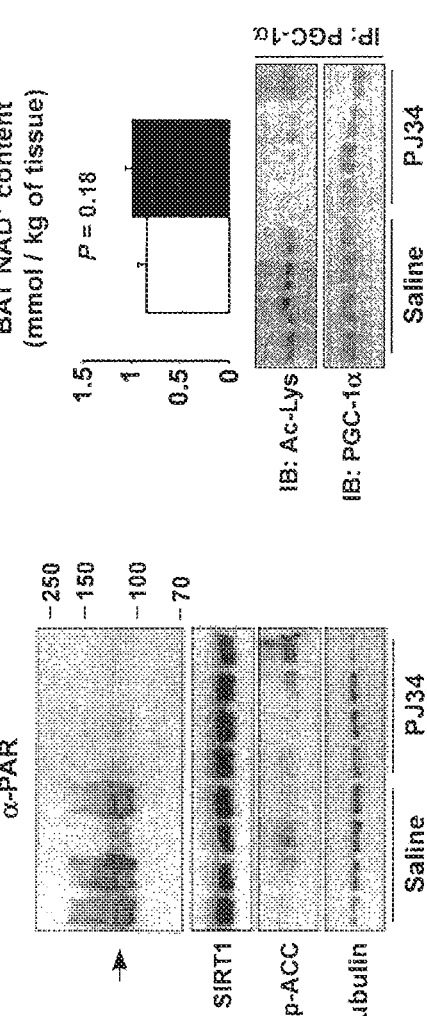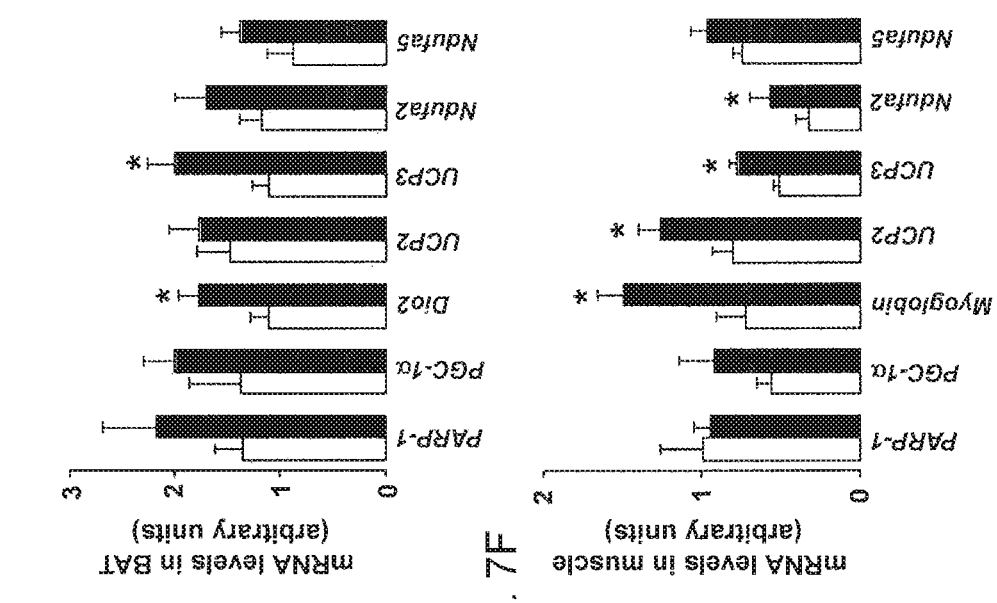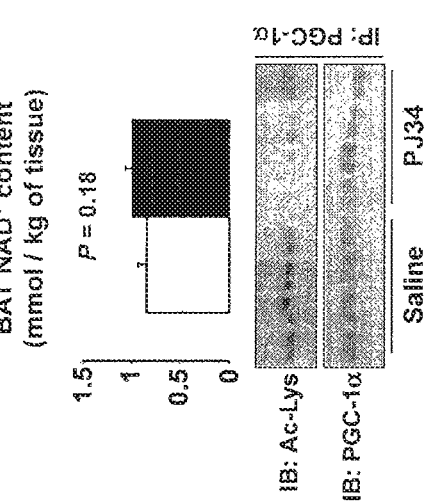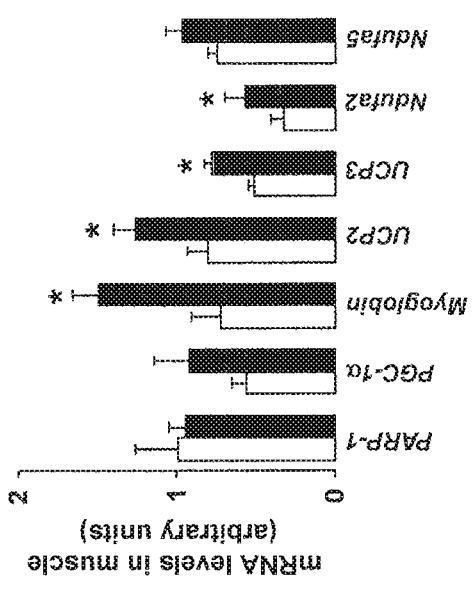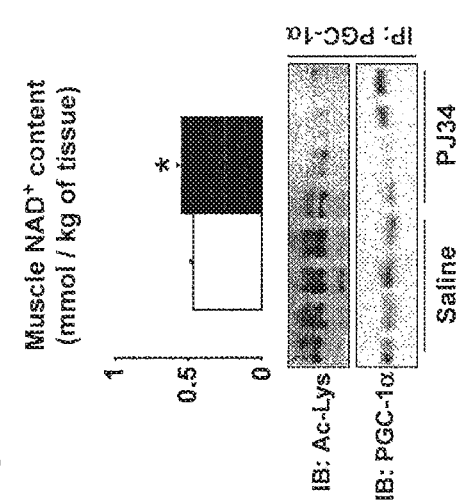

☐ PARP-1⁺/⁺  ■ PARP-1⁻/⁻

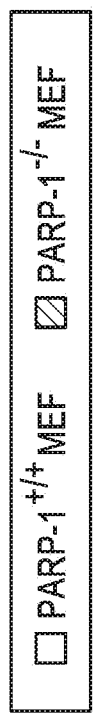
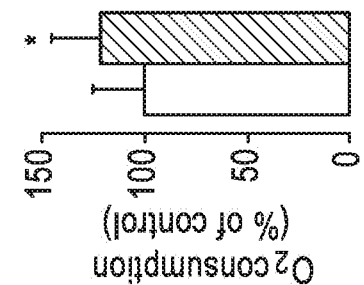
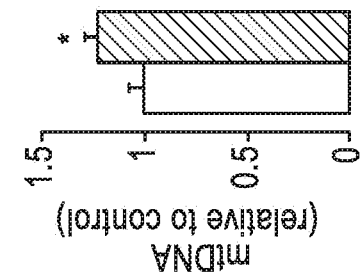
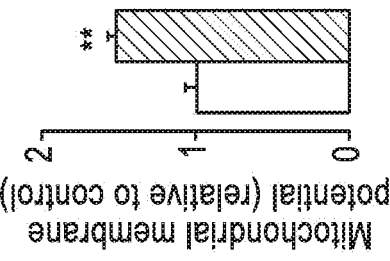
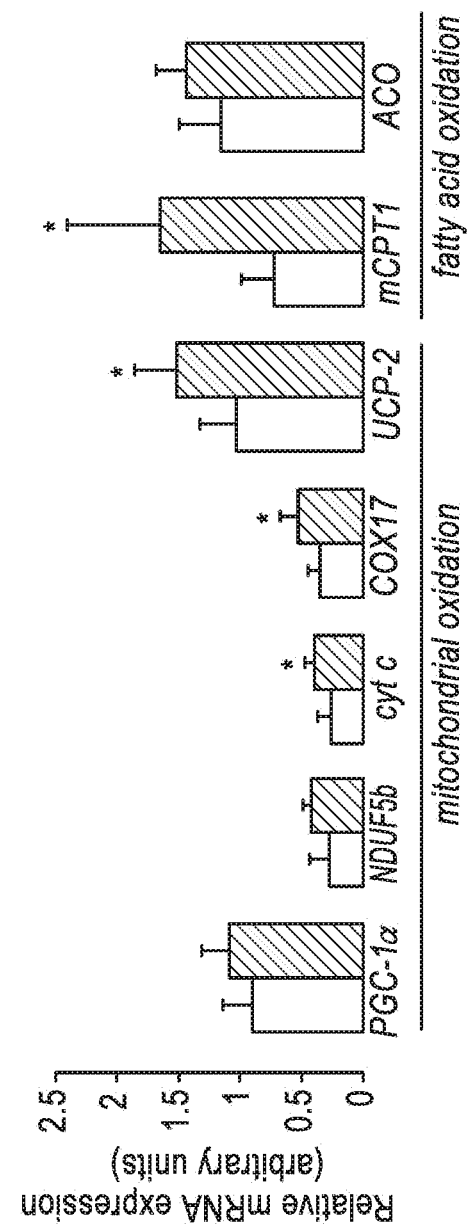
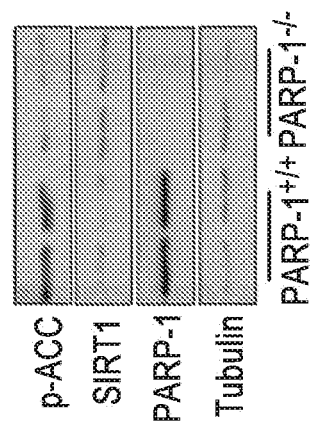

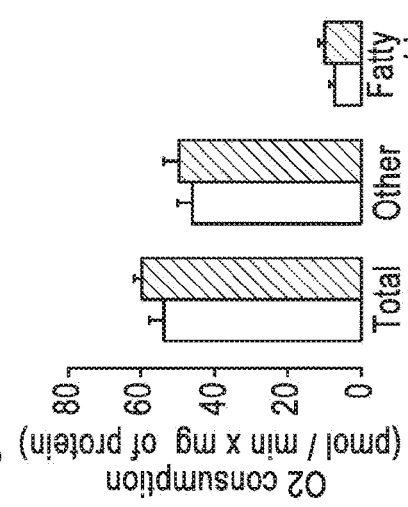
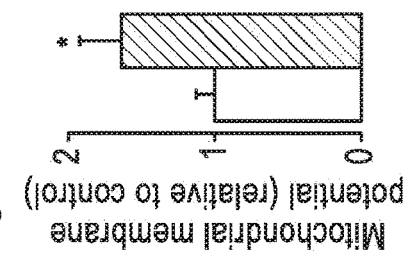
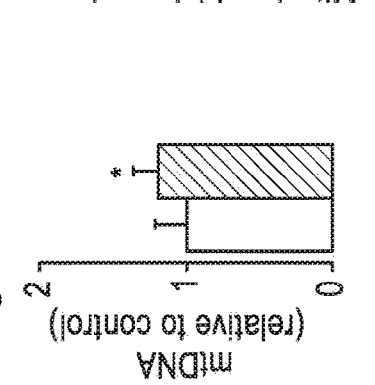
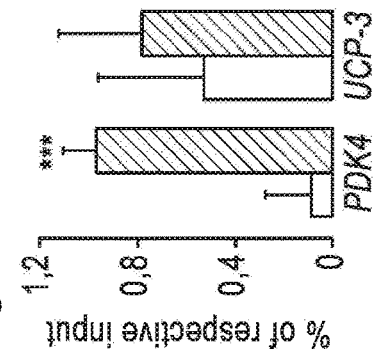
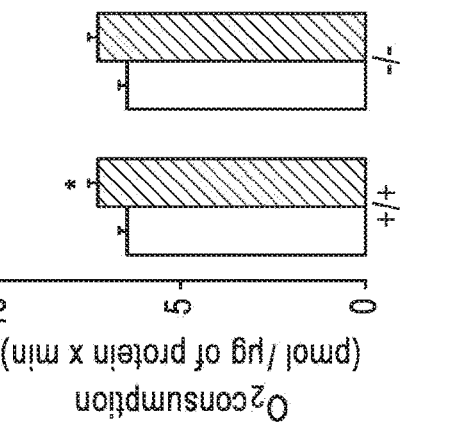
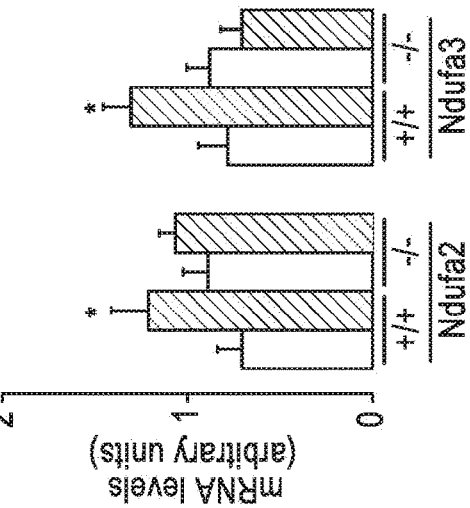
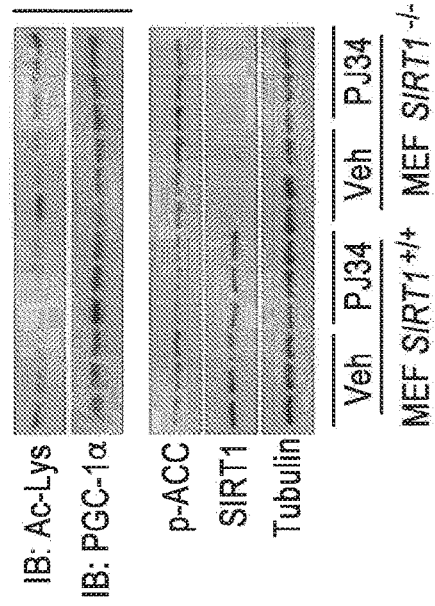

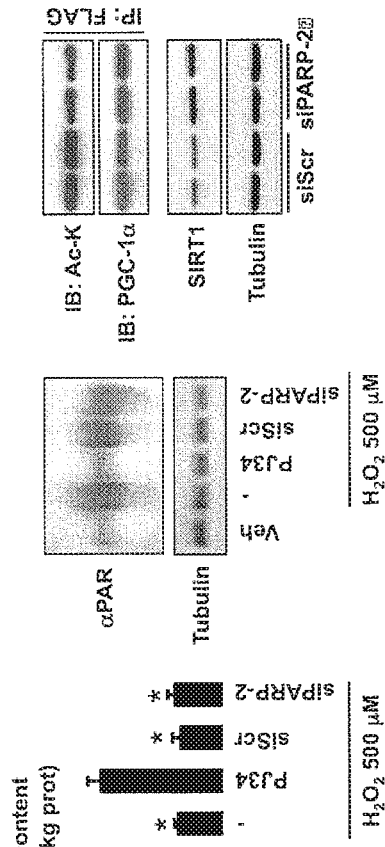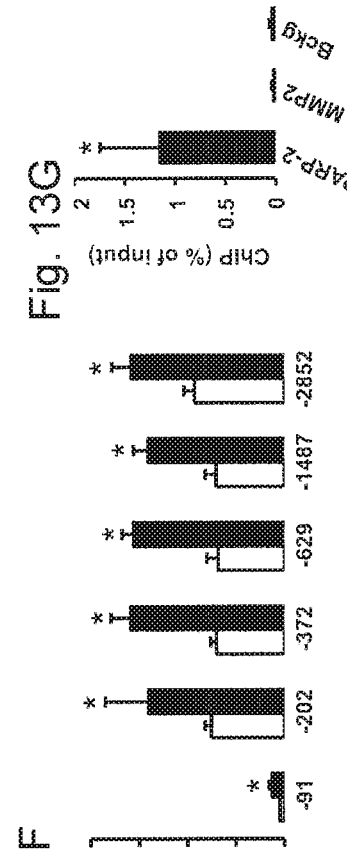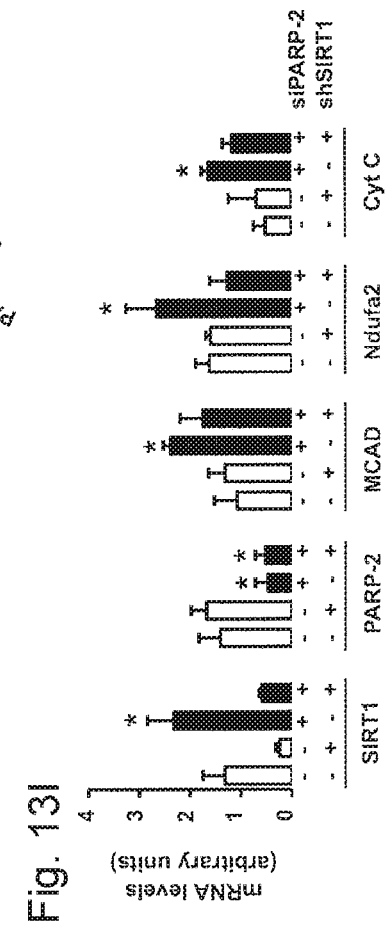
Fig. 13A, Fig. 13B, Fig. 13C, Fig. 13D, Fig. 13E, Fig. 13F, Fig. 13G, Fig. 13H, Fig. 13I

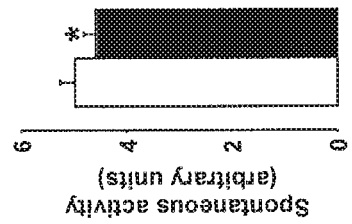
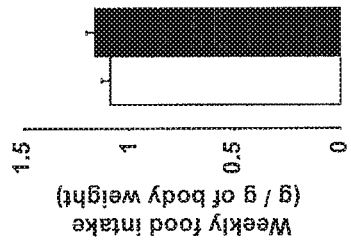
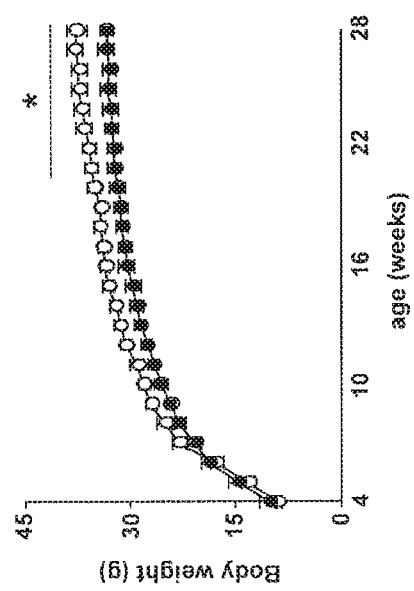
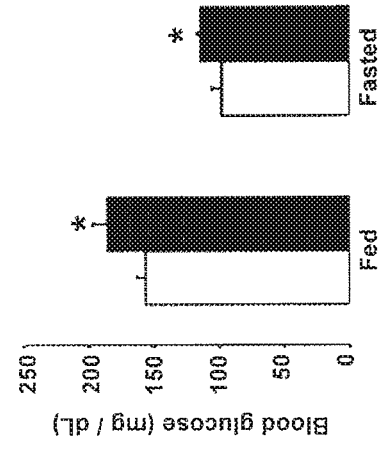
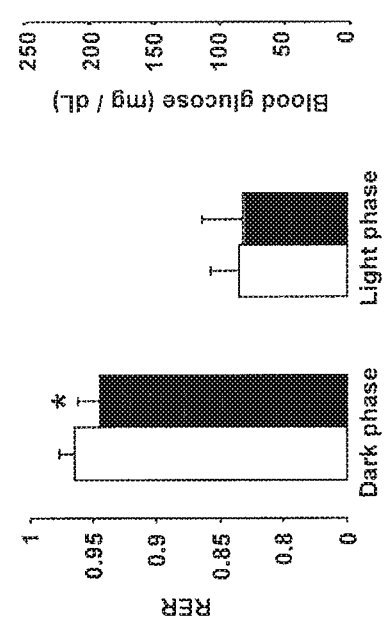
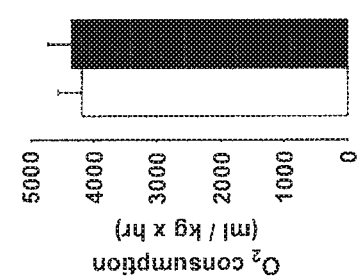

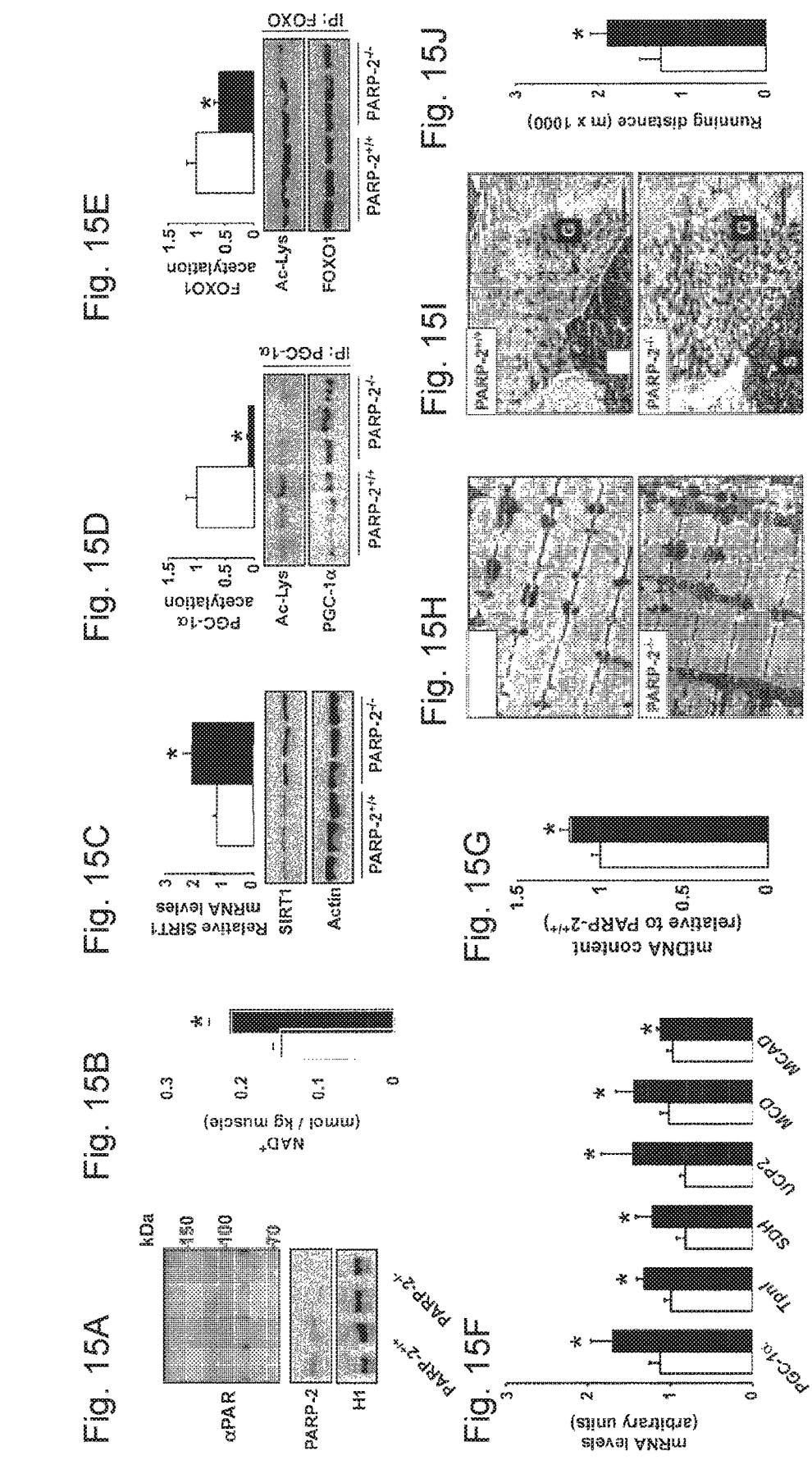

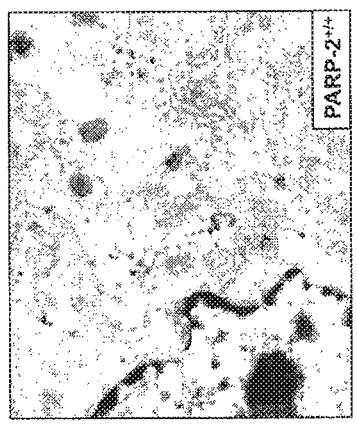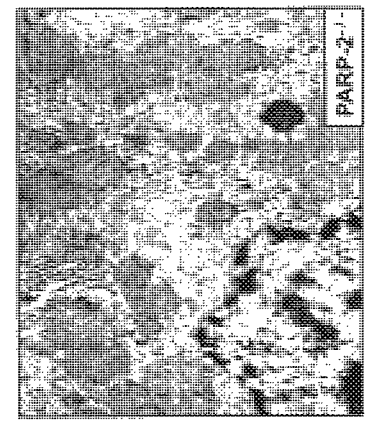
Fig. 16C
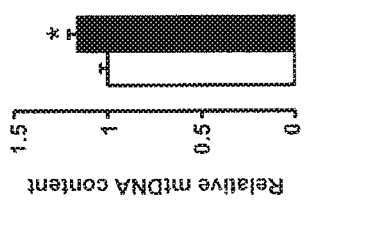
Fig. 16B
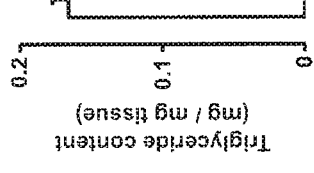
Fig. 16F
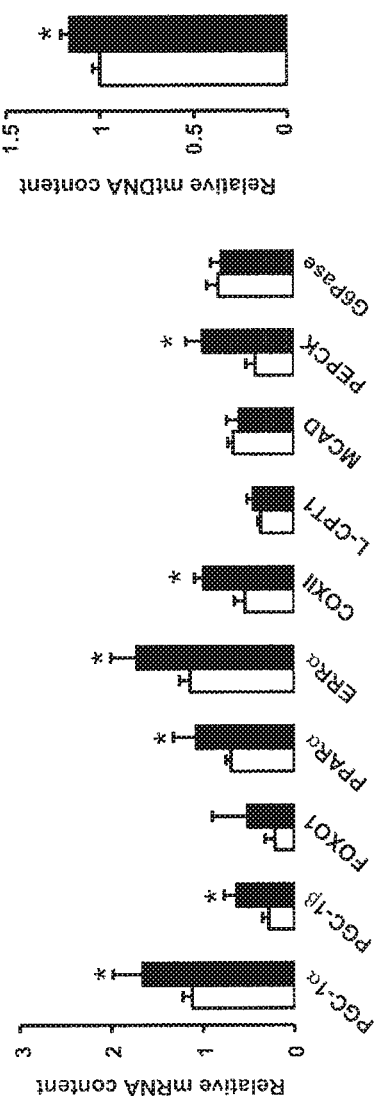
Fig. 16A
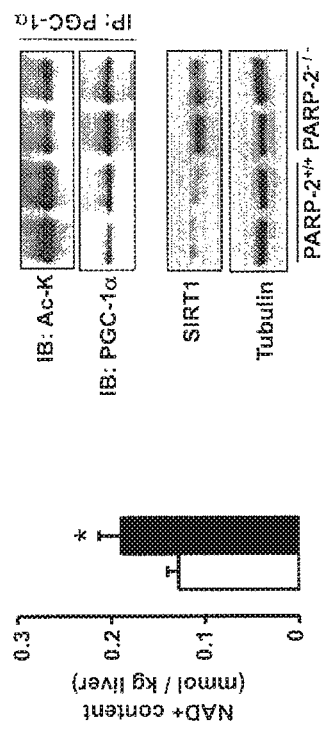
Fig. 16E
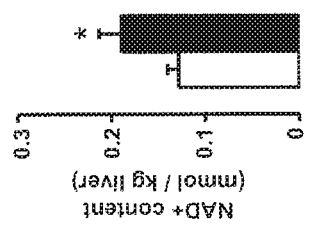
Fig. 16D

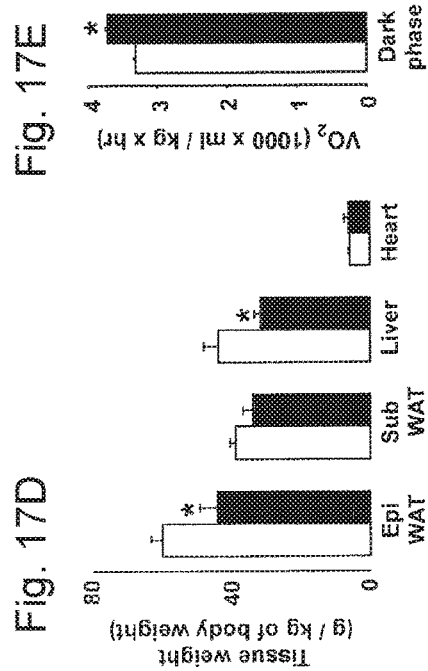
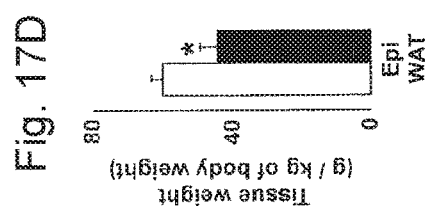
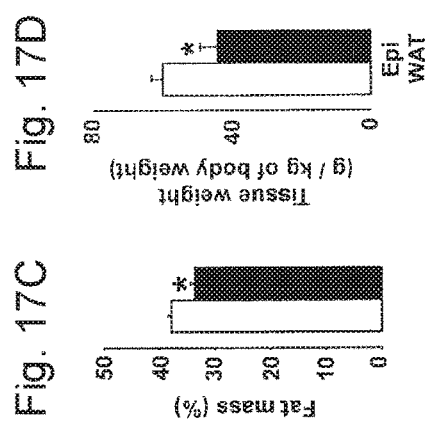
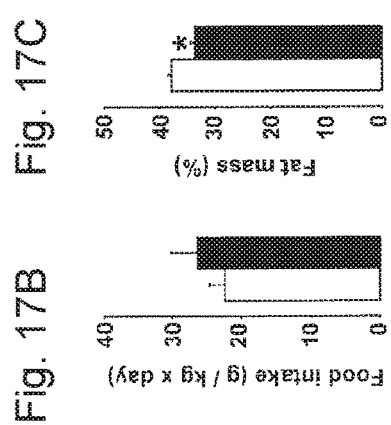
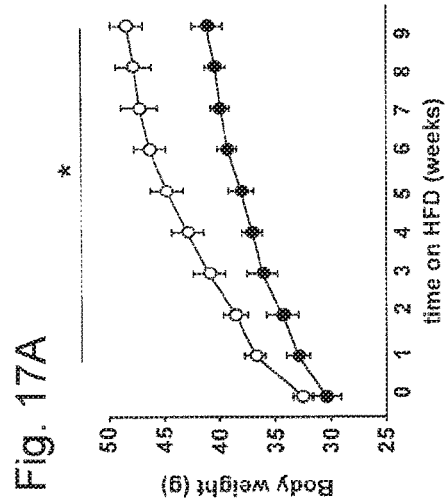
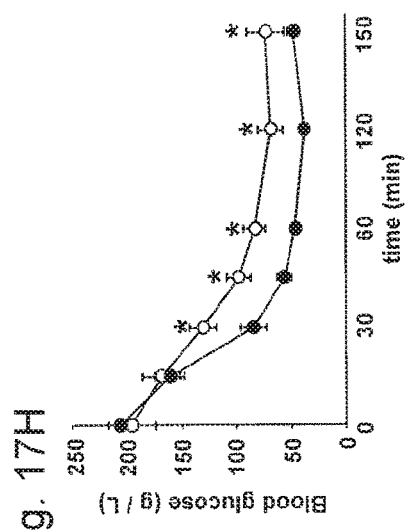
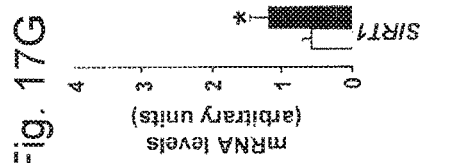
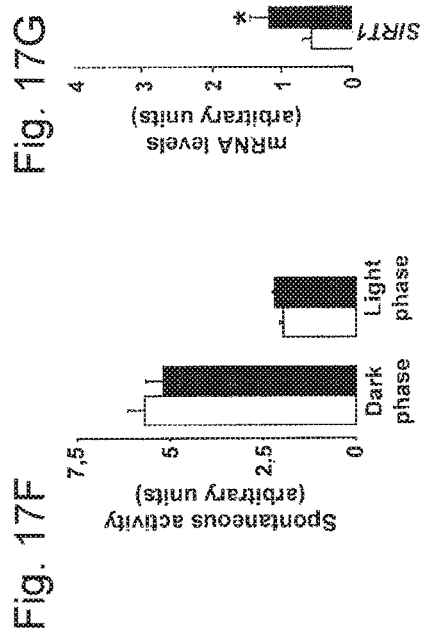

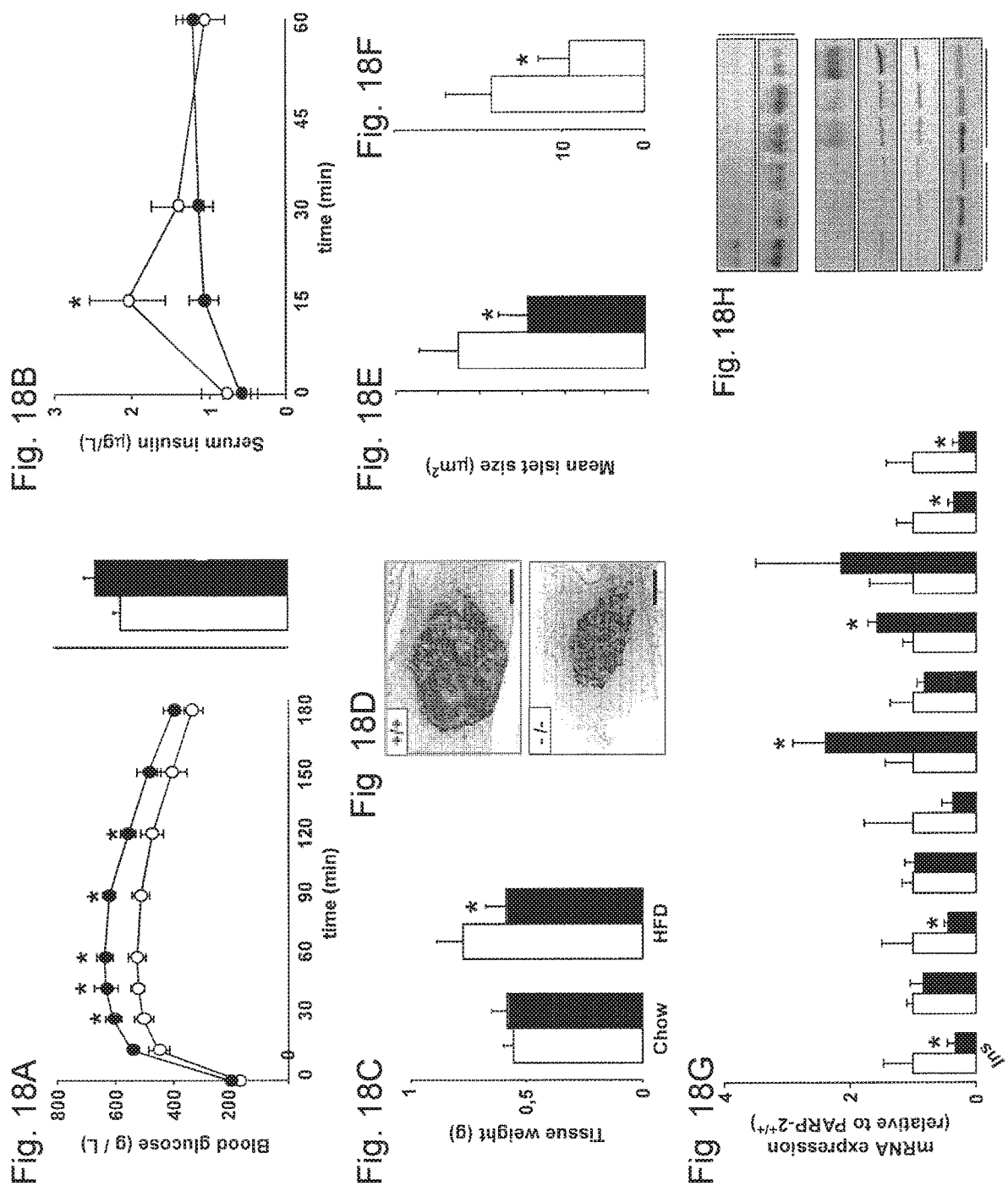

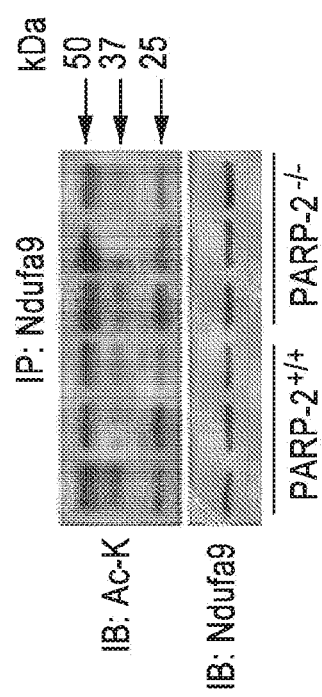
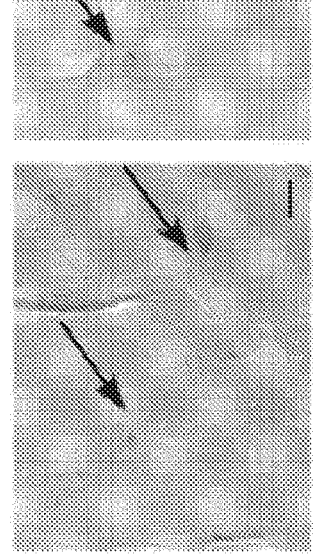
Fig. 20B
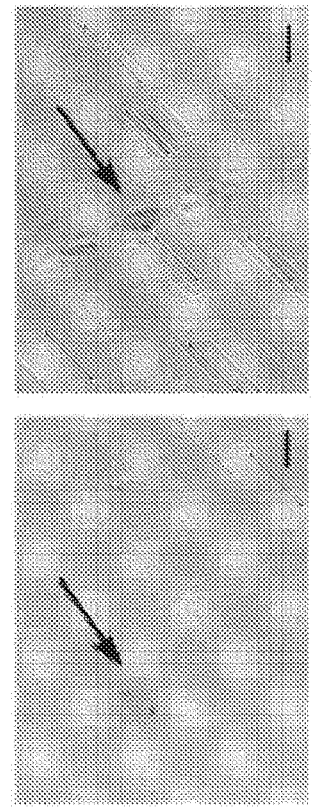
Fig. 20A

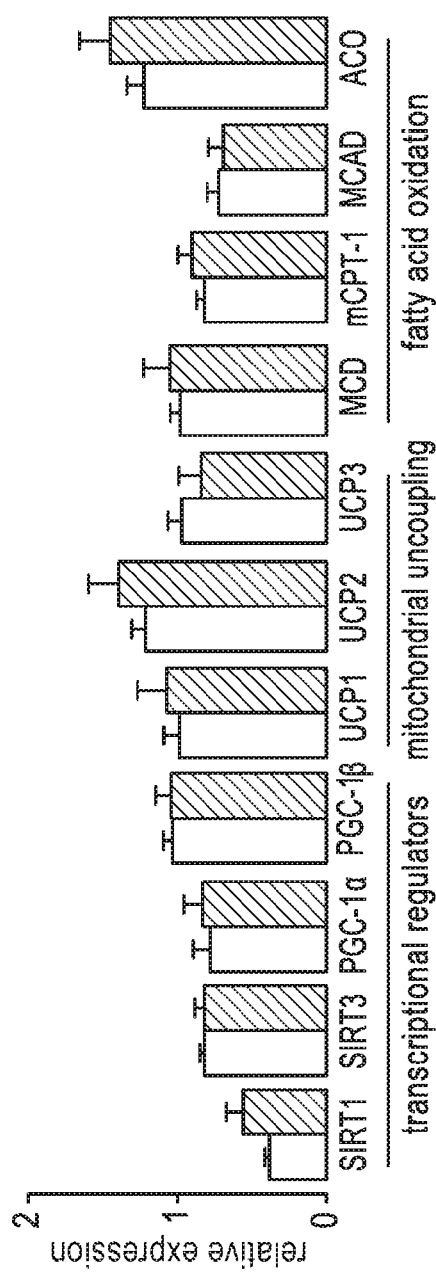
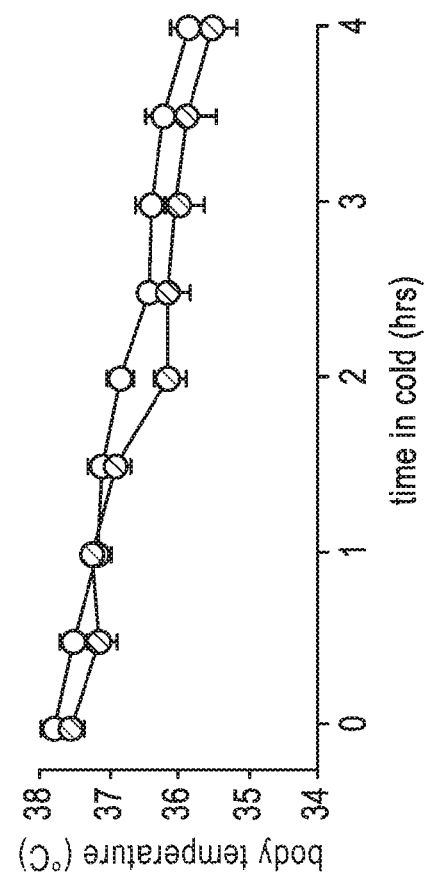
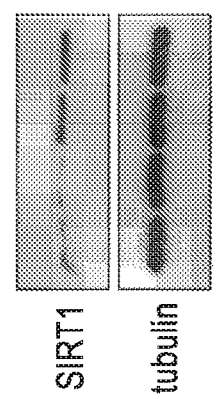

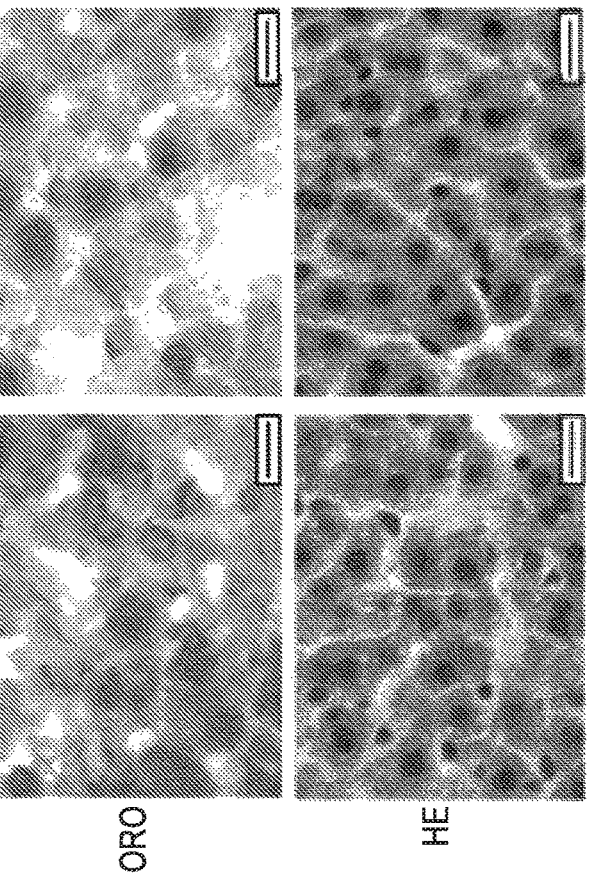
Fig. 22B
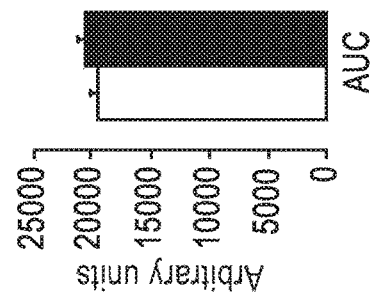
Fig. 22A
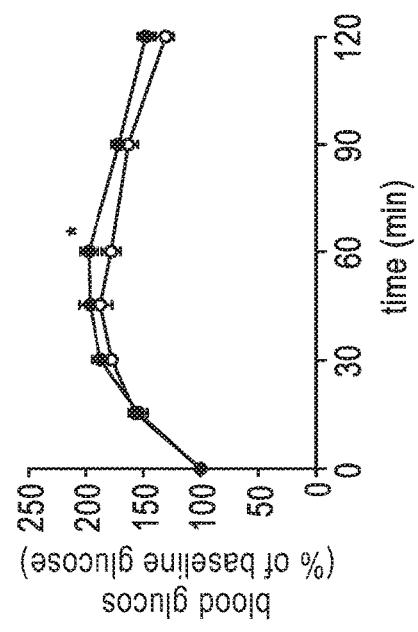
Fig. 22C
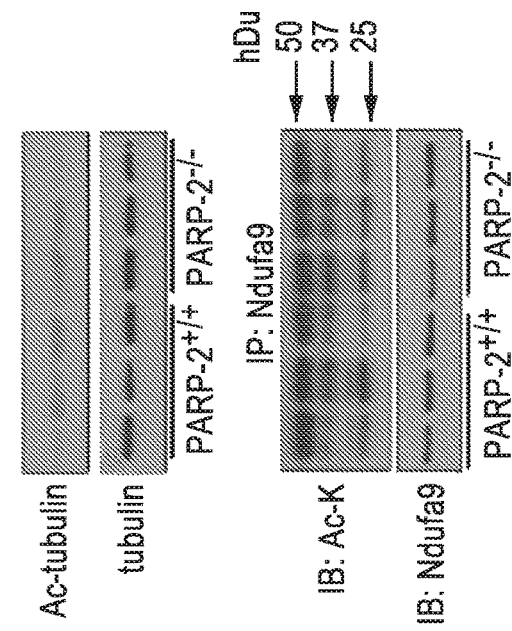

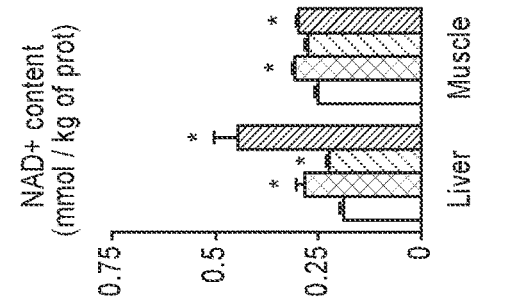
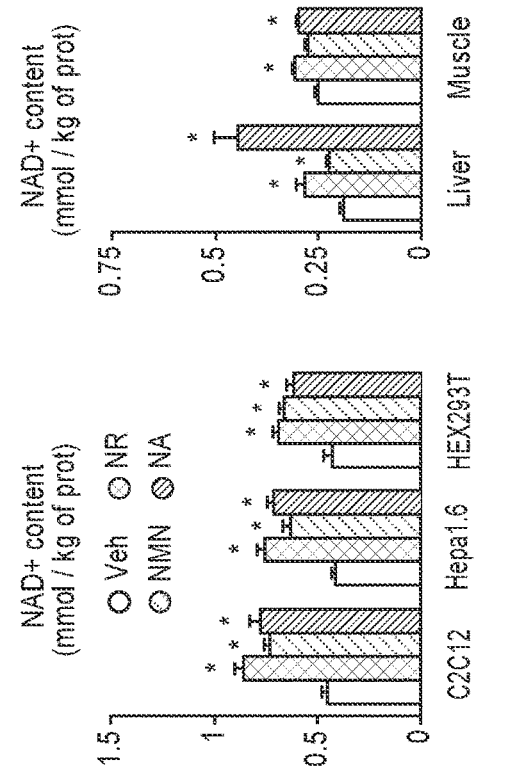
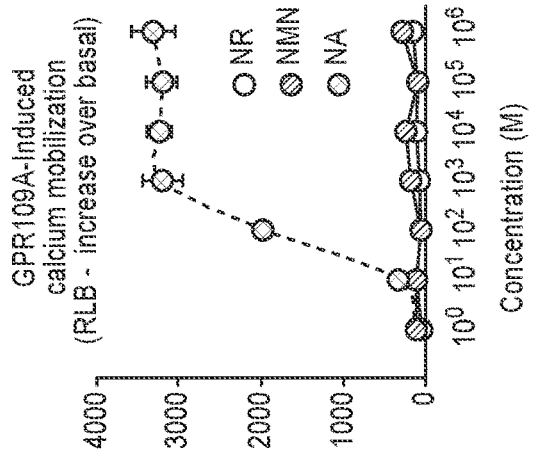
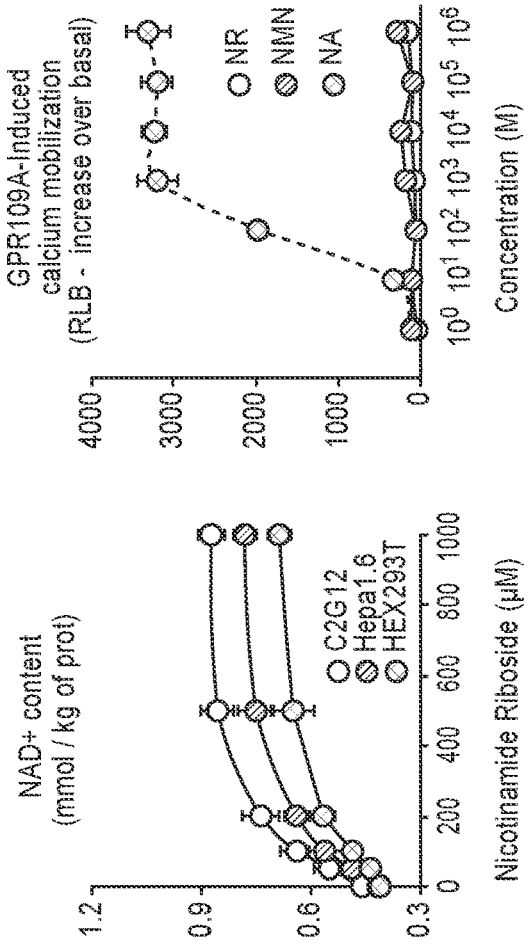
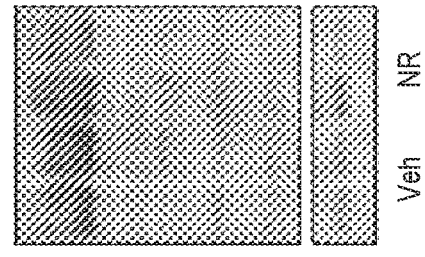
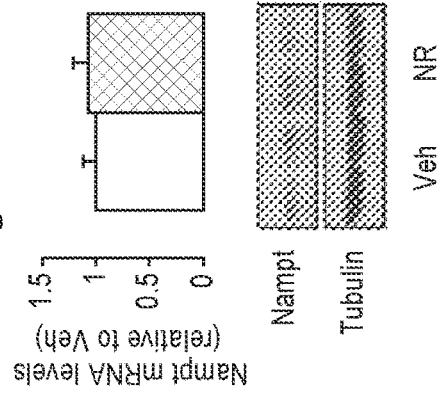
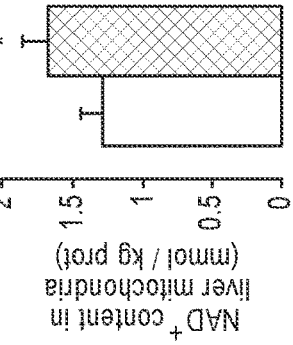
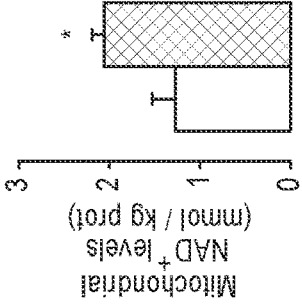

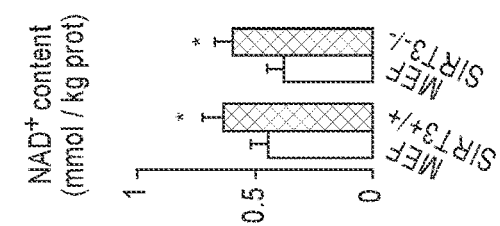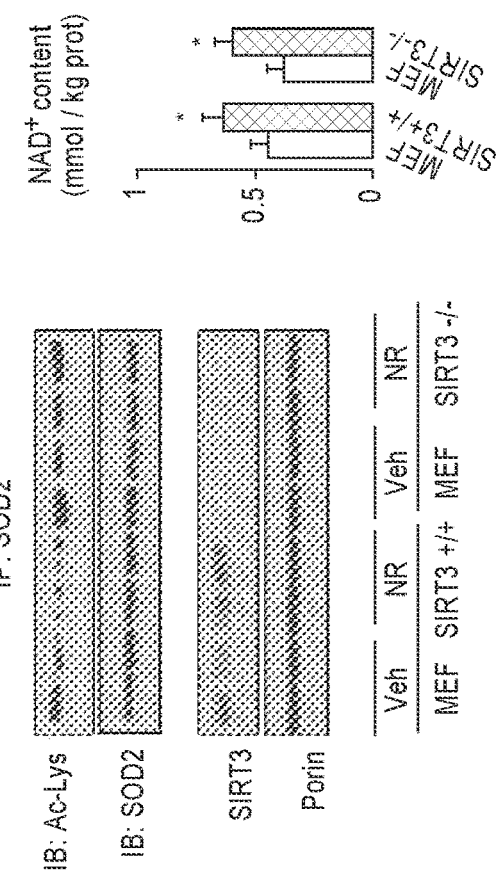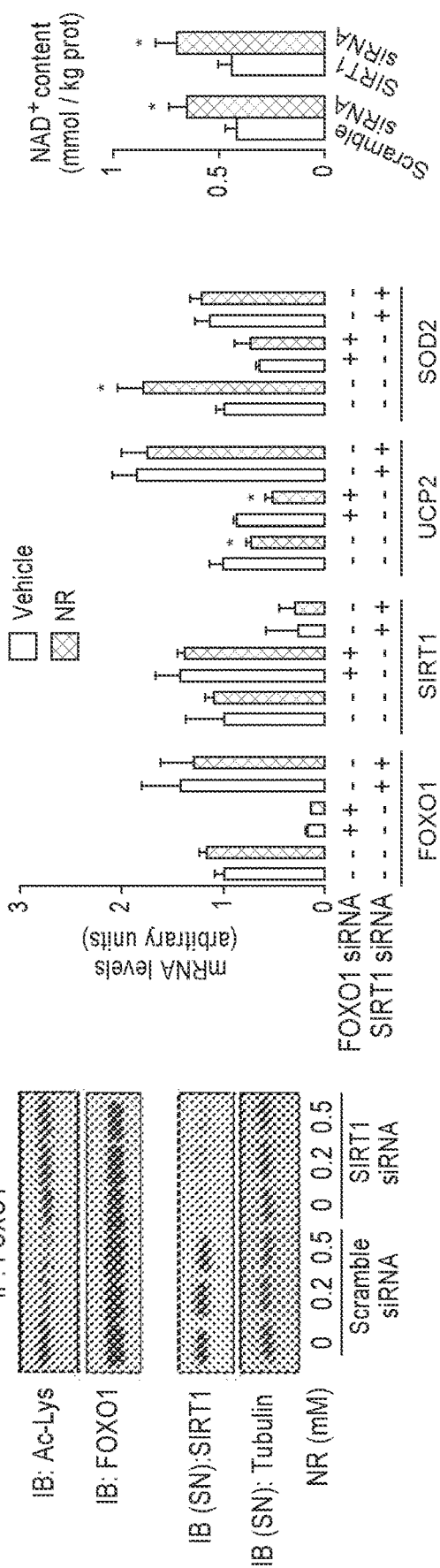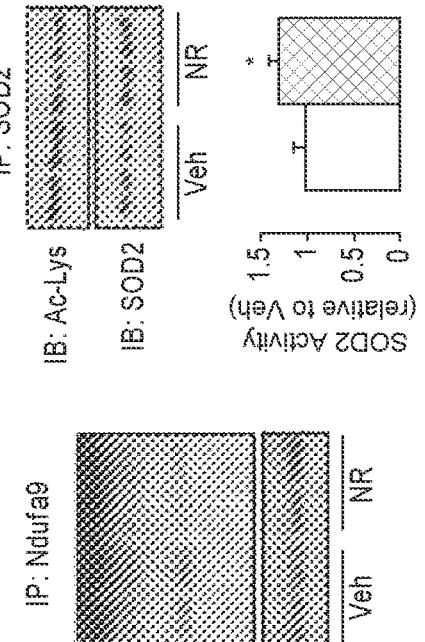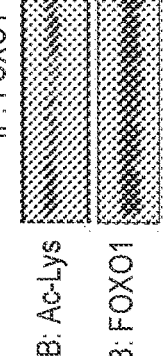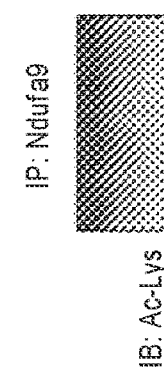

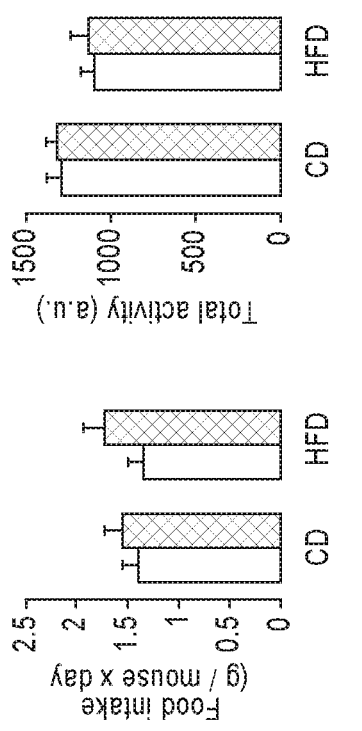
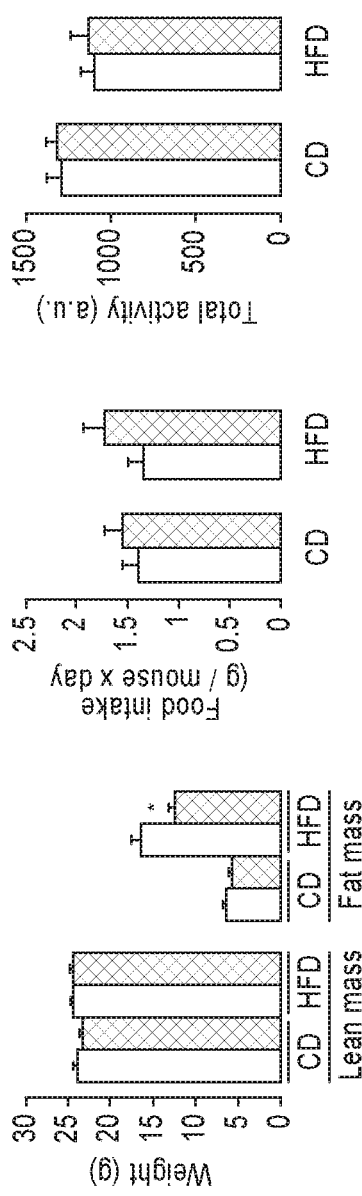
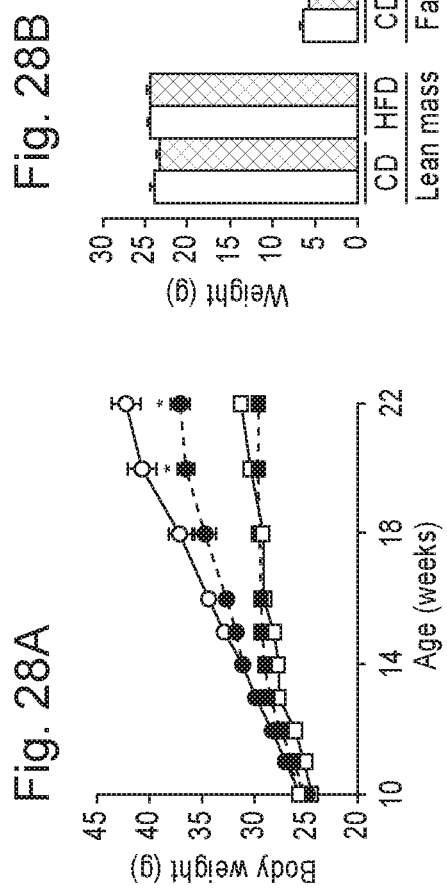
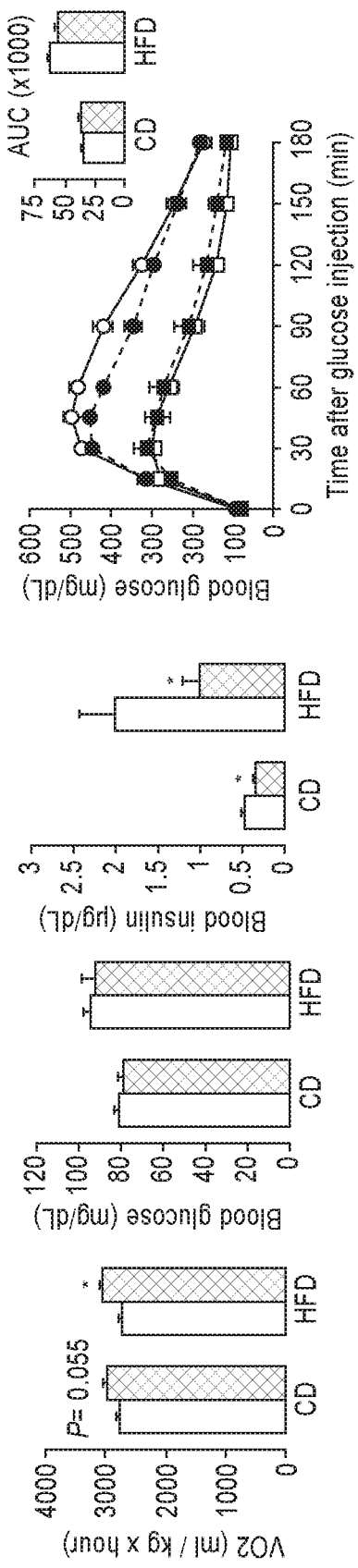

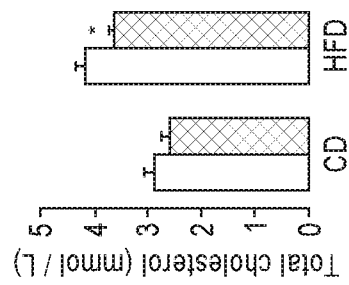
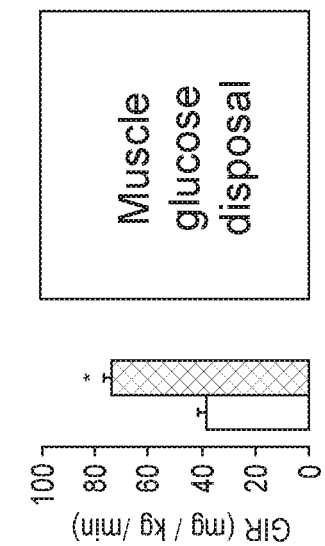
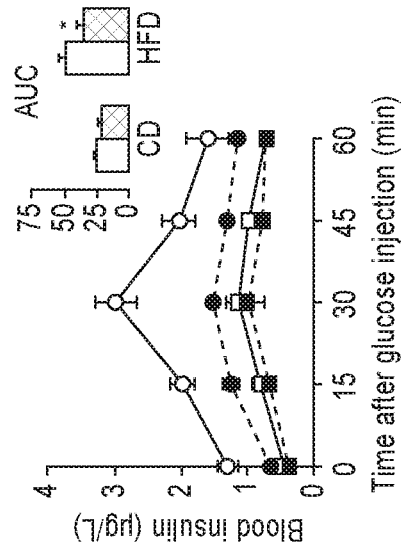

Fig. 29A
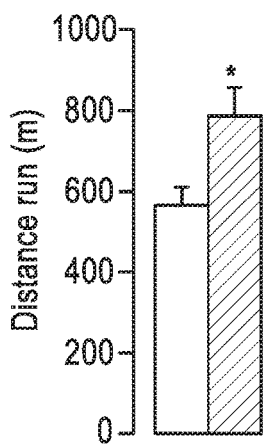
Fig. 29B
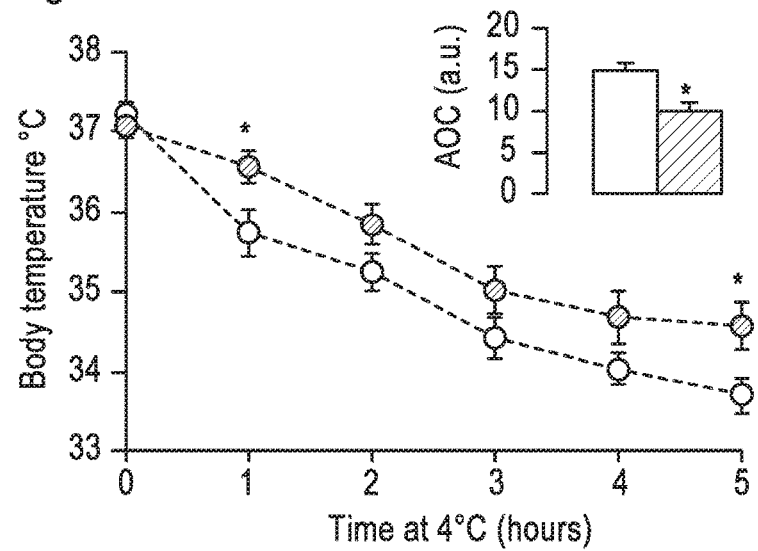
Fig. 29C
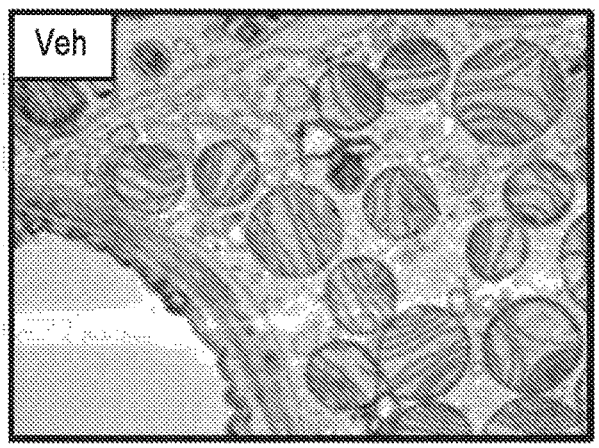
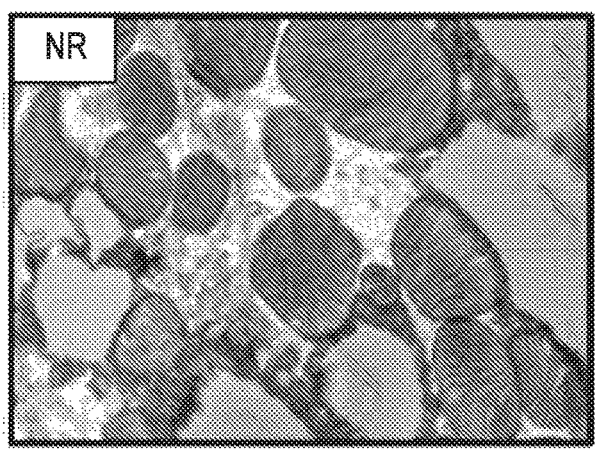
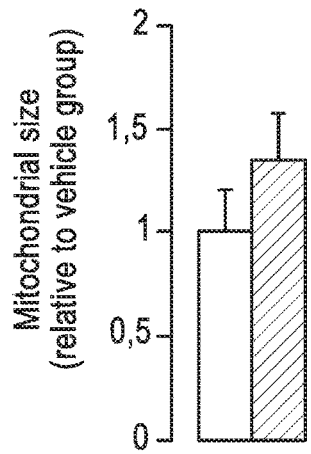
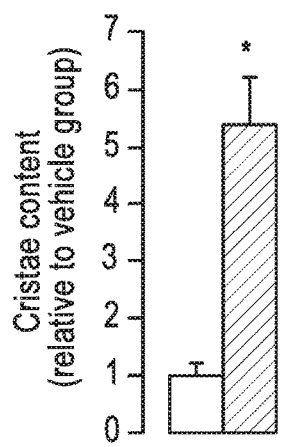

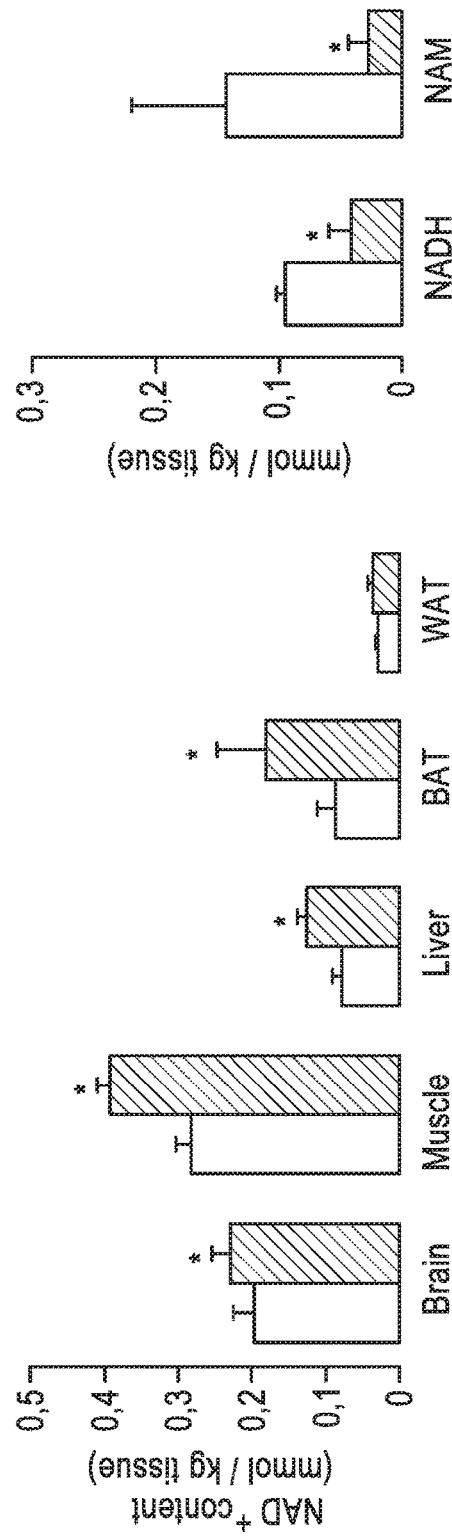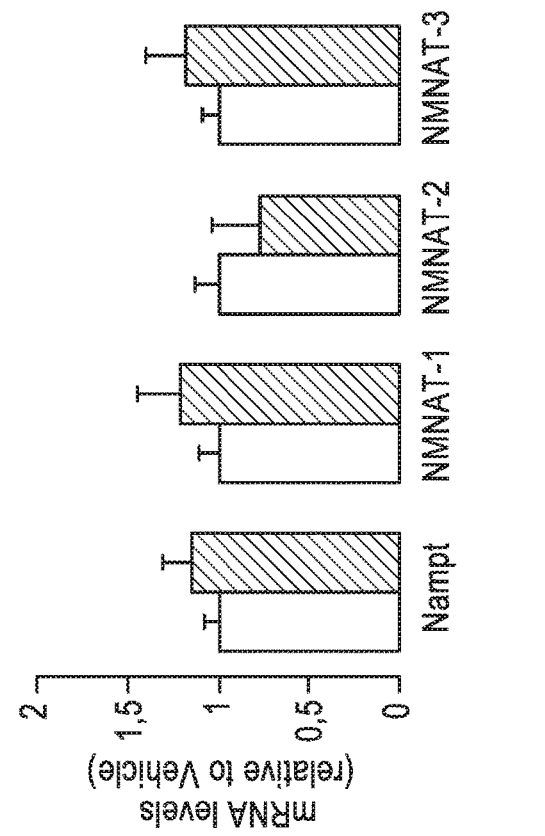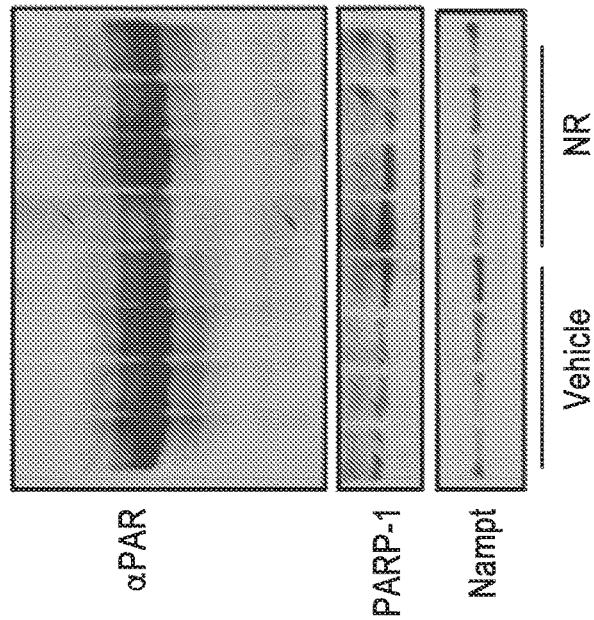

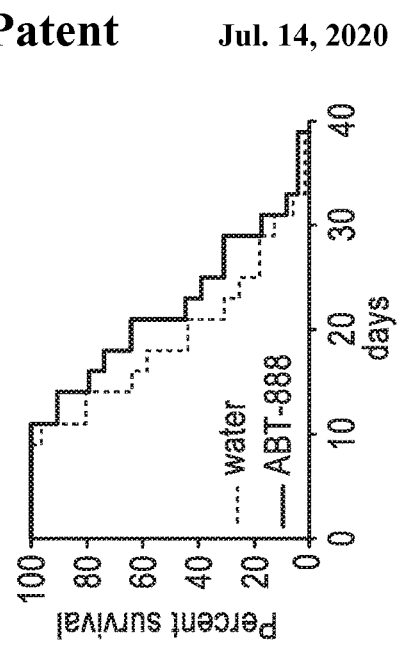
Fig. 34A
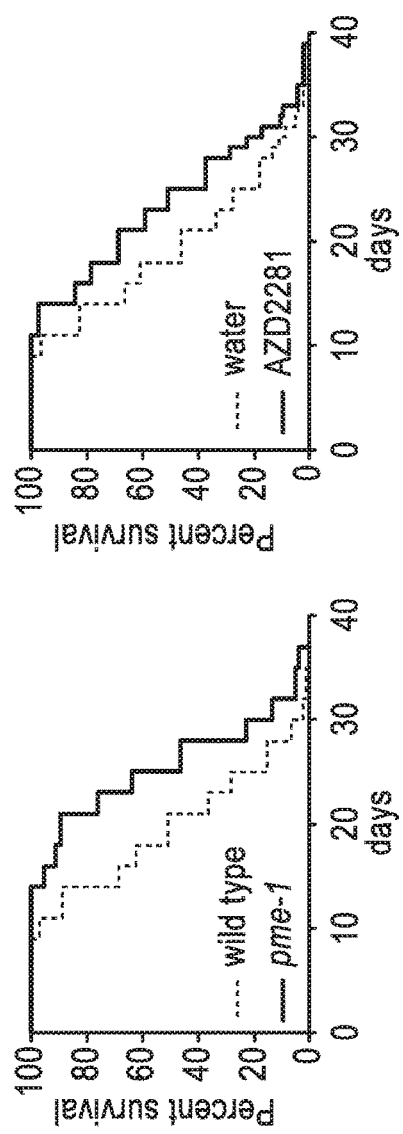
Fig. 34B
Fig. 34C
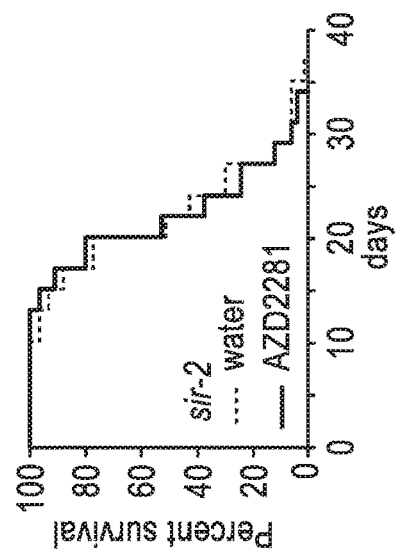
Fig. 34D
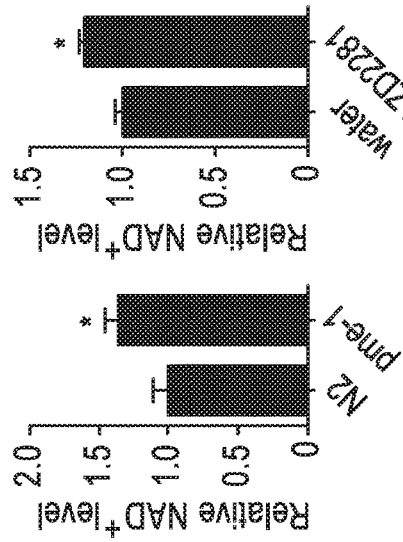
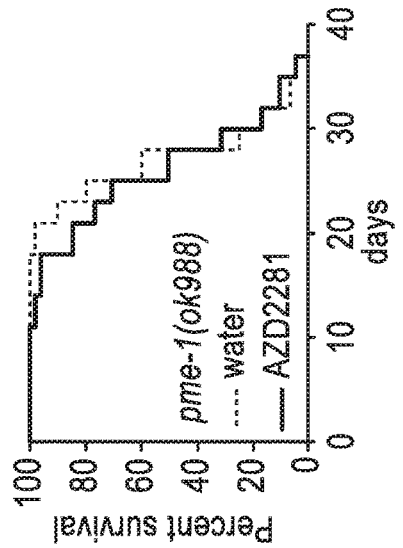
Fig. 34E Fig. 35A
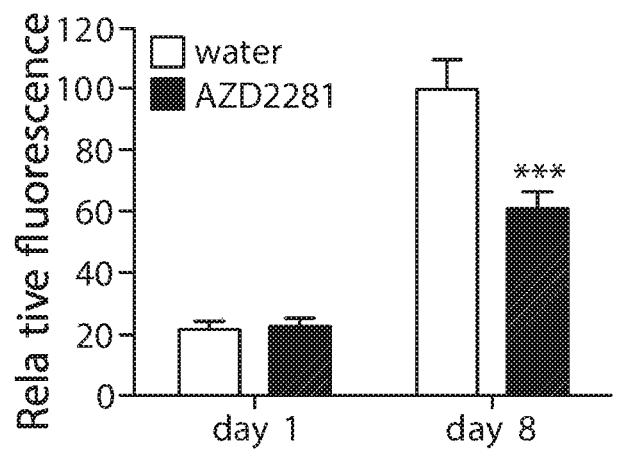
Fig. 35B
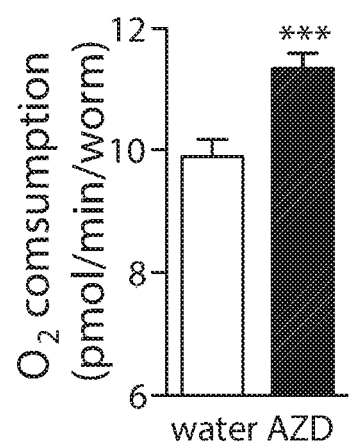
Fig. 35C
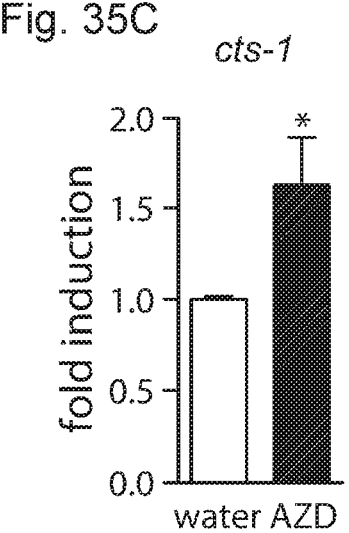
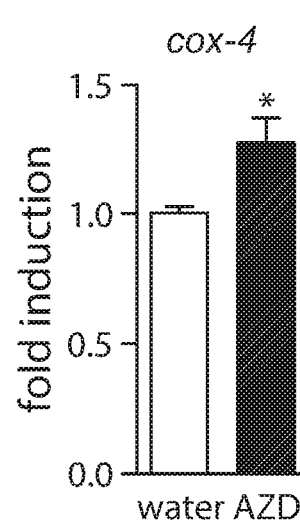
Fig. 35D
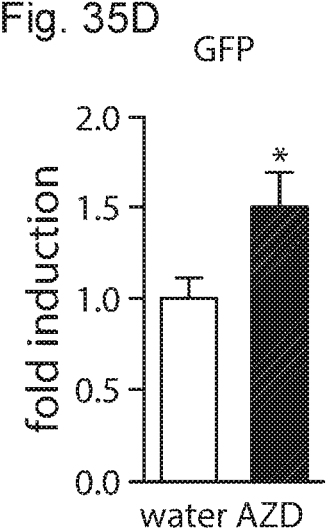

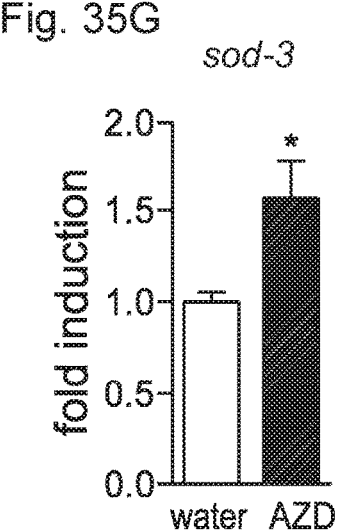

Fig. 36F
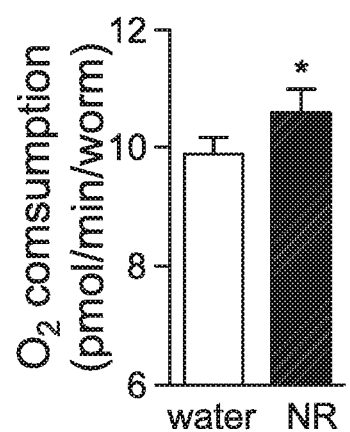
Fig. 36G  cts-1
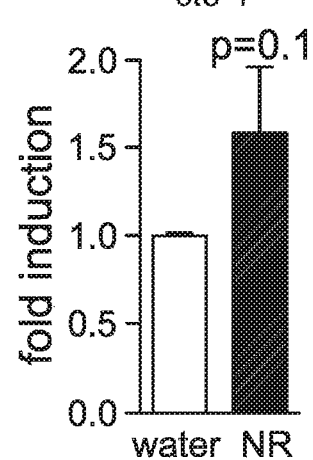
Fig. 36H  sod-3
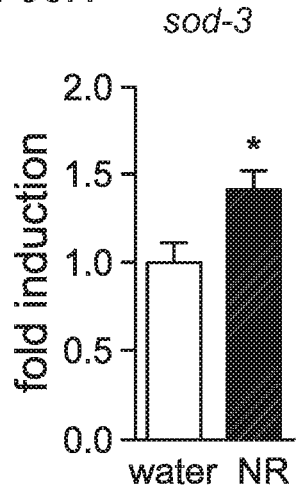
daf-16
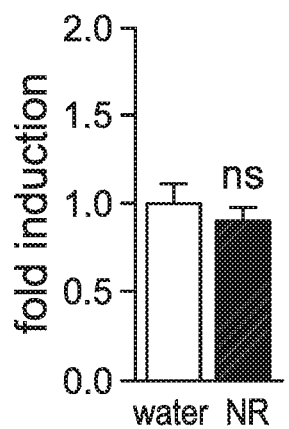

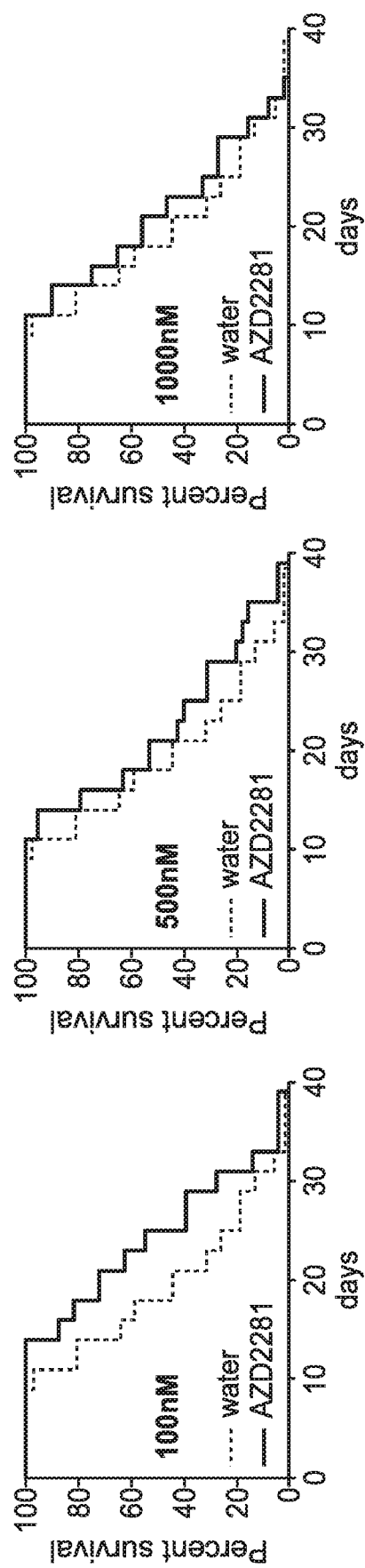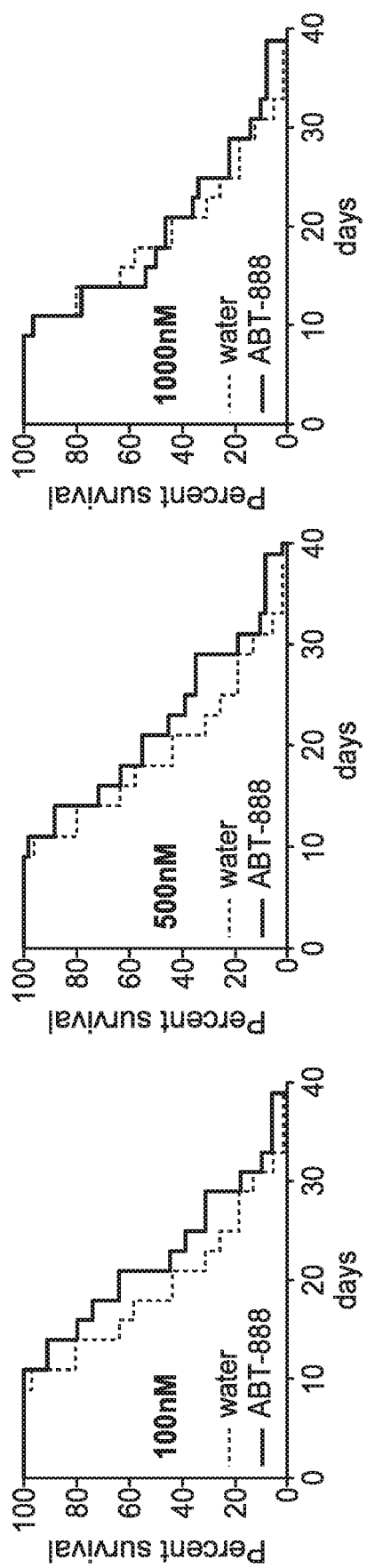

SEQUENCE LISTING

```
<160> NUMBER OF SEQ ID NOS: 162

<210> SEQ ID NO 1
<211> LENGTH: 22
<212> TYPE: DNA
<213> ORGANISM: Artificial Sequence
<220> FEATURE:
<223> OTHER INFORMATION: Synthesized primer

<400> SEQUENCE: 1
gacagactga tcgcagagaa ag                                              22

<210> SEQ ID NO 2
<211> LENGTH: 18
<212> TYPE: DNA
<213> ORGANISM: Artificial Sequence
<220> FEATURE:
<223> OTHER INFORMATION: Synthesized primer

<400> SEQUENCE: 2
tggagagccc cacacaca                                                   18

<210> SEQ ID NO 3
<211> LENGTH: 19
<212> TYPE: DNA
<213> ORGANISM: Artificial Sequence
<220> FEATURE:
<223> OTHER INFORMATION: Synthesized primer

<400> SEQUENCE: 3
cccagccgag tttgtcact                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthesized primer

<400> SEQUENCE: 4
ggcgatgagc accttctcta                                                 20

<210> SEQ ID NO 5
<211> LENGTH: 19
<212> TYPE: DNA
<213> ORGANISM: Artificial Sequence
<220> FEATURE:
<223> OTHER INFORMATION: Synthesized primer

<400> SEQUENCE: 5
cccaactgtg acttccatt                                                  19

<210> SEQ ID NO 6
<211> LENGTH: 20
<212> TYPE: DNA
<213> ORGANISM: Artificial Sequence
<220> FEATURE:
<223> OTHER INFORMATION: Synthesized primer

<400> SEQUENCE: 6
ggcatgtaac ccgtagcact                                                 20
```

<210> SEQ ID NO 7
<211> LENGTH: 20
<212> TYPE: DNA
<213> ORGANISM: Artificial Sequence
<220> FEATURE:
<223> OTHER INFORMATION: Synthesized primer

<400> SEQUENCE: 7
gctgcttgag agatgggttc                                                   20

<210> SEQ ID NO 8
<211> LENGTH: 19
<212> TYPE: DNA
<213> ORGANISM: Artificial Sequence
<220> FEATURE:
<223> OTHER INFORMATION: Synthesized primer

<400> SEQUENCE: 8
agttggtgtg gctggatca                                                    19

<210> SEQ ID NO 9
<211> LENGTH: 20
<212> TYPE: DNA
<213> ORGANISM: Artificial Sequence
<220> FEATURE:
<223> OTHER INFORMATION: Synthesized primer

<400> SEQUENCE: 9
cgtgatgcgt gcatcattga                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthesized primer

<400> SEQUENCE: 10
cattcacaaa gtaggccacc                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthesized primer

<400> SEQUENCE: 11
tggagagcac caagacagac a                                                 21

<210> SEQ ID NO 12
<211> LENGTH: 19
<212> TYPE: DNA
<213> ORGANISM: Artificial Sequence
<220> FEATURE:
<223> OTHER INFORMATION: Synthesized primer

<400> SEQUENCE: 12
tgccggagtc gacaatgat                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthesized primer

```
<400> SEQUENCE: 13
tccatcaggg tatcctctcc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthesized primer

<400> SEQUENCE: 14
ggaggcaagc ataagactgg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthesized primer

<400> SEQUENCE: 15
gcacgtctcc aatcctgaat                                              20

<210> SEQ ID NO 16
<211> LENGTH: 20
<212> TYPE: DNA
<213> ORGANISM: Artificial Sequence
<220> FEATURE:
<223> OTHER INFORMATION: Synthesized primer

<400> SEQUENCE: 16
tgaaccaaag ttgaccacca                                              20

<210> SEQ ID NO 17
<211> LENGTH: 19
<212> TYPE: DNA
<213> ORGANISM: Artificial Sequence
<220> FEATURE:
<223> OTHER INFORMATION: Synthesized primer

<400> SEQUENCE: 17
actgccactg caggatgag                                               19

<210> SEQ ID NO 18
<211> LENGTH: 20
<212> TYPE: DNA
<213> ORGANISM: Artificial Sequence
<220> FEATURE:
<223> OTHER INFORMATION: Synthesized primer

<400> SEQUENCE: 18
cacagcctca gcatcttcaa                                              20

<210> SEQ ID NO 19
<211> LENGTH: 23
<212> TYPE: DNA
<213> ORGANISM: Artificial Sequence
<220> FEATURE:
<223> OTHER INFORMATION: Synthesized primer

<400> SEQUENCE: 19
acattgtgcg ccgtgcctgt gaa                                          23

<210> SEQ ID NO 20
```

```
<211> LENGTH: 23
<212> TYPE: DNA
<213> ORGANISM: Artificial Sequence
<220> FEATURE:
<223> OTHER INFORMATION: Synthesized primer

<400> SEQUENCE: 20
agcctgcgca cactggcgtg aaa                                              23

<210> SEQ ID NO 21
<211> LENGTH: 25
<212> TYPE: DNA
<213> ORGANISM: Artificial Sequence
<220> FEATURE:
<223> OTHER INFORMATION: Synthesized primer

<400> SEQUENCE: 21
ccggatctac cttgctgctc acttt                                            25

<210> SEQ ID NO 22
<211> LENGTH: 26
<212> TYPE: DNA
<213> ORGANISM: Artificial Sequence
<220> FEATURE:
<223> OTHER INFORMATION: Synthesized primer

<400> SEQUENCE: 22
tagcaggtag aatccaagcg cgaaac                                           26

<210> SEQ ID NO 23
<211> LENGTH: 20
<212> TYPE: DNA
<213> ORGANISM: Artificial Sequence
<220> FEATURE:
<223> OTHER INFORMATION: Synthesized primer

<400> SEQUENCE: 23
gccggctcta tcctcctttg                                                  20

<210> SEQ ID NO 24
<211> LENGTH: 25
<212> TYPE: DNA
<213> ORGANISM: Artificial Sequence
<220> FEATURE:
<223> OTHER INFORMATION: Synthesized primer

<400> SEQUENCE: 24
tttgtatgca tcttgcacaa tcttt                                            25

<210> SEQ ID NO 25
<211> LENGTH: 23
<212> TYPE: DNA
<213> ORGANISM: Artificial Sequence
<220> FEATURE:
<223> OTHER INFORMATION: Synthesized primer

<400> SEQUENCE: 25
tggatggctg acagcagcct caa                                              23

<210> SEQ ID NO 26
<211> LENGTH: 24
<212> TYPE: DNA
<213> ORGANISM: Artificial Sequence
<220> FEATURE:
<223> OTHER INFORMATION: Synthesized primer

<400> SEQUENCE: 26
```

```
ctgaggatct gctcggaagc tttg                                          24
```

<210> SEQ ID NO 27
<211> LENGTH: 26
<212> TYPE: DNA
<213> ORGANISM: Artificial Sequence
<220> FEATURE:
<223> OTHER INFORMATION: Synthesized primer

<400> SEQUENCE: 27

```
gatcgcaatg ggtgcttttg atagaa                                        26
```

<210> SEQ ID NO 28
<211> LENGTH: 26
<212> TYPE: DNA
<213> ORGANISM: Artificial Sequence
<220> FEATURE:
<223> OTHER INFORMATION: Synthesized primer

<400> SEQUENCE: 28

```
agctgattgg caatgtctcc agcaaa                                        26
```

<210> SEQ ID NO 29
<211> LENGTH: 24
<212> TYPE: DNA
<213> ORGANISM: Artificial Sequence
<220> FEATURE:
<223> OTHER INFORMATION: Synthesized primer

<400> SEQUENCE: 29

```
ttgccctaca gctggctcat ttcc                                          24
```

<210> SEQ ID NO 30
<211> LENGTH: 24
<212> TYPE: DNA
<213> ORGANISM: Artificial Sequence
<220> FEATURE:
<223> OTHER INFORMATION: Synthesized primer

<400> SEQUENCE: 30

```
gcacccagat gattgggata ctgt                                          24
```

<210> SEQ ID NO 31
<211> LENGTH: 23
<212> TYPE: DNA
<213> ORGANISM: Artificial Sequence
<220> FEATURE:
<223> OTHER INFORMATION: Synthesized primer

<400> SEQUENCE: 31

```
gagtagctct tgtgctaccc agc                                           23
```

<210> SEQ ID NO 32
<211> LENGTH: 23
<212> TYPE: DNA
<213> ORGANISM: Artificial Sequence
<220> FEATURE:
<223> OTHER INFORMATION: Synthesized primer

<400> SEQUENCE: 32

```
aattgcttta ttctgcttcc acc                                           23
```

<210> SEQ ID NO 33
<211> LENGTH: 21
<212> TYPE: DNA

```
<213> ORGANISM: Artificial Sequence
<220> FEATURE:
<223> OTHER INFORMATION: Synthesized primer

<400> SEQUENCE: 33
gcaagaagca gatccagaaa c                                        21

<210> SEQ ID NO 34
<211> LENGTH: 26
<212> TYPE: DNA
<213> ORGANISM: Artificial Sequence
<220> FEATURE:
<223> OTHER INFORMATION: Synthesized primer

<400> SEQUENCE: 34
ggtcttcttc tgtctggtaa gtaagc                                   26

<210> SEQ ID NO 35
<211> LENGTH: 24
<212> TYPE: DNA
<213> ORGANISM: Artificial Sequence
<220> FEATURE:
<223> OTHER INFORMATION: Synthesized primer

<400> SEQUENCE: 35
gcaacaggag atttctgacc tcac                                     24

<210> SEQ ID NO 36
<211> LENGTH: 19
<212> TYPE: DNA
<213> ORGANISM: Artificial Sequence
<220> FEATURE:
<223> OTHER INFORMATION: Synthesized primer

<400> SEQUENCE: 36
ccagagatgc ctctgcttc                                           19

<210> SEQ ID NO 37
<211> LENGTH: 20
<212> TYPE: DNA
<213> ORGANISM: Artificial Sequence
<220> FEATURE:
<223> OTHER INFORMATION: Synthesized primer

<400> SEQUENCE: 37
gcacacattt ccccacactg                                          20

<210> SEQ ID NO 38
<211> LENGTH: 20
<212> TYPE: DNA
<213> ORGANISM: Artificial Sequence
<220> FEATURE:
<223> OTHER INFORMATION: Synthesized primer

<400> SEQUENCE: 38
cccaacctgc ccattctgat                                          20

<210> SEQ ID NO 39
<211> LENGTH: 20
<212> TYPE: DNA
<213> ORGANISM: Artificial Sequence
<220> FEATURE:
<223> OTHER INFORMATION: Synthesized primer

<400> SEQUENCE: 39
taccacaaac gcagcaaacc                                          20
```

<210> SEQ ID NO 40
<211> LENGTH: 20
<212> TYPE: DNA
<213> ORGANISM: Artificial Sequence
<220> FEATURE:
<223> OTHER INFORMATION: Synthesized primer

<400> SEQUENCE: 40
aagggacgcc attagaaacg        20

<210> SEQ ID NO 41
<211> LENGTH: 20
<212> TYPE: DNA
<213> ORGANISM: Artificial Sequence
<220> FEATURE:
<223> OTHER INFORMATION: Synthesized primer

<400> SEQUENCE: 41
cttcgaactt cctgctcctt        20

<210> SEQ ID NO 42
<211> LENGTH: 19
<212> TYPE: DNA
<213> ORGANISM: Artificial Sequence
<220> FEATURE:
<223> OTHER INFORMATION: Synthesized primer

<400> SEQUENCE: 42
ggccctgaaa agaactacg        19

<210> SEQ ID NO 43
<211> LENGTH: 20
<212> TYPE: DNA
<213> ORGANISM: Artificial Sequence
<220> FEATURE:
<223> OTHER INFORMATION: Synthesized primer

<400> SEQUENCE: 43
ggagctgctc atcttcaacc        20

<210> SEQ ID NO 44
<211> LENGTH: 20
<212> TYPE: DNA
<213> ORGANISM: Artificial Sequence
<220> FEATURE:
<223> OTHER INFORMATION: Synthesized primer

<400> SEQUENCE: 44
gcagtgacat ccccagtaca        20

<210> SEQ ID NO 45
<211> LENGTH: 21
<212> TYPE: DNA
<213> ORGANISM: Artificial Sequence
<220> FEATURE:
<223> OTHER INFORMATION: Synthesized primer

<400> SEQUENCE: 45
ggaaggcgag tgctaaatga a        21

<210> SEQ ID NO 46
<211> LENGTH: 24
<212> TYPE: DNA
<213> ORGANISM: Artificial Sequence
<220> FEATURE:

<223> OTHER INFORMATION: Synthesized primer

<400> SEQUENCE: 46
aaggtcttca cagagtctcg attg                                          24

<210> SEQ ID NO 47
<211> LENGTH: 20
<212> TYPE: DNA
<213> ORGANISM: Artificial Sequence
<220> FEATURE:
<223> OTHER INFORMATION: Synthesized primer

<400> SEQUENCE: 47
cctgctgata atcgggtcat                                               20

<210> SEQ ID NO 48
<211> LENGTH: 20
<212> TYPE: DNA
<213> ORGANISM: Artificial Sequence
<220> FEATURE:
<223> OTHER INFORMATION: Synthesized primer

<400> SEQUENCE: 48
ttgttgttgt tgccgatgtt                                               20

<210> SEQ ID NO 49
<211> LENGTH: 22
<212> TYPE: DNA
<213> ORGANISM: Artificial Sequence
<220> FEATURE:
<223> OTHER INFORMATION: Synthesized primer

<400> SEQUENCE: 49
gttaaatttt gcactcctgg ag                                            22

<210> SEQ ID NO 50
<211> LENGTH: 25
<212> TYPE: DNA
<213> ORGANISM: Artificial Sequence
<220> FEATURE:
<223> OTHER INFORMATION: Synthesized primer

<400> SEQUENCE: 50
aatgtgaaca ctgtcaagag gaaca                                         25

<210> SEQ ID NO 51
<211> LENGTH: 20
<212> TYPE: DNA
<213> ORGANISM: Artificial Sequence
<220> FEATURE:
<223> OTHER INFORMATION: Synthesized primer

<400> SEQUENCE: 51
tagaggcatc gaaagctggt                                               20

<210> SEQ ID NO 52
<211> LENGTH: 17
<212> TYPE: DNA
<213> ORGANISM: Artificial Sequence
<220> FEATURE:
<223> OTHER INFORMATION: Synthesized primer

<400> SEQUENCE: 52
caggcattgt gaagggg                                                  17

<210> SEQ ID NO 53
<211> LENGTH: 19
<212> TYPE: DNA
<213> ORGANISM: Artificial Sequence
<220> FEATURE:
<223> OTHER INFORMATION: Synthesized primer

<400> SEQUENCE: 53
ggccctgctt acaccattg                                            19

<210> SEQ ID NO 54
<211> LENGTH: 20
<212> TYPE: DNA
<213> ORGANISM: Artificial Sequence
<220> FEATURE:
<223> OTHER INFORMATION: Synthesized primer

<400> SEQUENCE: 54
cgtgcttgac cagaagttca                                           20

<210> SEQ ID NO 55
<211> LENGTH: 20
<212> TYPE: DNA
<213> ORGANISM: Artificial Sequence
<220> FEATURE:
<223> OTHER INFORMATION: Synthesized primer

<400> SEQUENCE: 55
tttccagcca tcgaataagg                                           20

<210> SEQ ID NO 56
<211> LENGTH: 20
<212> TYPE: DNA
<213> ORGANISM: Artificial Sequence
<220> FEATURE:
<223> OTHER INFORMATION: Synthesized primer

<400> SEQUENCE: 56
accacttgcc ttgaaccaac                                           20

<210> SEQ ID NO 57
<211> LENGTH: 20
<212> TYPE: DNA
<213> ORGANISM: Artificial Sequence
<220> FEATURE:
<223> OTHER INFORMATION: Synthesized primer

<400> SEQUENCE: 57
aaaacccctg gaaatcaacc                                           20

<210> SEQ ID NO 58
<211> LENGTH: 20
<212> TYPE: DNA
<213> ORGANISM: Artificial Sequence
<220> FEATURE:
<223> OTHER INFORMATION: Synthesized primer

<400> SEQUENCE: 58
agaaggatgc gcttctggta                                           20

<210> SEQ ID NO 59
<211> LENGTH: 20
<212> TYPE: DNA
<213> ORGANISM: Artificial Sequence
<220> FEATURE:
<223> OTHER INFORMATION: Synthesized primer

```
<400> SEQUENCE: 59
tccaccatta aatcgcacaa                                              20

<210> SEQ ID NO 60
<211> LENGTH: 20
<212> TYPE: DNA
<213> ORGANISM: Artificial Sequence
<220> FEATURE:
<223> OTHER INFORMATION: Synthesized primer

<400> SEQUENCE: 60
gctccatttt cgatgtcttg                                              20

<210> SEQ ID NO 61
<211> LENGTH: 25
<212> TYPE: DNA
<213> ORGANISM: Artificial Sequence
<220> FEATURE:
<223> OTHER INFORMATION: Synthesized primer

<400> SEQUENCE: 61
acctgaagaa tggcctatta catgg                                        25

<210> SEQ ID NO 62
<211> LENGTH: 20
<212> TYPE: DNA
<213> ORGANISM: Artificial Sequence
<220> FEATURE:
<223> OTHER INFORMATION: Synthesized primer

<400> SEQUENCE: 62
acagctcagg gtagagatgc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthesized primer

<400> SEQUENCE: 63
caagatcctg cagatgcaaa                                              20

<210> SEQ ID NO 64
<211> LENGTH: 20
<212> TYPE: DNA
<213> ORGANISM: Artificial Sequence
<220> FEATURE:
<223> OTHER INFORMATION: Synthesized primer

<400> SEQUENCE: 64
ttggagaagc acacgttctg                                              20

<210> SEQ ID NO 65
<211> LENGTH: 23
<212> TYPE: DNA
<213> ORGANISM: Artificial Sequence
<220> FEATURE:
<223> OTHER INFORMATION: Synthesized primer

<400> SEQUENCE: 65
caatgagcag atgctatttc atg                                          23

<210> SEQ ID NO 66
<211> LENGTH: 20
```

```
<212> TYPE: DNA
<213> ORGANISM: Artificial Sequence
<220> FEATURE:
<223> OTHER INFORMATION: Synthesized primer

<400> SEQUENCE: 66
caccaattag cactcgagca                                          20

<210> SEQ ID NO 67
<211> LENGTH: 18
<212> TYPE: DNA
<213> ORGANISM: Artificial Sequence
<220> FEATURE:
<223> OTHER INFORMATION: Synthesized primer

<400> SEQUENCE: 67
cggatccaga acatgggc                                            18

<210> SEQ ID NO 68
<211> LENGTH: 20
<212> TYPE: DNA
<213> ORGANISM: Artificial Sequence
<220> FEATURE:
<223> OTHER INFORMATION: Synthesized primer

<400> SEQUENCE: 68
ggcatctctc gcaaagtagc                                          20

<210> SEQ ID NO 69
<211> LENGTH: 20
<212> TYPE: DNA
<213> ORGANISM: Artificial Sequence
<220> FEATURE:
<223> OTHER INFORMATION: Synthesized primer

<400> SEQUENCE: 69
ggcaaacgca atggaactat                                          20

<210> SEQ ID NO 70
<211> LENGTH: 20
<212> TYPE: DNA
<213> ORGANISM: Artificial Sequence
<220> FEATURE:
<223> OTHER INFORMATION: Synthesized primer

<400> SEQUENCE: 70
agcacgttcc taagccttga                                          20

<210> SEQ ID NO 71
<211> LENGTH: 20
<212> TYPE: DNA
<213> ORGANISM: Artificial Sequence
<220> FEATURE:
<223> OTHER INFORMATION: Synthesized primer

<400> SEQUENCE: 71
ccgtgtgcct tatggaaact                                          20

<210> SEQ ID NO 72
<211> LENGTH: 18
<212> TYPE: DNA
<213> ORGANISM: Artificial Sequence
<220> FEATURE:
<223> OTHER INFORMATION: Synthesized primer

<400> SEQUENCE: 72
```
tggattgtgt ctgggcac                                                    18

<210> SEQ ID NO 73
<211> LENGTH: 23
<212> TYPE: DNA
<213> ORGANISM: Artificial Sequence
<220> FEATURE:
<223> OTHER INFORMATION: Synthesized primer

<400> SEQUENCE: 73
aaaggacagg atggaaggaa tca                                              23

<210> SEQ ID NO 74
<211> LENGTH: 24
<212> TYPE: DNA
<213> ORGANISM: Artificial Sequence
<220> FEATURE:
<223> OTHER INFORMATION: Synthesized primer

<400> SEQUENCE: 74
attaactggc agagtggcag gtaa                                             24

<210> SEQ ID NO 75
<211> LENGTH: 19
<212> TYPE: DNA
<213> ORGANISM: Artificial Sequence
<220> FEATURE:
<223> OTHER INFORMATION: Synthesized primer

<400> SEQUENCE: 75
ccacagctgc tgcagaaca                                                   19

<210> SEQ ID NO 76
<211> LENGTH: 18
<212> TYPE: DNA
<213> ORGANISM: Artificial Sequence
<220> FEATURE:
<223> OTHER INFORMATION: Synthesized primer

<400> SEQUENCE: 76
gaagggtcgc atggcaaa                                                    18

<210> SEQ ID NO 77
<211> LENGTH: 23
<212> TYPE: DNA
<213> ORGANISM: Artificial Sequence
<220> FEATURE:
<223> OTHER INFORMATION: Synthesized primer

<400> SEQUENCE: 77
aagtgtggaa ctctctggaa ctg                                              23

<210> SEQ ID NO 78
<211> LENGTH: 23
<212> TYPE: DNA
<213> ORGANISM: Artificial Sequence
<220> FEATURE:
<223> OTHER INFORMATION: Synthesized primer

<400> SEQUENCE: 78
gggttatctt ggttggcttt atg                                              23

<210> SEQ ID NO 79
<211> LENGTH: 23
<212> TYPE: DNA
<213> ORGANISM: Artificial Sequence
<220> FEATURE:
<223> OTHER INFORMATION: Synthesized primer

<400> SEQUENCE: 79
cctgaacatc gagtgtcgaa tat                                           23

<210> SEQ ID NO 80
<211> LENGTH: 25
<212> TYPE: DNA
<213> ORGANISM: Artificial Sequence
<220> FEATURE:
<223> OTHER INFORMATION: Synthesized primer

<400> SEQUENCE: 80
ggttcttctt ctgaatcttg cagct                                         25

<210> SEQ ID NO 81
<211> LENGTH: 18
<212> TYPE: DNA
<213> ORGANISM: Artificial Sequence
<220> FEATURE:
<223> OTHER INFORMATION: Synthesized primer

<400> SEQUENCE: 81
ggccgagatg tgcgaact                                                 18

<210> SEQ ID NO 82
<211> LENGTH: 22
<212> TYPE: DNA
<213> ORGANISM: Artificial Sequence
<220> FEATURE:
<223> OTHER INFORMATION: Synthesized primer

<400> SEQUENCE: 82
ttgttgatga gctggagcat gt                                            22

<210> SEQ ID NO 83
<211> LENGTH: 28
<212> TYPE: DNA
<213> ORGANISM: Artificial Sequence
<220> FEATURE:
<223> OTHER INFORMATION: Synthesized primer

<400> SEQUENCE: 83
ccagcacctt cagcttcagg tccttgat                                      28

<210> SEQ ID NO 84
<211> LENGTH: 28
<212> TYPE: DNA
<213> ORGANISM: Artificial Sequence
<220> FEATURE:
<223> OTHER INFORMATION: Synthesized primer

<400> SEQUENCE: 84
tgccggaagt tgagaggaaa tccaagat                                      28

<210> SEQ ID NO 85
<211> LENGTH: 23
<212> TYPE: DNA
<213> ORGANISM: Artificial Sequence
<220> FEATURE:
<223> OTHER INFORMATION: Synthesized primer

<400> SEQUENCE: 85
ggcccttgta aacaacaaaa tac                                           23

<210> SEQ ID NO 86
<211> LENGTH: 23
<212> TYPE: DNA
<213> ORGANISM: Artificial Sequence
<220> FEATURE:
<223> OTHER INFORMATION: Synthesized primer

<400> SEQUENCE: 86
ggcaacaaga gctgacagta aat                                              23

<210> SEQ ID NO 87
<211> LENGTH: 19
<212> TYPE: DNA
<213> ORGANISM: Artificial Sequence
<220> FEATURE:
<223> OTHER INFORMATION: Synthesized primer

<400> SEQUENCE: 87
tggcaggtag caccacagg                                                   19

<210> SEQ ID NO 88
<211> LENGTH: 22
<212> TYPE: DNA
<213> ORGANISM: Artificial Sequence
<220> FEATURE:
<223> OTHER INFORMATION: Synthesized primer

<400> SEQUENCE: 88
catctggtct tgcagcaact ct                                               22

<210> SEQ ID NO 89
<211> LENGTH: 25
<212> TYPE: DNA
<213> ORGANISM: Artificial Sequence
<220> FEATURE:
<223> OTHER INFORMATION: Synthesized primer

<400> SEQUENCE: 89
actccagcgt cgccatcagg attct                                            25

<210> SEQ ID NO 90
<211> LENGTH: 25
<212> TYPE: DNA
<213> ORGANISM: Artificial Sequence
<220> FEATURE:
<223> OTHER INFORMATION: Synthesized primer

<400> SEQUENCE: 90
taaacaggtg agactccagc aactt                                            25

<210> SEQ ID NO 91
<211> LENGTH: 22
<212> TYPE: DNA
<213> ORGANISM: Artificial Sequence
<220> FEATURE:
<223> OTHER INFORMATION: Synthesized primer

<400> SEQUENCE: 91
ccgcaaggga aagatgaaag ac                                               22

<210> SEQ ID NO 92
<211> LENGTH: 20
<212> TYPE: DNA
<213> ORGANISM: Artificial Sequence
<220> FEATURE:
<223> OTHER INFORMATION: Synthesized primer

<400> SEQUENCE: 92
tcgtttggtt tcggggtttc                                              20

<210> SEQ ID NO 93
<211> LENGTH: 24
<212> TYPE: DNA
<213> ORGANISM: Artificial Sequence
<220> FEATURE:
<223> OTHER INFORMATION: Synthesized primer

<400> SEQUENCE: 93
gccagcctct cctgatttta gtgt                                         24

<210> SEQ ID NO 94
<211> LENGTH: 24
<212> TYPE: DNA
<213> ORGANISM: Artificial Sequence
<220> FEATURE:
<223> OTHER INFORMATION: Synthesized primer

<400> SEQUENCE: 94
gggaacacaa aagacctctt ctgg                                         24

<210> SEQ ID NO 95
<211> LENGTH: 23
<212> TYPE: DNA
<213> ORGANISM: Artificial Sequence
<220> FEATURE:
<223> OTHER INFORMATION: Synthesized primer

<400> SEQUENCE: 95
ctatgtcgca gtatctgtct ttg                                          23

<210> SEQ ID NO 96
<211> LENGTH: 22
<212> TYPE: DNA
<213> ORGANISM: Artificial Sequence
<220> FEATURE:
<223> OTHER INFORMATION: Synthesized primer

<400> SEQUENCE: 96
gttatgatgt ctgtgtggaa ag                                           22

<210> SEQ ID NO 97
<211> LENGTH: 31
<212> TYPE: DNA
<213> ORGANISM: Artificial Sequence
<220> FEATURE:
<223> OTHER INFORMATION: Synthesized primer

<400> SEQUENCE: 97
gtttgtgtgc tatagatgat attttaaatt g                                 31

<210> SEQ ID NO 98
<211> LENGTH: 24
<212> TYPE: DNA
<213> ORGANISM: Artificial Sequence
<220> FEATURE:
<223> OTHER INFORMATION: Synthesized primer

<400> SEQUENCE: 98
cattaaacag tctacaaaac atat                                         24

<210> SEQ ID NO 99

```
<211> LENGTH: 21
<212> TYPE: DNA
<213> ORGANISM: Artificial Sequence
<220> FEATURE:
<223> OTHER INFORMATION: Synthesized primer

<400> SEQUENCE: 99
aaccctcctc cctctcaccc t                                              21

<210> SEQ ID NO 100
<211> LENGTH: 20
<212> TYPE: DNA
<213> ORGANISM: Artificial Sequence
<220> FEATURE:
<223> OTHER INFORMATION: Synthesized primer

<400> SEQUENCE: 100
acaccaatca gctcagagaa                                                20

<210> SEQ ID NO 101
<211> LENGTH: 20
<212> TYPE: DNA
<213> ORGANISM: Artificial Sequence
<220> FEATURE:
<223> OTHER INFORMATION: Synthesized primer

<400> SEQUENCE: 101
gaatgtcagg cctctaagaa                                                20

<210> SEQ ID NO 102
<211> LENGTH: 20
<212> TYPE: DNA
<213> ORGANISM: Artificial Sequence
<220> FEATURE:
<223> OTHER INFORMATION: Synthesized primer

<400> SEQUENCE: 102
caggaggtgt gtgacagcat                                                20

<210> SEQ ID NO 103
<211> LENGTH: 20
<212> TYPE: DNA
<213> ORGANISM: Artificial Sequence
<220> FEATURE:
<223> OTHER INFORMATION: Synthesized primer

<400> SEQUENCE: 103
ggagccaaga actcatcctg                                                20

<210> SEQ ID NO 104
<211> LENGTH: 20
<212> TYPE: DNA
<213> ORGANISM: Artificial Sequence
<220> FEATURE:
<223> OTHER INFORMATION: Synthesized primer

<400> SEQUENCE: 104
tctggcctgc tccttaggta                                                20

<210> SEQ ID NO 105
<211> LENGTH: 20
<212> TYPE: DNA
<213> ORGANISM: Artificial Sequence
<220> FEATURE:
<223> OTHER INFORMATION: Synthesized primer

<400> SEQUENCE: 105
```
aaggataagg gcgacagcaa                                                20

<210> SEQ ID NO 106
<211> LENGTH: 20
<212> TYPE: DNA
<213> ORGANISM: Artificial Sequence
<220> FEATURE:
<223> OTHER INFORMATION: Synthesized primer

<400> SEQUENCE: 106
tccaccaaga actctttcca                                                20

<210> SEQ ID NO 107
<211> LENGTH: 20
<212> TYPE: DNA
<213> ORGANISM: Artificial Sequence
<220> FEATURE:
<223> OTHER INFORMATION: Synthesized primer

<400> SEQUENCE: 107
ctgtcccgaa agggcattat                                                20

<210> SEQ ID NO 108
<211> LENGTH: 20
<212> TYPE: DNA
<213> ORGANISM: Artificial Sequence
<220> FEATURE:
<223> OTHER INFORMATION: Synthesized primer

<400> SEQUENCE: 108
cgttgcagtt gcctttcttg                                                20

<210> SEQ ID NO 109
<211> LENGTH: 22
<212> TYPE: DNA
<213> ORGANISM: Artificial Sequence
<220> FEATURE:
<223> OTHER INFORMATION: Synthesized primer

<400> SEQUENCE: 109
gtggggagcg tggcttcttc ta                                             22

<210> SEQ ID NO 110
<211> LENGTH: 24
<212> TYPE: DNA
<213> ORGANISM: Artificial Sequence
<220> FEATURE:
<223> OTHER INFORMATION: Synthesized primer

<400> SEQUENCE: 110
actgatccac aatgccacgc ttct                                           24

<210> SEQ ID NO 111
<211> LENGTH: 20
<212> TYPE: DNA
<213> ORGANISM: Artificial Sequence
<220> FEATURE:
<223> OTHER INFORMATION: Synthesized primer

<400> SEQUENCE: 111
cgagtgcccg tctggctata                                                20

<210> SEQ ID NO 112
<211> LENGTH: 18
<212> TYPE: DNA

<213> ORGANISM: Artificial Sequence
<220> FEATURE:
<223> OTHER INFORMATION: Synthesized primer

<400> SEQUENCE: 112
ggcagggtcc cagacatg                                                     18

<210> SEQ ID NO 113
<211> LENGTH: 24
<212> TYPE: DNA
<213> ORGANISM: Artificial Sequence
<220> FEATURE:
<223> OTHER INFORMATION: Synthesized primer

<400> SEQUENCE: 113
gtagcttatg aatgtgtgca actc                                              24

<210> SEQ ID NO 114
<211> LENGTH: 24
<212> TYPE: DNA
<213> ORGANISM: Artificial Sequence
<220> FEATURE:
<223> OTHER INFORMATION: Synthesized primer

<400> SEQUENCE: 114
gtcttgcgat cagctctttc atta                                              24

<210> SEQ ID NO 115
<211> LENGTH: 23
<212> TYPE: DNA
<213> ORGANISM: Artificial Sequence
<220> FEATURE:
<223> OTHER INFORMATION: Synthesized primer

<400> SEQUENCE: 115
gcactgcagc tcgcacatta caa                                               23

<210> SEQ ID NO 116
<211> LENGTH: 25
<212> TYPE: DNA
<213> ORGANISM: Artificial Sequence
<220> FEATURE:
<223> OTHER INFORMATION: Synthesized primer

<400> SEQUENCE: 116
ctcagacagt acctccttca ggaaa                                             25

<210> SEQ ID NO 117
<211> LENGTH: 20
<212> TYPE: DNA
<213> ORGANISM: Artificial Sequence
<220> FEATURE:
<223> OTHER INFORMATION: Synthesized primer

<400> SEQUENCE: 117
aggaagccgt tctgtgacat                                                   20

<210> SEQ ID NO 118
<211> LENGTH: 20
<212> TYPE: DNA
<213> ORGANISM: Artificial Sequence
<220> FEATURE:
<223> OTHER INFORMATION: Synthesized primer

<400> SEQUENCE: 118
ttgaaggagc tttgggaaga                                                   20

```
<210> SEQ ID NO 119
<211> LENGTH: 20
<212> TYPE: DNA
<213> ORGANISM: Artificial Sequence
<220> FEATURE:
<223> OTHER INFORMATION: Synthesized primer

<400> SEQUENCE: 119
aggggctgct gttgatggac                                               20

<210> SEQ ID NO 120
<211> LENGTH: 22
<212> TYPE: DNA
<213> ORGANISM: Artificial Sequence
<220> FEATURE:
<223> OTHER INFORMATION: Synthesized primer

<400> SEQUENCE: 120
caggggcact cgtacaggaa gc                                            22

<210> SEQ ID NO 121
<211> LENGTH: 23
<212> TYPE: DNA
<213> ORGANISM: Artificial Sequence
<220> FEATURE:
<223> OTHER INFORMATION: Synthesized primer

<400> SEQUENCE: 121
aaaggacagg atggaaggaa tca                                           23

<210> SEQ ID NO 122
<211> LENGTH: 24
<212> TYPE: DNA
<213> ORGANISM: Artificial Sequence
<220> FEATURE:
<223> OTHER INFORMATION: Synthesized primer

<400> SEQUENCE: 122
attaactggc agagtggcag gtaa                                          24

<210> SEQ ID NO 123
<211> LENGTH: 19
<212> TYPE: DNA
<213> ORGANISM: Artificial Sequence
<220> FEATURE:
<223> OTHER INFORMATION: Synthesized primer

<400> SEQUENCE: 123
gaactgcaca cagacctgc                                                19

<210> SEQ ID NO 124
<211> LENGTH: 21
<212> TYPE: DNA
<213> ORGANISM: Artificial Sequence
<220> FEATURE:
<223> OTHER INFORMATION: Synthesized primer

<400> SEQUENCE: 124
gactgggtta agccaatgct c                                             21

<210> SEQ ID NO 125
<211> LENGTH: 25
<212> TYPE: DNA
<213> ORGANISM: Artificial Sequence
<220> FEATURE:
```

```
<223> OTHER INFORMATION: Synthesized primer

<400> SEQUENCE: 125
tgtgaagtta ctgcaggagt gtaaa                                              25

<210> SEQ ID NO 126
<211> LENGTH: 26
<212> TYPE: DNA
<213> ORGANISM: Artificial Sequence
<220> FEATURE:
<223> OTHER INFORMATION: Synthesized primer

<400> SEQUENCE: 126
gcatagatac cgtctcttga tctgaa                                             26

<210> SEQ ID NO 127
<211> LENGTH: 20
<212> TYPE: DNA
<213> ORGANISM: Artificial Sequence
<220> FEATURE:
<223> OTHER INFORMATION: Synthesized primer

<400> SEQUENCE: 127
aggtggagga agcagtgaga                                                    20

<210> SEQ ID NO 128
<211> LENGTH: 20
<212> TYPE: DNA
<213> ORGANISM: Artificial Sequence
<220> FEATURE:
<223> OTHER INFORMATION: Synthesized primer

<400> SEQUENCE: 128
gcttggggtt gtgaaagaaa                                                    20

<210> SEQ ID NO 129
<211> LENGTH: 25
<212> TYPE: DNA
<213> ORGANISM: Artificial Sequence
<220> FEATURE:
<223> OTHER INFORMATION: Synthesized primer

<400> SEQUENCE: 129
aatccaccaa agctcacgcg tggaa                                              25

<210> SEQ ID NO 130
<211> LENGTH: 25
<212> TYPE: DNA
<213> ORGANISM: Artificial Sequence
<220> FEATURE:
<223> OTHER INFORMATION: Synthesized primer

<400> SEQUENCE: 130
tgatgtgtct ctcggtcaag ttcaa                                              25

<210> SEQ ID NO 131
<211> LENGTH: 23
<212> TYPE: DNA
<213> ORGANISM: Artificial Sequence
<220> FEATURE:
<223> OTHER INFORMATION: Synthesized primer

<400> SEQUENCE: 131
aagtgtggaa ctctctggaa ctg                                                23
```

```
<210> SEQ ID NO 132
<211> LENGTH: 23
<212> TYPE: DNA
<213> ORGANISM: Artificial Sequence
<220> FEATURE:
<223> OTHER INFORMATION: Synthesized primer

<400> SEQUENCE: 132
gggttatctt ggttggcttt atg                                              23

<210> SEQ ID NO 133
<211> LENGTH: 20
<212> TYPE: DNA
<213> ORGANISM: Artificial Sequence
<220> FEATURE:
<223> OTHER INFORMATION: Synthesized primer

<400> SEQUENCE: 133
tggagactgc tctggaaggt                                                  20

<210> SEQ ID NO 134
<211> LENGTH: 20
<212> TYPE: DNA
<213> ORGANISM: Artificial Sequence
<220> FEATURE:
<223> OTHER INFORMATION: Synthesized primer

<400> SEQUENCE: 134
tgctgctgtc ctcaaatacg                                                  20

<210> SEQ ID NO 135
<211> LENGTH: 20
<212> TYPE: DNA
<213> ORGANISM: Artificial Sequence
<220> FEATURE:
<223> OTHER INFORMATION: Synthesized primer

<400> SEQUENCE: 135
ccaaaaagac ctcgttcagc                                                  20

<210> SEQ ID NO 136
<211> LENGTH: 20
<212> TYPE: DNA
<213> ORGANISM: Artificial Sequence
<220> FEATURE:
<223> OTHER INFORMATION: Synthesized primer

<400> SEQUENCE: 136
atgtctccgg atcgtttcac                                                  20

<210> SEQ ID NO 137
<211> LENGTH: 28
<212> TYPE: DNA
<213> ORGANISM: Artificial Sequence
<220> FEATURE:
<223> OTHER INFORMATION: Synthesized primer

<400> SEQUENCE: 137 ccagcaccttt cagcttcagg tccttgat                                        28

<210> SEQ ID NO 138
<211> LENGTH: 28
<212> TYPE: DNA
<213> ORGANISM: Artificial Sequence
<220> FEATURE:
<223> OTHER INFORMATION: Synthesized primer
```

<400> SEQUENCE: 138
tgccggaagt tgagaggaaa tccaagat                                28

<210> SEQ ID NO 139
<211> LENGTH: 21
<212> TYPE: DNA
<213> ORGANISM: Artificial Sequence
<220> FEATURE:
<223> OTHER INFORMATION: Synthesized primer

<400> SEQUENCE: 139
accaagggct cagagcatgc a                                       21

<210> SEQ ID NO 140
<211> LENGTH: 23
<212> TYPE: DNA
<213> ORGANISM: Artificial Sequence
<220> FEATURE:
<223> OTHER INFORMATION: Synthesized primer

<400> SEQUENCE: 140
tggctttcag gagagtatct ttg                                     23

<210> SEQ ID NO 141
<211> LENGTH: 22
<212> TYPE: DNA
<213> ORGANISM: Artificial Sequence
<220> FEATURE:
<223> OTHER INFORMATION: Synthesized primer

<400> SEQUENCE: 141
ccgcaaggga aagatgaaag ac                                      22

<210> SEQ ID NO 142
<211> LENGTH: 20
<212> TYPE: DNA
<213> ORGANISM: Artificial Sequence
<220> FEATURE:
<223> OTHER INFORMATION: Synthesized primer

<400> SEQUENCE: 142
tcgtttggtt tcggggtttc                                         20

<210> SEQ ID NO 143
<211> LENGTH: 24
<212> TYPE: DNA
<213> ORGANISM: Artificial Sequence
<220> FEATURE:
<223> OTHER INFORMATION: Synthesized primer

<400> SEQUENCE: 143
gccagcctct cctgatttta gtgt                                    24

<210> SEQ ID NO 144
<211> LENGTH: 24
<212> TYPE: DNA
<213> ORGANISM: Artificial Sequence
<220> FEATURE:
<223> OTHER INFORMATION: Synthesized primer

<400> SEQUENCE: 144
gggaacacaa aagacctctt ctgg                                    24

<210> SEQ ID NO 145
<211> LENGTH: 21

-continued

```
<212> TYPE: DNA
<213> ORGANISM: Artificial Sequence
<220> FEATURE:
<223> OTHER INFORMATION: Synthesized primer

<400> SEQUENCE: 145
tcccgcagcc gagccgcggg g                                          21

<210> SEQ ID NO 146
<211> LENGTH: 27
<212> TYPE: DNA
<213> ORGANISM: Artificial Sequence
<220> FEATURE:
<223> OTHER INFORMATION: Synthesized primer

<400> SEQUENCE: 146
tcttccaact gcctctctgg ccctccg                                    27

<210> SEQ ID NO 147
<211> LENGTH: 24
<212> TYPE: DNA
<213> ORGANISM: Artificial Sequence
<220> FEATURE:
<223> OTHER INFORMATION: Synthesized primer

<400> SEQUENCE: 147
catttctcca cctcactgaa actg                                       24

<210> SEQ ID NO 148
<211> LENGTH: 23
<212> TYPE: DNA
<213> ORGANISM: Artificial Sequence
<220> FEATURE:
<223> OTHER INFORMATION: Synthesized primer

<400> SEQUENCE: 148
aatgtgttag tgcatgcaca cac                                        23

<210> SEQ ID NO 149
<211> LENGTH: 20
<212> TYPE: DNA
<213> ORGANISM: Artificial Sequence
<220> FEATURE:
<223> OTHER INFORMATION: Synthesized primer

<400> SEQUENCE: 149
aagggtggag gtgtcttggt                                            20

<210> SEQ ID NO 150
<211> LENGTH: 22
<212> TYPE: DNA
<213> ORGANISM: Artificial Sequence
<220> FEATURE:
<223> OTHER INFORMATION: Synthesized primer

<400> SEQUENCE: 150
gcttctttac actcctgcta aa                                         22

<210> SEQ ID NO 151
<211> LENGTH: 23
<212> TYPE: DNA
<213> ORGANISM: Artificial Sequence
<220> FEATURE:
<223> OTHER INFORMATION: Synthesized primer

<400> SEQUENCE: 151
```
ctaaggatgg tggagaacct tca                                    23

<210> SEQ ID NO 152
<211> LENGTH: 22
<212> TYPE: DNA
<213> ORGANISM: Artificial Sequence
<220> FEATURE:
<223> OTHER INFORMATION: Synthesized primer

<400> SEQUENCE: 152
cgcgcttaat agtgtccatc ag                                     22

<210> SEQ ID NO 153
<211> LENGTH: 22
<212> TYPE: DNA
<213> ORGANISM: Artificial Sequence
<220> FEATURE:
<223> OTHER INFORMATION: Synthesized primer

<400> SEQUENCE: 153
atccaattgt gccaagcact aa                                     22

<210> SEQ ID NO 154
<211> LENGTH: 25
<212> TYPE: DNA
<213> ORGANISM: Artificial Sequence
<220> FEATURE:
<223> OTHER INFORMATION: Synthesized primer

<400> SEQUENCE: 154
ccaccatttt gatagtttcc atagg                                  25

<210> SEQ ID NO 155
<211> LENGTH: 22
<212> TYPE: DNA
<213> ORGANISM: Artificial Sequence
<220> FEATURE:
<223> OTHER INFORMATION: Synthesized primer

<400> SEQUENCE: 155
ctcgacaact tcccagataa cc                                     22

<210> SEQ ID NO 156
<211> LENGTH: 25
<212> TYPE: DNA
<213> ORGANISM: Artificial Sequence
<220> FEATURE:
<223> OTHER INFORMATION: Synthesized primer

<400> SEQUENCE: 156
ggtacaggtt gcgatagatg atagc                                  25

<210> SEQ ID NO 157
<211> LENGTH: 20
<212> TYPE: DNA
<213> ORGANISM: Artificial Sequence
<220> FEATURE:
<223> OTHER INFORMATION: Synthesized primer

<400> SEQUENCE: 157
gccccaattc gcgccaagga                                        20

<210> SEQ ID NO 158
<211> LENGTH: 20
<212> TYPE: DNA
<213> ORGANISM: Artificial Sequence

```
<220> FEATURE:
<223> OTHER INFORMATION: Synthesized primer

<400> SEQUENCE: 158
aggttggcgg cagttctggg                                              20

<210> SEQ ID NO 159
<211> LENGTH: 20
<212> TYPE: DNA
<213> ORGANISM: Artificial Sequence
<220> FEATURE:
<223> OTHER INFORMATION: Synthesized primer

<400> SEQUENCE: 159
ttcttccatg tccgggatag                                              20

<210> SEQ ID NO 160
<211> LENGTH: 20
<212> TYPE: DNA
<213> ORGANISM: Artificial Sequence
<220> FEATURE:
<223> OTHER INFORMATION: Synthesized primer

<400> SEQUENCE: 160
ccccactctt ctcgaatcag                                              20

<210> SEQ ID NO 161
<211> LENGTH: 25
<212> TYPE: DNA
<213> ORGANISM: Artificial Sequence
<220> FEATURE:
<223> OTHER INFORMATION: Synthesized primer

<400> SEQUENCE: 161
gctggacgtg atcttactga ttacc                                        25

<210> SEQ ID NO 162
<211> LENGTH: 24
<212> TYPE: DNA
<213> ORGANISM: Artificial Sequence
<220> FEATURE:
<223> OTHER INFORMATION: Synthesized primer

<400> SEQUENCE: 162
gtagcagagc ttctccttga tgtc                                         24
```

METHODS OF TREATING MITOCHONDRIAL DYSFUNCTION

RELATED APPLICATIONS

This application is a continuation of U.S. Ser. No. 15/293,640, filed Oct. 14, 2016, which is a continuation of U.S. Ser. No. 13/984,157, filed Nov. 20, 2013. U.S. Ser. No. 13/984,157 is a national stage application, filed under 35 U.S.C. § 371, of International Application No. PCT/IB2012/001146, filed Feb. 15, 2012, which claims the benefit of provisional applications U.S. Ser. No. 61/443,052 filed Feb. 15, 2011 and U.S. Ser. No. 61/446,303, filed Feb. 24, 2011. The contents each of which are herein incorporated by reference in their entireties.

INCORPORATION OF SEQUENCE LISTING

The contents of the text file named "EPFL-003C01US_ST25.txt", which was created on Oct. 12, 2016 and is 31 KB in size, are hereby incorporated by reference in their entirety

FIELD OF THE INVENTION

The present invention relates generally to methods of increasing intracellular $NAD^+$ for the treatment of various mitochondrial disorders, including but not limited to metabolic disorders, neurodegenerative diseases, and chronic inflammatory diseases, and diseases associated with aging.

BACKGROUND OF THE INVENTION

Mitochondria are cellular organdies present in most eukaryotic cells. One of their primary functions is oxidative phosphorylation, a process through Which energy derived from metabolism of fuels like glucose or fatty acids is converted to ATP, which is then used to drive various energy-requiring biosynthetic reactions and other metabolic activities. Mitochondria have their own genomes, separate from nuclear DNA, comprising rings of DNA with about 16,000 base pairs in human cells. Each mitochondrion may have multiple copies of its genome, and individual cells may have hundreds of mitochondria.

Mitochondrial dysfunction contributes to various disease states. Some mitochondrial diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

In addition to congenital disorders involving inherited defective mitochondria, acquired mitochondrial dysfunction contributes to diseases, particularly neurodegenerative disorders associated with aging like Parkinson's, Alzheimer's, Huntington's Diseases. The incidence of somatic mutations in mitochondrial DNA rises exponentially with age; diminished respiratory chain activity is found universally in aging people. Mitochondrial dysfunction is also implicated in excitotoxic neuronal injury, such as that associated with seizures or ischemia. Other disorders associated with mitochondrial dysfunction include chronic inflammatory disorders and metabolic disorders While a number of drugs have been developed over the years to treat the various mitochondrial dysfunction, these drugs can often have side effects or are effective only for a limited time period. Thus a need exists for therapeutic strategies for treating mitochondrial dysfunction

SUMMARY OF THE INVENTION

The invention features methods of treating disorders associated with mitochondrial dysfunction by administering to subject suffering from or susceptible to developing a metabolic disorder one or more compounds that increases intracellular nicotinamide adenine dinucleotide ($NAD^+$) in an amount sufficient to activate SIRT1 or SIRT3.

Also included in the invention are methods of promoting oxidative metabolism by administering to subject suffering from or susceptible to developing a metabolic disorder one or more compounds that increases intracellular nicotinamide adenine dinucleotide ($NAD^+$) in an amount sufficient to activate SIRT1 or SIRT3.

In another aspect the invention provide a method of increasing the concentration of $NAD^+$ within the mitochondria by contacting mitochondria with nicotinamide riboside (NR).

Further included in the invention is a method of activating mitochondrial sirtulin by contacting mitochondria with nicotinamide riboside (NR). The sirtulin is SIRT3, SIRT4 or SIRT5.

Disorders associated with mitochondrial dysfunction is a metabolic disorder, a neurodegenerative disease, a chronic inflammatory disease, or an aging related disorder. For example, the metabolic disorder is obesity or type II diabetes.

The compound is a NAD booster, a PARP-1 inhibitor, an AMPK activator or combination thereof.

In another aspect the invention provides methods of treating cancer comprising administering to subject suffering from or susceptible to developing a cancer a PARP inhibitor and a NAD+ booster, a PARP inhibitor and an AMPK agonist, or an AMPK agonist and a NAD+ booster.

PARP inhibitors include for example, PJ34, TIQ, TES-500, TES-501, BSI-202, Iniparib, AZD2281, Olaparib, ABT-888, Veliparib, AG014699, CEP 9722, or MK 4827. Alternatively, a PARP-1 inhibitor is a nucleic acid that inhibits PARP-1 expression or activity.

A NAD booster includes for example tryptophan, nicotinamide riboside (NR), nicotinic acid (NA), nicotinamide (NAM), N-formylkynurenine, quinolinic acid, nictotinamide riboside kinase (NRK) or nicotinamide mononucleotide (NMN).

An AMPK agonist is 5-aminoimidazole-4-carboxamide-1-b-D-riboside, PT-1, A-769662 (Abbott), Adiponectin, Leptin, Ghrelin, Cannabinoids, alpha-lipoic acid, Interleukin-6 (IL-6), Resveratrol, Quercetin, Metformin, Berberine, Curcumine, Epigallocatechin-3-gallate (green tea), Thiazolidinediones, such as rosiglitazone and pioglitazone or Dinitrophenol (DNP).

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIGS. 1A-1J. Increased energy expenditure and adaptive thermogenesis in PARP-1$^{-/-}$ mice. FIG. 1A. PARP-1$^{+/+}$ and $^{-/-}$ male mice (n=8/9) were weighed weekly to analyze body weight evolution. FIG. 1B. Total white adipose tissue (WAT) was weighed upon autopsy. FIG. 1C. Average weekly food consumption throughout the study. FIG. 1D. O2 consumption and FIG. 1E. respiratory-/- quotient (RQ) of PARP-1$^{+/+}$ and male mice (n=9/9) were measured by indirect calorimetry. FIG. 1F. Thermogenic capacity was determined upon acute exposure of PARP-1$^{+/+}$ and $^{-/-}$ mice to 4° C. for the indicated times (n=6/5 males). FIG. 1G. Oral glucose tolerance test was performed (n=5/5 males) and the area under curve (AUC) is shown on the top right, expressed in arbitrary units. FIGS. 1H-1J. Peripheral and hepatic insulin responsiveness of PARP-1$^{+/+}$ and PARP-1$^{-/-}$ mice was assessed by euglycemic-hyperinsulinemic clamp. (FIG. 1H) Glucose infusion rates (GIR), (FIG. 1I) hepatic glucose production (HGP) and (FIG. 1J) glucose uptake in different tissues are all shown as mean+/-SEM. Throughout the figure, * indicates statistical difference vs. PARP-1$^{+/+}$ mice at p<0.05.

FIG. 2A. PARP-1 autoPARylation band (arrowhead) was analyzed in 100 Rg of total protein extract from gastrocnemius muscle obtained from 16 week-old wild-type C57Bl/6J mice fed ad libitum or fasted for 24 h before sacrifice at 8:00 am. 50 µg of protein were used to determine PARP-1 and tubulin protein expression. FIG. 2B. C57Bl/6J mice were fed chow or a high-fat diet for 12 weeks and gastrocnemius muscle were analyzed as described in FIG. 2A. FIG. 2C. PARP-P$^{+/+}$ and -/- male mice. (n=10/10) were fed chow (represented as circles) or a high-fat diet (represented as squares) from the age of eight weeks onwards and body weight was monitored weekly. FIG. 2D. The total WAT mass, individual WAT depots, and organ weights were determined upon autopsy (E—epididymal, SC—subcutaneous, P—perirenal), (FIG. 2E) An oral glucose tolerance test and (FIG. 2F) an intraperitoneal insulin tolerance test were performed on high-fat fed PARP-1$^{+/+}$ and $^{-/-}$ male mice at 12 weeks of age (n=10/10). The area under curve (AUC) of the oral glucose tolerance test is shown on the top-right side of panel (FIG. 2E), expressed in arbitrary units. In the figure, * indicates statistical difference vs. PARP-1$^{+/+}$ mice at p<0.05.

FIGS. 3A-3H. Increased mitochondrial activity in brown adipose tissue (BAT) and gastrocnemius muscle of PARP-1$^{-/-}$ mice. FIG. 3A. BAT and after of PARP-P1$^{+/+}$ and $^{-/-}$ was photographed weighed autopsy and mice (11.5 months of age, n=8/9 males). BAT content (relative to total body weight), is shown at the bottom of the image. FIG. 3B. BAT mitochondrial DNA (mtDNA) was quantified by qPCR. FIG. 3C. mRNA levels of the indicated genes were determined by RT-qPCR in the BAT. FIG. 3D. Transmission electron micrographs of representative BAT sections show increased mitochondrial content in PARP-1$^{-/-}$ mice. FIGS. 3E-3F. 25 µg of total protein extracts from (FIG. 3E) BAT or (FIG. 3F) gastrocnemius muscles of PARP-1$^{+/+}$ and $^{-/-}$ mice were used to analyze the abundance of mitochondrial complexes. FIG. 3G. SDH staining of sections from the gastrocnemius and soleus muscles of PARP-1$^{+/+}$ and $^{-/-}$. FIG. 3H. mRNA levels of the indicated genes were measured by RT-qPCR in gastrocnemius muscle. Throughout the figure, white bars represent PARP-1$^{+/+}$ mice, while black bars represent PARP1$^{-/-}$ mice. * indicates statistical difference vs. PARP-1$^{+/+}$ mice at p<0.05.

FIGS. 4A-4G. The absence of PARP-1 raises NAD$^+$ levels and activates SIRT1. FIG. 4A. Protein PARylation was determined by anti-PAR staining on formalin-fixed 7 µm BAT and muscle tissue sections of PARP-1$^{+/+}$ and $^{-/-}$ mice. The white bar is equivalent to 10 µm. (FIG. 4B) NAD$^+$ and (FIG. 4C) NAM levels in BAT and muscle were determined by mass spectrometry. FIGS. 4D-4E. PARP-1, SIRT1 and actin (as loading control) protein content on (FIG. 4D) BAT and (FIG. 4E) skeletal muscle was determined by Western blotting using 100 µg of total protein lysate. PGC-1α and FOXO1 acetylation was examined by immunoprecipitation. FIG. 4F. Tubulin and acetylated-tubulin levels were estimated in gastrocnemius muscle from PARP-1$^{+/+}$ and $^{-/-}$ mice. FIG. 4G. The Ndufa9 subunit of mitochondrial complex I was immunoprecipitated from 400 µg of total protein from gastrocnemius muscle and acetylation levels of the complex were analyzed by western blotting. * indicates statistical difference vs. PARP-1$^{+/+}$ mice at p<0.05. Abbreviations can be found in the text.

FIGS. 5A-5F. PARP-1 knock-down promotes SIRT1 activity and oxidative metabolism. FIGS. 5A-5C. HEK293T cells were transfected with either a scramble (as control) or a PARP-1 shRNA and HA-PGC-1α for 48 h. FIG. 5A. Total cell lysates were then obtained to analyze PARP-1 protein and PARP-1 autoPARylation (arrowhead). FIG. 5B. Intracellular NAD+ levels was measured on total acid extracts. FIG. 5C. Total protein lysates were used to analyze PGC-1α deacetylation in HA immunoprecipitates. FIGS. 5D-5F. HEK293T cells were transfected with either a pool of PARP-1 siRNAs, a pool of SIRT1 siRNAs, or different combinations of both using the corresponding scramble siRNAs as control (−). Additionally, the cells were simultaneously transfected with HA-PGC-1α for 48 h. Then, (FIG. 5D) relative mitochondrial DNA content, (FIG. 5E) mRNA levels of the markers indicated and (FIG. 5F) total O$_2$ consumption were analyzed as described. * indicates statistical difference vs. respective control sh/siRNA-transfected cells at p<0.05.

FIGS. 6A-6I. Pharmacological PARP-1 inhibition activates SIRT1 and enhances mitochondrial function in cultured cells. FIGS. 6A-6C. C2C12 myotubes, which express FLAG-HA-PGC-1α, were treated for 6 hrs with either PBS (as vehicle), H$_2$O$_2$ (500 µM) or H2O2 and PJ34 (1 µM). Then, (FIG. 6A) total protein extracts were obtained to test the markers indicated, (FIG. 6B) Intracellular NAD+ and SIRT1 protein levels were measured and (FIG. 6C) PGC-1α acetylation was tested in FLAG immunoprecipitates. Tubulin was measured on the supernatants to ensure equal protein input. FIG. 6D. C2C12 mytobues were treated with PJ34 (1 mM) for the times indicated and acidic extracts were evaluate NAD$^+$ obtained to intracellular levels. FIGS. 6E-6F. C2C12 myotubes, which express FLAG-HA-PGC-1α, were treated for 24 h with PBS (as vehicle) or with the PARP inhibitor PJ34 (1 µM, unless otherwise stated). (FIG. 6E)- PARP-1 protein and PARP-1 autoPARylation (arrowhead) were then determined by Western blotting and (FIG. 6F) intracellular NAD$^+$ content and PGC-α acetylation levels were measured. FIGS. 6G-6I. C2C12 myotubes differentiated for 48 h were infected with FLAG-HA-PGC-1α and a control or a SIRT1 shRNA. 48 h later, myotubes were treated with PJ34 for 24 hrs (unless otherwise stated). Then, (FIG. 6G) PGC-1α acetylation levels were quantified by immunoprecipitation. 50 Rg of total protein extracts were used to measure the other markers indicated. FIG. 6H. mRNA expression levels of selected genes were quantified 48 hrs by RT-qPCR reactions; abbreviations are listed in the text. FIG. 6I. Cellular $O_2$ consumption was measured 48 hrs after PJ34 treatment as described, * indicates statistical vs. vehicle-treated group at $p<0.05$.

FIGS. 7A-7F. Pharmacological PARP-1 inhibition increases $NAD^+$ levels and phenocopies SIRT1 activation in vivo, C57Bl/6J male mice received daily injections with PJ34 (2×10 mg/kg/day i.p.) or saline (n=10/10) for 5 days before sacrifice; then FIGS. 7A-7B. Global PARylation, p-ACC and SIRT1 levels were determined by using 100 Rg of total protein extracts from (FIG. 7A) BAT and (FIG. 7B) gastrocnemius muscle. The PARP-1 autoPARylation band is indicated by an arrowhead. FIGS. 7C-7D. $NAD^+$ levels and PGC-1 acetylation levels were determined in (FIG. 7C) BAT and (FIG. 7D) in muscle. To detect PGC-1 acetylation, 1 mg of BAT and 2 mg of protein from gastrocnemius muscle were used to immunoprecipitate PGC-1α using 5 μg of antibody. Then acetyl-lysine levels were evaluated by western blot. FIGS. 7E-7F. mRNA expression levels of selected genes in (FIG. 7E) BAT and (FIG. 7F) gastrocnemius muscle were quantified by RT-qPCR; abbreviations are listed in the text. * indicates statistical vs. vehicle-treated group at $p<0.05$.

FIG. 8A. Oxygen consumption was determined in PARP-1$^{+/+}$ and $^{-/-}$ mice (n=6/6) as described in the Materials and Methods. TEE-total energy expenditure, REE-resting energy expenditure. FIG. 8B. Spontaneous activity was determined during indirect calorimetry in CLAMS using PARP-1$^{+/+}$ and (n=9/9). Asterisks indicate significant difference between cohorts, where * $p<0.05$.

FIG. 9A. mRNA expression levels of selected genes were quantified by RT-qPCR reactions in the liver of PARP-1$^{+/+}$ and $^{-/-}$ mice (n=9/9); abbreviations are listed in the text. Asterisks indicate significant difference between cohorts, where * $p<0.05$; * $p<0.001$. FIG. 9B. mRNA expression of PARP-1 were quantified in different metabolic tissues of C57Bl/6J male mice (n=5). Asterisks indicate significant difference between the respective tissue and liver, where * $p<0.001$.

FIGS. 11A-11E. Assessment of mitochondrial function and protein levels in PARP-1$^{+/+}$ and −/− MEFs. In PARP-1$^{+/+}$ and $^{-/-}$ primary MEFs (n=3/3) oxygen consumption (FIG. 11A), mitochondrial DNA content (FIG. 11B), mitochondrial membrane potential (FIG. 11C), mRNA expression (FIG. 11D), phospho-ACC, SIRT1 and PARP-1 protein levels (FIG. 11E) was determined. Abbreviations are listed in the text. Asterisks indicate significant difference between cohorts, where * $p<0.05$, ** $p<0.01$.

FIGS. 12A-12G. Assessment of mitochondrial function upon−/−pharmacological. PARP inhibition in C2C12 cells and SIRT1 MEFs. FIG. 12A. Promoter occupancy of PGC-1α was quantified after PJ34 treatment on the PDK4 and UCP-3 promoters (1 μM, 48 h) (n=3/3). Mitochondrial DNA (FIG. 12B), mitochondrial membrane potential (FIG. 12C) was characterized in differentiated C2C12 myofibers after PJ34 treatment (1 μM, 48 h) (n=3/3). FIG. 12D. Substrate contribution to biological oxidation was determined as described in the Materials and Methods. FIGS. 12E-12G. PGC-1 acetylation, ACC phosphorylation, SIRT1 protein levels (FIG. 12E), expression of mRNAs encoding for mitochondrial proteins (FIG. 12F) and O2 consumption (FIG. 12G) were determined in SIRT1$^{+/+}$ and MEF$^{-/-}$ cells.

FIGS. 13A-13I. PARP-2 regulates oxidative metabolism by acting as a transcriptional repressor of SIRT1. FIG. 13A. PARP-2 protein and mRNA levels were analyzed in C2C12 myotubes carrying stably transfected scramble or PARP-2 shRNA. FIG. 13B. $NAD^+$ content was evaluated in C2C12 myotubes treated with PJ34 (24 hrs, 1 mM) or carrying a stable transfection of a scramble or a PARP-2 shRNA. $H_2O_2$ treatment was performed for 1 hr. FIG. 13C. Total protein extracts from C2C12 mytotubes treated as in FIG. 13B were used to test total PARylation. FIG. 13D. Scramble or PARP-2 shRNA were stably transfected in C2C12 myotubes that were infected with FLAG-PGC-1. After 48 hr, total protein extracts were obtained and used for FLAG immunoprecipitation and to test the markers indicated. FIG. 13E. SIRT1 mRNA levels were analyzed in C2C12 myotubes carrying a stable transfection with either scramble or a PARP-2 siRNA. FIG. 13F. The activity of nested deletions of the SIRT1 promoter was measured after PARP-2 depletion in C2C12 cells. FIG. 13G. The presence of PARP-2 on the SIRT1 (−1-91) and K19 promoter was assessed in C2C12 cells by ChIP assays. FIGS. 13H-13I. $O_2$ consumption (FIG. 13H) and snRNA levels of the markers indicated (FIG. 13I) were measured in C2C12 myotubes carrying a stable transfection with either a scramble (−) or a PARP-2 (+) shRNA and infected with adenovirus encoding for either a scramble (−) or a SIRT1 (+) shRNA. Unless otherwise indicated, white bars represent scramble shRNA transfected myotubes and black bars represent PARP-2 shRNA transfected myotubes. All results are expressed as mean±SD * indicates statistical difference vs. PARP-2$^{+/+}$ mice at $p<0.05$.

FIGS. 14A-14F. General physiologic characteristics of PARP-2$^{-/-}$ mice. FIG. 14A. PARP-2$^{+/+}$ and male mice (n=15/13) were weighed weekly and FIG. 14B. food consumption was measured. FIGS. 14C-14E. PARP-2$^{+/+}$ and male mice on a chow diet (n=6/6, age of 3 months) were subjected to indirect calorimetry, where (FIG. 14C) locomotor activity, (FIG. 14D) $O_2$ consumption and (FIG. 14E) RER were determined. FIG. 14F. Fed and fasted blood glucose levels. * indicates statistical difference vs. PARP-2$^{+/+}$ mice at $p<0.05$.

FIGS. 15A-15J. PARP-2$^{-/-}$ muscles have higher SIRT1 activity, mitochondrial content and oxidative profile. FIG. 15A. PARylation and PARP-2 levels in gastrocnemius muscle were determined by western blot. PARP-2 levels were determined in nuclear extracts, and histone 1 (H1) was used as loading. FIG. 15B. $NAD^+$ control levels in gastrocnemius muscle of 4-months oldPARP-2+/+ and male mice (n=4 and 8, respectively) were determined by HPLC/MS. FIG. 15C. SIRT1 mRNA and protein levels were determined in total muscle mRNA or protein extracts. FIG. 15D. PGC-1α and FIG. 15E. FOXO1 acetylation lysine levels were examined after immunoprecipitation. Quantifications are shown on top of the respective images. FIG. 15F. Gene expression of the indicated genes in the gastrocnemius muscle of PARP-2$^{+/+}$ and $^{-/-}$ mice was evaluated by RT-qPCR. FIG. 15G. Quantification of mitochondrial DNA by qPCR. (FIG. 15H) Transmission electron micrographs and (FIG. 15I) SDH staining of representative gastrocnemius muscle sections show increased mitochondrial content (PARP-2$^{+/+}$ and $^{-/-}$ male mice n=15 and 13, respectively; age of 7 months). Scale bar in FIG. 15I=100 m. FIG. 15J. Endurance treadmill test was performed as described. White bars represent PARP-2$^{+/+}$ mice, while black bars represent PARP-2$^{-/-}$ mice. * indicates statistical difference vs. PARP-2$^{+/+}$ mice at p<0.05.

FIGS. 16A-16F. PARP-2$^{-/-}$ mice display higher mitochondrial content in liver. FIG. 16A. mRNA expression in livers from PARP-2+/+ analysis and male (n=16/13, respectively; 6 months of age) mice fed a chow diet. FIG. 16B. Relative liver mitochondrial DNA (mtDNA) content was estimated by RT-qPCR. FIG. 16C. Transmission electron microscopic images of liver sections demonstrate higher mitochondrial number in PARP-2$^{-/-}$ mice. FIG. 16D. Total intrahepatic NAD$^+$ content was measured by HPLC/MS. FIG. 16E. Total liver protein extracts were used to evaluate SIRT1 protein levels and immunoprecipitate PGC-1 to examine PGC-1 acetylation levels. FIG. 16F. Liver triglyceride content was estimated after methanol/chloroform lipid extraction as described. White bars represent PARP-2$^{+/+}$ mice, while black bars represent PARP-2$^{-/-}$ mice. * indicates statistical difference vs. PARP-2$^{+/+}$ mice at p<0.05.

FIGS. 17A-17H. PARP-2$^{-/-}$ mice are protected against diet-induced body weight gain and insulin resistance. FIG. 17A. 6 month old PARP-2+/+ and $^{-/-}$ male mice (n=7 and 9, respectively) fed on high fat diet were weighed weekly. FIG. 17B. Food intake was monitored during high-fat feeding FIG. 17C. Body fat mass composition was evaluated through EchoMRI. FIG. 17D. The weight of the tissues indicated was determined upon autopsy at the end of the high-fat feeding period. (FIG. 17E) VO$_2$ and (FIG. 17F) spontaneous activity was determined by indirect calorimetry. Quantification of the mean values during light and dark phases are shown. FIG. 17G. mRNA expression levels in gastrocnemius muscles from PARP-2$^{+/+}$ and $^{-/-}$ mice after 12 weeks of high-fat diet was determined by qRT-PCR. FIG. 17H. Glucose excursion after an intraperitoneal insulin tolerance test. White bars and circles represent PARP-2$^{+/+}$ mice, while black bars and circles represent PARP-2$^{-/-}$ mice. * indicates statistical difference vs. PARP-2$^{+/+}$ mice at p<0.05.

FIGS. 18A-18H. Pancreatic abnormalities render PARP-2$^{-/-}$ mice glucose intolerant after high-fat feeding. FIG. 18A. Plasma glucose levels during an intraperitoneal glucose tolerance test (IPGTT) in 9-month old PARP-2$^{+/+}$ and $^{-/-}$ male mice (n=7 and 9, respectively) fed a high fat diet for 12 weeks. The area under the curve of the glucose curves is shown at the right. FIG. 18B. Insulin levels during the first hour of the IPGTT in FIG. 18A. FIG. 18C. Comparison of total pancreas weight between PARP-2$^{+/+}$ and $^{-/-}$ mice on chow and high-fat diet. FIG. 18D. Pancreas from PARP-2$^{+/+}$ and $^{-/-}$ mice after high-fat diet were stained for insulin (scale bar=50 Rm) and FIG. 18E. Mean islet size was quantified. FIG. 18F. Total insulin content in pancreas was measured as described. FIG. 18G. Gene expression in the pancreas of PARP-2$^{+/+}$ and $^{-/-}$ mice was measured by RT-qPCR. FIG. 18H. Pancreatic total protein extracts were used to test the abundance of SIRT1, and subunits from the respiratory complexes I and III. FOXO1 was also immunoprecipitated to determine relative FOXO1 acetylation levels. Through the figure, white bars and circles represent PARP-2$^{+/+}$ mice, while black bars and circles represent PARP-2$^{-/-}$ mice. * indicates statistical difference vs. PARP-2$^{+/+}$ mice at p<0.05.

FIG. 19A. Total and mitochondrial NAD$^+$ was determined as described in Experimental procedures in C2C12 cells transduced with either scramble (white bars) or a PARP-2 (black bars) shRNA. FIG. 19B. PARP-2 and SIRT1 were immunoprecipitated from C2C12 cells and blotted for the markers indicated. FIG. 19C. ChIP assay was performed in HEK293T cells and the interaction of PARP-2 with the SIRT1-91 bp promoter region (black bars) or the K19 promoter (white bars) was evaluated by qPCR. FIG. 19D. Alignment of the SIRT1 promoter of different vertebrate species was performed using the ClustalW software. The green field indicates the murine −1-91 region, where PARP-2 interacts. * indicates statistical difference between the PARP-2 IP and the unspecific antibody binding at P<0.05.

FIGS. 20A-20B. PARP-2 deletion does not lead to the accumulation of DNA damage and does not influence SIRT2 and SIRT3 activity in muscle. FIG. 20A. Representative image of the TUNEL reaction in the gastrocnemius muscle of young (3 months of age) and old (11 months of age) PARP-2$^{+/+}$ and $^{-/-}$ male mice (n=3/3/4/3; young PARP-2$^{+/+}$/ young PARP-2$^{-/-}$/old PARP-2$^{+/+}$/old PARP-2$^{-/-}$) to determine the amount of DNA strand breaks. The bar represents 1 m. Arrows represent TUNEL-positive nuclei indicative of DNA damage. FIG. 20B. The acetylation status of tubulin, a SIRT2 target, was evaluated using specific antibodies, while the activity of SIRT3 activity was evaluated by the acetylation status of Ndufa9 (37 kDa) immunoprecipitates.

FIGS. 21A-21C. PARP-2 deletion does not have a major impact on BAT gene expression and function. FIG. 21A. SIRT1 protein levels were detected in the BAT of PARP-2$^{+/+}$ and $^{-/-}$ male mice by Western blotting. FIG. 21B. BAT mRNA expression pattern was determined in PARP-2$^{+/+}$ and male mice (n=16/13) by RT-qPCR. FIG. 21C. PARP-2$^{+/+}$ and $^{-/-}$ mice n=6/6) were exposed to cold (4° C.), as described in Experimental procedures. White bars and circles represent PARP-2$^{+/+}$ mice and black bars or circles represent PARP-2$^{-/-}$ mice. All results are expressed as mean±SD.

FIGS. 22A-22C. PARP-2$^{-/-}$ livers display reduced lipid accumulation, in the absence of changes in SIRT2 and SIRT3 activity or gluconeogenic potential. FIG. 22A. The acetylation of SIRT2 and SIRT3 targets (tubulin and Ndufa9, respectively) were determined by the use of specific antibodies (acetyl-tubulin) or by immunoprecipitation (Ndufa9). FIG. 22B. Liver morphology and lipid content was assessed by hematoxilin-eosin (HE) and Oil-Red O (ORO) stainings. The bar represents 10 μm. FIG. 22C. Gluconeogenesis was assessed by intraperitoneal pyruvate PARP-2+/+—tolerance test in (white bar and circles) and/—(black bar and circles) male mice (n=10/9) as described in materials and methods. The area under curve (AUC) is shown at the right of the panel * indicates statistical difference PARP-2$^{+/+}$ vs. PARP-2$^{-/-}$ mice at p<0.05.

FIG. 23A. Morphology and lipid accumulation the liver of PARP-2$^{+/+}$ and $^{-/-}$ male mice (n=16/13) after 12 weeks of high-fat diet was visualized with hematoxilin-eosin (HE) and Oil Red-O staining. The bar represents 20 μm. FIG. 23B. Triglyceride quantity was determined after lipid extraction from PARP-2$^{+/+}$ (white bar) or PARP-2$^{-/-}$ (black bar) livers as described in the methods. * indicates statistical difference PARP-2$^{+/+}$ HFD vs. PARP-2$^{-/-}$ HFD mice at p<0.05.

FIG. 24A. Total NAD+ was determined from the pancreas of PARP-2$^{+/+}$ (white bar) and $^{-/-}$ male mice (black bar) (n=7/5). FIG. 24B. The absence of an interaction between pancreatic PARP-2 and FOXO-1 was evidenced by immunprecipitation experiments. FIG. 24C. The pancreas of PARP-1$^{+/+}$ and $^{-/-}$ male mice (n=3/3) were stained for insulin (bar=50 μm). FIG. 24D. Insulin content in the pancreas from PARP-1$^{+/+}$ (white bar) or –/– (black bar) mice was determined by ELISA.

FIG. 25A. C2C12 myotubes were treated for 24 hrs with different PARP inhibitors at the concentrations indicated. FIG. 25B. C2C12 myotubes were treated with PBS (Veh), PJ34 (1 mM) or TES501 at the concentrations indicated. FIG. 25C. C2C12 myotubes were treated with PJ34 or TES501 for the times indicated. * indicates statistical difference vs. untreated or vehicle treated cells at p<0.05.

FIGS. 26A-26H. Nicotinamide Riboside supplementation increases NAD$^+$ content and sirtuin activity in cultured mammalian cells. FIG. 26A. C2C12 myotubes, Hepa1.6 and HEK293T cells were treated with nicotinamide riboside (NR) for 24 hrs and acidic extracts were obtained to measure total NAD$^+$ intracellular content. FIG. 26B. GPR109A-expressing Chem-4 cells were loaded with 3 μM Fura-2-acetoxymethyl ester derivative (Fura-2/AM) for 30 min at 37° C. Then, cells were washed with Hank's balanced salt solution and calcium flux in response to nicotinic acid (NA; as positive control), NR and nicotinamide mononucleotide (NMN) at the concentrations indicated was determined as indicated in methods. FIG. 26C. C2C12 myotubes, Hepa1.6 and HEK293T cells were treated with either PBS (as Vehicle) or 0.5 mM of NR, NMN or NA for 24 hrs. Then total NAD$^+$ intracellular content was determined as in FIG. 26A. FIG. 26D. C57Bl/6J mice were fed with chow containing vehicle (water) or either NR, NMN or NA at 400 mg/kg/day (n=8 mice per group). After one week, NAD$^+$ content was determined in liver and quadriceps muscle. FIG. 26E. HEK293T cells were treated with NR (0.5 mM, black bars) or vehicle (white bars) for 4 hrs. Then, cells were harvested and mitochondria were isolated for NAD$^+$ measurement. FIG. 26F. C57Bl/6J mice were fed with chow containing vehicle (water) or NR at 400 mg/kg/day (n=8 mice per group). After one week, mitochondria were isolated from their livers to measure NAD$^+$ content. FIG. 26G. HEK293T cells were treated with either PBS (as Vehicle) or 0.5 mM of NR for 24 hrs. Then mRNA and protein was extracted to measure Nampt levels by RT-qPCR and western blot, respectively. FIG. 26H. REK293T cells were treated with either PBS (as Vehicle) or 0.5 mM of NR for 24 hrs. Then protein homogenates were obtained to test global PARylation and PARP-1 levels. Throughout the figure, all values are presented as mean+/–SD. * indicates statistical significant difference vs. respective vehicle group at P<0.05. Unless otherwise stated, the vehicle groups are represented by white bars, and NR groups are represented by black bars.

FIGS. 27A-27G. Nicotinamide Riboside supplementation increases sirtuin activity in cultured mammalian cells. FIG. 27A. HEK293T cells were transfected with a pool of either scramble siRNAs or SIRT1 siRNAs. After 24 hrs, cells were treated with vehicle (PBS) or NR at the concentrations indicated, and, after an additional 24 hrs, total protein extracts were obtained. FOXO1 acetylation was tested after FOXO1 immunoprecipitation (IP) from 500 μg of protein, while tubulin and SIRT1 levels were evaluated in the supernatant of the IP. FIG. 27B. HEK293T cells were transfected with a pool of either scramble siRNAs, FOXO1 siRNAs or SIRT1 siRNAs. After 24 hrs, cells were treated with NR (0.5 mM; black bars) or vehicle (PBS; white bars) for additional 24 hrs. Then total mRNA was extracted and the mRNA expression levels of the markers indicated was evaluated by qRT-PCR. FIG. 27C. HEK293T cells were transfected with a pool of either scramble siRNAs, FOXO1 siRNAs or sun siRNAs. After 24 hrs, cells were treated with NR (0.5 mM; black bars) or vehicle (PBS; white bars) for additional 24 hrs. Then acidic extracts were obtained to measure intracellular NAD$^+$ levels. FIGS. 27D-27E. HEK293T cells were treated with NR (0.5 mM) or vehicle (PBS) for 24 hrs and total protein extracts were obtained to measure (FIG. 27D) Ndufa9 or (FIG. 27E) SOD2 acetylation after IP. The extracts were also used to measure SOD2 activity (bottom panel). FIGS. 27F-27G. SIRT3$^{+/+}$ and SIRT3$^{-/-}$ mouse embryonic fibroblasts (MEFs) were treated with NR (0.5 mM) or vehicle (PBS) for 24 hrs and either (FIG. 27F) total extracts to test SOD2 acetylation were obtained or (FIG. 27G) acidic extracts were used to measure intracellular NAD$^+$ content. Throughout the figure, all values are presented as mean+/–SD. * indicates statistical significant difference vs. respective vehicle group at P<0.05. Unless otherwise stated, the vehicle groups are represented by white bars, and NR groups are represented by black bars.

FIGS. 28A-28K. NR supplementation prevents diet-induced obesity by enhancing energy expenditure and reduces cholesterol levels. 10-week-old C57Bl/6J mice were fed with either chow (CD) or high fat diet (RFD) mixed with either water (as vehicle) or NR (400 mg/kg/day) (n=10 mice per group). FIG. 28A. Body weight evolution was monitored during 12 weeks. FIG. 28B. Body composition was evaluated after 8 weeks of diet through Echo-MRI. FIGS. 28C-28E. Food intake, activity and $VO_2$ were evaluated using indirect calorimetry. FIGS. 28F-28G. Blood glucose and insulin levels were measured in animals fed with their respective diets for 16 weeks after a 6 hr fast. FIGS. 28H-28I. After 10 weeks on their respective diets (CD=squares; RFD=circles) an intraperitoneal glucose tolerance test was performed in mice that were fasted overnight. At the indicated times blood samples were obtained to evaluate either (FIG. 28H) glucose or (FIG. 28I) insulin levels. Areas under the curve are shown at the top-right of the respective panels (FIG. 28J) Hyperinsulinemic-euglycemic clamps were performed on either CD or CD-NR mice (4 weeks of treatment). Glucose infusion rates (GIR) and muscle glucose uptake were calculated after the test. FIG. 28K. Serum levels of total cholesterol were measured in animals fed with their respective diets for 16 weeks, after a 6 hr fast. Throughout the figure, white represent the vehicle group and black represent the NR-supplemented mice. All values are presented as mean+/–SD. * indicates statistical significant difference vs. respective vehicle treated group.

FIGS. 29A-29C. NR enhances skeletal muscle and BAT oxidative function. 10-week-old C57Bl/6J mice were fed a high fat diet (HFD) mixed with either water (as vehicle; white bars and circles) or NR (400 mg/kg/day; black bars and circles) (n=10 mice per group). FIG. 29A. An endurance exercise test was performed using a treadmill in mice fed with either HFD or HFD-NR for 12 weeks. FIG. 29B. A cold-test was performed in mice fed with either HFD or HFD-NR for 9 weeks. The area over the curve (AOC) is shown on the top right of the graph. FIG. 29C. Electron microscopy of the BAT was used to analyze mitochondrial content and morphology. The size and cristae content of mitochondria was quantified as specified in methods. Throughout the figure, all values are shown as mean+/−SD. * indicates statistical significant difference vs. vehicle supplemented group at P<0.05.

FIGS. 30A-30D. Chronic INR supplementation increases plasma and intracellular NAD$^+$ content in a tissue-specific manner. Tissues from C57Bl/6J mice were collected after 16 weeks of HFD supplemented with either water (as vehicle; white bars) or N$^R$ (400 mg/kg/day; black bars). FIG. 30A. NAD$^+$ levels were measured in acidic extracts obtained from different tissues. FIG. 30B. NADH and NAM levels were measured in gastrocnemius muscle. FIG. 30C. Quadriceps muscle protein homogenates were obtained to test global PARylation, PARP-1 and Nampt protein levels. FIG. 30D. Total mRNA was isolated from quadriceps muscles and the mRNA levels of the markers indicated were measured by RT-qPCR. Throughout the figure, all values are expressed as mean+/−SD. * indicates statistical significant difference vs. respective vehicle treated group.

FIG. 31A. Total protein extracts were obtained from quadriceps muscle and brain indicated to evaluate the acetylation levels of FOXO1 and SOD2 through immunoprecipitation assays, using 1 and 0.5 mg of protein, respectively. FIG. 31B. Total mRNA from quadriceps muscle and brain was extracted to measure the abundance of the markers indicated by RT-qPCR. FIG. 31C. Mitochondrial DNA content was measured in DNA extracted from quadriceps muscle and brain. The results are expressed a mitochondrial copy number relative to genomic DNA. FIG. 31D. The abundance of mitochondrial marker proteins in 20 μg of protein from total quadriceps muscle and brain lysates. Throughout the figure, all values are shown as mean+/−SD. * indicates statistical significant difference vs. vehicle supplemented group at P<0.05.

FIG. 33A. Total protein PARylation was evaluated in liver and muscle of young (6 months) and aged (24 months) C57BL/6J mice, and was accompanied by (FIG. 33B) decreased NAD+ levels, and (FIG. 33C) PGC-1 hyperacetylation. FIG. 33D. Aged C. elegans displayed higher total protein PARylation levels, which were largely attenuated in pme-1 mutants. FIG. 33E. Aging decreased worm NAD+, in both wildtype and in pme-1 mutant worms, with a higher level of NAD+ in the pre-1 mutant during aging. Two-way ANOVA revealed significant difference with age (p<0.008) and genotype (p=0.02). FIG. 33F. pme-1 mutant worms accumulated less of the aging pigment lipofuscin compared to wild type worms. Bar graphs are expressed as mean±SEM, * p≤0.5;  p≤0.01; * p≤0.001.

FIGS. 34A-34E. Longevity in C. elegans with pme-1 mutation or PARP inhibition. FIG. 34A. pme-1 (ok988) mutant worms displayed 29.4% mean lifespan extension. FIG. 34B. PARP inhibition by AZD2281 (100 nM) or ABT-888 (100 nM), extended lifespan by 22.9% and 15% respectively, FIG. 34C in a pme-1-dependent manner. FIG. 34D. pme-1 mutation and PARP inhibition increased NAD+ levels in C. elegans at day 4 of adulthood. FIG. 34E. PARP inhibition by AZD2281 (100 nM) does not extend lifespan in the sir-2.1(ok434) mutant. Bar graphs are expressed as mean±SEM, *p<0.05.

FIGS. 35A-35I. PARP inhibition increases mitochondrial function and ROS defense, FIG. 35A. AZD2281 decreased the accumulation of the aging pigment lipofuscin. FIG. 35B. Oxygen consumption was increased in day 3 adult worms after AZD2281. (AZD). FIG. 35C. Quantitative RT-PCR analysis of AZD2281-treated worms at day 3 of adulthood shows increased expression of genes involved in mitochondrial oxidative metabolism. FIGS. 35D-35E. The effects of AZD on mitochondrial content and morphology in body wall muscle. Stars represent nuclei, insets show higher magnification of a small section of the image, marked by the dashed rectangle. FIG. 35F. AZD2281 decreased ROS, as measured by mitoSOX, accompanied by an increase in sod-3::GFP. FIGS. 35G-35H. Quantitative-RT-PCR for oxidative stress regulators in vehicle- and AZD2281-treated worms. FIG. 35I. AZD2281 fails to extend lifespan in daf-16(mu86) mutant worms. Bar graphs are expressed as mean±SEM, * p≤0.05;  p≤0.01; * p≤0.001.

FIGS. 36A-36J. Supplementation of C. elegans with the NAD+ precursor NR mimics the metabolic and lifespan effects of PARP mutation or inhibition. Supplementation of NAD$^+$ precursors NR (500 RM) in wild type N2 worms increases (FIG. 36A) NAD$^+$ and (FIGS. 36B-36C) lifespan in a sir-2-dependent manner. FIGS. 36D-36E. The effects of NR on mitochondrial content and morphology in body wall muscle. Stars represent nuclei, insets show higher magnification of a small section of the image, marked by the dashed rectangle. FIG. 36F. Oxygen consumption was increased in day 3 adult worms after NR. FIGS. 36G-36H. Quantitative-RT-PCR of the expression of oxidative stress-related genes in wild-type and NR-treated worms. FIG. 36I. NR effects on lifespan are daf-16-dependent. FIG. 36J. Scheme summarizing how NAD$^+$ precursors and PARP inhibitors increase lifespan through activation of sir-2.1. Bar graphs are expressed as mean±SEM, *p<0.05; **p<0.01.

FIGS. 37A-37B. Lifespan analyses with different concentrations of PARP inhibitors. FIGS. 37A-37B. Worm lifespan was measured after treatment with PARP inhibitors AZD2281 (FIG. 37A) or ABT-888 (FIG. 37B). See Table S1 for statistics.

FIGS. 38A-3B. Worm lifespan was measured after treatment with NAD+ precursors NR (FIG. 38A) or NAM (FIG. 38B), See Table S1 for statistics.

FIG. 39A, NAM increased NAD+ levels in C. elegans at day 4 of adulthood. FIG. 39B. NAM increased worm lifespan by 18%. FIG. 39C. Oxygen consumption was increased in day 3 adult worms after NAM. FIG. 39D. Quantitative-RT-PCR of NAM-treated worms revealed a trend for increased cts-1 expression, and expression of sod-3 was increased whereas daf-16 was unchanged FIG. 39E. NAM increased mitochondrial content in body wall muscle. Bar graphs are expressed as mean±SEM, *p<0.05; ** p<0.01.

FIG. 40. Is a schematic illustrating how one can modulate of energy metabolism by impacting on NAD$^+$ levels. This scheme illustrates that in addition to inhibiting NAD+ consumption (e.g. through PARP inhibitors) or changing the ratio between NAD+/NADH (e.g. through AMPK activators) also providing more NAD+ precursors (e.g. Nicotinamide Riboside (NR), Nicotinic acid (NA), Nicotinamide (NAM), Nicotinamide mononucleotide (NMN), Tryptophan) could be used to increase NAD+ levels.

DETAILED DESCRIPTION OF THE INVENTION

Figure 2A:
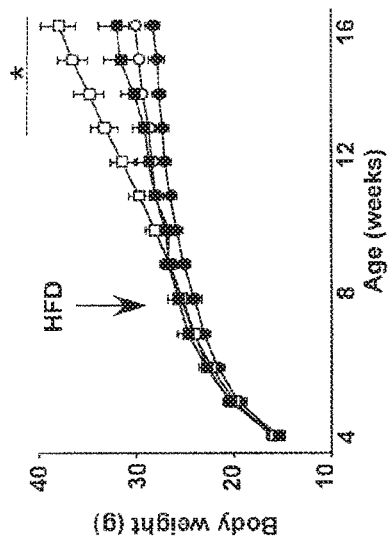
FIGS. 2A-2F, PARP-1$^{-/-}$ mice are protected against high fat feeding-induced metabolic abnormalities.

The invention is based upon the discovery of new pathways to regulate intracellelluar $NAD^+$. The inventors have shown that a decrease in poly(ADP-ribose) polymerase-1 (PARP-1) activity induces intracellular $NAD^+$, SIRT1. and SIRT3 activity and that a decrease on poly(ADP-ribose) polymerase-2 (PARP-2) activity induces SIRT1 and SIRT3 activity. More specifically, it was discovered that inhibition of PARP-1 and PARP-2 promotes oxidative metabolism and oxidative stress defense. Similar effects can be obtained through boosting NAD+ levels by providing NAD+ precursors such as nicotinamide riboside or nicotinic acid. Furthermore, the inventors have also discovered that NAD+ is an aging biomarker. Specifically, the inventors have shown that NAD+ levels and sirtuin activity are reduced in aged mice and *C. elegans*. Restoration of NAD+ levels, by genetic or pharmacological reduction of PARP-1 PARP-2 or by increasing the supply of NAD+ precursors prevents age-associated metabolic decline and extends lifespan in a sir-2.1-dependent fashion.

Regulation of intracellular NAD+ levels are useful in treating or alleviating a symptom of various disorders in which aberrant (i.e., increase or decrease) mitochondrial function is involved. For example, regulation of intracellular NAD+ levels is useful in treating or alleviating a symptom of mitochondrial disorders which include diseases with inherited and/or acquired mitochondrial dysfunction, such as Charcot-Marie-Tooth disease, Type 2A2, Mitochondrial Encephalopathy Lactic Acidosis and Stroke (MELAS), Leigh Syndrome, Barth Syndrome, Leber's optic neuropathy, fatty acid oxidation disorders, inherited forms of deafness and blindness, metabolic abnormalities induced by exposure to toxic chemicals and/or drugs (e.g. cisplatin induced deafness, gentamycin induced deafness). In addition, the methods of the invention are also useful at treating or alleviating a symptom of metabolic disorders, neurodegenerative disorders, aging related disorders or chronic inflammatory disorders, all characterized by mitochondrial dysfunction.

Intracellular NAD+ levels control the activity of the type III deacetylase SIRT1 (Lin et al., 2000), allowing it to act as a metabolic sensor and fine-tune transcriptional programs to drive the utilization of different energetic substrates (Gerhart-Hines et al., 2007; Rodgers et al., 2005). Overexpression studies have revealed how enhancing the activity of SIRT1 or of its orthologs promotes longevity in lower eukaryotes (reviewed by (Canto and Auwerx, 2009)) and protects against high-fat diet (HFD)-induced metabolic disease in mice (Banks et al., 2008; Pfluger et al., 2008), which in turn may also indirectly sustain a more healthy ageing process. These attractive properties of SIRT1 activation have spurred a quest to identify SIRT1 "activators" that could be used pharmacologically in situations of metabolic stress and damage. Most of the previous attempts to pharmacologically activate SIRT1 have relied on the discovery of direct small molecule SIRT1 agonists. This strategy has identified compounds, like resveratrol or SRT1720 (Borra et al., 2005; Howitz et al., 2003; Kaeberlein et al., 2005; Milne et al., 2007; Pacholec et al., 2010), whose ability to directly interact and activate SIRT1 is still under debate (Borra et al., 2005; Canto et al., 2010; Dai et al., 2010; Kaeberlein et al., 2005; Pacholec et al., 2010; Urn et al., 2009). Consequently, there is a strong interest to develop alternative strategies to activate SIRT1. Given the $NAD^+$-sensing abilities of SIRT1, another potential way to activate it would be by increasing intracellular $NAD^+$ levels. The present invention is based on the hypothesis that SIRT1 can be activated by specific inhibition of other cellular NAD+-consuming activities.

Poly(ADP-ribose) polymerase (PARP)-1 constitutes one of the major $NAD^+$ consumers in the cell (Schraufstatter et al., 1986; Shieh et al., 1998). PARP-1 is activated upon binding to damaged or abnormal DNA (Durkacz et al., 1980; Kun et al., 2002), and catalyzes the formation of poly(ADP-ribose) polymers (PAR) onto different acceptor proteins, including PARP-1 itself (auto-PARylation), using $NAD^+$ as substrate (Adamietz, 1987; Burkle, 2005; Chambon et al., 1963). To test the influence of PARP-1 on SIRT1 activity and on metabolic homeostasis we used both a genetic strategy, exploiting PARP-1 deficient (PARP-1$^{-/-}$) mouse (Menissier-de Murcia et al., 1997) and cellular models, and a pharmacological approach, to inhibit PARP-1 activity. The combined results as described herein of these complimentary studies demonstrate how a reduction or ablation of PARP-1 activity increases $NAD^+$ levels and SIRT1 activity, which, in turn, promotes mitochondrial content and function, culminating in a solid protection against metabolic disease.

PARP-2 has a structurally similar catalytic domain (amino acids 202-593) as PARP-1 (Oliver et al., 2004). Accordingly, we also evaluated the effect of PARP-2 inhibition on intracellular $NAD^+$ levels and global metabolism in cells or organs. The potential relevance of PARP-2 for $NAD^+$ homeostasis, which would impact on sum activity and global metabolism, prompted us hence to fully examine the metabolic phenotype of germline PARP-2$^{-/-}$ mice. The data shown herein demonstrates that the absence of PARP-2 activates SIRT1 and promotes mitochondrial biogenesis in muscle. However, our data also reveals that the absence of PARP-2 leads to pancreatic failure upon high-fat feeding, underscoring the possibility of developing drugs that selectively inhibit specific PARP proteins for metabolic indications.

Accordingly the invention features methods of promoting oxidative metabolism and treating, alleviating a symptom or delaying the onset of a disorder associated with aberrant mitochondrial function by administering to a subject a compound that increases intracellular nicotinamide adenine dinucleotide ($NAD^+$) in an amount sufficient to activate SIRT1 or SIRT3. Also included in the invention are methods of treating, alleviating a symptom or delaying the onset cancer by one or more compounds that increases intracellular nicotinamide adenine dinucleotide ($NAD^+$) in an amount sufficient to activate SIRT1 or SIRT3. The subject is suffering from or susceptible to developing the disorder.

The invention further provides methods of increasing concentration of $NAD^+$ within the mitochondria by contacting mitochondria with nicotinamide riboside. In another aspect, the invention provides a method of activating mitochondrial sirtuins. Mitochondrial sirtuins include for example SIRT3, SIRT4 and SIRT5.

Compounds that increase $NAD^+$ include inhibitors of the poly (ADP-ribose) polymerase (PARPs) family of proteins, NAD+ boosters and AMPK agonists. The compounds can be administered alone or in combination.

Members of the PARPs family of protein include PARP-1, PARP-2, PARP-3, PARP-4, PARP-5a, PARP5b, PARP-6, PARP-7, PARP-8, PARP-9, PARP-10, PARP-12, PARP-13, PARP-14, PARP-15, and PARP-16. Preferably, the compound is a PARP-1 inhibitor.

A PARP-1 inhibitor is a compound that decreases expression or activity of PARP-1. A decrease in PARP-1 expression or activity is defined by a reduction of a biological function of the PARP-1 protein. A PARP-1 biological function includes for example, the catalysis of lipid molecules between phospholipid membranes or the transfer of lipid from high density lipoproteins (HDL) to low density lipoproteins (LDL). PARP-1 expression is measured by detecting a PARP-1 transcript or protein or by measuring PARylation activity. PARP-1 inhibitors are known in the art or are identified using methods described herein. For example, a PARP-1 inhibitor is identified by detecting an increase of intracellular $NAD^+$. Intracellular $NAD^+$ is detected by methods known in the art such the methods disclosed herein.

The PARP-1 inhibitor is for example an antisense PARP-1 nucleic acid, a PARP-1 specific short-interfering RNA, or a PARP specific ribozyme.

By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense PARP-1 nucleic acid sequence, an anti-sense PARP-1 nucleic acid sequence or both. Optionally, the siRNA is constructed such that a single transcript has both the sense and complementary antisense sequences from the target gene, e.g., a hairpin.

Binding of the siRNA to a PARP-1 transcript in the target cell results in a reduction in PARP-1 production by the cell. The length of the oligonucleotide is at least 10 nucleotides and may be as long as the naturally-occurring PARP-1 transcript. Preferably, the oligonucleotide is 19-25 nucleotides in length. Most preferably, the oligonucleotide is less than 75, 50, 25 nucleotides in length.

Exemplary PARP-1 inhibitors, which inhibit NAD+ consumption, also include small molecule inhibitors such as PJ34, TIQ, TES-500, TES-501, BSI-202 or Iniparib, AZD2281 or Olaparib, ABT-888 or Veliparib, AG014699, CEP 9722 MK 4827, Other PARP-1 inhibitors are known in the art.

Other examples of molecules that can raise NAD+ levels, independently of PARP inhibition, are compounds that induce NAD+ synthesis (i.e. NAD boosters), such as tryptophan, nicotinamide riboside (NR), niacin, nicotinic acid (NA), nicotinamide (NAM), N-formylkynurenine, Quionlinic acid, nicotinamide riboside kinase (NRK) or nicotinamide mononucleotide (NMN).

Exemplary compounds that also induce NAD+ levels, independent of the stimulation of NAD+ synthesis or the inhibition of NAD+ usage, include small molecule activators of AMP activated kinase (AMPK), such as 5-aminoimidazole-4-carboxamide-1-b-D-riboside, PT-1, A-769662 (Abbott), Adiponectin, Leptin, Ghrelin, Cannabinoids, alpha-lipoic acid, Interleukin-6 (IL-6), Resveratrol, Quercetin, Metformin, Berberine, Curcumine, Epigallocatechin-3-gallate (green tea), Thiazolidinediones, such as rosiglitazone and pioglitazone or Dinitrophenol (DNP).

The present invention provides for both prophylactic and therapeutic methods of treating a subject at risk of (or susceptible to) a disorder or having a disorder associated with aberrant (e.g., insufficient) metabolism. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Oxidative metabolism is promoted by exposing, e.g., contacting a tissue or cell with a compound that increases that increases intracellular nicotinamide adenine dinucleotide ($NAD^+$) in an amount sufficient to activate SIRT1. By promoting oxidative metabolism is meant an increase in oxygen consumption compared to a tissue or cell that has not been in contact with compound. Tissues or cells are directly contacted with compound. Alternatively, the compound is administered systemically. The compound is administered in an amount sufficient to increase (e.g., activate) SIRT1 or SIRT3. Oxidative metabolism is measured by known in the art, such as by the methods described herein.

The methods are useful to treat, alleviate the symptoms of, or delay the onset of a disorder associated with aberrant mitochondrial function. Disorders associated with aberrant mitochondrial function include for example metabolic disorders, neurodegenerative disorders aging related disorders and chronic inflammatory disorders. Mitochondrial disorders include also diseases with inherited and/or acquired mitochondrial dysfunction, such as Charcot-Marie-Tooth disease, Type 2A2, Mitochondrial Encephalopathy Lactic Acidosis and Stroke (MELAS), Leigh syndrome, Barth syndrome, Leber's optic neuropathy, Fatty acid oxidation disorders, Inherited forms of deafness and blindness, metabolic abnormalities induced by exposure to toxic chemicals and/or drugs (e.g. cisplatin induced deafness).

Metabolic disorders include for example, type II diabetes, obesity, hyperglycemia, glucose intolerance, insulin resistance (i.e., hyperinsulinemia, metabolic syndrome, syndrome X), hypercholesterolemia, hypertension, hyperlipoproteinemia, hyperlipidemia (e.g., dyslipidemia), hypertriglylceridemia, cardiovascular disease, atherosclerosis, peripheral vascular disease, kidney disease, ketoacidosis, thrombotic disorders, nephropathy, diabetic neuropathy, diabetic retinopathy, sexual dysfunction, dermatopathy, dyspepsia, hypoglycemia, cancer or edema.

Neurodegenerative disorders include diseases such as Dementia, Alzheimer's disease, Parkinson's disease, and Huntington's disease.

Chronic inflammatory diseases include disease such as celiac disease, vasculitis, lupus, chronic obstructive pulmonary disease (COPD), irritable bowel disease, atherosclerosis, arthritis, and psoriasis.

Aging related disorders includes disease such as cancer, dementia, cardiovascular disease, such as arteriosclerosis, hypertension, diabetes mellitus (type I or type II) arthritis, cataracts, Alzheimer's disease and osteoporosis.

The subject is suffering from or a susceptible to developing a metabolic disorder. Subjects suffering from or at risk of developing a metabolic disorder are identified by methods known in the art. For example diabetes is diagnosed by for example by measuring fasting blood glucose levels or insulin or by glucose tolerance test. Normal adult glucose levels are 60-126 mg/dl. Normal insulin levels are 7 mU/mL±3 mU. Hypertension is diagnosed by a blood pressure consistently at or above 140/90. Cardiovascular disease is diagnosed by measuring Cholesterol levels. For example, LDL cholesterol above 137 or total cholesterol above 200 is indicative of cardiovascular disease. Hyperglycemia is diagnosed by a blood glucose level higher than 10 mmol/l (180 mg/dl). Glucose intolerance is diagnosed by a two-hour glucose levels of 140 to 199 mg per dL (7.8 to 11.0 mmol)

on the 75-g oral glucose tolerance test. Insulin resistance is diagnosed by a fasting serum insulin level of greater than approximately 60 pmol/L. Hypoglycemia is diagnosed by a blood glucose level lower than 2.8 to 3.0 mmol/L (50 to 54 mg/dl). Obesity is diagnosed for example, by body mass index. Body mass index (BMI) is measured ($kg/m^2$(or $lb/in^2 \times 704.5$)). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e., fat mass impedes current), estimates % fat) is measured. The parameters for normal, overweight, or obese individuals is as follows: Underweight: BMI<18.5; Normal: BMI 18.5 to 24.9; Overweight: BMI=25 to 29.9. Overweight individuals are characterized as having a waist circumference of >94 cm for men or >80 cm for women and waist to hip ratios of ≥0.95 in men and ≥0.80 in women. Obese individuals are characterized as having a BMT of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of ≥35.≥

The methods described herein lead to a reduction in the severity or the alleviation of one or more symptoms of the metabolic disorder. Symptoms of diabetes include for example elevated fasting blood glucose levels, blood pressure at or above 140/90 mm/Hg; abnormal blood fat levels, such as high-density lipoproteins (HDL) less than or equal to 35 mg/dL, or triglycerides greater than or equal to 250 mg/dl, (mg/dL=milligrams of glucose per deciliter of blood). Efficacy of treatment is determined in association with any known method for diagnosing the metabolic disorder. Alleviation of one or more symptoms of the metabolic disorder indicates that the compound confers a clinical benefit.

The compounds, e.g., PARP-1 inhibitors (also referred to herein as "active compounds") of the invention, and derivatives, fragments, analogs and homologs thereof, can be incorporated into pharmaceutical compositions suitable for administration. Such compositions typically comprise the peptide or mimetic, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, Which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Mitochondrial disorders are diagnosed for example in combination with abnormalities of glucose and lipid homeostasis, ketone bodies and abnormalities in acid/base balance and abnormal levels of other metabolites in the blood.

Neurodegenerative disorders are diagnosed for example by physical and neurological examination, family history, Electroencephalograms (EEGs) MRI and CAT scans.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PARP-1 inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

EXAMPLES

Example 1 General Methods

Materials. All chemicals, including PJ34 (Garcia et al., 2001), were from Sigma-Aldrich unless stated otherwise.

Animal Experiments. Male PARP-1$^{+/+}$ and PARP-1$^{-/-}$ mice on a pure C57Bl/6J background (Menissier-de Murcia et al., 1997) were used. Mice were housed separately, had ad libitum access to water and standard rodent chow (10 kcal % of fat, Safe, Augy, France) or to a high calorie, high fat diet (60 kcal % of fat, Research. Diets, New Brunswick, N.J., USA), and were kept under a 12 h dark-light cycle. In other animal experiments, 8 weeks-old male C57Bl/6J mice were purchased from Charles River and powder chow (D12450B) and high fat (D12492) diets were from Research Diets Inc (New Brunswick, N.J., USA). 80 ml of water per kg of powder CD were used to make food pellets. 40 ml of water per kg of powder HFD were used to make food pellets. For NR, NMN and NA supplemented diets, the appropriate amount of these compounds was added to the water used to create the pellets, taking into account the differences in the daily intake of each diet. Mice were housed separately, had ad libitum access to water and food and were kept under a 12 h dark-light cycle. Mice were fed with homemade pellets from 10 weeks of age. To make the pellets, the powder food was mixed with water (vehicle) or with NR. All animal experiments were carried out according to local national and EU ethical guidelines. To monitor body weight, mice were weighed and the food consumption was measured each week on the same day. In case of PJ34 treatment, mice received each 12 h (at 7:00 and 19:00) 10 mg/kg PJ34 by intraperitoneal injection for 5 continuous days. In all studies animals were killed (at 14:00) either after $CO_2$ inhalation or cervical dislocation after 6 h of fasting (starting at 8:00), and tissues were collected and processed as specified below. Oral glucose tolerance test, intraperitoneal insulin tolerance test, free fatty acid (FFA) and triglycerides were determined as described (Lagouge et al., 2006). Plasma insulin and was determined in heparinized plasma samples using specific ELISA kits (Mercodia). Blood samples were collected in heparinized tubes and plasma was isolated after centrifugation. Plasma parameters were measured using a Cobas c111 (Roche Diagnostics). Thermoadaptation was performed as described (Lagouge et al., 2006). We measured $O_2$ consumption, $CO_2$ production, and spontaneous locomotor activity in an open circuit indirect calorimetry system (Sabre systems, Las Vegas, Nev., USA) over 24-48 has described (Dali-Youcef et al., 2007; Lagouge et al., 2006; Watanabe et al., 2006). Energy expenditure was obtained by using an energy equivalent of 20.1 J/ml $O_2$. The respiratory quotient was the ratio of $CO_2$ production over $O_2$ consumption. During actimetry, beamline crossings were summarized each 15 minutes. The sum of beamline crosses for each 15 min period were plotted against time and AUC was calculated for each mouse that was average in each experimental cohort. Euglycemic-hyperinsulinemic clamps were performed in PARP-1$^{-/-}$ and $^{+/+}$ male mice (n=4 mice per genotype; age=4 months) exactly as previously described (Feige et al, 2008).

Homozygous PARP-2$^{-/-}$ and littermate PARP-2$^{+/+}$ mice (Menissier-de Murcia et al., 2003) and PARP-1$^{-/-}$ and PARP-1$^{+/+}$ mice (Menissier-de Murcia et al., 1997), on a mixed C57BL/6J/SV129 background (87.5%/12.5%) background, from heterozygous crossings were used. Mice were housed separately, had ad libitum access to water and food, and were kept under a 12/12 h dark-light cycle. Mice were selected for the study at the age of 4 weeks and were kept on chow diet (10 kcal % of fat, Safe, Augy, France). For a part of the animals, food was changed by a high fat diet (HFD, 60 kcal % of fat, Research Diets, New Brunswick, N.J., USA) at the age of 16 weeks. Each week on the same day mice were weighed and the food-consumption was measured. $O_2$ consumption ($VO_2$), $CO_2$ production, respiratory exchange ratios (RER), and actimetry were measured by CLAMS of Colombus Instruments, total body fat was measured by echoMRI as described (Lagouge et al., 2006; Watanabe et al., 2006). Endurance test was performed as described in (Canto et al., 2009). Intraperitoneal glucose and insulin tolerance tests (IPGTT and IPITT, respectively) were performed as previously described (Feige et al, 2008). The animals were killed after 6 h of fasting by $CO_2$ asphyxiation and tissues were collected. Total body fat content was then examined at autopsy, by weighing the subcutaneous, gonadal, mesenterial, retroperitoneal and BAT associated fat depots. Liver triglyceride was determined after Folch extraction using a commercial triglyceride kit (Roche). Pancreas and plasma insulin content was determined from acidic extracts using a commercial ELISA kit (Mercodia) (Champy et al., 2004).

Histology and Microscopy. Haematoxylin-eosin (HE), Oil Red-O and succinate-dehydrogenase (SDH) stainings were performed on 7 m tissue sections as described (Lagouge et al., 2006; Picard et al., 2002). Transmission electron microscopy (TEM) investigation was performed on glutaraldehyde-fixed, osmium tetroxyde stained ultrafine sections (Watanabe et al., 2006). PAR was detected in tissues using a monoclonal anti-PAR antibody (Alexis) and Mouse-on-mouse kit (Vector Laboratories) on 7 μm formalin-fixed tissues using as described in (Garcia et al., 2001). A specific binding of the secondary antibody was controlled on sections where the primary antibody was omitted. Mitochondrial size and cristae content was analyzed as previously described in St-Pierre et al. (St-Pierre, J., Lin, J., Krauss, S., Tarr, P. T., Yang, R., Newgard, C. B., and Spiegelman, B. M, Bioenergetic analysis of peroxisome proliferator-activated receptor gamma coactivators 1alpha and 1beta (PGC-1alpha and PGC-1beta) in muscle cells. J Biol Chem 278, 26597-26603 (2003)).

Cell Culture, Transfection, Adenoviral Infection and Mitochondrial Characterization. HEK293T, MEF and C2C12 cells were cultured in DMEM (4.5 g/l glucose, 10% FCS). PARP-1$^{+/+}$ and PARP-1$^{-/-}$ MEFs were prepared as described in (Menissier-de Murcia et al., 1997). SIRT1 and MEFs were kindly provided by Fred Alt (Chea et al., 2005). SIRT3 MER were established according to standard techniques from conditional SERT3$^{-/-}$ mice. (Picard, F., Gehin, M., Annicotte, J., Rocchi, S., Champy, M. F., O'Malley, B. W., Chambon, P., and Auwerx, J. (2002). SRC-1 and TIF2 control energy balance between white and brown adipose tissues. Cell 111, 931-941.) Deletion of the SIRT3 gene was induced via infection with adenovirus encoding for the Cre recombinase. HEK293T cells were transfected using JetPei reagent (Polyplus Transfections, Illkirch, France) according to the manufacturer's instructions. C2C12 cells were differentiated in DMEM (4.5 g/L glucose, 2% horse serum) after reaching confluency for 2 days, followed by 2 days of PJ34 treatment (10 μM). PARP-1 shRNA constructs were described in (Shah et al., 2005). Human PARP-1 and siR-NAs were obtained from Dharmacon (Thermo Scientific). The adenovirus encoding for FLAG-HA-PGC-1α, control and SIRT1 shRNAs were a kind gift from Pere Puigserver and were used (MOI=100) in C2C12 myotubes as described (Canto et al., 2009). Mitochondrial charge determination was performed as described (Bai et al., 2001) and DNA strand breaks were quantified by TUNEL assays according to the manufacturer's instructions (Millipore).

Murine Hepa1.6 and HEK293T cells were maintained in 4.5 g/L glucose DMEM, 10% FCS. For the transfection of HEK293T cells JetPei was used (Polyplus transfections, Illkirch, France) according to the description of the company. PARP-2 depletion and overexpression took place as described in (Bai et al. 2007).

C2C12 cells were maintained in 4.5 g/L glucose DMEM, 10% FCS and were differentiated in 4.5 g/L glucose DMEM, 2% horse serum for 2 days, when cells were considered myofibers. PARP-2 was depleted from C2C12 cells using lentiviral shRNA system (MISSION Lentiviral Vectors, Sigma-Aldrich). The vectors contained the interfering and control sequences described in (Bai et al. 2007). C2C12 cells were transduced with 20 MOI virus and were selected with 2.5 g/ml puromycin. Cells withstanding puromycin selection were subcultured. In all subsequent cell culture steps puromycin selection was constantly maintained. The efficiency of knock-down at the mRNA level was assessed by RT-qPCR.

mRNA and mtDNA Analysis. Total RNA was prepared using TRIzol (Invitrogen) according to the manufacturer's instructions. RNA was treated with DNase, and 2 μg of RNA was used for reverse transcription (RT). cDNA was purified on QIAquick PCR cleanup columns (Qiagen, Valencia, Calif., USA). 50× diluted cDNA was used for RT-quantitative PCR (RT-VCR) VCR) reactions (Bai et al., 2007). The RT-qPCR reactions were performed using the Light-Cycler system (Roche Applied Science) and a qPCR Supermix (Qiagen) with the primers for mice summarized in Table 1 and 4, and with the primers for worms summarized on Table 7. mtDNA quantification was performed as described (Lagouge et al., 2006) with the primers indicated in Table 2 and 5.

Immunoprecipitation, SDS-PAGE, Western Blotting. Cells were lysed in lysis buffer (50 mM Tris, 100 nM KCl, EDTA 1 mM, NP40 1%, nicotinamide 5 mM, Na-butyrate 1 in M, protease inhibitors pH7.4). Proteins were separated by SDS-PAGE and transferred onto nitrocellulose membranes. The origin of the primary and secondary antibodies used can be found as supplemental experimental procedures. Reactions were developed by enhanced chemiluminescence (Amersham, Little Chalfont, UK), PGC-1α, FOXO1 and Ndufa9 acetylation levels were analyzed by immunoprecipitation from cellular or nuclear lysates of tissues with anti-PGC-1α (Millipore), anti-FOXO1 (Cell Signaling, Danvers, Mass., USA) and anti-Ndufa9 (Abcam) antibody followed by Western blot using an acetyl-lysine antibody (Cell Signaling) that was normalized to total PGC-1a/FOXO1/Ndufa9 levels (Lagouge et al., 2006; Rodgers et al., 2005). In HEK293T cells HA-tagged PGC-1α was overexpressed and was immunoprecipitated using an anti-HA. In C2C12 myotubes, FLAG-HA tagged PGC-1α was introduced through adenoviral delivery 2 days before treatments, then IP was performed using anti-FLAG antibody and samples were processed as described. All blots were quantified by densitometry using ImageJ software. Poly(ADP-Ribose) detection was performed as previously described with slight modifications (Bai et al., PARP-1 inhibition increases mitochondrial metabolism through SIRT1 activation. Cell Metab 13, 461-468. (2011)) Briefly, PAR was detected by using a monoclonal anti-PAR antibody (Alexis, Lausanne Switzerland) by Western blotting of total protein lysates, using either 50 g of total worm protein lysates, 50 g of liver protein lysate or 200 g of muscle total protein extracts. PGC-1 acetylation was determined using PGC-1 immunoprecipitates from 2 mg of protein extracts, as described in Canto et al. (Canto et al., AMPK regulates energy expenditure by modulating NAD+ metabolism and SIRT1 activity. Nature 458, 1056 (2009)).

Chromatin Immunoprecipitation (ChIP). ChIP was performed according to (Bai et al., 2007). FLAG-HA-PGC-1 (Rodgers et al., 2005) was introduced by adenoviral transfer into C2C12 myotubes after 48 h of differentiation and cells were cultured for an additional 2 days. Cells were then exposed to 1 M PJ34 in saline for 24 h. Thereafter ChIP was performed using anti-FLAG (Sigma) and anti-TNF-R1 (Santa Cruz) as described (Bai et al., 2007). Pelleted DNA was quantified by qPCR using the primers against PDK4 and UCP-3 promoters flanking the nuclear receptor site (Table 3 and 6). The results were normalized for the signal of the respective inputs (vehicle/PJ34-treated) and were expressed as a percentage. The signal of anti-TNF-R1 (non-specific antibody) was subtracted from the anti-FLAG signal (specific) and the specific signal was plotted. Primers for ChIP are summarized in Supplementary Table 3 and 6.

Antibodies Used for Western Blot Applications. PARP-1 (Erdelyi et al., 2009), PAR (Alexis, Lausanne, Switzerland), SIRT1 (Millipore), FOXO1 (Cell Signaling), haemagglutinin (Sigma), Complex I (Ndufa9) (Abeam), Complex IV (COXI) and V (subunit) (Molecular probes), FLAG (Sigma), and actin (Sigma) were detected using a polyclonal rabbit antibodies. SIRT1 (Millipore), actin (Sigma), PARP-2 (rabbit polyclonal antibody raised against full length mouse PARP-2) and H1 (kindly provided by S. Muller, IBMC, Strasbourg). FOXO1 and SOD2 antibodies were from Santa Cruz Biotechnology, and Acetyl-tubulin antibodies were from Sigma Inc. Antibodies for mitochondrial markers were purchased from Mitosciences. The secondary antibody was IgG-peroxidase conjugate (Sigma, 1:10000).

Constructs, and Reporter Assays SIRT1 promoter constructs were described in (Nemoto et al., 2004), pSuper-siPARP2, pSuper-scrPARP2 and pBabe-PARP2 were described in (Bai et al., 2007). Adenovirus for SIRT1 knockdown is reported in (Rodgers et al., 2005).

SIRT1 Promoter Reporter Assay HEK293T cells seeded in 6 well plates, after the depletion or overexpression of PARP-2, were transfected with 1.6 g SIRT1 promoter reporter construct, 1 g of pBabe/pBabe-PARP-2/pSuper-shPARP-2/pSuper-scrPARP-2 and 0.4 g pCMV-Gal. Ten hours after transfection cells were scraped then luciferase and -galactosidase activity were determined. Luciferase activity was expressed as luciferase activity/-galactosidase activity.

$NAD^+$ NAM Determination. $NAD^+$ levels in cultured cells were determined using a commercial kit (Enzychrom™, BioAssays Systems, CA). For tissue samples $NAD^+$ and NAM levels were determined as described in (Sauve et al., 2005). In brief, to a weighed aliquot of frozen pulverized tissue we added as standards, $^{18}O\text{-}NAD^+$ (typically 2.00 nmol) and $^{18}O$-NAM (typically 2.00 nmol). 70 L of ice-cold 7% perchloric acid was then added and the sample was vortexed and sonicated three times, then centrifuged. Clear supernatant was removed and neutralized by additions of 3 M NaOH and 1 M phosphate buffer (pH=9), then centrifuged. Clear supernatant was injected onto HPLC C-18 column with 20 mM ammonium acetate eluent to separate $NAD^+$ and NAM from other cellular components, $NAD^+$ and NAM peaks (260 nm absorbance) were collected. Collections were lyophilized to dryness and subjected to MALDI-TOF analysis. For $NAD^+$ measurement, ratio of intensities for m/z=664 and 666 peaks, corresponding to $^{16}O$- and $^{18}O\text{-}NAD^+$ isotopomers, was multiplied by 2.00 nmol and then divided by tissue weight to determine NAD+ concentration in the sample. For NAM the ratio of intensities for m/z=123 and 125 peaks, corresponding to $^{16}O$- and $^{18}O$-NAM isotopomers, was multiplied by 2.00 nmol and then divided by tissue weight to determine NAM concentration in the sample. Corrections were applied for isotopic abundance. Other NAD metabolites were determined as previously described (Yang and Sauve, Synthesis of nictotinamide riboside and derivatives: effective agents for increasing nictinomide adenine dinucleotide concentrations in mammalian cells. J Med Chem 50, 6458-6461 (2006)).

Oxygen Consumption in Cultured Cells. Cellular $O_2$ consumption was measured using a Seahorse bioscience XF24 analyzer with thirty biological replicates per condition, in 24 well plates at 37° C., exactly as described (Canto et al., 2009). C2C12 were infected with an adenovirus encoding for FLAG-HA-PGC-1 and either scramble or SIRT1 shRNAs 48 h previous to $O_2$ consumption measurements. Then myotubes were treated with 1 μM PJ34 for 48 h. In order to measure the contribution of fatty acid oxidation to global $O_2$ consumption, total cellular $O_2$ consumption was measured for 6 successive 2 min measurements at 5 min intervals. Then, 50 μl of etomoxir (1 M; Calbiochem, San Diego, Calif., USA) were added and, after 15 mM, 6 successive 2 min measurements were performed at 5 min intervals. The remaining $O_2$ consumption was attributed to non-lipid substrates, while the difference with the initial $O_2$ consumption values was considered due to fatty acid oxidation.

Intraperitoneal Pyruvate Tolerance Test (ipPTT) Intraperitoneal pyruvate tolerance test was performed as described (Yao et al., 2006). Increase in blood glucose was expressed as percentage of baseline glucose level.

Sequence Alignment Sequences of SIRT1 promoter was acquired for the indicated vertebrate species from Pubmed. The initial 300 bp segment (−1 to −300) was aligned using the ClustalW algorithm (at the World Wide Web (www) ebi.ac.uk/Tools/msa/clustalw2/) and the sequences homologous to the murine −1--204 (corresponding to the two shortest SIRT1 promoter construct) were displayed.

Cold Exposure Cold exposure was performed as described (Lagouge et al., 2006).

Endurance Test Endurance exercise tests were performed as described in Lagouge et al., 2006 on C57Bl/6J mice fed with HFD or HFD-NR for 12 weeks. Chow fed PARP-2 mice were subjected to a resistance running test, using a variable speed belt treadmill enclosed in a plexi glass chamber with a stimulus device consisting of a shock grid attached to the rear of the belt (Columbus). Animals were acclimatized to the chamber for 5 days preceding the running test. For the habituation, mice run at 12 m/min for 10 minutes with a 5° incline. For the actual test, we used a protocol at 5° incline where, beginning at 10 m/min, speed increased gradually by 1 m/min every 5 minutes. The distance run and the number of shocks were monitored during the test, and exhaustion was assumed when mice received more than 50 shocks in a 2.5 minutes interval. Mice were removed from the treadmill upon exhaustion. After high-fat diet, a few modifications were introduced: habituation was performed for 5 days preceding the test running at 10 m/min for 10 minutes with no inclination. For the actual test, we used a protocol with no incline where, beginning at 8 m/min, speed increased gradually by 1 m/min every 5 minutes.

Hyperinsulinemic-euglycemic clamps were performed as described (Lagouge et al., 2006).

Islet Size Determination Islet size was determined on insulin-stained slides. From each pancreas several consecutive sections (3-11) were made and all were stained for insulin. All islets on each section were photographed on a Zeiss Axioscope microscope and a Zeiss Axiocam camera with special care to avoid duplicate photographing the same islet multiple times. The area of the islets was measured using the Image J freeware that was converted into $m^2$ by determining the original size of a large islet.

Mitochondrial DNA Measurement The assay was performed as described (Lagouge et al., 2006). DNA. was extracted using the standard proteinase K digestion following phenol-chloroform extraction. Mitochondrial and genomic DNA was determined using specific primers in qPCR reactions (primers summarized in Table 2 and 5.) and was expressed as percentage of WT.

Muscle Nuclear Protein Isolation The protocol was slightly modified, as described (Edelman et al., 1965). Gastrocnemius muscle was removed from animals after 6 hours of fasting and was frozen immediately in liquid $N_2$. All manipulations were carried out on ice. Tissues were homogenized in 2 ml homogenization buffer H1 (0.32 M sucrose; 1 mM $MgCl_2$; 0.2 mM $K_2HPO_4$; 0.6 mM $KH_2PO_4$; pH 6.8) by Ultra TURAX (~1000 rpm). The homogenate was obtained in a Potter-Elvhejem tissue grinder. Next the suspension was filtered through a 70 μm then a 40 μm nylon net (BD Falcon). After each filtration homogenate volume was adjusted to 2 ml with H1 buffer. After filtration the homogenate was centrifuged at 800 g for 5 minutes and then the pellet was washed with additional 1 ml H1. The pellet was desiccated at 21° C. for 5 minutes and resuspended in N2 buffer (2.15 M sucrose; 1 mM $MgCl_2$; 3.5 mM $K_2HPO_4$; pH 6.8). Suspension was centrifuged at 16000 g for 2 hours and the pellet was suspended in lysis buffer (62.5 mM TRIS pH 6.8; 2% SDS; 10% glycerol; 1 mM PMSF; 50 mM: DTT; 1× protease inhibitor cocktail). The pellet was resuspended in 200 μl lysis buffer. The lysate was passed through a 22G needle (20×) then centrifuged at 10000 rpm for 10 min. The supernatant was used in further experiments as nuclear extract.

Determination of Protein Acetylation Status PGC-1α, FOXO1 and Ndufa9 acetylation was analyzed by immunoprecipitation of PGC-1, FOXO1 and Nduf9a from nuclear lysates of tissues with anti-PGC-1α (Millipore), anti-FOXO1 (1 mg, Cell Signaling, Danvers, Mass., USA), or Ndufa9 (Abeam) antibody followed by Western blot using an acetyl-lysine antibody (Cell Signaling) that was normalized to total PGC-1α/FOXO1/Ndufa9 (Canto et al., 2009). Tribulin acetylation was assessed by Western blotting of total protein samples by acetylated tubulin-specific antibody (Sigma) that was then normalized for total tubrilin (Santa Cruz).

GPR109A—Calcium Mobilization Assay. Ready-to-Assai™ GRP109A Nicotinic Acid Receptor Cells were used to measure calcium mobilization as specified by the manufacturer (Millipore). Calcium flux was determined using excitation at 340 and 380 nm in a fluorescence spectrophotometer (Victor X4, Perkin Elmer) in a 180 seconds time course, adding the ligand at 60 seconds. Internal validation was made using 0.1% Triton X-100 for total fluorophore release and 10 mM EGTA to chelate free calcium. Similarly, GPR109A specificity was internally validated using control cells devoid of GRP109A overexpression. Liver triglyceride measurement Liver triglycerides were measured from 20 mg of liver tissue using a variation of the Folch method, as described in Bai et al. (Bai et al., PARP-2 regulates SIRT1 expression and whole-body energy expenditure. (2011). Cell Metab 13, 450-460.

Statistics. For the statistical analysis in the animal studies, all data was verified for normal distribution. To assess significance we performed Student's t-test for independent samples. Values are expressed as mean+/−SEM unless otherwise specified. Survival analyses were performed using the Kaplan Meier method and the significance of differences between survival curves calculated using the log rank test. Differences between two groups were assessed using two-tailed t-tests. To compare the interaction between age and genotype, two-way ANOVA tests were performed. Calculation of mean lifespan and SEM were calculated using the R software. Analysis of variance, assessed by Bonferroni's multiple comparison test, was used When comparing more than two groups. The statistical software used was GraphPad Prism 5 (GraphPad Software, Inc.) and all p-values <0.05 were considered significant.

*C. elegans* Strains *C. elegans* strains were cultured at 20° C. on nematode growth media agar plates seeded with *E. coli* strain OP50 unless stated otherwise. Strains used were wild-type Bristol N2, RB1042 pme-1 (ok988) I, CF1038 daf-16(mu86) I, VC199 sir-2.1(ok434) IV, KN259 (huIs33 [sod-3::GFP+pRE4(rol-6(su1006))] and SJ4103 (zcIs14 [myo-3::GFP(mit)]). Strains were provided by the *Caenorhabditis* Genetics Center (University of Minnesota).

Worm Lifespan Analysis Lifespan tests were performed as described in Mouchiroud et al (L. Mouchiroud et al., Pyruvate imbalance mediates metabolic reprogramming and mimics lifespan extension by dietary restriction in *Caenorhabditis elegans*. Aging Cell 10, 39 (2011)). Briefly, 60-100 animals were used per conditions and scored every other day. All lifespan experiments were performed at 20° C. Animals that crawled off the plate or had an <<exploded vulva>> phenotype were censored. Treatments with PARP inhibitors—AZD2281 (also known as KU59436, olaparib), and ABT888 (also known as veliparib)— or $NAD^+$ precursors—nicotinamide riboside (NR) and nicotinamide (NAM)—were added at the indicated concentration just before pouring the plates. Animals were exposed to compounds during the full life from eggs until death. To ensure a permanent exposure to the compound, plates were changed twice a week. All the compounds used in this study were dissolved in a water stock solution.

Fluorescence Analysis Quantification of GFP expression and endogenous gut fluorescence were carried out according to the protocol as described in Yamamoto et al. (Yamamoto et al., NCoR1 is a conserved physiological modulator of muscle mass and oxidative function. Cell 147, 827 (2011)). Briefly, GFP was monitored in day 1 or day 3 adults. Fluorimetric assays were performed using a Victor X4 multilabel plate reader (Perkin-Elmer Life Science). Eighty worms were picked at random (20 worms per well of a black-walled 96-well plate) and each well was read four times and averaged. Each experiment was repeated at least three times. Endogenous gut fluorescence was monitored at day 1, day 4 and day 8 by following the same protocol as described before.

Confocal Microscopy and Image Processing Worms were immobilized with 6 mM solution of tetramisole hydrochloride (Sigma, Buchs, Switzerland) in M9 and mounted on 6% agarose pads on glass slides. Images of worms were acquired using Zeiss LSM 700 Upright confocal microscope (Carl Zeiss AG, Oberkochen, Germany) under non-saturating exposure conditions. All the snapshots were taken from the same part of *C. elegans*: muscles from the upper part of the worm, excluding the regions of oesophagus and vulva. For each condition multiple worms were observed and imaged. Image processing was performed with the Fiji software. One of the critical issues during the imaging process was the position of the worm, as it influences the level of background. For the uniformity of the represented images, contrast and brightness were adjusted in order, to eliminate the undesirable background signal. Neither of these manipulations was affecting the mitochondrial shape. Tracing of the mitochondrial network contour was done by the use of Gaussian blur filter followed by the application of Laplacian operator.

MitoSox Staining MitoSox staining was performed as previously described with slight modification (W. Yang, S. Hekimi, A mitochondrial superoxide signal triggers increased longevity in *Caenorhabditis elegans*. PLoS Biology 8, e1000556 (2010)). Briefly, a population of 100 worms was recovered in 1 ml of M9 buffer, washed three times to remove residual bacteria, and resuspended in 200 μl of 1:200 MitoSox stock solution (initial stock solution was dissolved at 1 mM in DMSO). After 20 minutes of treatment, worms were washed five times in 1 ml of M9 buffer to eliminate the MitoSox reagent, and then transferred in a black-walled 96-well plate for reading. Fluorescence produced by the Mitosox reaction was measured as described before.

Worm Respiration Assays Oxygen consumption was measured using the Seahorse XF24 equipment (Seahorse Bioscience Inc., North Billerica, Mass.) as described in Yamamoto et al. Typically, 200 animals per conditions were recovered from NGM plates with M9 medium, washed three times in 2 mLM9 to eliminate residual bacteria, and resuspended in 500 μL M9 medium. Worms were transferred in 24-well standard Seahorse plates (#100777-004) (50 worms per well) and oxygen consumption was measured 6 times. Respiration rates were normalized to the number of worms in each individual well. NAD measurement by HPLC For NAD+ quantification, approximately 1000 worms were collected in M9 buffer, washed five times to remove residual bacteria and flash-frozen in liquid nitrogen and stored at −80° C. until analysis. Extraction was started by adding 250 μl of 1.6M perchloric acid on frozen samples, followed by extensive homogenization in a Qiagen tissuelyser, and centrifugation at 20.000 g for 15 min. The supernatant was recovered and neutralized with a 3M potassium carbonate solution. After centrifugation, 100 μl of supernatant was filtered and used for NAD measurement using an HPLC system (Agilent) with a Supelco LC-18-T column (Sigma), as described in Yoshino et al. (Yoshino, K. F. Mills, M. J. Yoon, S. Imai, Nicotinamide Mononucleotide, a Key NAD (+) Intermediate, Treats the Pathophysiology of Diet- and Age-Induced Diabetes in Mice. Cell Metab 14, 528 (2011)).

Figure 8A:
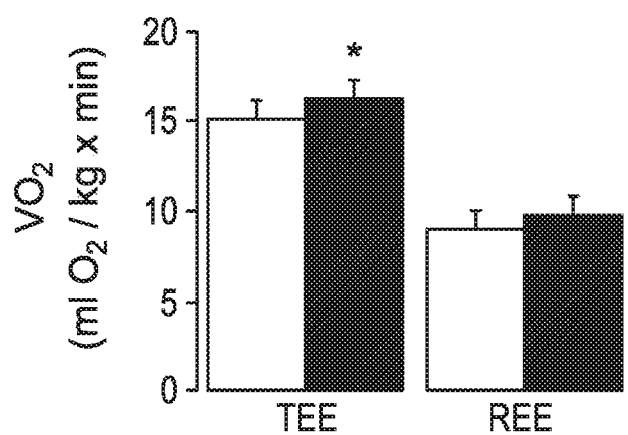
FIGS. 8A-8B. Increased spontaneous locomotor activity and energy expenditure in the PARP-1$^{-/-}$ mice during night.
Figure 8B:
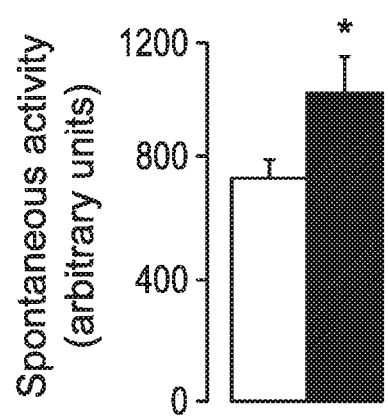

Example 2 PARP-1$^{-/-}$ Mice are Leaner and Display Increased Energy Expenditure A striking initial observation was that PARP-1$^{-/-}$ mice on chow weighed less (FIG. 1A) and accumulated less fat than wild-type (WT, PARP-1$^{+/+}$) littermates upon aging (FIG. 1B). This happened despite the fact that the PARP-1$^{-/-}$ mice consumed significantly more food (FIG. 1C). The effects of PARP-1 deletion on body mass and food intake were observed in both males and females (data not shown). During indirect calorimetry, PARP-1$^{-/-}$ mice also consumed more O2 (FIG. 1D), suggesting that their decreased body weight might be a consequence of increased energy expenditure (EE). Interestingly, resting energy expenditure (REE) was not different (FIGS. 8A-8B), suggesting that the increase could be attributed to changes at night, when the mice are active. In line with this, spontaneous locomotor activity was significantly increased at night in PARP-1$^{-/-}$ mice (FIG. 8B). Consistently, the respiratory quotient was also higher in PARP-1$^{-/-}$ mice during the dark phase (FIG. 1E), suggesting increased glucose oxidation rates during the feeding period. PARP-1$^{-/-}$ mice could also better maintain their body temperature upon cold exposure (FIG. 1F), indicating improved adaptive thermogenesis.

From a metabolic perspective, PARP-1$^{-/-}$ mice were more glucose tolerant (FIG. 1G) and had a tendency towards lower fasting glucose levels (4.30±0.17 mM in PARP-1$^{+/+}$ mice vs. 3.98±0.18 mM in PARP-1$^{-/-}$ mice; p=0.058) despite having similar fasting insulin levels (data not shown). When submitted to a euglycemic-hyperinsulinemic clamp, PARP-1$^{-/-}$ mice did not present any major difference in glucose infusion rates (GIR) (FIG. 1H), or hepatic glucose production (HGP) (FIG. 1I), but, supporting their better glucose tolerance, they displayed a tendency towards higher glucose uptake in muscle (FIG. 1J). Also In line with the lower fat mass and improved glucose tolerance, serum triglyceride (1.04±0.07 mM in PARP-1$^{+/+}$ mice vs. 0.84±0.05 mM in PARP-1$^{-/-}$ mice; p=0.048) and free fatty acid levels (0.93±0.09 mEq/L in PARP-1$^{+/+}$ mice vs. 0.72+ 0.03 mEq/L in PARP-1$^{-/-}$ mice; p=0.040) were reduced in PARP-1$^{-/-}$ mice. Overall, these results indicate that PARP-1$^{-/-}$ mice, even on chow diet, have higher energy expenditure than WT mice, resulting in a leaner phenotype and better thermogenic and metabolic profile.

Figure 2B:
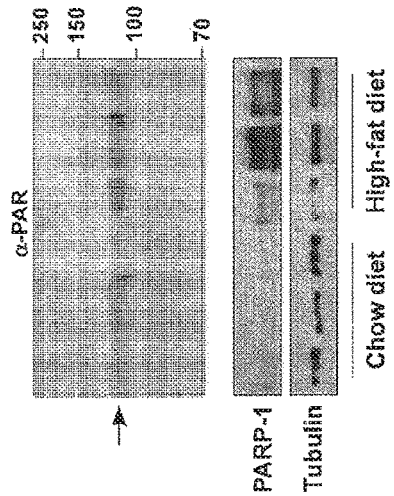

Example 3 PARP-1 Protein Levels and Activity are Regulated by Metabolic Challenges The striking impact of PARP-1 deletion on metabolism made us wonder whether PARP activity would be dynamically regulated in normal mice upon physiological changes in nutrient availability. To test this hypothesis we analyzed whether nutrient scarcity (fasting) or overload (high-fat diet) would have an effect on PARP-1 activity. A 24-hr fast promoted a significant reduction in PARP activity, as manifested by the lower PARP-1 autoPARylation levels, which reflect global PARylation activity (Adamietz, 1987) (FIG. 2A). This change happened in the absence of changes in total PARP-1 levels, suggesting a lower activity of the enzyme (FIG. 2A). In contrast, nutrient overload induced by high-fat feeding promoted a robust increase in PARP-1 protein levels and PARP activity (FIG. 2B). Together, these data indicate that PARP-1 levels and activity are positively regulated by nutrient availability.

Example 4 PARP-1$^{-/-}$ Mice are Resistant to HFD-Induced Diabesity

Figure 2C:
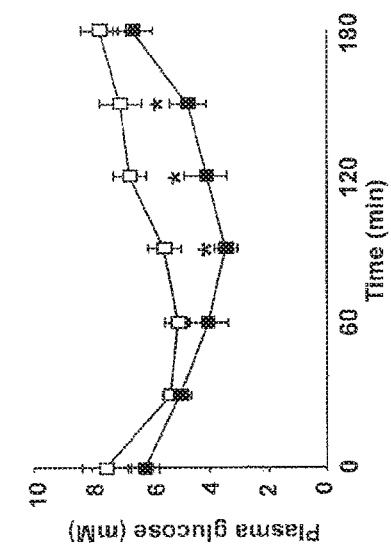
Figure 2D:
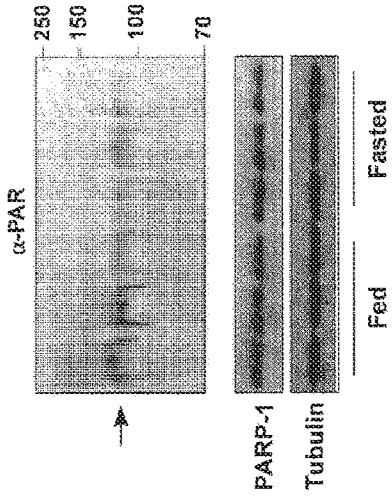
Figure 2E:
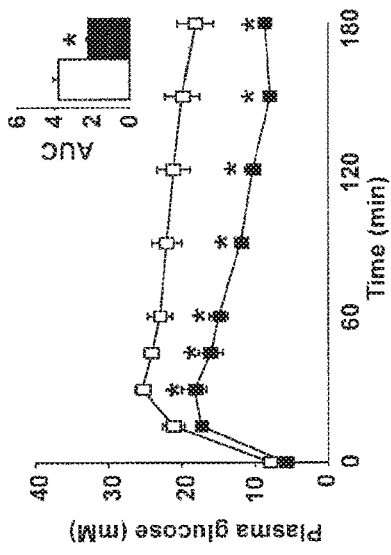
Figure 2F:
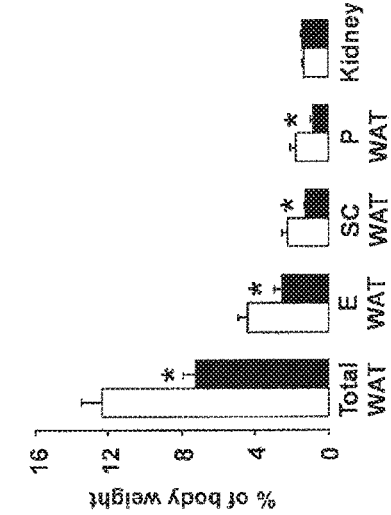

Given the above data, indicating that nutrient availability dynamically regulates PARP activity, and the lean phenotype promoted by PARP-1 deletion, it was speculated that PARP-1 could be involved in the development of high-fat diet-induced metabolic disease. To test this hypothesis, we fed PARP-1$^{+/+}$ and PARP-1$^{-/-}$ mice with a high-fat diet for two months. As expected, PARP-1$^{-/-}$ mice gained less weight after high fat feeding (FIG. 2C). The blunted body weight gain was due to a decrease in white fat mass, as manifested by the decreased weight of all the fat depots analyzed (FIG. 2D). The weight of other tissues, such as pancreas, heart or kidney, was similar between the two genotypes (FIG. 2D and data not shown). In contrast to the moderately improved glucose tolerance of PARP-1$^{-/-}$ mice on chow diet, a more pronounced reduction in the area under the curve (AUC) in the oral glucose tolerance test was now evident in PARP-1$^{-/-}$ mice upon HFD (FIG. 2E). Finally, in line with the protection against body weight gain, the PARP-1 deletion also rendered mice fed with HFD more insulin sensitive (FIG. 2F). As in chow diet, serum insulin levels were not different between the two genotypes (data not shown). Furthermore, while no differences in serum triglyceride levels could be found after 8 weeks of FWD between PARP-1$^{+/+}$ and $^{-/-}$ mice (data not shown), PARP-1$^{-/-}$ mice had lower serum free fatty acid levels (0.66±0.05 mEq/L in PARP-1$^{+/+}$ mice vs. 0.53±0.03 mEq/l in PARP-1$^{-/-}$ mice: p=0.026). As a whole, these experiments show that PARP-1$^{-/-}$ mice are protected against HFD-induced obesity and metabolic disorders.

Example 5 Higher Mitochondrial Content in Brown Adipose Tissue and Muscle from PARP-1$^{-/-}$ Mice The phenotypic impact of the PARP-1 deletion on energy expenditure and metabolic fitness suggested that the mitochondrial activity of PARP-1$^{-/-}$ mice might be enhanced in metabolic tissues, such as skeletal muscle and brown adipose tissue (BAT). The influence of PARP-1 deletion on BAT biology was evidenced by the fact that PARP-1$^{-/-}$ mice had a relatively higher amount of BAT, when expressed as percentage of total body weight, and by the more intense red morphological appearance of the BAT (FIG. 3A). Furthermore, PARP-1$^{-/-}$ BAT contained more mitochondria based on the increased mitochondrial DNA content (FIG. 3B). This higher mitochondrial DNA content in PARP-1$^{-/-}$ mice was in line with increased expression of genes involved in mitochondrial uncoupling (Uncoupling protein-1 (UCP1) and UCP3), fatty acid oxidation (Medium chain acylcoenzyme A dehydrogenase, (MCAD)) and respiration (Ndufa2, Ndufb2, Ndufb5, Cytochrome c (cyt c), COX17) (FIG. 3C). Additionally, the expression of Deiodinase-2 (Dio2) was higher in PARP-1$^{-/-}$ mice, suggesting increased thyroid. hormone activation in the BAT (FIG. 3C). Furthermore, the increased mitochondrial content in PARP-1$^{-/-}$ BAT was also evidenced by transmission electron microscopy (FIG. 3D) and by the higher protein expression of specific subunits from different respiratory complexes (FIG. 3E).\

As in BAT, the protein levels of mitochondrial respiratory complexes were also markedly induced in the gastrocnemius muscle of PARP-1$^{-/-}$ mice (FIG. 3F). In line with this, succinate dehydrogenase (SDH) staining (FIG. 3G) and expression analysis of muscle fiber isotype genes (Troponin I (Trop I), Myosin heavy chain I (MHCI); FIG. 3H) indicated an increase in the number of oxidative fibers, characterized by a higher mitochondrial content than glycolytic fibers. Similar to what was observed in BAT, the increased mitochondrial content was linked to an upregulation of the expression of genes encoding mitochondrial proteins (FIG. 3H).

Figure 9A:
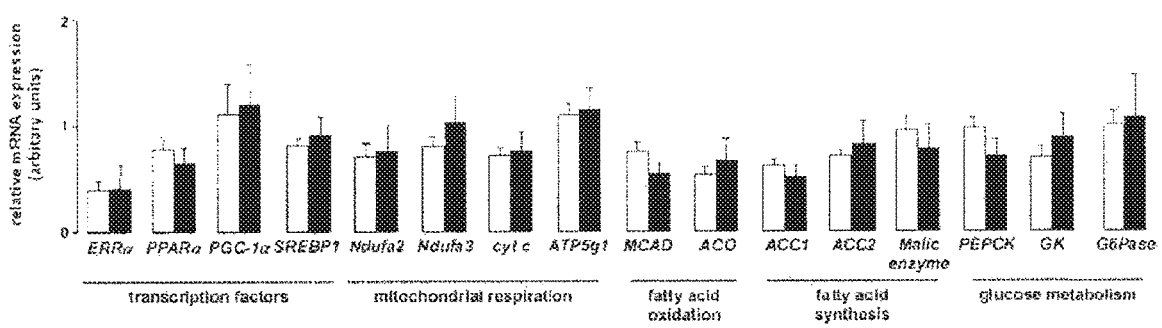
FIGS. 9A-9B. Gene expression of different metabolic genes and PARP1 in metabolic tissues.
Figure 9B:
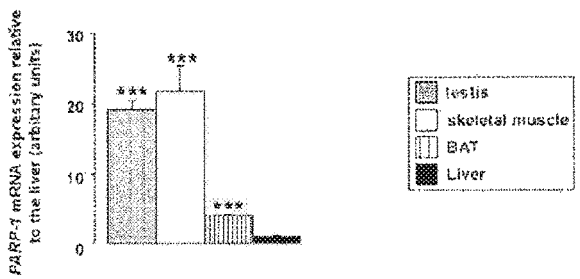
Figure 10A:
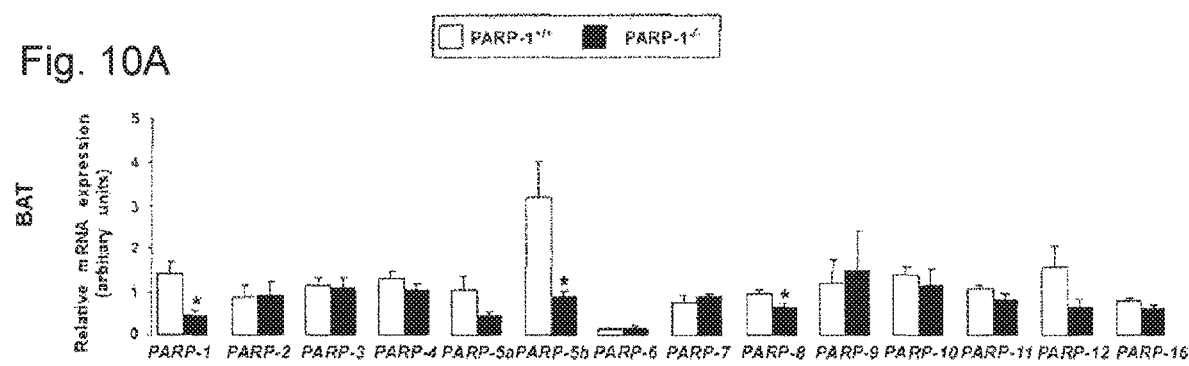
FIGS. 10A-10B. Gene expression pattern of the different members of the PARP family in the BAT and gastrocnemius muscle. RT-qPCR reactions were performed on cDNA populations from the BAT (FIG. 10A) and the gastrocnemius muscle (FIG. 10B) of PARP-1$^{+/+}$ and $^{-/-}$ male mice (n=7/5). Asterisks indicate significant difference between cohorts, where * $p<0.05$; *** $p<0.001$.
Figure 10B:
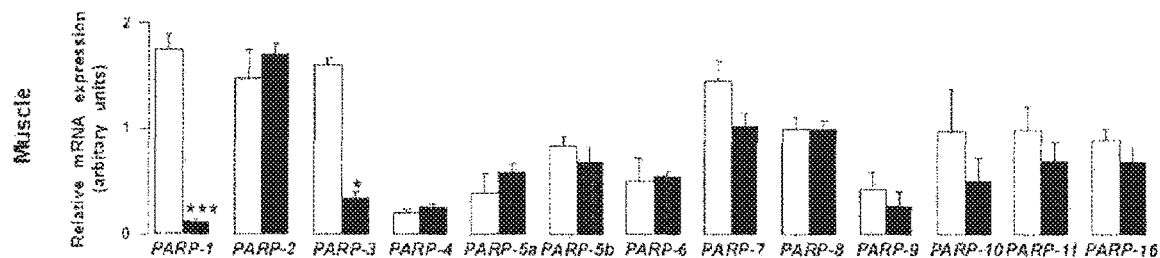

Another crucial tissue for whole body metabolism is the liver and we investigated the expression of a large set of genes encoding for transcription factors (Estrogen receptor related—(ERR), Peroxisome proliferator activated receptor—(PPAR α), Peroxisome-proliferator-activated receptor-gamma co-activator 1 (PGC-1α), Sterol regulatory element-binding protein (SREBP1)), proteins involved in mitochondrial respiration (Ndufa2, Ndufa3, cyt c, ATP5g1), in fatty acid oxidation (MCAD, ACO), in fatty acid synthesis (Malic enzyme, acetyl-CoA carboxylase-1 and -2 (ACC-1, -2)) and in glucose metabolism (Phosphoenol pyruvate carboxykinase (PEPCK), Glucokinase (GK), glucose-6 phosphatase (G6Pase)) (FIG. 9A). The lack of significant changes in the expression of this metabolic geneset suggested that the absence of PARP-1 has only a minor metabolic impact in the liver, potentially explained by the very low expression of PARP-1 in the liver relative to skeletal muscle or BAT (FIG. 9B).

Example 6 BAT Mice and Muscle from PARP-1$^{-/-}$ Display Higher NAD$^+$ Content and SIRT1 Activity The above results illustrate that PARP-1$^{-/-}$ mice have more mitochondria in BAT and in muscle, a tissue which was also enriched in oxidative fibers. This phenotype resembles many of the features expected from SIRT1 activation (Baur et al., 2006; Feige et al., 2008; Lagouge et al., 2006; Milne et al., 2007). PARP-1 is a major NAD$^+$-consumer in the cell (Shieh et al., 1998; Sims et al., 1981), making it tempting to speculate that in limits NAD$^+$ normal conditions, PARP-1 availability for SIRT1.

Therefore, the lack of PARP-1 activity could lead to higher NAD$^+$ levels and, consequently, activate SIRT1. PARP-1 is considered to be the enzyme that drives most of the PARP activity in the cell (Shieh et al., 1998; Sims et al., 1981). In agreement with this, the ablation of PARP-1 reduced PARylation in both BAT and muscle (FIG. 4A). The expression of the other known PARP enzymes was not induced in BAT and muscle of PARP-1$^{-/-}$ mice (FIGS. 3A-B), explaining the lack of compensation on global PARylation. Importantly, terminal dUTP nick-end labeling (TUNEL) assays revealed that the number of DNA. strand breaks was not increased in PARP-1$^{-/-}$ tissues (data not shown), confirming previous observations indicating that PARP-1 deletion by itself does not lead to the accumulation of DNA damage (Allinson et al., 2003; Fong et al., 2009). Consequent to the attenuated NAD$^+$-consuming PARylation activity, a robust increase in NAD+ content was observed in the BAT and muscle of PARP-1$^{-/-}$ mice (FIG. 4B). Interestingly, the levels of nicotinamide (NAM), a NAD$^+$-derived metabolite that inhibits sirtuin activity (Bitterman et al., 2002), were not altered (FIG. 4C), indicating that the effect is specific for NAD+. We next tested the increase in NAD+ whether levels affected the activity of SIRT1.

Indicative of SIRT1 activation and supporting the increase in mitochondrial content, PGC-1 acetylation levels in BAT (FIG. 4D) and skeletal muscle (FIG. 4E) of PARP-1$^{-/-}$ mice were significantly reduced by ~40% and ~90%, respectively, compared to PARP-1+/+ mice. The deacetylation of another SIRT1 target, forkhead box O1 (FOXO1), was also significantly reduced by ~60% in BAT (FIG. 4D) and ~40% in muscle (FIG. 4E), further supporting that the loss of PARP-1 activity leads to generalized SIRT1 activation. Remarkably, SIRT1 protein levels were robustly increased in muscle and BAT from PARP-1$^{-/-}$ mice (FIGS. 4D and 4E) contributing to elevated SIRT1 activity. While not significantly different in BAT (FIG. 4D), PGC-1 protein levels were also higher in the muscles from PARP-1$^{-/-}$ mice (FIG. 4E).

It is important to note that altered NAD$^+$ levels could potentially impact on the activity of not just SIRT1, but also other sirtuins. Hence, we explored the activity of the closest SIRT1 homologs that are also expressed in different cellular compartments: SIRT2 (North et al., 2003) and SIRT3 (Schroer et al., 2002), which act as cytoplasmatic and mitochondrial sirtuins, respectively. The acetylation level of tubulin, an established SIRT2 target (North et al., 2003), was not altered in the gastrocnemius muscle of PARP-1−/− mice (FIG. 4F). Likewise, the acetylation levels of Complex I, a target for SIRT3 (Ahn et al., 2008) even showed a slight, but not significant, tendency to increase on the PARP-1$^{-/-}$ muscles (FIG. 4G). These observations indicate that not all sirtuins increase their activity in response to the changes in NAD$^+$ levels induced by PARP-1 ablation.

Example 7 Knocking-Down PARP-1 in Cultured Cells Enhances Oxidative Metabolism

Given the effects of the somatic ablation of PARP-1 on SIRT1 activity and mitochondrial content in transgenic mice, we next evaluated Whether reducing PARP-1 activity in an acute fashion could constitute a useful mechanism to increase cellular NAD$^+$ levels and improve energy metabolism. For this purpose, we knocked-down PARP-1. expression in HEK293T cells. With this approach, we reduced PARP-1 protein levels by ~80%, which dramatically reduced global intracellular PARP activity as manifested in the low auto-poly(ADP-ribosyDation of PARP-1 (FIG. 5A). The reduction of PARP activity in this cell model perfectly recapitulated all our in vivo findings. First of all, the reduction in PARP-1 activity increased the NAD$^+$ content (FIG. 5B) and subsequently enhanced SIRT1 function, as evidenced by the strong decrease in PGC-1 acetylation levels (FIG. 5C). Importantly, this change happened in the absence of changes in SIRT1 protein levels (FIG. 5C), indicating that the changes NAD$^+$ might act as the main drivers of SIRT1 activity. These changes in SIRT1 and PGC-1 activity culminated in robust increase in mitochondrial DNA content (FIG. 5D), mitochondrial-related gene expression (CPT-1b, MCAD, UCP3 and PPAR) (FIG. 5E), and cellular O$_2$ consumption (FIG. 5F). These observations indicate that reduction of PARP-1 levels, even in an acute fashion, activate SIRT1 and promote mitochondrial biogenesis and oxidative metabolism. Importantly, the majority of this oxidative phenotype was dependent on SIRT1 action, as evidenced by results showing that most of the metabolic effects elicited by PARP-1 depletion were lost when SIRT1 was simultaneously knocked-down (FIGS. 5D-F).

We next aimed to consolidate these observations with the use of MEF cells from PARP-1$^{+/+}$ and PARP-1$^{-/-}$ mice. In line with the data obtained from the PARP-1 knockdown experiments, MEFs from PARP-1$^{-/-}$ mice showed enhanced O$_2$ consumption (FIG. 11A), increased mitochondrial content (FIG. 11B), mitochondrial membrane potential (FIG. 11C) and higher expression of genes involved in mitochondrial function (e.g. PGC-1, NDUF5b, cyt c, COX17, UCP-2, mCPT-1, ACO) (FIG. 11D). In line with the observations made on tissues from PARP-1 null mice, PARP-1$^{-/-}$ MEFs displayed increased SIRT1 protein content (FIG. 11E). Together, the observations in two different cellular models fully support that a reduction in PARP-1 levels promotes mitochondrial gene expression and oxidative metabolism.

Example 8 Pharmacological Inhibition of PARP Activity Enhances Oxidative Metabolism Via SIRT1

To test the dynamic interplay between SIRT1 and PARP-1, we exposed C2C12 myotubes to H$_2$O$_2$ (500 μM, 6 hrs). H$_2$O$_2$ is a very well-known activator of PARP-1 (Schraufstatter et al., 1986) and, accordingly, increased protein PARylation, as manifested by the slow migration band, in the absence of changes in total PARP-1 levels (FIG. 6A). This increase in PARP-1 activity led to a marked decrease in intracellular NAD$^+$ levels (FIG. 6B). It is important to note that H$_2$O$_2$ treatment did not affect SIRT1 protein levels (FIG. 6B). However, due to the lower NAD$^+$ bioavailability, SIRT1 activity was markedly lower, as testified by the hyperacetylation of PGC-1a (FIG. 6C). We also tested whether inhibition of PARP activity, using the global PARP activity inhibitor PJ34 (Garcia et al., 2001), would prevent the decrease SIRT1 activity during H$_2$O$_2$ treatment (FIG. 6A). Confirming our hypothesis, PARP inhibition prevented the decrease in intracellular NAD$^+$ (FIG. 6B) and enhanced SIRT1 function (FIG. 6C), despite the fact that SIRT1 protein levels did not change.

While the above results clearly indicate that PARP-1 activation limits SIRT1 activity and that PARP inhibitors relieve this limitation, it is generally assumed that basal PARP activity is rather low. However, recent evidence indicates that PARP-1 activity is not necessarily linked to DNA-damage and that it even fluctuates in a circadian fashion (Asher et al., 2010). Therefore it is tempting to speculate that prolonged PARP inhibition, even in the absence of DNA damage will favor NAD$^+$, accumulation and, potentially, SIRT1 activity. In line with this hypothesis, inhibition of PARP activity with PJ34 led to a gradual increase in NAD$^+$, becoming significant 24 hrs after the initiation of the treatment (FIG. 6D). After 24 hrs, PJ34 treatment robustly decreased basal PARP activity (FIG. 6E), while PARP-1 protein and mRNA levels remained unchanged (FIG. 6E and data not shown). The increase in NAD promoted by PJ34 at 24 hrs happened in a dose dependent manner (FIG. 6F). We further confirmed the increase in NAD$^+$ content upon PARP-1 inhibition using another, structurally unrelated PARP inhibitor, TIQ-A (data not shown) (Chiarugi et al., 2003), this dose-dependent increase in NAD$^+$ importantly correlated with SIRT1. activation, as illustrated by the deacetylation of PGC-1α (FIG. 6F). It is important to note that, while compounds like resveratrol impact on SIRT1 through AMP-activated protein kinase (AMPK) (Canto et al., 2010; Urn et al., 2010), PJ34 does not alter AMPK activity as reflected by the unchanged acetyl-CoA carboxylase (ACC) phosphorylation levels (FIG. 6G). Similarly, 24 hrs treatment with PJ34 did not change SIRT1 protein levels (FIG. 6G). Together, these observations suggest that it is mainly the increase in NAD$^+$ promoted by PJ34 that is responsible for the activation of SIRT1. Consequent to PGC-1α deacetylation and activation, PJ34 treatment increased PGC-1α recruitment to target-genes, as manifested in ChIP experiments using the PDK4 promoter (FIG. 12A). This led to the induction of mitochondrial biogenesis, as manifested in the increased expression of several mitochondrial genes, including Ndufa2, Ndufa3, MCAD, PDK4 and UCP3 (FIG. 6H), and higher mitochondrial DNA content (FIG. 12B). In addition, PJ34-treated myotubes displayed enhanced oxidative metabolism, as testified by the higher mitochondrial potential (FIG. 12C) and O$_2$ consumption rates (FIG. 6 I). A closer analysis indicated that the increase in O$_2$ consumption could not be attributed solely to an increase in fatty acid oxidation, but rather to the combination of enhanced oxidation of lipid and non-lipid substrates (FIG. 12D).

Interestingly, when SIRT1 expression was knocked-down in C2C12 myotubes by the use of specific shRNAs the effects of PJ34 on PGC-1α acetylation, were blunted (FIG. 6G). The major role of SIRT1 in mediating PJ34-induced PGC-1α deacetylation was further confirmed in mice, where PJ34 was totally unable to decrease PGC-1α acetylation levels (FIG. 12E). In line with the impaired PGC-1α activation, mitochondrial gene expression and $O_2$ consumption, were also largely blunted by the SIRT1 knock-down in C2C12 myotubes (FIGS. 6H-I) and in SIRT1 MEF cells (FIGS. 12F-G), indicating that SIRT1 is an important mediator of PJ34 actions. It must be noted, however, that PJ34-treatment also has SIRT1-independent effects, as reflected by the persistent increase in UCP3 mRNA expression even. when SIRT1 expression was knocked-down (FIG. 6H). This could be explained by the fact that PJ34-induced increase in UCP3 expression is not regulated through the binding of PGC-1 to its promoter, as evidenced by the ChIP experiment (FIG. 12A). These results indicate that the acute pharmacological inhibition of PARP activity in cellular models recapitulates the phenotypic characteristics of the PARP-1$^{-/-}$ mice, and underscores that most of these effects are mediated by SIRT1. The metabolic effects of PJ34 in C2C12 cells encouraged us to test whether these effects also persisted in vivo. To explore this possibility, we injected mice with PJ34 (10 mg/kg) twice a day for 5 days. The treatment did not cause a difference in body weight or in food consumption (data not shown), but was enough to robustly decrease PARP activity in BAT and muscle (FIGS. 7A and B, respectively). Importantly, neither SIRT1 protein levels nor AMPK activity, as reflected by the phosphorylation levels of ACC, were affected by PJ34 treatment (FIGS. 7A and B). Consequent to the decrease in PARPactivity, NAD+ levels edged up in PJ34-treated animals, even though the increase was only statistically significant in muscle (FIGS. 7C-D). This increase in NAD$^+$ levels correlated with higher SIRT1. activity, as manifested by the reduced PGC-1α acetylation levels (FIGS. 7C-D). While both BAT (FIG. 7E) and muscle (FIG. 7F) displayed a tendency to a higher expression of a number of mitochondrial genes (such as Ndufa2, Ndufa5, UCP2 and UCP3), the increase was more robust in muscle than in BAT, in correlation with the higher increase in NAD$^+$. In muscle, the increase in mitochondrial gene expression induced by PJ34 was accompanied by an increase in Myoglobin mRNA levels, which facilitates oxygen delivery into muscle fibers (FIG. 7F). In BAT, and in line with the results observed in PARP-1$^{-/-}$ mice, Dio2 mRNA was significantly induced by PJ34, suggesting thyroid hormone activation (FIG. 7E). Interestingly, and despite the short duration of the treatment, PJ34 caused a tendency to improve the serum metabolite profile, as manifested by the reduction in blood glucose (9.94±0.28 mM in vehicle vs. 9.19±0.58 mM with PJ34; p=0.05), triglycerides (1.21±0.08 mM in vehicle vs. 1.11±0.04 mM with PJ34; p=0.08) and free fatty acid levels (1.59±0.06 mEq/L in vehicle vs. 1.44±0.03 mEq/L with PJ34; p=0.03). All these data indicate that PJ34 treatment also in vivo phenocopies part of the oxidative features induced by PARP-1 gene deletion.

Example 9 Role of PARP-2 as a Regulator of SIRT1 Activity

In order to examine the potential role of PARP-2 as a regulator of SIRT1 activity, we generated C2C12 myocytes stably transfected with either a scrambled or a PARP-2 shRNA. PARP-2 mRNA and protein content is reduced by 80% in myotubes from cells carrying the PARP-2 shRNA (FIG. 13A). We next evaluated whether this deficiency in PARP-2 activity affects NAD$^+$ homeostasis. While inhibition of total PARP activity with the inhibitor NAD$^+$ PJ34 leads to increased intracellular content, a reduction in PARP-2 by itself did not affect (FIGS. 19A-19D) NAD$^+$ total (FIG. 13B) or mitochondrial levels.

Figure 19A:
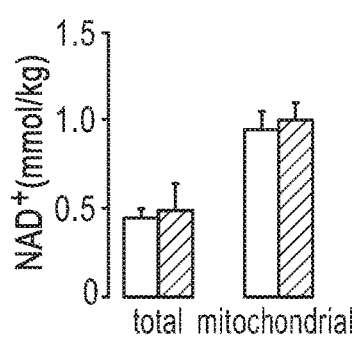
FIGS. 19A-19D. PARP-2 influences SIRT1 activity by directly regulating the SIRT1 promoter.
Figure 19B:
Figure 19C:
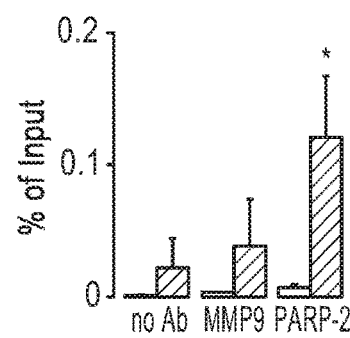
Figure 19D:
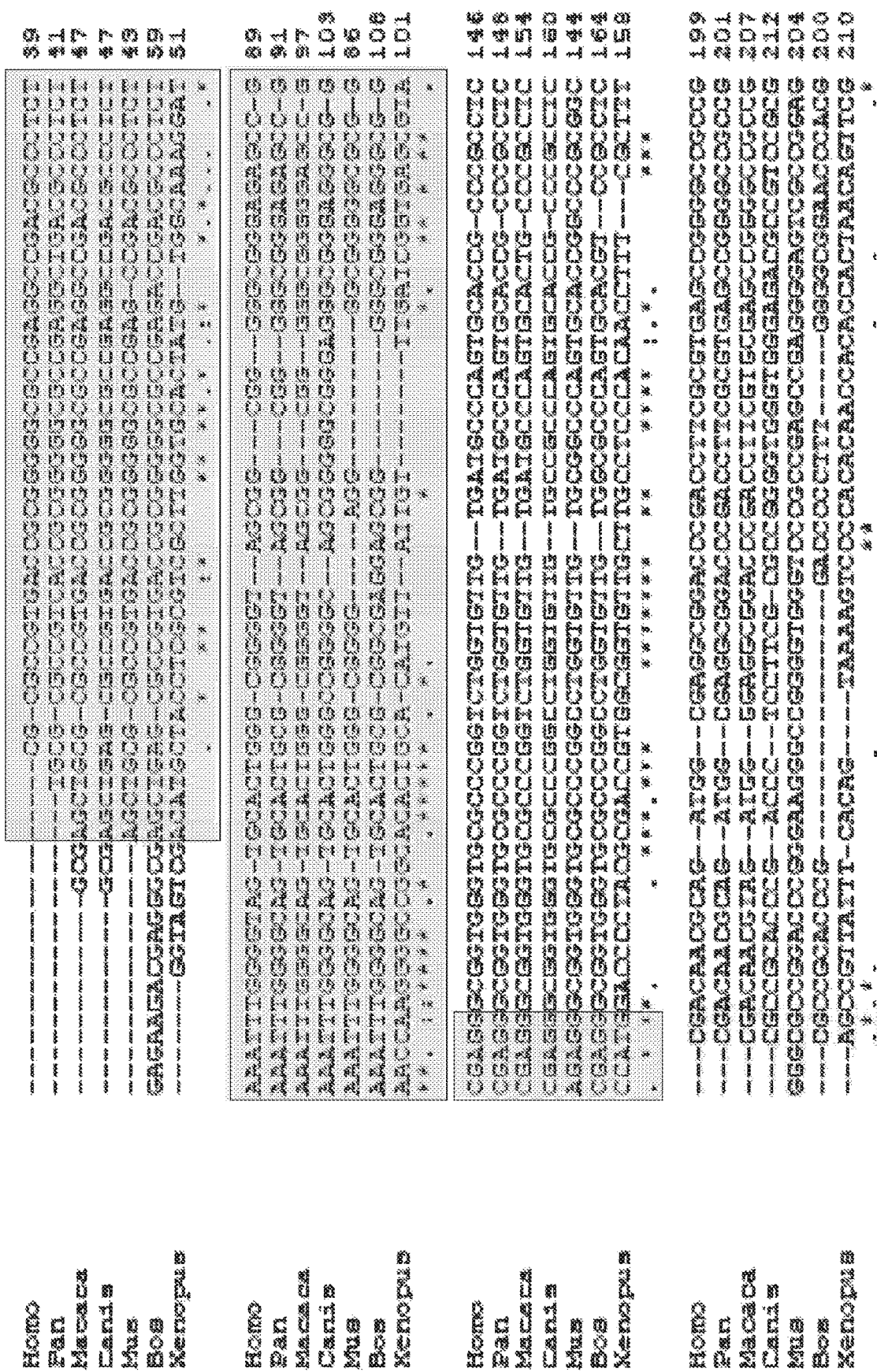

Similarly, knocking down. PARP-2 did not prevent $H_2O_2$-induced NAD$^+$ depletion, while global inhibition of PARP activity with PJ34 did (FIG. 13B). To further sustain our observations we analyzed the impact of the PARP-2 knock-down on global PARP activity by checking H2O2-induced protein PARylation, While PJ34 completely reversed $H_2O_2$-induced PARylation, the knock-down of PARP-2 could not prevent protein hyperPARylation (FIG. 13C). These results confirm that PARP-2 is a secondary PARP activity in the cell, as already demonstrated previously (Ame et al., 1999; Shieh et al., 1998). Furthermore, it also suggests that PARP-2 depletion has little impact on NAD$^+$ homeostasis, Given the absence of an impact on NAD$^+$ homeostasis, it was surprising to observe that myotubes in which PARP-2 had been knocked down, displayed higher SIRT1 activity, as demonstrated by reduced PGC-1 acetylation (FIG. 13D, top panels). We could not find any direct interaction between PARP-2 and SIRT1 (FIG. 19B), indicating that changes in SIRT1 activity are not likely to happen through direct post-translational modification by PARP-2. Rather, the increase in SIRT1 activity was linked to increased SIRT1 content (FIG. 1D, bottom panels). The increase in SIRT1 protein was concomitant to an increase in SIRT1 mRNA levels (FIG. 13E). To explore why SIRT1. mRNA levels were increased by transcriptional induction, we used a reporter construct in which serial deletions of the mouse SIRT1 promoter region controlled luciferase expression (FIG. 13F). These studies demonstrated that knocking down PARP-2 promoted a 2-fold increase in SIRT1 transcription through the very proximal promoter region (−91 bp), an effect that was maintained for the whole upstream regulatory region that was analyzed (FIG. 13F). In chromatin immunoprecipitation (ChIP) assays, PARP-2 was shown to bind directly to the proximal SIRT1 promoter (region comprised between the transcription start site and −91 bp) in C2C12 myotubes (FIG. 13G). The direct binding of PARP-2 on the SIRT1 promoter was also observed in a non-murine cell line, like 293HEK cells (FIG. 19C), as this proximal −91 by region is extremely conserved along evolution (FIG. 19D). All these results suggest that PARP-2 acts as a direct negative regulator of the SIRT1 promoter. Consequently, a reduction of PARP-2 levels induces SIRT1 transcription, leading to higher SIRT1 protein levels and activity. An expected consequence of this increase in SIRT1 activity is that a reduction in PARP-2 content should lead to higher mitochondrial gene expression, by the activation of PGC-1α through deacetylation, and to increased $O_2$ consumption. This hypothesis turned out to be correct, as cellular $O_2$ consumption was increased in PARP-2 knock-down cells (FIG. 13H), concomitant to the increase in expression of genes related to lipid and mitochondrial metabolism, such as Medium Chain Acyl coenzyme A Dehydrogenase (MCAD), NADH Dehydrogenase [Ubiquinone] 1 alpha subcomplex subunit 2 (Ndufa2) and Cytochrome C (Cyt) (FIG. 13I). Furthermore, using adenoviruses encoding for a shRNA for SIRT1, we demonstrated that the increase in SIRT1 activity contributed in a major fashion to the oxidative phenotype of PARP-2 deficient myotubes (FIGS. 13H-I).

Example 10 Knocking-Down PARP-2 in Mice Promotes an Increase in the Use of Fat

All the experiments above illustrate that reducing PARP-2 activity might be useful to increase SIRT1 activity and, consequently, potentiate oxidative metabolism. In order to gain further insight in this mechanism, we next examined the metabolic profile of the PARP-2$^{-/-}$ mice. PARP-2$^{-/-}$ mice were smaller and leaner then their PARP-$2^{+/+}$ littermates (FIG. 14A). The fact that there was no difference in food intake between the PARP-$2^{-/-}$ and PARP-$2^{+/+}$ mice (FIG. 14B) and that spontaneous locomotor activity was lower in the PARP-$2^{-/-}$ mice (FIG. 14C), suggested that the difference in weight gain was due to altered energy expenditure (EE). Indirect calorimetry, however, only indicated a slight tendency towards a higher $O_2$ consumption in chow fed PARP-$2^{-/-}$ mice compared to wild type littermates under basal conditions (FIG. 14D). Interestingly, RQ values indicate that during the dark phase PARP-$2^{-/-}$ mice use lipid substrates as energy source at proportionally higher rates than the PARP-$2^{+/+}$ littermates (FIG. 14E). Strikingly, PARP-$2^{-/-}$ mice were mildly hyperglycemic in both fed and fasted states (FIG. 2F), linked to a tendency towards lower blood insulin levels in both fed (2.52±0.24 µg/L for PARP-$2^{+/+}$ vs. 1.77±0.13 µg/L for PARP-$2^{-/-}$ mice) and fasted (0.77±0.07 µg/L for PARP-$2^{+/+}$ vs. 0.71±0.11 µg/L for PARP-$2^{-/-}$ mice) states. Overall, these results illustrate that PARP-2 deletion promotes an increase in the use of fat as main energy source, associated with a leaner phenotype.

Example 11 SIRT1 mRNA and Protein Levels were Increased in Muscles from PARP-$2^{-/-}$ Mice At the molecular level, PARP-2 deletion was not linked to higher DNA damage in either young or old mice (FIG. 20A). In line with these in vitro data, we could not detect a significant change in protein PARylation in PARP-$2^{-/-}$ mice, as determined by western blotting (FIG. 15A). In contrast to the data from C2C12 myotubes, PARP-$2^{-/-}$ muscles contained more $NAD^+$ (FIG. 15B). The data from cultured myotubes suggests that the increase in $NAD^+$ levels observed in muscle tissue might be secondary to the leaner phenotype rather than a direct consequence of the reduction in PARP-2 function per se. In line with the role of PARP-2 as a negative regulator of the SIRT1 promoter, SIRT1 mRNA and protein levels were increased in muscles from PARP-$2^{-/-}$ mice (FIG. 15C). The combination of higher $NAD^+$ and higher SIRT1 protein provides an excellent scenario to increase SIRT1 activity. Confirming this hypothesis, the acetylation levels of two different SIRT1 substrates, the peroxisome proliferator-activated receptor (PPAR) coactivator-1 (PGC-1) (FIG. 15D) and the forkhead box O1 (FOXO1) transcription factor (FIG. 15E), were markedly decreased in muscles from PARP-$2^{-/-}$ mice. Importantly, the acetylation status of SIRT2 and SIRT3 targets, such as tubulin and Ndufa9, respectively, was not affected by PARP-2 deletion, indicating that PARP-$2^{-/-}$ deletion is not affecting the activity of the closest SIRT1 homologs (FIG. 20B).

Example 12 PARP-2 Deletion Influences Mitochondrial Biogenesis

PGC-1α and FOXO1 are transcriptional activators strongly linked to the regulation of mitochondrial biogenesis and oxidative metabolism. Consequent to their activation through deacetylation, the expression of transcriptional regulators of oxidative metabolism (PGC-1α), of biomarkers of oxidative muscle fibers (troponin I (tpnI)), and of mitochondrial proteins (succinate dehydrogenase (SDH), uncoupling protein 2 (UCP2)) and lipid oxidation enzymes (malonyl-CoA decarboxylase (MCD), MCAD) were increased in gastrocnemius muscle of the PARP-$2^{-/-}$ mice (FIG. 15F). The increase in mitochondrial content was further evidenced by the higher mitochondrial DNA content (FIG. 15G) and by the more prominent mitochondria observed upon transmission electron microscopy analysis of the gastrocnemius muscle (FIG. 15H). The increased mitochondrial biogenesis clearly promoted a more oxidative phenotype of the PARP-$2^{-/-}$ muscles, as reflected by the prominent increase in SDH positive oxidative muscle fibers (FIG. 15I). As a physiological consequence of this increased oxidative muscle profile, PARP-$2^{-/-}$ mice performed much better than their PARP-$2^{+/+}$ littermates on a treadmill endurance test (FIG. 15J). As a whole, these results indicate that PARP-2 deletion promotes mitochondrial biogenesis in muscle, increasing the oxidative and endurance profile of the fibers.

We also explored whether PARP-2 deletion could also influence mitochondrial biogenesis in other highly metabolic tissues, such as in brown adipose tissue (BAT) and liver. In BAT, despite higher SIRT1 content (FIG. 3A), we were unable to detect changes in the expression of the main metabolic genes (FIG. 21B). Supporting the minor impact of PARP-2 deletion on BAT function, body temperature dropped similarly in PARP-$2^{+/+}$ and PARP-$2^{-/-}$ mice upon cold exposure (FIG. 21C). This suggested that BAT is unlikely to contribute significantly to the differences in EE observed in the PARP-$2^{-/-}$ mice. In contrast, PARP-2 deletion had strong effects on the expression of diverse regulators of mitochondrial metabolism in the liver, including PGC-1α, PGC-1, FOXO1, PPAR, estrogen-related receptor (ERR) and Cytochrome C oxidase subunit II (COXII) (FIG. 16A). Consistently, PARP-$2^{-/-}$ livers displayed a higher mitochondrial content, as evidenced by the increase in mitochondrial DNA levels (FIG. 16B) and by the appearance of more mitochondria upon electron microscopy (FIG. 16C). As in muscle, liver $NAD^+$ content was higher in PARP-$2^{-/-}$ mice (FIG. 16D), which, together with the higher amounts of SIRT1 protein, translated into increased SIRT1 activation (FIG. 16E). In line with what was observed in muscle, no changes in the activity of SIRT2 and SIRT3, the closest SIRT1 homologs, was detected (FIG. 22A). The observation that PARP-$2^{-/-}$ livers had a tendency towards a reduced triglyceride content both upon oil red O staining (FIG. 22B) and direct biochemical measurement (FIG. 16F) is consistent with the induction of oxidative metabolism. Despite the increase in phosphoenolpyruvate carboxykinase (PEPCK) expression in PARP-$2^{-/-}$ mice and the increased capacity of liver for oxidative metabolism, PARP-$2^{-/-}$ mice responded similar to PARP-$2^{+/+}$ littermates upon a pyruvate-tolerance test (FIG. 22C), probably due to the similar expression of another rate-limiting enzyme, the glucose-6-phosphatase (G6Pase) (FIG. 16A).

Figure 23A:
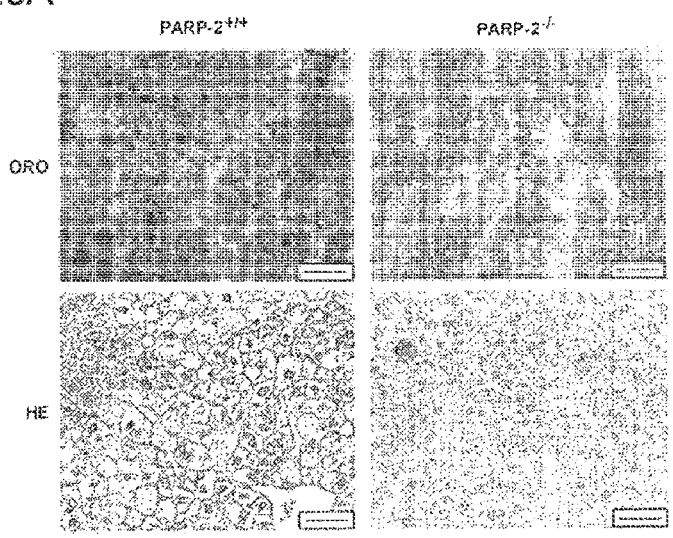
FIGS. 23A-23B. PARP-2$^{-/-}$ livers are protected from high-fat diet-induced lipid accumulation.
Figure 23B:
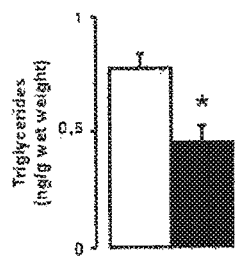

Example 13 PARP-$2^{-/-}$ Mice are Protected from Body Weight Gain and Insulin Resistance Upon High-Fat Feeding The increased mitochondrial biogenesis and oxidative phenotype observed in the skeletal muscle and liver of PARP-$2^{-/-}$ mice incited us to test how these mice would respond to high-fat diet (RFD) feeding. PARP-$2^{-/-}$ mice were protected against weight gain when fed a HFD (FIG. 17A), despite a similar food intake (FIG. 17B). This leaner phenotype was associated with a reduced body fat mass, as evidenced by Echo-MRI analysis (FIG. 17C). This reduction in fat content was clearly more pronounced (20% decrease) in the epididimal fat depots, which is equivalent to visceral fat in man, than in the subcutaneous fat pads (FIG. 17D). The weight of the PARP-$2^{-/-}$ livers was also markedly reduced (FIG. 17D), consequent to a lower triglyceride accumulation (FIGS. 23A-B). Accentuating what was observed in chow-fed mice, PARP-2$^{-/-}$ mice on high fat diet displayed now significantly higher $O_2$ consumption rates (FIG. 17E). The increase in $VO_2$ was not due to increased activity (FIG. 17F), indicating that high-fat fed PARP-2$^{-/-}$ mice have higher basal EE. As expected, the expression of the transcriptional regulators governing EE (SIRT1, PGC-1), was increased in gastrocnemius from PARP-2$^{-/-}$ mice when compare d to their PARP-2$^{+/+}$ littermates after the HFD (FIG. 17G). The expression of several genes involved in fatty acid uptake and oxidation (muscle carnitine palmitoyltansferase 1b (mCPT1b), peroxisomal acyl-coenzyme A oxidase 1 (ACOX1), MCD, MCAD), mitochondrial electron transport and oxidative phosphorylation (Ndufa2, Cyt C, COXIV) followed a similar pattern as these transcriptional regulators and were maintained at a higher level in the PARP-2$^{-/-}$ muscle (FIG. 17G). Consequent to the much leaner and oxidative phenotype, PARP-2$^{-/-}$ mice remained more insulin-sensitive than their wild-type littermates after high-fat feeding (FIG. 17H), and their endurance performance was markedly better (data not shown). These results clearly indicate that PARP-2$^{-/-}$ mice are protected from body weight gain and insulin resistance upon high-fat feeding, linked to a better muscle oxidative phenotype.

Figure 24A:
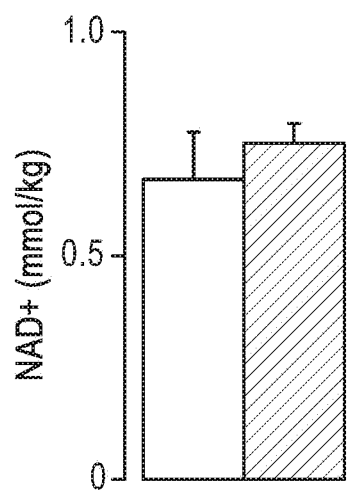
FIGS. 24A-24D. The pancreas of PARP-2$^{-/-}$, but not PARP-1$^{-/-}$ mice, is hypofunctional upon high-fat feeding.
Figure 24B:
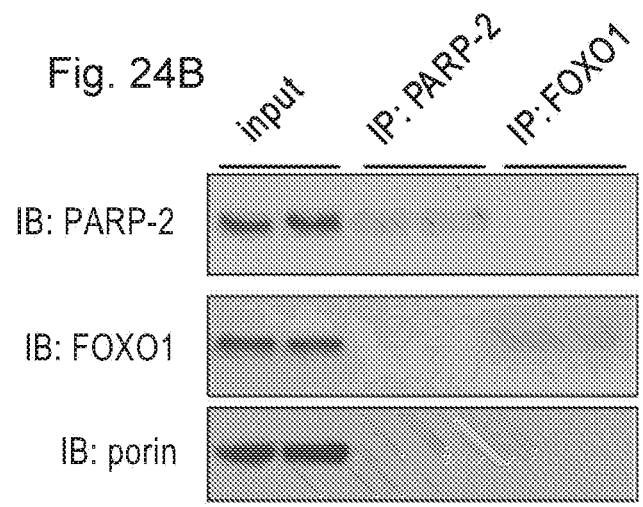
Figure 24C:
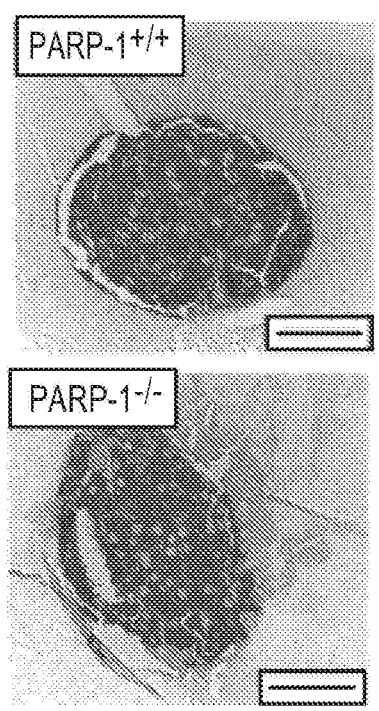
Figure 24D:
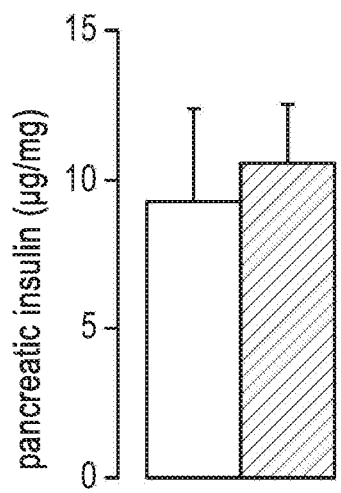
Figure 25B:
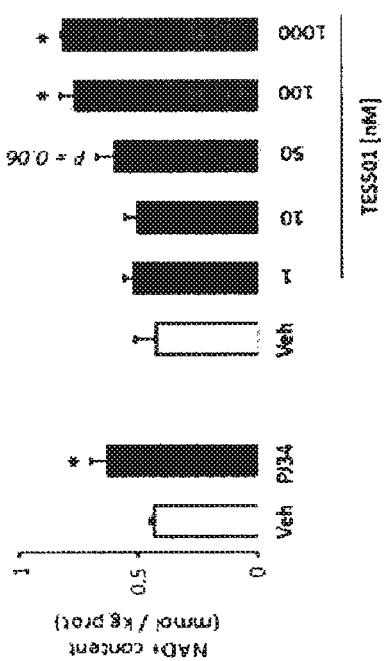
FIGS. 25A-25C. PARP inhibitors are a useful tool to increase intracellular NAD$^+$ content.
Figure 25A:
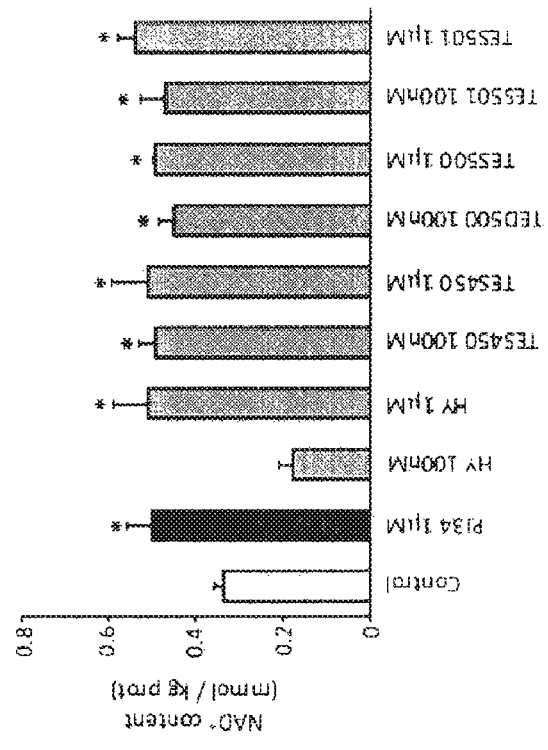
Figure 25C:
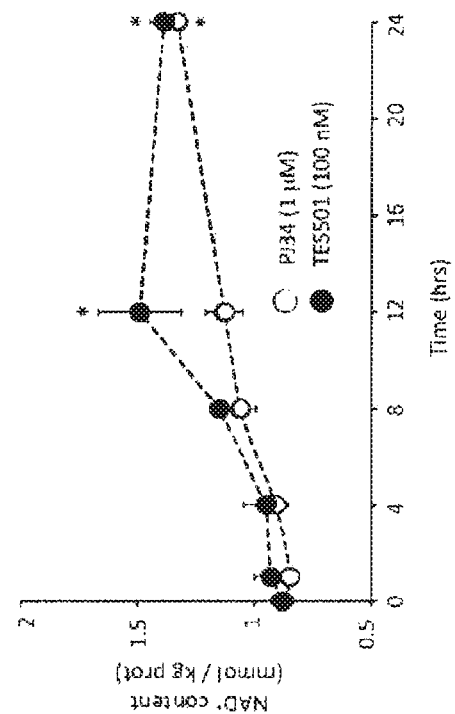

Example 14 PARP-2$^{-/-}$ Were More Glucose Intolerant Compared to Their PARP-2$^{+/+}$ Littermates after High-Fat Feeding To our surprise, despite their lower body weight and higher insulin sensitivity, PARP-2–/– mice were more glucose intolerant compared to their PARP-2$^{+/+}$ littermates after high-fat feeding (FIG. 18A), and still displayed fasting hyperglycemia (172.44±20.11 mg/dL for PARP-2$^{+/+}$ vs. 203.34±10.26 mg/dL for PARP-2$^{-/-}$). The fact that PARP-2$^{-/-}$ mice are also more insulin sensitive (FIG. 17H) suggested that this glucose intolerance could be related to defects in the insulin-release upon a glucose load. Confirming this hypothesis, the insulin peak after an intraperitoneal glucose injection in PARP-2$^{-/-}$ mice was blunted in PARP-2$^{-/-}$ mice (FIG. 18B). Furthermore, fasting blood insulin levels were lower in PARP-2$^{-/-}$ mice (0.87±0.24 µg/L for PARP-2$^{+/+}$ vs. 0.58±0.16 µg/L for PARP-2$^{-/-}$ mice). These observations led us to examine the pancreas from PARP-2$^{-/-}$ mice. High-fat diet increased the pancreatic mass in wild-type mice, but not in PARP-2 deficient mice (FIG. 18C). Histological analysis of the pancreas of PARP-2$^{+/+}$ and PARP-2$^{-/-}$ mice revealed that islet size was smaller in PARP-2$^{-/-}$ mice after high-fat feeding (FIGS. 18D and 18E). This reduction in islet size translated into a robust reduction in pancreatic insulin content (FIG. 18F). When pancreatic gene expression was analyzed in pancreas from PARP-2$^{+/+}$ and PARP-2$^{-/-}$ mice, it became evident that, in addition to an increase in some mitochondrial-related genes (mitochondrial transcription factor A (TFAm), citrate synthase (CS)), the pancreas of PARP-2$^{-/-}$ mice had severe reductions in the expression of a number of key genes for pancreatic function (such as glucokinase (GK) and Kir6.2) and proper-cell growth (pancreatic and duodenal homeobox 1 (pdx1)) (FIG. 18G). Given the reduced insulin content and pdx1 expression it was also not surprising that expression of the insulin gene (Ins) was decreased in the PARP-2$^{-/-}$ pancreas (FIG. 18G). As in other tissues, PARP-2 deletion led to higher SIRT1 protein levels in pancreas (FIG. 18H), which translated not only into higher mitochondrial protein content, as manifested by complex I (39 kDa subunit) and complex III (47 kDa subunit) levels, (FIG. 18H) but also in the constitutive deacetylation of FOXO1 (FIG. 18H). NAD$^+$ levels were similar in pancreas form PARP-2$^{+/+}$ and $^{-/-}$ mice (FIG. 24A) The deacetylation and activation of FOXO1 could underpin the pancreatic phenotype of the PARP-2 mice, as FOXO1 activity compromises pancreatic growth by acting as a negative regulator of pdx1 (Kitamura et al., 2002). Altogether, these results illustrate that high-fat diet leads to altered expression of key genes involved in pancreatic-cell proliferation and function in PARP-2 deficient mice, culminating into a reduced pancreatic islet size and insulin content, explaining the glucose intolerance despite their leaner and more insulin-sensitive phenotype.

Example 15 NR Increases Intracellular and Mitochondrial NAD$^+$ Content in Mammalian Cells and Tissues NR treatment dose-dependently increased intracellular NAD$^+$ levels in murine and human cell lines (FIG. 26A), with maximal effects at concentrations between 0.5 and 1 mM. In C2C12 myotubes, the $K_m$ for NR uptake was 172.3±17.6 µM, with a $V_{max}$ of 204.2±20.5 pmol/mg of protein/min. Unlike NA, both NR and another well-described NAD$^+$ precursor, NMN (Revollo et al., 2007), did not activate GPR109A (FIG. 26B), hence constituting valuable candidates to increase NAD$^+$ levels without activating GPR109A. Strikingly, the ability of NR to increase intracellular NAD$^+$ in mammalian cells was, at least, similar to that of these other precursors (FIG. 26C). We next evaluated the efficacy of NR, NMN and NA to increase NAD$^+$ in vivo by supplementing mouse chow with NR, NMN or NA at 400 mg/kg/day for one week. All compounds increased NAD$^+$ levels in liver, but only NR and NA significantly enhanced muscle NAD$^+$ content. (FIG. 26D). These results illustrate how NR administration is a valid tool to boost NAD$^+$ levels in mammalian cells and tissues without activating GPR109A.

Given the existence of different cellular NAD$^+$ pools and the relevance of mitochondrial NAD$^+$ content for mitochondrial and cellular function, we also analyzed whether NR treatment would affect mitochondrial NAD$^+$ levels. In contrast to what has been observed with other strategies aimed to increase NAD$^+$ bioavailability, such as PARP inhibition, we found that mitochondrial NAD$^+$ levels were enhanced in cultured cells (FIG. 26E) and mouse liver (FIG. 26F) after NR supplementation. This is, to our knowledge, the first nutritional intervention that increases mitochondrial NAD$^+$ levels.

To further solidify our data, we also wondered whether the enhanced NAD$^+$ levels upon NR treatment could derive from alterations in the NAD$^+$ salvage pathway or PARP activity However, we could not see any change in Nampt mRNA or protein content in response to NR treatment (FIG. 26G). Similarly, PARP activity and PARP-1 content were not affected by NR (FIG. 26H). Altogether, these results suggest that NR increases NAD$^+$ by direct NAD$^+$ biosynthesis rather than by indirectly affecting the major NAD$^+$ salvage (Nampt) or consumption (PARPs) pathways. Importantly, this increase in NAD$^+$ was not linked to changes in cellular glycolytic rates or ATP levels, which would be expected if NAD$^+$/NADH ratios had been altered to the point of compromising basic cellular functions.

Example 16 NR Treatment Enhances SIRT1 and SIRT3 Activity

The ability of NR to increase intracellular NAD$^+$ levels both in vivo and in vitro prompted us to test whether it could activate sirtuin enzymes. Confirming this hypothesis, NR dose-dependently decreased the acetylation of FOXO1 in a SIRT1-dependent manner (FIG. 27A). This deacetylation of FOXO1 by SIRT1 upon NR treatment resulted in its transcriptional activation, leading to higher expression of target genes, such as Gadd45, Catalase, Sod1 and Sod2. The lack of changes in SIRT1 protein levels upon NR treatment (FIG. 27A) suggests that NR increases SIRT1. activity by enhancing $NAD^+$ bioavailability. The higher SIRT1 activity in NR-treated cells was supported by mRNA expression analysis. Consistent with SIRT1 being a negative regulator of Ucp2 expression, NR decreased Ucp2 mRNA levels (FIG. 27B). Importantly, knocking down Sirt1 prevented the action of NR on Ucp2 expression (FIG. 27B). Similarly, the higher expression of a FOXO1 target gene, Sod2, upon NR treatment was also prevented by the knockdown of either Foxo1 or Sirt1 (FIG. 27B). This suggested that NR leads to a higher Sod2 expression thought the activation of SIRT1, which then deacetylates and activates FOXO1. Importantly, the knock-down of SIRT1 did not compromise the ability of NR to increase intracellular $NAD^+$ content, indicating that NR uptake and metabolism into $NAD^+$ is not affected by SIRT1 deficiency (FIG. 27C).

In line with the increase in mitochondrial $NAD^+$ levels (FIGS. 1E-F) and the potential consequent activation of mitochondrial sirtuins, NR also reduced the acetylation status of Ndufa9 and SOD2 (FIGS. 27D and 27E, respectively), both targets for SIRT3 (Ahn et al., 2008; Qiu et al., 2010). SOD2 deacetylation has been linked to a higher intrinsic activity. In line with these observations, NR treatment enhanced SOD2 activity (FIG. 27E). To ensure that NR-induced SOD2 deacetylation was consequent to SIRT3 activation, we used mouse embryonic fibroblast (MEFs) established from SIRT3 KO mice. The absence of SIRT3 was reflected by the higher basal acetylation of SOD2 (FIG. 27F). Importantly, NR was unable to decrease the acetylation status of SOD2 in $SIRT3^{-/-}$ MEFs (FIG. 27F), despite that $NAD^+$ levels increased to similar levels as in $SIRT3^{+/+}$ MEFs (FIG. 27G). These results clearly indicate that NR triggers SIRT3 activity, probably by increasing mitochondrial $NAD^+$ levels, inducing the concomitant deacetylation of its mitochondrial targets. Strikingly, not all sirtuins were affected by NR, as the acetylation of tubulin, a target of the cytoplasmic SIRT2, was not altered.

Example 17 NR Supplementation Enhances Energy Expenditure

Given the promising role of sirtuins to protect against metabolic disease, we next evaluated the effects of long-term NR administration in vivo. We fed 10-week-old male C57Bl/6J mice with either chow (CD) or high-fat diet (RFD), supplemented or not with NR at 400 mg/kg/day. While NR had no effect on the body weight (BW) on CD, HFD-induced body weight gain was significantly attenuated by NR (FIG. 28A), due to reduced fat mass (FIG. 28B). This was visibly translated into a significant lower weight of the epididymal depot in NR-fed mice. Importantly, this was not due to redistribution of lipids to other tissues, most notably to liver, which actually contained 40% less triglycerides.

The reduced body weight gain of NR-fed mice upon HFD was not due to reduced food intake, as NR-fed mice actually had a tendency to eat more, especially on HFD conditions (FIG. 28C). Similarly, NR did not affect the activity pattern of mice (FIG. 28D), indicating that the lower BW on HFD was not consequent to different physical activity. Rather, the phenotype was due to enhanced energy expenditure (EE). Mice on CD had a marked tendency to display higher $O_2$ consumption rates when fed with NR, and this tendency became clearly significant under HFD conditions (FIG. 28E). Of note, NR-fed mice became more flexible in their use of energy substrates, as reflected in the higher amplitude of the changes in RER between feeding and fasting periods in CD conditions. Altogether, these results indicate that NR lowers HFD-induced BW gain by enhancing EE.

From a metabolic perspective, NR- and vehicle-fed mice had similar fasting blood glucose levels in either CD or HFD conditions (FIG. 28F). However, fasting insulin levels were much lower in NR-supplemented mice (FIG. 28G). This lower insulin/glucose ratio is indicative of insulin sensitization after NR administration. This speculation was further supported by glucose tolerance tests. NR promoted a slight, albeit not significant, improvement in glucose tolerance (FIG. 28H) in mice fed a HFD, accompanied by a robust reduction in insulin secretion (FIG. 28I). Therefore, NR-fed mice on HFD display a better glucose disposal with lower insulin levels. In order to conclusively establish whether NR fed mice were more insulin sensitive, we performed hyperinsulinemic-euglycemic clamps on CD and CD-NR mice. We chose not to perform this analysis on the HFD groups in order to avoid the possible influence of differential BW. Mice supplemented with NR required an almost 2-fold higher glucose infusion rate to maintain euglycemia (FIG. 28J). This was consequent to a very marked increase in insulin-induced muscle glucose uptake (FIG. 28J). This observation unequivocally demonstrates that NR-fed mice are more insulin-sensitive. Furthermore, NR partially prevented the increase in total (FIG. 28K) and LDL cholesterol levels induced by HFD, even though HDL-cholesterol levels were unaffected. The amelioration of cholesterol profiles is fully in line with previous observations from the use of other $NAD^+$ precursors, such as NA.

Example 18 NR Enhances the Oxidative Performance of Skeletal Muscle and Brown Adipose Tissue NR-fed mice had a clear tendency to display a better endurance performance than vehicle fed mice. This tendency was significantly accentuated upon HFD (FIG. 29A), suggesting an enhanced muscle oxidative performance. Similarly, NR-fed mice, both on Cd and HFD, showed enhanced thermogenic capacity, as manifested in the ability to maintain body temperature during cold exposure (FIG. 29B). The latter observation hints toward an improvement in brown adipose tissue (BAT) oxidative performance. To gain further insight into the ability of BAT and muscle to enhance their oxidative performance, we performed some histological analysis. Gastrocnemius muscles from NR mice displayed a more intense SDH staining than their vehicle-fed littermates, indicating a higher oxidative profile. Electron microscopy revealed that mitochondria in BAT of NR-fed mice, despite not being significantly larger, had more abundant cristae (FIG. 29C), which has been linked to increased respiratory capacity. Altogether, the above results suggest that NR supplemented mice display a higher oxidative capacity due to enhanced mitochondrial function.

Example 19 Chronic NR Feeding Increases $NAD^+$ In Vivo in a Tissue-Specific Manner We next wondered how chronic NR feeding would affect $NAD^+$ metabolism in mice. Chronic NR supplementation increased $NAD^+$ levels in both CD and HFD (FIG. 30A)

conditions in some tissues, including liver and muscle, but not in others, such as brain or white adipose tissue (WAT). Interestingly, NAD$^+$ was also higher in the BAT of NR-fed mice, but only on HFD (FIG. 30B and. These differences could be due to the differential expression of NRKs in tissues. NRKs initiate NR metabolism into NAD$^+$. There are two mammalian NRKs: NRK1 and NRK2. While we found NRK1 expressed ubiquitously, NRK2 was mainly present in cardiac and skeletal muscle tissues, as previously described, but also detectable in BAT and liver, in line with the better ability of these tissues to respond to NR.

We also tested whether the increase in NAD$^+$ would be concomitant to changes in other NAD$^+$ metabolites. Strikingly, NADH and nicotinamide (NAM) levels were largely diminished in muscles from NR-fed mice (FIG. 30B), indicating that NR specifically increases NAD$^+$, but not necessarily other by-products of NAD$^+$ metabolism. We analyzed in vivo whether the activity of major NAD$^+$ degrading enzymes or the levels of Nampt could also contribute to the increase in NAD$^+$ after chronic NR supplementation. As previously observed in HEK293T cells (FIGS. 26G-H), PARP-1 levels and global PARylation were similar in muscle (FIG. 30C) and livers from NR- and vehicle-fed mice, indicating that the enhanced NAD$^+$ content cannot be explained by differential NAD$^+$ consumption through PARP activity. Nampt mRNA (FIG. 30D) and protein (FIG. 30C) levels were also similar in NR and vehicle fed mice, suggesting that NAD$^+$ salvage pathways do not explain the differences in NAD$^+$ levels. We furthermore could not detect differences in mRNA expression of the different NMN adenylyltransferase (NMNAT) enzymes (FIG. 30D). Altogether, these results reinforce the notion that the higher NAD$^+$ levels observed in tissues from NR-fed mice is consequent to an increase in direct NAD$^+$ synthesis from NR.

Example 20 NR Enhances Sirtuin Activity In Vivo

Figure 31A:
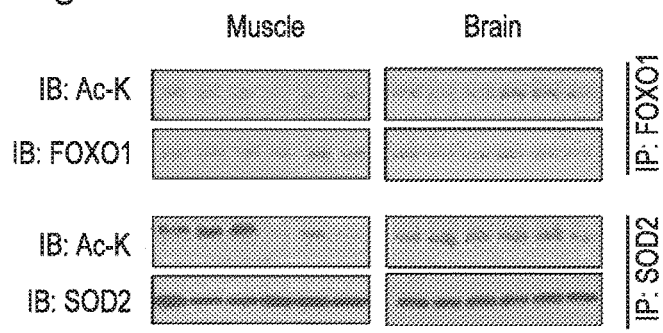
FIGS. 31A-31D. NR stimulates sirtuin activity in vivo and enhances mitochondrial gene expression. Tissues from C57Bl/6J mice were collected after 16 weeks of HFD supplemented with either water (as vehicle; white bars) or NR (400 mg/kg/day; black bars).

Higher NAD$^+$ levels were also accompanied by higher sirtuin activity in vivo. A prominent deacetylation of SIRT1 and SIRT3 targets (FOXO1 and SOD2, respectively) was observed in the skeletal muscle, liver and BAT, where NAD$^+$ content was induced by NR, but not in brain and WAT, where NAD$^+$ levels were unaffected by NR supplementation (FIG. 31A). We also evaluated PGC-1α acetylation as a second readout of SIRT1 activity. We were unable to detect PGC-1α in total lysates from WAT or brain, but in muscle, liver and BAT PGC-1α was deacetylated upon NR treatment. These observations highlight how NR can only induce sirtuin activity in tissues where NAD$^+$ accumulates. Like in cultured cells, we could not detect changes in the acetylation status of the SIRT2 target tubulin, suggesting either that increasing NAD$^+$ might not affect the activity of all sirtuins equally, that the increase is only compartment-specific or that additional regulatory elements, like class I and II HDACs, also contribute to tubulin acetylation status.

Figure 31B:
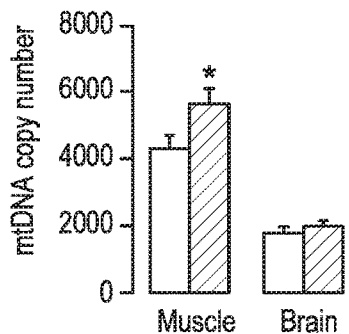
Figure 31C:
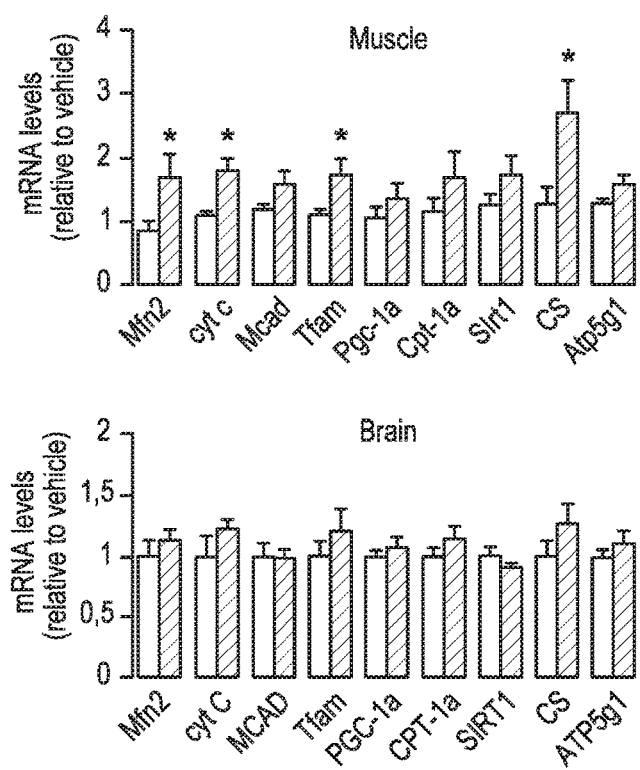
Figure 31D:
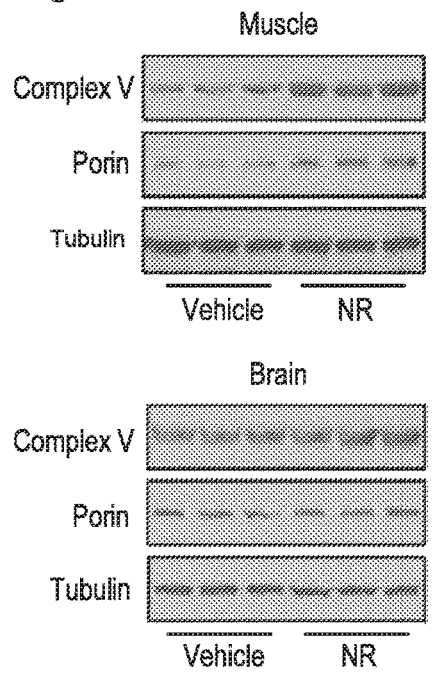
Figure 32:
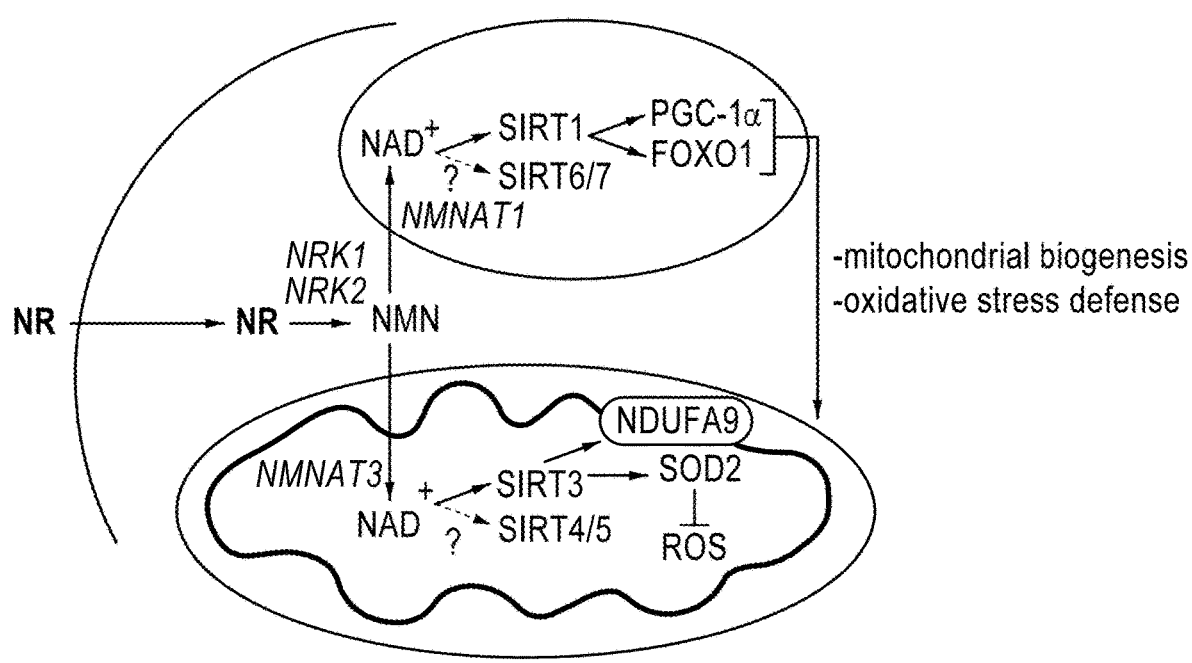
FIG. 32. Schematic representation of the different actions of NR in metabolic homeostasis. The scheme summarizes the hypothesis by which NR supplementation would increase NAD$^+$ content in key metabolic tissues, leading to SIRT1 and SIRT3 activation and the deacetylation and modulation of the activity of key metabolic regulators. This model does not rule out the participation of additional mechanisms of action for NR to achieve its beneficial effects. Abbreviations can be found in the text and enzymes are indicated in italics.

In line with the changes in acetylation levels of PGC-1α, a key transcriptional regulator of mitochondrial biogenesis, we could observe either an elevated expression or a strong tendency towards an increase (P<0.1) of nuclear genes encoding transcriptional regulators of oxidative metabolism (Sirt1, PGC-1α; mitochondrial transcription factor A (Tfam)) and mitochondrial proteins (Mitofusin 2 (MX), Cytochrome C (Cyt C), Medium Chain Acyl-coA Dehydrogenase (MCAD), Carnitine palmitoyltransferase-1b (CPT-1b), Citrate Synthase (CS) or ATP synthase lipid binding protein (ATP5g1)) in quadriceps muscles from NR-fed mice (FIG. 31B). Conversely, in brain, where NAD$^+$ and sirtuin activity levels were not affected by NR feeding, the expression of these genes was not altered (FIG. 31B). Consistently also with enhanced mitochondrial biogenesis, mitochondrial DNA content was increased in muscle, but not in brain from NR-fed mice (FIG. 31C). Finally, mitochondrial protein content also confirmed that mitochondrial function was only enhanced in tissues in which NAD$^+$ content was increased (FIG. 31D). This way, while muscle, liver and BAT showed a prominent increase in mitochondrial proteins (Complex V—ATP synthase subunit α and porin), such change was not observed in brain or WAT. Altogether, these results suggest that NR feeding increases mitochondrial biogenesis in a tissue-specific manner, consistent with the tissue-specific nature of the increases in NAD$^+$ and sirtuin activity observed in NR-fed mice. The higher number of mitochondria, together with the different morphological mitochondrial profiles found in NR-fed mice (FIG. 29C) would contribute to explain the higher oxidative profile, energy expenditure and protection against metabolic damage observed upon NR feeding.

Example 21 PARP Activity and NAD+ in Aged Mammals and Worms

Figure 33A:
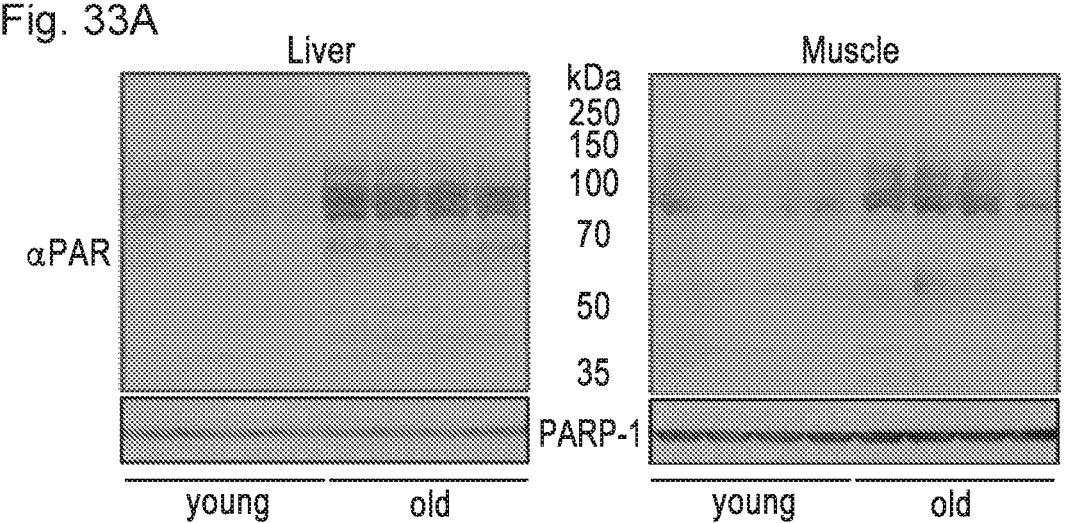
FIGS. 33A-33F. PARP activity and NAD+ in aged mammals and worms.
Figure 33B:
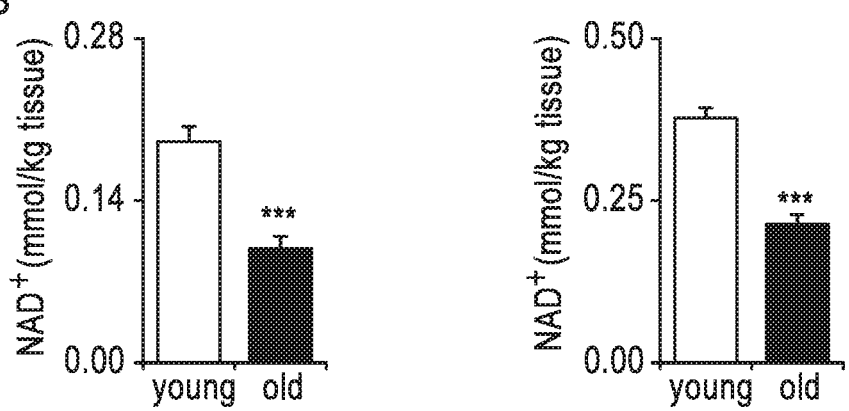
Figure 33C:
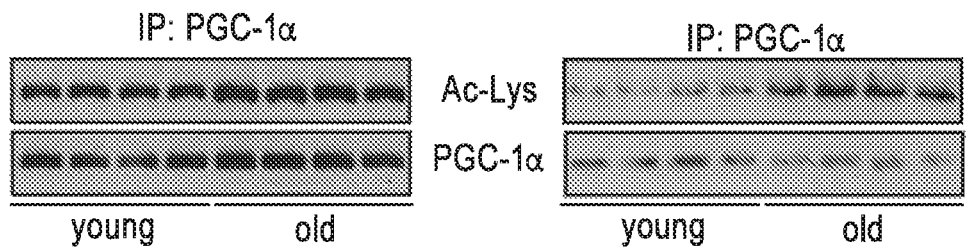
Figure 33D:
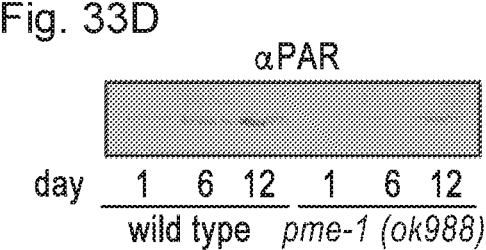
Figure 33E:
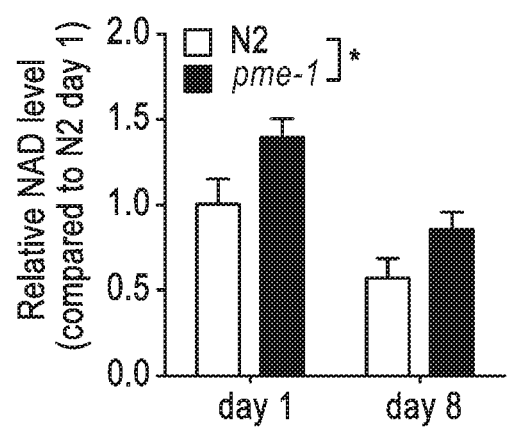
Figure 33F:
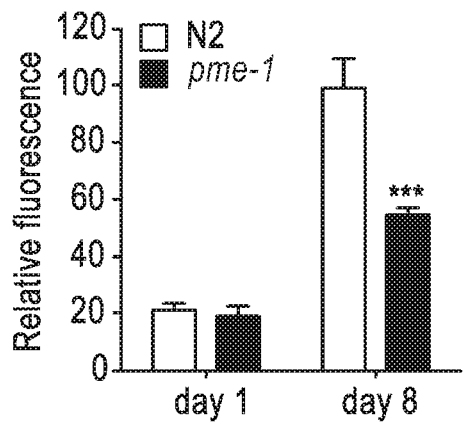

The PARP proteins, with PARP1 and PARP2 representing the main PARP activities in mammals, were classically described as DNA repair proteins, but recent studies have linked these proteins to metabolism. Furthermore, an association between PARPs and lifespan has been postulated, but a causal role remained unclear. To establish the role of PARPs in aging, we compared global PARylation in young versus old mice (24 and 103 weeks). Both in liver and muscle of aged mice, PARylation was markedly increased (FIG. 33A). In line with the hypothesis that PARP proteins are prime NAD$^+$ consumers, NAD$^+$ levels were robustly decreased in older mice (FIG. 33B). Changes in NAD+ are generally translated into altered SIRT1 activity. The lower NAD+ levels in aged mice were indeed reflected in hyperacetylation of the SIRT1 substrate PGC1, indicative of reduced SIRT1 activity (FIG. 33C). To evaluate the possible contribution of PARP activity and NAD$^+$ metabolism in the aging process, we turned to C. elegans, where it is easier to evaluate the impact of genetic or pharmacological manipulations on. The aging-associated and NAD+ lifespan PARylation changes were evolutionary conserved as PARylation was also markedly increased with age in nematodes (FIG. 33D), and NAD+ levels were lower (FIG. 33E). Changes in PARylation and NAD+ were attenuated in worms in which the PARP1 homolog—pme-1 (15)—was mutated (FIGS. 33D-E). The residual PARylation is consistent with the presence of a second PARP gene, pme-2, the worm homolog of the less active PARP2 protein. We further analyzed the natural aging process in worms by monitoring the accumulation of the aging-associated lipid peroxidation product lipofuscin, which was robustly reduced in pme-1 worms (FIG. 33 F). Together, these data suggest that disturbance of the PARP/NAD$^+$-signaling network in aging is evolutionary conserved.

Example 22 Longevity in C. Elegans with Pme-1 Mutation or PARP Inhibition

We next aimed to determine the causal role of PARPs in aging. Strikingly, pme-1 deficient worms displayed a 29% mean lifespan extension (FIG. 34A, p<0.001, see Table 8 for statistics). To inhibit PARP activity we also fed worms from eggs until death with two chemically distinct pan-PARP inhibitors, i.e. AZD2281 (KU59436, olaparib), or ABT-888 (veliparib), resulting in a 15-23% lifespan extension (FIG. 34B, p<0.001 for AZD2281, p<0.05 for ABT-888; FIGS. 37A-37B; Table 8). The lifespan of the pme-1 mutant was not further extended by AZD2281, confirming that pme-1 is the major worm PARP activity (FIG. 34C). Consistent with the hypothesis of NAD+ as a possible mediator of these effects, both deletion of pane-1 gene or pharmacological PARP inhibition significantly NAD+ increased levels (FIG. 34D). Although the role of SIRT1 or its homologs in lifespan extension under basal, unstressed, conditions is subject of intense debate, it holds a central position in healthspan regulation in the context of disease or cellular stress. Given the NAD+ dependence of SIRT1, we analyzed epistasis by treating sir-2.1 (ok434) mutant worms with AZD2281. In this context, we lost the AZD2281-induced longevity in the sir-2.1(ok434) mutant (FIG. 34E), confirming sir-2.1 dependence of the lifespan extension.

Example 23 PARP Inhibition Increases Mitochondrial Function and ROS Defense

Figure 35E:
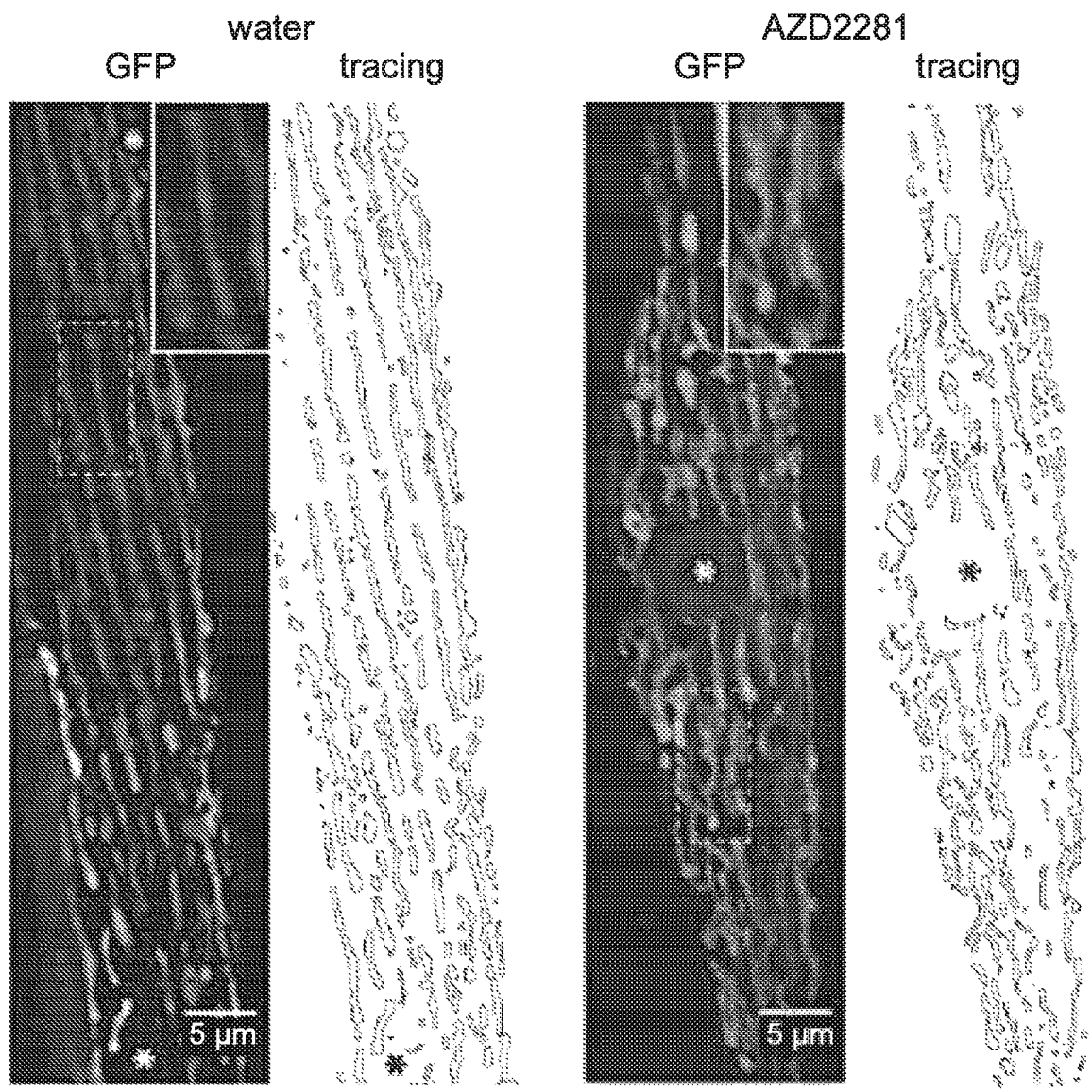

Consistent with delayed aging, and in line with the data in pme-1 mutants, AZD2281 reduced lipofuscin accumulation (FIG. 35A). As NAD+ and SIRT1 are thought to influence oxidative metabolism, we functionally characterized mitochondrial activity in AZD2281-treated worms by measuring oxygen consumption rates. At day 3 of adulthood, AZD2281 robustly increased respiration (FIG. 35B), in line with increased expression of citrate synthase (cts-1) and cytochrome c oxidase subunit 4 (cox-4) (FIG. 35C). By using confocal microscopy in the pmyo-3::mito::GFP reporter, which expresses mitochondria-targeted GFP in the muscle, we also observed a more intense fluorescence signal after AZD2281, indicating a more dense mitochondrial network (FIGS. 35D-E).

Figure 35F:
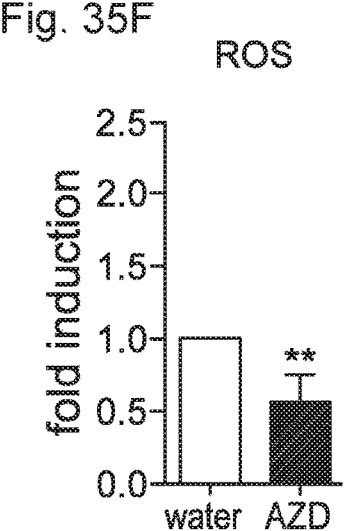
Figure 35G:
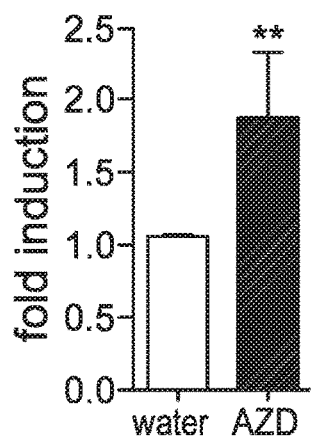
Figure 35H:
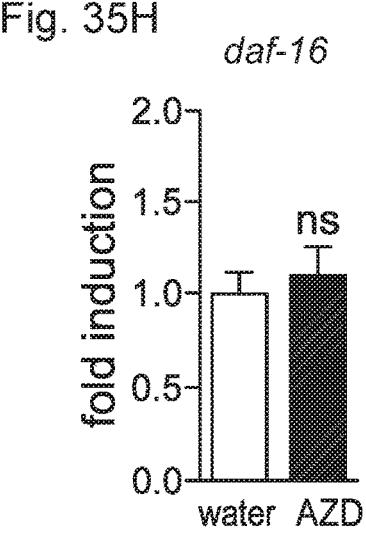
Figure 35I:
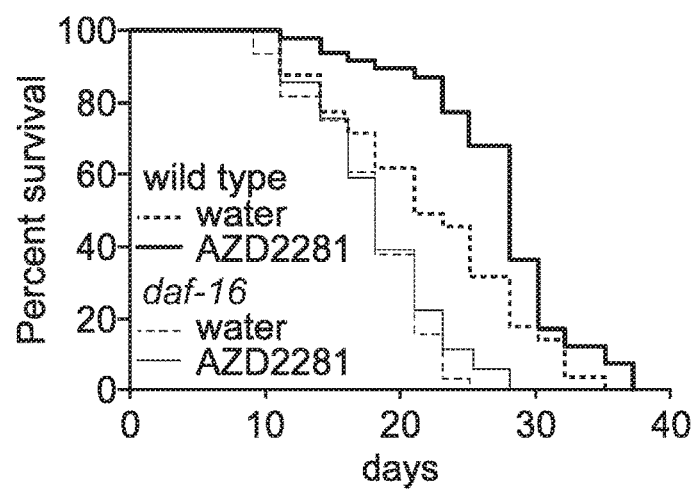

As changes in mitochondrial metabolism can cause oxidative stress, we measured reactive oxygen species (ROS) during early adulthood using the mitoSOX probe, which indicates specific mitochondrial superoxide production. At day 3, ROS production was decreased in AZD2281-treated worms, paralleled with a marked induction of the mitochondrial antioxidant gene, sod-3 (FIGS. 35F-G). The best-characterized transcriptional regulator of antioxidant defense is daf-16, the *C. elegans* FOXO3A homolog. AZD2281 failed to increase lifespan in daf-16 mutants (FIG. 35I), suggesting that the induction of antioxidant defense is key for AZD2281 to grant longevity. Of relevance, FOXO3A has been described as a deacetylation target for SIRT1 in mammals, and daf-16 was shown to interact with sir-2. AZD2281 did not change expression of daf-16 (FIG. 35H), in line with its reported regulation by subcellular distribution rather than transcription.

Figure 36A:
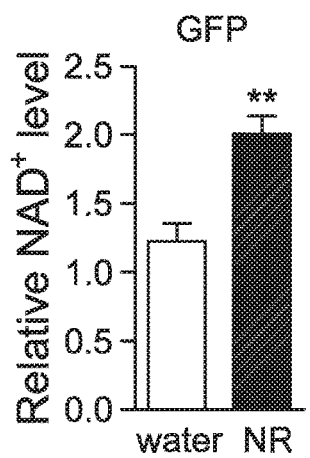
Figure 36B:
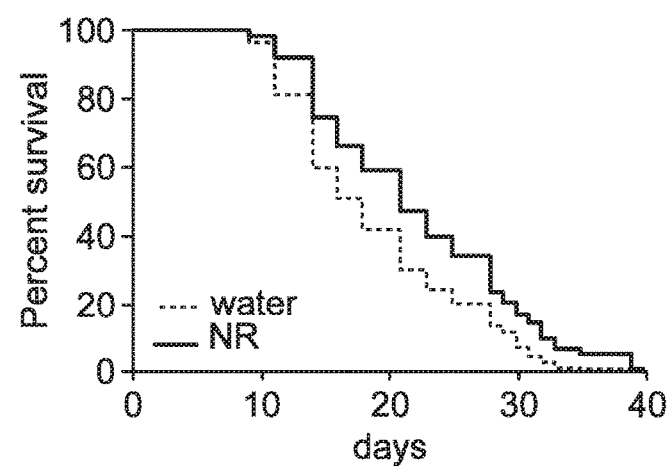
Figure 36C:
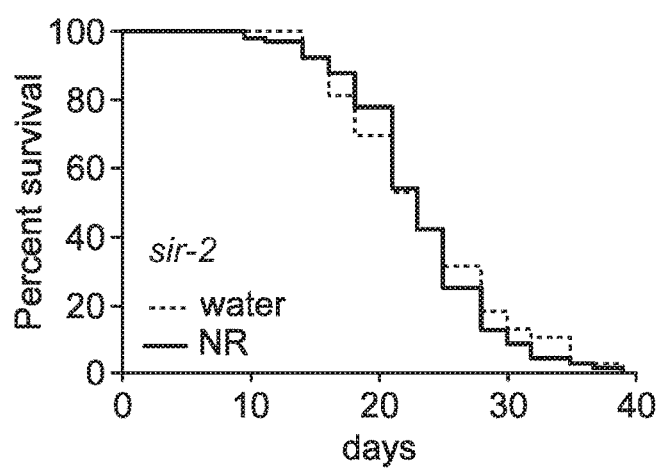
Figure 39A:
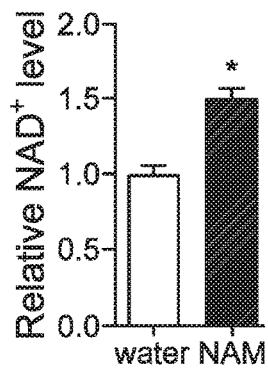
FIGS. 39A-39E. The NAD precursor NAM increases NAD+ levels, lifespan, mitochondrial function and ROS defense.
Figure 39B:
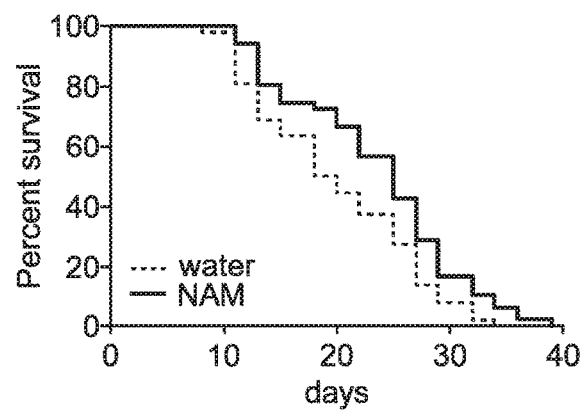

Example 24 Supplementation of *C. Elegans* with the NAD+ Precursor NR Mimics the Metabolic Lifespan Effects of PARP Mutation or Inhibition In addition to their role in NAD+ metabolism, PARP proteins could in theory, also impact longevity through. PARylation of specific proteins. To confirm our hypothesis that it is indeed the increase in NAD+ that induces longevity upon PARP inhibition, we analyzed the impact of raising NAD+ levels through providing worms with different NAD+ precursors. We focused on NAD+ the salvage pathway precursors, nicotinamide (NAM) and NAM riboside (NR). NAM is the end-product of the sirtuin and PARP reaction, whereas NR is a recently discovered vitamin—both can serve as precursors of NAD (re-)synthesis. Consistent with their function as NAD+ precursors, NAM and NR increased NAD+ levels (FIG. 36A, FIG. 39A). Strikingly, treatment of *C. elegans* with these NAD+ precursors also extended lifespan (FIG. 36B, FIGS. 38A-B, FIG. 39B, see Table 8 for statistics) in a sir-2.1-dependent fashion (FIG. 36C).

Figure 36D:
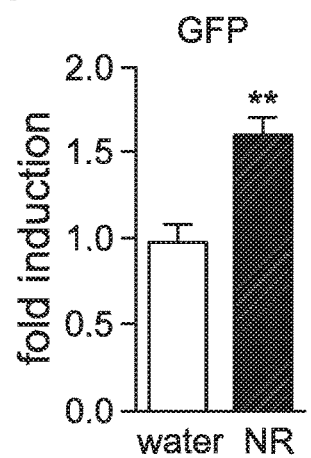
Figure 36E:
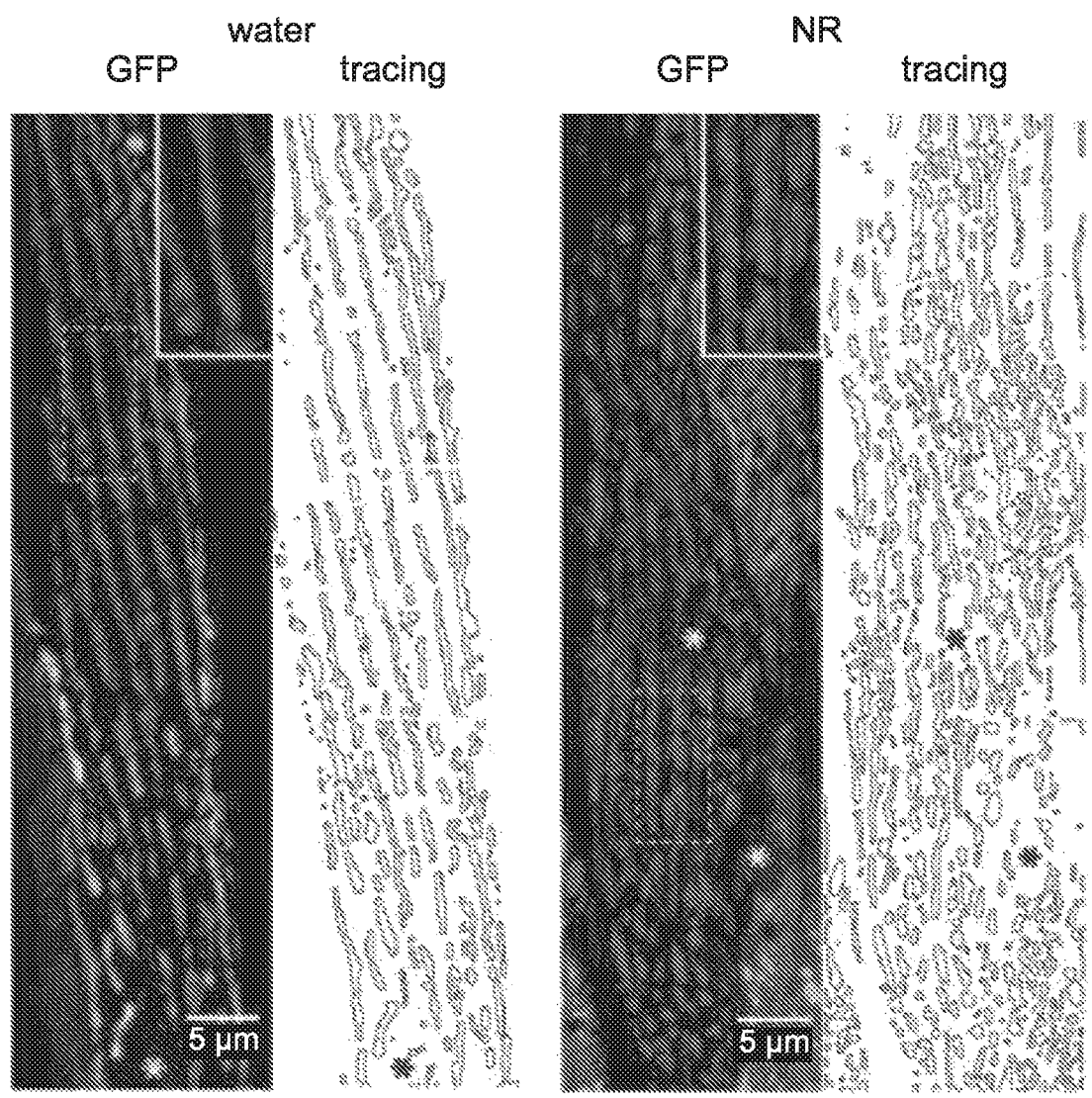
Figure 36I:
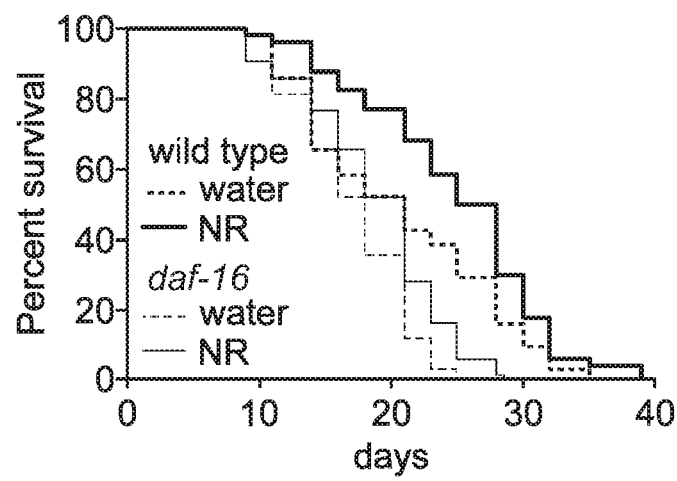
Figure 39C:
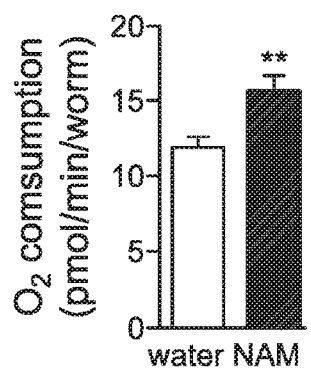
Figure 39D:
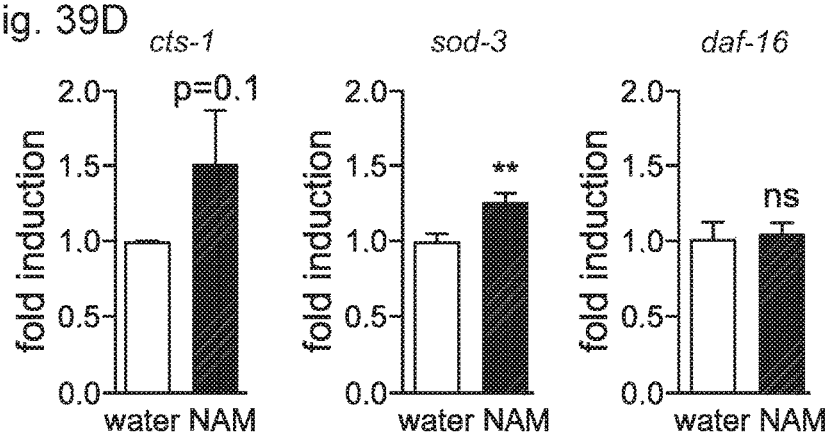
Figure 39E:
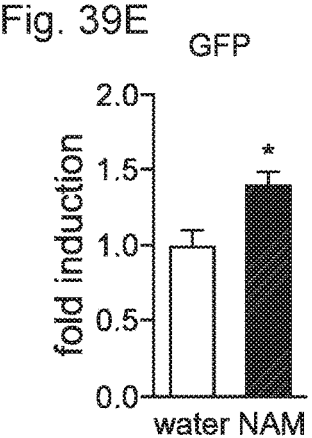

As was observed for AZD2281, NR and NAM also increase muscle mitochondrial content (FIG. 36D, FIG. 39E) and affect mitochondrial morphology (FIG. 36E). Similarly, both NAM and NR increased respiration at day 3 (FIG. 36F, FIG. 39C) with a trend for increased cts-1 expression (FIG. 36G, FIG. 3C), and significantly higher sod-3 expression, without affecting daf-16 mRNA levels (FIG. 36H, FIG. 39D), thereby mimicking the effects of PARP inhibition on lifespan and mitochondrial metabolism. Importantly, the lifespan extension of NR was also completely abolished in daf-16 mutant worms (FIG. 36I). The fact that two independent strategies to boost NAD+ levels promote a similar phenotype strengthens the hypothesis that NAD+ might be a critical metabolite influencing mitochondrial fitness and lifespan in a sir2.1-dependent way.

Figure 36J:
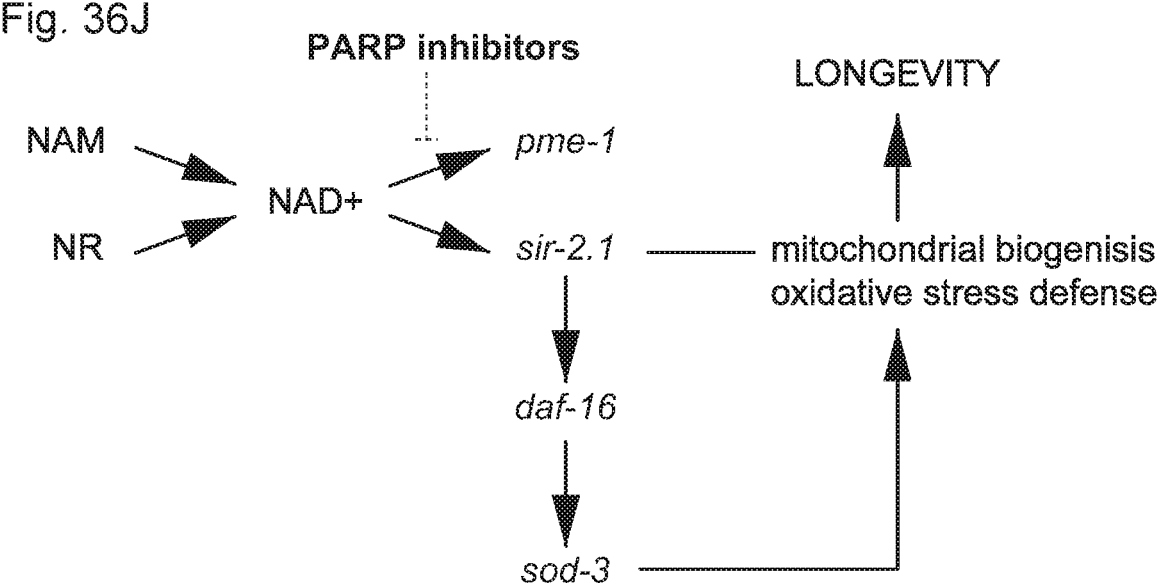
Figure 38A:
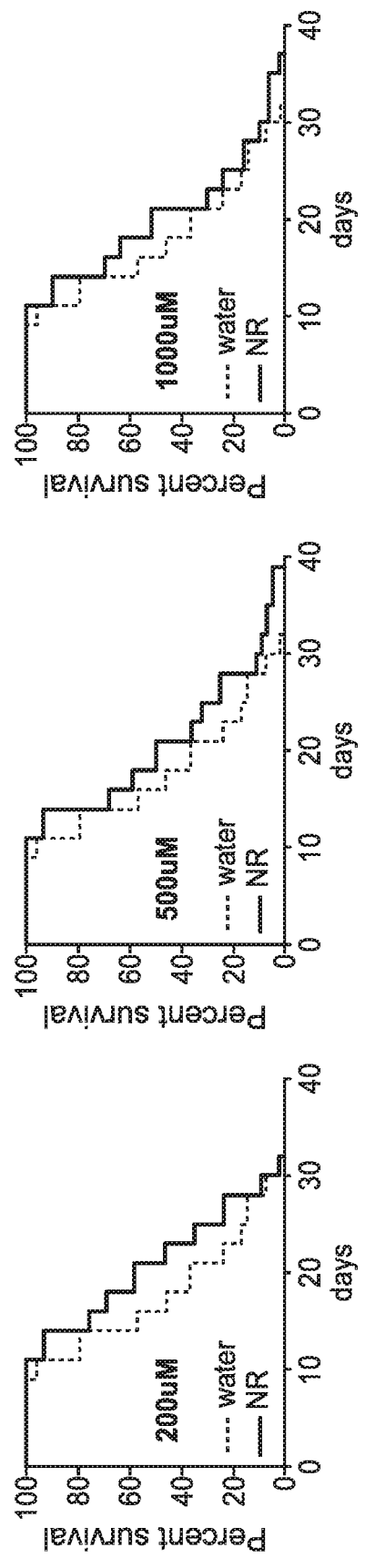
FIGS. 38A-38B. Lifespan analyses with different concentrations of NAD+ precursors.
Figure 38B:
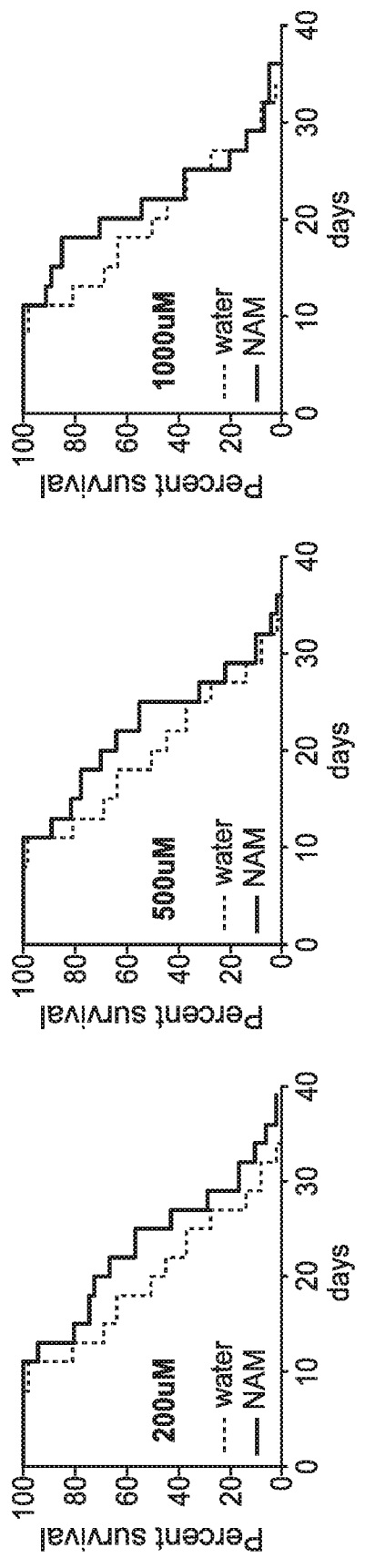

To summarize, NAD+ our data indicate that PARP activity, by modulating availability, plays an important role to preserve (mitochondrial) fitness. Not only is PARylation increased and are NAD+ levels reduced in aged worms and mice, but we also show that interventions aimed to safeguard NAD+ levels curb the aging process and extend lifespan in *C. elegans*. Furthermore, our data also provide evidence for a role of sir-2.1 in lifespan regulation, at least in the context of increased availability of its substrate NAD+. We hence propose a model in which elevation of NAD+ levels activate sir-2.1, resulting in the deacetylation of daf-16, which improves oxidative stress defense through sod-3 (FIG. 36J). The fact that PARP inhibitors and NAD+ precursors also increase NAD+ levels in mammals suggests that these beneficial metabolic effects may also apply to humans and warrants further validation.

TABLE 1

| Gene | Primers | |
|---|---|---|
| ACC1 | 5'-GACAGACTGATCGCAGAGAAAG-3' | 5'-TGGAGAGCCCCACACACA-3' |
| ACC2 | 5'-CCCAGCCGAGTTTGTCACT-3' | 5'-GGCGATGAGCACCTTCTCTA-3' |
| ACO | 5'-CCCAACTGTGACTTCCATT-3' | 5'-GGCATGTAACCCGTAGCACT-3' |
| ATP5g1 | 5'-GCTGCTTGAGAGATGGGTTC-3' | 5'-AGTTGGTGTGGCTGGATCA-3' | qRT-PCR primers for quantification of gene expression

TABLE 1-continued qRT-PCR primers for quantification of gene expression

| Gene | Primers |
|------|---------|
| COX17 | 5'-CGTGATGCGTGCATCATTGA-3'  5'-CATTCACAAAGTAGGCCACC-3' |
| Cyclophyllin B | 5'-TGGAGAGCACCAAGACAGACA-3'  5'-TGCCGGAGTCGACAATGAT-3' |
| Cytochrome C | 5'-TCCATCAGGGTATCCTCTCC-3'  5'-GGAGGCAAGCATAAGACTGG-3' |
| Dio2 | 5'-GCACGTCTCCAATCCTGAAT-3'  5'-TGAACCAAAGTTGACCACCA-3' |
| ERR | 5'-ACTGCCACTGCAGGATGAG-3'  5'-CACAGCCTCAGCATCTTCAA-3' |
| GK | 5'-ACATTGTGCGCCGTGCCTGTGAA-3'  5'-AGCCTGCGCACACTGGCGTGAAA-3' |
| G6Pase | 5'-CCGGATCTACCTTGCTGCTCACTTT-3'  5'-TAGCAGGTAGAATCCAAGCGCGAAAC-3' |
| Mahe enzyme | 5'-GCCGGCTCTATCCTCCTTTG-3'  5'-TTTGTATGCATCTTGCACAATCTTT-3' |
| MCD | 5'-TGGATGGCTGACAGCAGCCTCAA-3'  5'-CTGAGGATCTGCTCGGAAGCTTTG-3' |
| MCAD | 5'-GATCGCAATGGGTGCTTTTGATAGAA-3'  5'-AGCTGATTGGCAATGTCTCCAGCAAA-3' |
| mCPT1 | 5'-TTGCCCTACAGCTGGCTCATTTCC-3'  5'-GCACCCAGATGATTGGGATACTGT-3' |
| Myosin 1 | 5'-GAGTAGCTCTTGTGCTACCCAGC-3'  5'-AATTGCTTTATTCTGCTTCCACC-3' |
| Myosin 2A | 5'-GCAAGAAGCAGATCCAGAAAC-3'  5'-GGTCTTCTTCTGTCTGGTAAGTAAGC-3' |
| Myosin 2X | 5'-GCAACAGGAGATTTCTGACCTCAC-3'  5'-CCAGAGATGCCTCTGCTTC-3' |
| Ndufa2 | 5'-GCACACATTTCCCCACACTG-3'  5'-CCCAACCTGCCCATTCTGAT-3' |
| Ndufb3 | 5'-TACCACAAACGCAGCAAACC-3'  5'-AAGGGACGCCATTAGAAACG-3' |
| Ndufb5 | 5'-CTTCGAACTTCCTGCTCCTT-3'  5'-GGCCCTGAAAAGAACTACG-3' |
| PARP-1 | 5'-GGAGCTGCTCATCTTCAACC-3'  5'-GCAGTGACATCCCCAGTACA-3' |
| PARP-2 | 5'-GGAAGGCGAGTGCTAAATGAA-3'  5'-AAGGTCTTCACAGAGTCTCGATTG-3' |
| PARP-3 | 5'-CCTGCTGATAATCGGGTCAT-3'  5'-TTGTTGTTGTTGCCGATGTT-3' |
| PARP-4 | 5'-GTTAAATTTTGCACTCCTGGAG-3'  5'-AATGTGAACACTGTCAAGAGGAACA-3' |
| PARP-5a | 5'-TAGAGGCATCGAAAGCTGGT-3'  5'-CAGGCATTGTGAAGGGG-3' |
| PARP-5b | 5'-GGCCCTGCTTACACCATTG-3'  5'-CGTGCTTGACCAGAAGTTCA-3' |
| PARP-6 | 5'-TTTCCAGCCATCGAATAAGG-3'  5'-ACCACTTGCCTTGAACCAAC-3' |
| PARP-7 | 5'-AAAACCCCTGGAAATCAACC-3'  5'-AGAAGGATGCGCTTCTGGTA-3' |
| PARP-8 | 5'-TCCACCATTAAATCGCACAA-3'  5'-GCTCCATTTTCGATGTCTTG-3' |
| PARP-9 | 5'-ACCTGAAGAATGGCCTATTACATGG-3'  5'-ACAGCTCAGGGTAGAGATGC-3' |
| PARP-10 | 5'-CAAGATCCTGCAGATGCAAA-3'  5'-TTGGAGAAGCACACGTTCTG-3' |
| PARP-11 | 5'-CAATGAGCAGATGCTATTTCATG-3'  5'-CACCAATTAGCACTCGAGCA-3' |
| PARD-12 | 5'-CGGATCCAGAACATGGGC-3'  5'-GGCATCTCTCGCAAAGTAGC-3' |
| PARP-14 | 5'-GGCAAACGCAATGGAACTAT-3'  5'-AGCACGTTCCTAAGCCTTGA-3' |
| PARP-16 | 5'-CCGTGTGCCTTATGGAAACT-3'  5'-TGGATTGTGTCTGGGCAC-3' |
| PDK4 | 5'-AAAGGACAGGATGAAAGGAATCA-3'  5'-ATTAACTGGCAGAGTGGCAGGTAA-3' |
| PEPCK | 5'-CCACAGCTGCTGCAGAACA-3'  5'-GAAGGGTCGCATGGCAAA-3' |
| PGC-1 | 5'-AAGTGTGGAACTCTCTGGAACTG-3'  5'-GGGTTATCTTGGTTGGCTTTATG-3' |
| PPAR | 5'-CCTGAACATCGAGTGTCGAATAT-3'  5'-GGTTCTTCTTCTGAATCTTGCAGCT-3' |
| SREBP1 | 5'-GGCCGAGATGTGCGAACT-3'  5'-TTGTTGATGAGCTGGAGCATGT-3' |
| Troponin I | 5'-CCAGCACCTTCAGCTTCAGGTCCTTGAT-3'  5'-TGCCGGAAGTTGAGAGGAAATCCAAGAT-3' |

TABLE 1-continued qRT-PCR primers for quantification of gene expression

| Gene | Primers |
| --- | --- |
| UCP1 | 5'-GGCCCTTGTAAACAACAAAATAC-3' 5'-GGCAACAAGAGCTGACAGTAAAT-3' |
| UCP2 | 5'-TGGCAGGTAGCACCACAGG-3' 5'-CATCTGGTCTTGCAGCAACTCT-3' |
| UCP3 | 5'-ACTCCAGCGTCGCCATCAGGATTCT-3' 5'-TAAACAGGTGAGACTCCAGCAACTT-3' |

TABLE 2

Primers for mtDNA determinations

| | |
| --- | --- |
| mtDNA specific (murine) | 5'-CCGCAAGGGAAAGATGAAAGAC-3' 5'-TCGTTTGGTTTCGGGGTTTC-3' |
| nuclear specific (murine) | 5'-GCCAGCCTCTCCTGATTTTAGTGT-3' 5'-GGGAACACAAAAGACCTCTTCTGG-3' |
| mtDNA specific (human) | 5'-CTATGTCGCAGTATCTGTCTTTG-3' 5'-GTTATGATGTCTGTGTGGAAAG-3' |
| nuclear specific (human) | 5'-GTTTGTGTGCTATAGATGATATTTTAAATTG-3' 5'-CATTAAACAGTCTACAAAACATAT-3' |

TABLE 3

ChIP primers

| | |
| --- | --- |
| PDK4 | 5'-AACCCTCCTCCCTCTCACCCT-3' 5'-ACACCAATCAGCTCAGAGAA-3' |
| UCP-3 | 5'-GAATGTCAGGCCTCTAAGAA-3' 5'-CAGGAGGTGTGTGACAGCAT-3' |

TABLE 4

RT-PCR primers for quantification of gene expression

| Gene | Primers |
| --- | --- |
| ACO | CCCAACTGTGACTTCCATTGGCATGTAACCCGTAGCACT |
| ATP5g1 | GCTGCTTGAGAGATGGGTTCAGTTGGTGTGGCTGGATCA |
| COX17 | CGTGATGCGTGCATCATTGACATTCACAAAGTAGGCCACC |
| Citrate | GGAGCCAAGAACTCATCCTGTCTGGCCTGCTCCTTAGGTA |
| Cyclophyllin B | TGGAGAGCACCAAGACAGACATGCCGGAGTCGACAATGAT |
| Cytochrome C | TCCATCAGGGTATCCTCTCCGGAGGCAAGCATAAGACTGG |
| Dio2 | GCACGTCTCCAATCCTGAATTGAACCAAAGTTGACCACCA |
| ERR | ACTGCCACTGCAGGATGAGCACAGCCTCAGCATCTTCAA |
| FOXO1 | AAGGATAAGGGCGACAGCAATCCACCAAGAACTCTTTCCA |
| G6Pase | CCGGATCTACCTTGCTGCTCACTTTTAGCAGGTAGAATCCAAGCGCGAAAC |
| GK | ACATTGTGCGCCGTGCCTGTGAAAGCCTGCGCACACTGGCGTGAAA |
| Kir6.2 | CTGTCCCGAAAGGGCATTATCGTTGCAGTTGCCTTTCTTG |
| Insulin | GTGGGGAGCGTGGCTTCTTCTAACTGATCCACAATGCCACGCTTCT |
| Insulin receptor | CGAGTGCCCGTCTGGCTATAGGCAGGGTCCCAGACATG |
| LCAD | GTAGCTTATGAATGTGTGCAACTCGTCTTGCGATCAGCTCTTTCATTA |
| L-CPT1 | GCACTGCAGCTCGCACATTACAACTCAGACAGTACCTCCTTCAGGAAA |

TABLE 4-continued

RT-PCR primers for quantification of gene expression

| Gene | Primers |
|---|---|
| MCD | TGGATGGCTGACAGCAGCCTCAACTGAGGATCTGCTCGGAAGCTTTG |
| MCAD | GATCGCAATGGGTGCTTTTGATAGAAAGCTGATTGGCAATGTCTCCAGCAAA |
| mCPT1 | TTGCCCTACAGCTGGCTCATTTCCGCACCCAGATGATTGGGATACTGT |
| Ndufa2 | GCACACATTTCCCCACACTGCCCAACCTGCCCATTCTGAT |
| PEPCK | CCACAGCTGCTGCAGAACAGAAGGGTCGCATGGCAAA |
| PPAR | AGGAAGCCGTTCTGTGACATTTGAAGGAGCTTTGGGAAGA |
| PC | AGGGGCTGCTGTTGATGGACCAGGGGCACTCGTACAGGAAGC |
| PDK4 | AAAGGACAGGATGGAAGGAATCAATTAACTGGCAGAGTGGCAGGTAA |
| SDH | GAACTGCACACAGACCTGCGACTGGGTTAAGCCAATGCTC |
| SIRT1 | TGTGAAGTTACTGCAGGAGTGTAAAGCATAGATACCGTCTCTTGATCTGAA |
| SIRT3 | AGGTGGAGGAAGCAGTGAGAGCTTGGGGTTGTGAAAGAAA |
| PDX1 | AATCCACCAAAGCTCACGCGTGGAATGATGTGTCTCTCGGTCAAGTTCAA |
| PGC-1 | AAGTGTGGAACTCTCTGGAACTGGGGTTATCTTGGTTGGCTTTATG |
| PGC-1 | TGGAGACTGCTCTGGAAGGTTGCTGCTGTCCTCAAATACG |
| TFAm | CCAAAAAGACCTCGTTCAGCATGTCTCCGGATCGTTTCAC |
| Troponin I | CCAGCACCTTCAGCTTCAGGTCCTTGATTGCCGGAAGTTGAGAGGAAATCCAAGAT |
| UCP1 | GGCCCTTGTAAACAACAAAATACGGCAACAAGAGCTGACAGTAAAT |
| UCP2 | ACCAAGGGCTCAGAGCATGCATGGCTTTCAGGAGAGTATCTTTG |
| UCP3 | ACTCCAGCGTCGCCATCAGGATTCTTAAACAGGTGAGACTCCAGCAACTT |

TABLE 5

Primers for mtDNA determination.

| mtDNA specific (murine) | 5'-CCGCAAGGGAAAGATGAAAGAC-3' 5'-TCGTTTGGTTTCGGGGTT-3' |
|---|---|
| Nuclear specific (murine) | 5'-GCCAGCCTCTCCTGATTTTAGTGT-3' 5'-GGGAACACAAAAGACCTCTTCTGG-3' |

TABLE 6

Primers for ChIP

| SIRT1-91 | 5'-TCCCGCAGCCGAGCCGCGGGG-3<br>5'-TCTTCCAACTGCCTCTCTGGCCCTCCG-3' |
|---|---|
| Human K19 | 5'-CATTTCTCCACCTCACTGAAACTG-3' 5'-AATGTGTTAGTGCATGCA-3' |
| Murine K19 | 5'-AAGGGTGGAGGTGTCTTGGT-3' 5'-GCTTCTTTACACTCC-3' |

TABLE 7

RT-PCR primers for quantification of gene expression

| Gene | Forward | Reverse |
|---|---|---|
| sod-3 (C08A9.1) | CTAAGGATGGTGGAGAACCTTCA | CGCGCTTAATAGTGTCCATCAG |
| daf-16 (R13H8.1) | ATCCAATTGTGCCAAGCACTAA | CCACCATTTTGATAGTTTCCATAGG |

TABLE 7-continued

RT-PCR primers for quantification of gene expression

| Gene | Forward | Reverse |
|---|---|---|
| cts-1 (T20G5.1) | CTCGACAACTTCCCAGATAACC | GGTACAGGTTGCGATAGATGATAGC |
| cox-4 (W09C5.8) | GCCCCAATTCGCGCCAAGGA | AGGTTGGCGGCAGTTCTGGG |
| rrn-1.1 (F31C3.7) | TTCTTCCATGTCCGGGATAG | CCCCACTCTTCTCGAATCAG |
| act-1 (T04C12.6) | GCTGGACGTGATCTTACTGATTACC | GTAGCAGAGCTTCTCCTTGATGTC |

TABLE 8

Summary of lifespan experiments

| strains and culture conditions | mean lifespan ± SE (days) | variation compared to control (%) | P-values against control | N(trials) |
|---|---|---|---|---|
| N2 | 19.7 ± 0.61 | | | 96/24(2) |
| pme-1(ok988) | 25.5 ± 0.52 | +29.4 | <10$^{-3}$ | 91/29(2) |
| N2 + water | 20.1 ± 0.59 | | | 138/42(3) |
| N2 + AZD 100 nM | 24.7 ± 0.55 | +22.9 | <10$^{-3}$ | 141/39(3) |
| N2 + water | 19.4 ± 0.98 | | | 55/5(1) |
| N2 + ABT 100 nM | 22.3 ± 1.01 | +15.0 | 0.05 | 52/8(1) |
| N2 + water | 19.8 ± 0.87 | | | 53/7(1) |
| pme-1(ok988) + water | 27.2 ± 0.55 | +37.4 | <10$^{-3}$ | 49/11(1) |
| N2 + AZD 100 nM | 22.8 ± 0.9 | +15.2 | 0.02 | 48/12(1) |
| pme-1(ok988) + AZD 100 nM | 26.1 ± 0.78 | +31.2 | ns$^a$ | 49/11(1) |
| N2 + water | 20.5 ± 0.737 | | | 83/37(2) |
| sir-2.1(ok434) + water | 22.9 ± 0.624 | +11.7 | ns | 88/32(2) |
| N2 + AZD 100 nM | 24.7 ± 0.669 | +20.5 | <10$^{-3}$ | 89/31(2) |
| sir-2.1(ok434) + AZD 100 nM | 21.9 ± 0.528 | +6.7 | ns$^b$ | 84/36(2) |
| N2 + water | 21.7 ± 1.24 | | | 30/30(1) |
| daf-16(mu86) + water | 17.5 ± 0.69 | -19.3 | 0.0009 | 36/24(1) |
| N2 + AZD 100 nM | 26.5 ± 0.77 | +22.1 | 0.004 | 41/19(1) |
| daf-16(mu86) + AZD 100 nM | 18.2 ± 0.76 | -16.1 | ns$^c$ | 37/23(1) |
| N2 + water | 19.5 ± 0.51 | | | 186/52(4) |
| N2 + NR 500 nM | 23.5 ± 0.56 | +20.1 | <10$^{-3}$ | 172/68(4) |
| N2 + water | 20.7 ± 0.80 | | | 79/41(2) |
| sir-2.1(ok434) + water | 23.4 ± 0.67 | +13.0 | ns | 80/40(2) |
| N2 + NR 500 nM | 24.9 ± 0.68 | +20.3 | 0.0008 | 86/34(2) |
| sir-2.1(ok434) + NR 500 nM | 23.2 ± 0.61 | +12.0 | ns$^b$ | 76/44(2) |
| N2 + water | 20.7 ± 0.80 | | | 79/41(2) |
| daf-16(mu86) + water | 17.1 ± 0.47 | -17.4 | <10$^{-3}$ | 76/44(2) |
| N2 + NR 500 nM | 24.9 ± 0.68 | +20.3 | 0.0008 | 86/34(2) |
| daf-16(mu86) + NR 500 nM | 19.1 ± 0.51 | -7.8 | 0.01 $^c$ | 88/32(2) |
| N2 + water | 19.9 ± 0.95 | | | 54/6(1) |
| N2 + NAM 200 nM | 23.5 ± 1.03 | +18.1 | 0.01 | 50/10(1) |
| N2 + NAM 500 nM | 22.6 ± 0.92 | +13.5 | ns | 52/8(1) |
| N2 + NAM 1000 nM | 21.8 ± 0.85 | +9.5 | ns | 46/14(1) |
| N2 + water | 19.4 ± 0.97 | | | 55/5(1) |
| N2 + AZD 100 nM | 24.5 ± 0.94 | +25.6 | 0.001 | 52/8(1) |
| N2 + AZD 500 nM | 22.2 ± 1.15 | +14.4 | 0.03 | 48/12(1) |
| N2 + AZD 1000 nM | 21.2 ± 0.96 | +9.2 | ns | 53/7(1) |
| N2 + water | 19.4 ± 0.97 | | | 55/5(1) |
| N2 + ABT 100 nM | 22.5 ± 1.05 | +16.0 | 0.04 | 52/8(1) |
| N2 + ABT 500 nM | 22.1 ± 1.20 | +13.9 | ns | 49/11(1) |
| N2 + ABT 1000 nM | 20.0 ± 1.23 | +3.6 | ns | 50/10(1) |
| N2 + water | 17.9 ± 0.84 | | | 54/6(1) |
| N2 + NR 200 nM | 21.1 ± 0.88 | +17.9 | 0.04 | 44/16(1) |
| N2 + NR 500 nM | 20.6 ± 1.02 | +15.1 | 0.04 | 43/17(1) |
| N2 + NR 1000 nM | 20.0 ± 0.89 | +11.7 | ns | 50/10(1) |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Adamietz, P. (1987). Poly(ADP-ribose) synthase is the major endogenous nonhistone acceptor for poly(ADP-ribose) in alkylated rat hepatoma cells. Eur J Biochem 169, 365-372.

Ahn, B. H., Kim, H. S., Song, S., Lee, I. H., Liu, J., Vassilopoulos, A., Deng, C. X., and Finkel, T. (2008). A role for the mitochondrial deacetylase Sirt3 in regulating energy homeostasis. Proc Natl Acad Sci USA 105, 14447-14452.

Aksoy, P., Escande, C., White, T. A., Thompson, M., Soares, S., Benech, J. C., and Chini, E. N. (2006). Regulation of SIRT1 mediated NAD dependent deacetylation: a novel role for the multifunctional enzyme CD38. Biochem Biophys Res Commun 349, 353-359.

Allinson, S. L., Dianova, I I, and Dianov, G. L. (2003). Poly(ADP-ribose) polymerase in base excision repair: always engaged, but not essential for DNA damage processing. Acta Biochim Pol 50, 169-179.

Ame, J. C., Rolli, V., Schreiber, V., Niedergang, C., Apiou, F., Decker, P., Muller, S., Hoger, T., Menissier-de Murcia, J., and de Murcia, G. (1999). PARP-2, A novel mammalian DNA damage-dependent poly(ADP-ribose) polymerase. J BiolChem 274, 17860-17868.

Ame, J. C., Spenlehauer, C., and de Murcia, G. (2004). The PARP superfamily. Bioessays 26, 882-893.

Asher, G., Reinke, H., Altmeyer, M., Gutierrez-Arcelus, M., Hottiger, M. O., and Schibler, U. (2010). Poly(ADP-ribose) polymerase 1 participates in the phase entrainment of circadian clocks to feeding. Cell 142, 943-953.

Bai, P., Bakondi, E., Szabo, E., Gergely, P., Szabo, C., and Virag, L. (2001). Partial protection by poly(ADP-ribose) polymerase inhibitors from nitroxyl-induced cytotoxicity in thymocytes. Free Radic Biol Med 31, 1616-1623.

Bai, P., Houten, S. M., Huber, A., Schreiber, V., Watanabe, M., Kiss, B., de Murcia, G., Auwerx, J., and Menissier-de Murcia, J. (2007). Poly(ADP-ribose) polymerase-2 controls adipocyte differentiation and adipose tissue function through the regulation of the activity of the retinoid X receptor/peroxisome proliferator-activated receptor-gamma heterodimer. J Biol Chem 282, 37738-37746.

Balint, B. L., Szanto, A., Math, A., Bauer, U. M., Gabor, P., Benko, S., Puskas, L. G., Davies, P. J., and Nagy, L. (2005). Arginine methylation provides epigenetic transcription memory for retinoid-induced differentiation in myeloid cells. Mol Cell Biol 25, 5648-5663.

Banks, A. S., Kon, N., Knight, C., Matsumoto, M., Gutierrez-Juarez, R., Rossetti, L., Gu, W., and Accili, D. (2008). SirT1 gain of function increases energy efficiency and prevents diabetes in mice. Cell Metab 8, 333-341.

Barbosa, M. T., Soares, S. M., Novak, C. M., Sinclair, D., Levine, J. A., Aksoy, P., and Chini, E. N. (2007). The enzyme CD38 (a NAD glycohydrolase, EC 3.2.2.5) is necessary for the development of diet-induced obesity. Faseb J 21, 3629-3639.

Baur, J. A., Pearson, K. J., Price, N. L., Jamieson, H. A., Lerin, C., Kalra, A., Prabhu, V. V., Allard, J. S., Lopez-Lluch, G., Lewis, K., et al. (2006). Resveratrol improves health and survival of mice on a high-calorie diet. Nature 444, 337-342.

Bitterman, K. J., Anderson, R. M., Cohen, H. Y., Latorre-Esteves, M., and Sinclair, D. A. (2002). Inhibition of silencing and accelerated aging by nicotinamide, a putative negative regulator of yeast sir2 and human SIRT1. J Biol Chem 277, 45099-45107.

Borra, M. T., Smith, B. C., and Denu, J. M. (2005). Mechanism of human SIRT1 activation by resveratrol. J Biol Chem 280, 17187-17195.

Brunet, A., Sweeney, L. B., Sturgill, J. F., Chua, K. F., Greer, P. L., Lin, Y., Tran, H., Ross, S. E., Mostoslaysky, R., Cohen, H. Y., Hu, L. S., Cheng, H. L., Jedrychowski, M. P., Gygi, S. P., Sinclair, D. A., Alt, F. W., and Greenberg, M. E. (2004). Stress-dependent regulation of FOXO transcription factors by the SIRT1. deacetylase. Science. 303, 2011-2015.

Burkle, A. (2005). Poly(ADP-ribose). The most elaborate metabolite of NAB+. FEBS J 272, 4576-4589.

Buteau, J., and Accili, D. (2007). Regulation of pancreatic beta-cell function by the forkhead protein FoxO1. Diabetes Obes Metab 9 Suppl 2, 140-146.

Canto, C., and Auwerx, J. (2009). Caloric restriction, SIRT1 and longevity. Trends Endocrinol Metab 20, 325-331.

Canto, C., Gerhart-Hines, Z., Feige, J. N., Lagouge, M., Noriega, L., Milne, J. C., Elliott, P. J., Puigserver, P., and Auwerx, J. (2009). AMPK regulates energy expenditure by modulating NAD+ metabolism and SIRT1 activity. Nature 458, 1056-1060.

Canto, C., Jiang, L. Q., Deshmukh, A. S., Mataki, C., Coste, A., Lagouge, M., Zierath, J. R., and Auwerx, J. (2010). Interdependence of AMPK and SIRT1 for metabolic adaptation to fasting and exercise in skeletal muscle. Cell 11, 213-219.

Chambon, P., Weill, J. D., and Mandel, P. (1963). Nicotinamide mononucleotide activation of new DNA-dependent polyadenylic acid synthesizing nuclear enzyme. Biochem Biophys Res Commun 11:39-43, 39-43.

Champy, M. F., Selloum, M., Piard, L., Zeitler, V., Caradec, C., Chambon, P., and Auwerx, J. (2004). Mouse functional genomics requires standardization of mouse handling and housing conditions. Mamm. Genome. 15, 768-783

Chen, D., Bruno, J., Easlon, E., Lin, S. J., Cheng, H. L., Alt, F. W., and Guarente, L. (2008). Tissue-specific regulation of SIRT1 by calorie restriction. Genes Dev 22, 1753-1757.

Chen, D., Steele, A. D., Lindquist, S., and Guarente, L. (2005). Increase in activity during calorie restriction requires Sirt1. Science 310, 1641.

Chiarugi, A., Meli, E., Galvani, M., Picca, R., Baronti, R., Camaioni, E., Costantino, G., Marinozzi, M., Pellegrini-Giampietro, D. E., Pellicciari, R., et al. (2003). Novel isoquinolinone-derived inhibitors of poly(ADP-ribose) polymerase-1: pharmacological characterization and neuroprotective effects in an in vitro model of cerebral ischemia. J Pharmacol Exp Ther 305, 943-949.

Chua, K. F., Mostoslaysky, R., Lombard, D. B., Pang, W. W., Saito, S., Franco, S., Kaushal, D., Cheng, H. L., Fischer, M. R., Stokes, N., et al. (2005). Mammalian SIRT1 limits replicative life span in response to chronic genotoxic stress. Cell. Metab 2, 67-76.

Dai, H., Kustigian, L., Carney, D., Case, A., Considine, T., Hubbard, B. P., Pemi, R. B., Riera, T. V., Szczepankiewicz, B., Vlasuk, G. P., et al. (2010). SIRT1 activation by small molecules: kinetic and biophysical evidence for direct interaction of enzyme and activator. J Biol Chem 285, 32695-32703.

Dali-Youcef, N., Mataki, C., Coste, A., Messaddeq, N., Giroud, S., Blanc, S., Kochi, C., Champy, M. F., Chambon, P., Fajas, L., et al. (2007). Adipose tissue-specific inactivation of the retinoblastoma protein protects against diabesity because of increased energy expenditure. Proc Natl Acad Sci USA 104, 10703-10708.

Devalaraja-Narashimha, K., and Padanilam, B. J. (2010). PARP I deficiency exacerbates diet-induced obesity in mice. J Endocrinol 205, 243-252.

Durkacz, B. W., Omidiji, O., Gray, D. A., and Shall, S. (1980). (ADP-ribose)n participates in DNA excision repair. Nature 283, 593-596.

El Ramy, R., Magroun, N., Messadecq, N., Gauthier, L. R., Boussin, F. D., Kolthur-Seetharam, U., Schreiber, V., McBurney, M. W., Sassone-Corsi, P., and Dantzer, F. (2009). Functional interplay between Parp-1 and SirT1 in genome integrity and chromatin-based processes. Cell Mol Life Sci 66, 3219-3234.

Edelman, J. C., Edelman, P. M., Kniggee, K. M., and Schwartz, I. L. (1965). Isolation of skeletal muscle nuclei. J Cell Biol 27, 365-377.

Erdelyi, K., Bai, P., Kovacs, I., Szabo, E., Mocsar, G., Kakuk, A., Szabo, C., Gergely, P., and Virag, L. (2009). Dual role of poly(ADP-ribose) glycohydrolase in the regulation of cell death in oxidatively stressed A549 cells. Faseb J 23, 3553-3563.

Feige, J. N., Lagouge, M., Canto, C., Strehle, A., Houten, S. M., Milne, J. C., Lambert, P. D., Mataki, C., Elliott, P. J., and Auwerx, J. (2008). Specific SIRT1 activation mimics low energy levels and protects against diet-induced metabolic disorders by enhancing fat oxidation. Cell Metab 8, 347-358.

Fong, P. C., Boss, D. S., Yap, T. A., Tutt, A., Wu, P., Mergui-Roelvink, M., Mortimer, P., Swaisland, H., Lau, A., O'Connor, M. J., et al. (2009). Inhibition of Poly(ADP-Ribose) Polymerase in Tumors from BRCA Mutation Carriers. N Engl J Med 24, 123-434.

Frescas, D., Valenti, L., and Accili, D. (2005). Nuclear trapping of the forkhead transcription factor FoxO1 via Sirt-dependent deacetylation promotes expression of glucogenetic genes. J Biol Chem 280, 20589-20595.

Fulco, M., Cen, Y., Zhao, P., Hoffman, E. P., McBurney, M. W., Sauve, A. A., and Sartorelli, V. (2008). Glucose restriction inhibits skeletal myoblast differentiation by activating SIRT1 through AMPK-mediated regulation of Nampt. Dev Cell 14, 661-673.

Garcia, S. F., Virag, L., Jagtap, P., Szabo, E., Mabley, J. G., Liaudet, L., Marton, A., Hoyt, D. G., Murthy, K. G., Salzman, A. L., et al. (2001). Diabetic endothelial dysfunction: the role of poly(ADP-ribose) polymerase activation. Nat Med 7, 108-113.

Gerhart-Hines, Z., Rodgers, J. T., Bare, O., Lerin, C., Kim, S. H., Mostoslaysky, R., Alt, F. W., Wu, Z., and Puigserver, P. (2007). Metabolic control of muscle mitochondrial function and fatty acid oxidation through SIRT1/PGC-1alpha. Embo J 26, 1913-1923.

Gross, D. N., van den Heuvel, A. P., and Birnbaum, M. J. (2008). The role of FoxO in the regulation of metabolism. Oncogene 27, 2320-2336.

Haenni, S. S., Hassa, P. O., Altmeyer, M., Fey, M., Imhof, R., and Hottiger, M. O. (2008). Identification of lysines 36 and 37 of PARP-2 as targets for acetylation and autoADP-ribosylation. Int. J. Biochem. Cell Biol. 40(10), 2274-2283.

Haigis, M. C., and Guarente, L. P. (2006). Mammalian sirtuins—emerging roles in physiology, aging, and calorie restriction. Genes Dev 20, 2913-2921.

Haigis, M. C., and Sinclair, D. A. (2010). Mammalian sirtuins: biological insights and disease relevance. Annu 5, 253-295.

Hood, D. A. (2009). Mechanisms of exercise-induced mitochondrial biogenesis in skeletal muscle. Appl Physiol Nutr Metab 34, 465-472.

Houtkooper, R. H., Canto, C., Wanders, R. J., and Auwerx, J. (2010). The secret life of NAD+: an old metabolite controlling new metabolic signaling pathways. Endocr Rev 31, 194-223.

Howitz, K. T., Bitterman, K J., Cohen, H. Y., Lamming, D. W., Lavu, S., Wood, J. G., Zipkin, R. E., Chung, P., Kisielewski, A., Zhang, L. L., et al. (2003). Small molecule activators of sirtuins extend *Saccharomyces cerevisiae* lifespan. Nature 425, 191-196.

Jagtap, P., and Szabo, C. (2005). Poly(ADP-ribose) polymerase and the therapeutic effects of its inhibitors. Nat Rev Drug Discov 4, 421-440.

Ju, B. G., Lunyak, V. V., Perissi, V., Garcia-Bassets, I., Rose, D. W., Glass, C. K., and Rosenfeld, M. G. (2006). A topoisomerase IIbeta-mediated dsDNA break required for regulated transcription. Science 312, 1798-1802.

Kaeberlein, M., McDonagh, T., Heitweg, B., Hixon, J., Westman, E. A., Caldwell, S. D., Napper, A., Curtis, R., DiStefano, P. S., Fields, S., et al. (2005). Substrate-specific activation of sirtuins by resveratrol. J Biol Chem 280, 17038-17045.

Kaneto, H., Matsuoka, T. A., Miyatsuka, T., Kawamori, D., Katakami, N., Yamasaki, Y., and Matsuhisa, M. (2008). PDX-1 functions as a master factor in the pancreas. Front Biosci 13, 6406-6420.

Kawamori, D., Kaneto, H., Nakatani, Y., Matsuoka, T. A., Matsuhisa, M., Hori, M., and Yamasaki, Y. (2006). The forkhead transcription factor Foxo1 bridges the JNK pathway and the transcription factor PDX-1 through its intracellular translocation. J Biol Chem 281, 1091-1098.

Kitamura, T., Nakae, J., Kitamura, Y., Kido, Y., Biggs, W. H., 3rd, Wright, C. V., White, M. F., Arden, K. C., and Accili, D. (2002). The forkhead transcription factor Foxo1 links insulin signaling to Pdx1 regulation of pancreatic beta cell growth. J Clin Invest 110, 1839-1847.

Knight, M. I., and Chambers, P. J. (2001). Production, extraction, and purification of human poly(ADP-ribose) polymerase-1 (PARP-1) with high specific activity. Protein Expr Purif 23, 453-458.

Kolthur-Seetharam, U., Dantzer, F., McBurney, M. W., de Murcia, G., and Sassone-Corsi, P. (2006). Control of AIF-mediated cell death by the functional interplay of SIRT1 and PARP-1 in response to DNA damage. Cell Cycle 5, 873-877.

Krishnakumar, R., Gamble, M. J., Frizzell, K. M., Berrocal, J. G., Kininis, M., and Kraus, W. L. (2008). Reciprocal binding of PARP-1 and histone H1 at promoters specifies transcriptional outcomes. Science 319, 819-821.

Kun, E., Kirsten, E., and Ordahl, C. P. (2002). Coenzymatic activity of randomly broken or intact double-stranded DNAs in auto and histone H1 trans-poly(ADP-ribosylation), catalyzed by poly(ADP-ribose) polymerase (PARP I). J Biol Chem 277, 39066-39069.

Lagouge, M., Argmann, C., Gerhart-Hines, Z., Meziane, H., Lerin, C., Daussin, F., Messadeq, N., Milne, J., Lambert, P., Elliott, P., et al. (2006). Resveratrol Improves Mitochondrial Function and Protects against Metabolic Disease by Activating SIRT1 and PGC-1.alpha. Cell 127, 1109-1122.

Lin, S. J., Defossez, P. A., and Guarente, L. (2000). Requirement of NAD and SIR2 for life-span extension by calorie restriction in *Saccharomyces cerevisiae*. Science 289, 2126-2128.

Lopez-Lluch, G., Hunt, N., Jones, B., Zhu, M., Jamieson, H., Hilmer, S., Cascajo, M. V., Allard, J., Ingram, D. K., Navas, P., et al. (2006). Calorie restriction induces mitochondrial biogenesis and bioenergetic efficiency. Proc Natl Acad Sci USA 103, 1768-1773.

MacDonald, P. E., Joseph, J. W., and Rorsman, P. (2005). Glucose-sensing mechanisms in pancreatic beta-cells. Philos Trans R Soc Lond B Biol. Sci 360, 2211-2225.

Malik, R., Kashyap, A., Bonsai, K., Sharma, P., Rayasam, O. V., Davis, J. A., Bora, R. S., Ray, A., and Saini, K. S. (2009). Comparative deacetylase activity of wild type and mutants of SIRT1. Biochem Biophys Res Commun 391, 739-743.

Menissier-de Murcia, J., Niedergang, C., Trucco, C., Ricoul, M., Dutrillaux, B., Mark, M., Oliver, F. J., Masson, M., Dierich, A., LeMeur, M., et al. (1997). Requirement of poly(ADP-ribose) polymerase in recovery from DNA damage in mice and in cells. Proc Nati Acad Sci USA 94, 7303-7307.

Menissier-de Murcia, J., Ricoul, M., Tartier, L., Niedergang, C., Huber, A., Dantzer, F., Schreiber, V., Ame, J. C., Dierich, A., LeMeur, M., Sabatier, L., Chambon, P., and de Murcia, G. (2003). Functional interaction between PARP-1 and PARP-2 in chromosome stability and embryonic development in mouse. EMBO J. 22, 2255-2263.

Milne, J. C., Lambert, P. D., Schenk, S., Carney, D. P., Smith, J. J., Gagne, D. J., Jin, L., Boss, O., Perth, R. B., Vu, C. B., et al. (2007). Small molecule activators of SIRT1 as therapeutics for the treatment of type 2 diabetes. Nature 450, 712-716.

Moynihan, K. A., Grimm, A. A., Plueger, M. M., Bernal-Mizrachi, E., Ford, E., Cras-Meneur, C., Permutt, M. A., and Imai, S. (2005). Increased dosage of mammalian Sir2 in pancreatic beta cells enhances glucose-stimulated insulin secretion in mice. Cell Metab. 2, 105-117.

Narkar, V. A., Downes, M., Yu, R. T., Embler, E., Wang, Y. X., Banayo, E., Mihaylova, M. M., Nelson, M. C., Zou, Y., Juguilon, H., et al. (2008). AMPK and PPARdelta agonists are exercise mimetics. Cell 134, 405-415.

Nemoto, S., Fergusson, M. M., and Finkel, T. (2004). Nutrient availability regulates SIRT1 through a forkhead-dependent pathway. Science. 306, 2105-2108.

North, B. J., Marshall, B. L., Borra, M. T., Denu, J. M., and Verdin, E. (2003). The human Sir2 ortholog, SIRT2, is an NAD+-dependent tubulin deacetylase. Mol Cell 11, 437-444

Oliver, A. W., Ame, J. C., Roe, S. M., Good, V., de Murcia, O., and Pearl, L. H. (2004). Crystal structure of the catalytic fragment of murine poly(ADP-ribose) polymerase-2. Nucleic Acids Res. 32, 456-464.

Pacholec, M., Bleasdale, J. E., Chrunyk, B., Cunningham, D., Flynn, D., Garofalo, R. S., Griffith, D., Griffor, M., Loulakis, P., Pabst, B., et al. (2010). SRT1720, SRT2183, SRT1460, and resveratrol are not direct activators of SIRT1. J 285, 8340-8351.

Pfluger, P. T., Herranz, D., Velasco-Miguel, S., Serrano, M., and Tschop, M. H. (2008). Sirt1 protects against high-fat diet-induced metabolic damage. Proc Natl Acad Sci USA 105, 9793-9798.

Picard, F., Gehin, M., Annicotte, J., Rocchi, S., Champy, M. F., O'Malley, B. W., Chambon, P., and Auwerx, J. (2002). SRC-1 and T1F2 control energy balance between white and brown adipose tissues. Cell. 111, 931-941.

Picard, F., Kurtev, M., Chung, N., Topark-Ngarm, A., Senawong, T., hado De, O. R., Leid, M., McBurney, M. W., and Guarente, L. (2004). Sirt1 promotes fat mobilization in white adipocytes by repressing PPAR-gamma. Nature. 429, 771-776.

Pillai, J. B., Gupta, M., Rajamohan S. B., Lang, R., Raman, J., and Gupta, M. P. (2006). Poly(ADP-ribose) polymerase-1-deficient mice are protected from angiotensin II-induced cardiac hypertrophy. Am J Physiol Heart Circ Physiol 291, H1545-111553.

Pillai, J. B., Russell, H. M., Raman, J., Jeevanandam, V., and Gupta, M. P. (2005). Increased expression of poly(ADP-ribose) polymerase-1 contributes to caspase-independent myocyte cell death during heart failure. Am J Physiol Heart Circ Physiol 288, H486-H496.

Pillai, Isbatan, A., Imai, S., and Gupta, M. P. (2005). Poly(ADP-ribose) polymerase-1-dependent cardiac myocyte cell death during heart failure is mediated by NAD+ depletion and reduced Sir2alpha deacetylase activity. J. Biol. Chem. 280, 43121-43130.

Rajamohan, S. B., Pillai, V. B., Gupta, M., Sundaresan, N. R., Konstatin, B., Samant, S., Hottiger, M. O., and Gupta, M. P. (2009). SIRT1 promotes cell survival under stress by deacetylation-dependent deactivation of poly (ADP-ribose) polymerase 1. Mol Cell Biol 29(15), 4116-4129.

Rodgers, J. T., Lerin, C., Haas, W., Gygi, S. P., Spiegelman, B. M., and Puigserver, P. (2005). Nutrient control of glucose homeostasis through a complex of PGC-1alpha and SIRT1. Nature 434, 113-118.

Sakamaki, J., Daitoku, H., Yoshimochi, K., Miwa, M., and Fukamizu, A. (2009). Regulation of FOXO1-mediated transcription and cell proliferation by PARP-1. Biochem Biophys Res Commun 382, 497-502.

Sauve, A. A. (2009). Pharmaceutical strategies for activating sirtuins. Curr Pharm Des 15, 45-56.

Sauve, A. A., Moir, R. D., Schramm, V. L., and Willis, I. M. (2005). Chemical activation of Sir2-dependent silencing by relief of nicotinamide inhibition. Mol Cell 17, 595-601.

Schraufstatter, I. U., Hinshaw, D. B., Hyslop, P. A., Spragg, R. G., and Cochrane, C. G. (1986). Oxidant injury of cells. DNA strand-breaks activate polyadenosine diphosphate-ribose polymerase and lead to depletion of nicotinamide adenine dinucleotide. J Clin Invest 77, 1312-1320.

Schwer, B., North, B. J., Frye, R. A., Ott, M., and Verdin, E. (2002). The human silent information regulator (Sir)2 homologue hSIRT3 is a mitochondrial nicotinamide adenine dinucleotide-dependent deacetylase. J Cell Biol 158, 647-657.

Shah, R. G., Ghodgaonkar, M. M., Affar el, B., and Shah, G. M. (2005). DNA vector-based RNAi approach for stable depletion of poly(ADP-ribose) polymerase-1. Biochem Biophys Res Commun 331, 167-174.

Shieh, W. M., Ame, J. C., Wilson, M. V., Wang, Z. Q., Koh, D. W., Jacobson, M. K., and Jacobson, E. L. (1998). Poly (ADP-ribose) polymerase null mouse cells synthesize ADP-ribose polymers. J Biol Chem 273, 30069-30072.

Sims, J. L., Berger, S. J., and Berger, N. A. (1981). Effects of nicotinamide on NAD and poly(ADP-ribose) metabolism in DNA-damaged human lymphocytes. J Supramol Struct Cell Biochem 16, 281-288.

Smith, B. C., Hallows, W. C., and Denu, J. M. (2009). A continuous microplate assay for sirtuins and nicotinamide-producing enzymes. Anal Biochem 394, 101-109.

Tremblay, G. B., Tremblay, A., Copeland, N. G., Gilbert, D. J., Jenkins, N. A., Labrie, F., and Giguere, V. (1997). Cloning, chromosomal localization, and functional analysis of the murine estrogen receptor beta. Mol Endocrinol 11, 353-365.

Um, H. J., Bae, J. H., Park, J. W., Suh, H., Jeong, N. Y., Yoo, Y. H., and Kwon, T. K. (2010). Differential effects of resveratrol and novel resveratrol derivative, HS-1793, on endoplasmic reticulum stress-mediated apoptosis and Akt inactivation. Int J Oncol 36, 1007-1013.

Um, J. H., Park, S. J., Kang, H., Yang, S., Foretz, M., McBurney, M. W., Kim., M. K., Viollet, B., and Chung, J. H. (2009). AMP-activated protein kinase-deficient mice are resistant to the metabolic effects of resveratrol. Diabetes 59, 554-563.

Vousden, K. H., and Ryan, K. M. (2009). p53 and metabolism. Nat Rev Cancer 9, 691-700

Watanabe, M., Houten, S. M., Mataki, C., Christoffolete, M. A., Kim, B. W., Sato, H., Messaddeq, N., Harney, J. W., Ezaki, O., Kodama, T., et al. (2006). Bile acids induce energy expenditure by promoting intracellular thyroid hormone activation. Nature 439, 484-489.

Yang, H., Yang, T., Baur, J. A., Perez, E., Matsui, T., Carmona, J. J., Lamming, D. W., Souza-Pinto, N. C., Bohr, V. A., Rosenzweig, A., et al. (2007). Nutrient-sensitive mitochondrial NAD+levels dictate cell survival. Cell 130, 1095-1107.

Yao, X. H., Chen, L., and Nyomba, B. L. (2006). Adult rats prenatally exposed to ethanol have increased gluconeogenesis and impaired insulin response of hepatic gluconeogenic genes. J Appl Physiol 100, 642-648.

Yelamos, J., Schreiber, V., and Dantzer, F. (2008). Toward specific functions of poly(ADP-ribose) polymerase-2. Trends Mol. Med. 14, 169-178.

Yu, J., and Auwerx, J. (2009). Protein deacetylation by SIRT1: An emerging key post-translational modification in metabolic regulation. Pharmacol Res 62(1), 35.

We claim:

1. A method of treating a disorder associated with mitochondrial dysfunction, the method comprising administering to a subject in need thereof:
   (a) a poly(ADP-ribose) polymerase (PARP) inhibitor; and
   (b) one or more compounds that increases intracellular and mitochondrial nicotinamide adenine dinucleotide (NAD$^+$) in an amount sufficient to induce Sirtuin 1 (SIRT1) or Sirtuin 3 (SIRT3) protein expression,
   wherein the PARP inhibitor is N-(6-Oxo-5,6-dihydrophenanthridin-2-yl)-(N,N-dimethylamino)acetamide hydrochloride (PJ34), Thieno[2,3-c]isoquinolin-5-one (TIQ), 4-iodo-3-nitrobenzamide (Iniparib or BSI-201), 4-[[3-[4-(cyclopropanecarbonyl)piperazine-1-carbonyl]-4-fluorophenyl]methyl]-2H-phthalazin-1-one (Olaparib or AXD2281), 2-[(2R)-2-methylpyrrolidin-2-yl]-1H-benzimidazole-4-carboxamide (Veliparib or ABT-888), 6-fluoro-2-[4-(methylaminomethyl)phenyl]-3,10-diazatricyclo[6.4.1.04,13]trideca-1,4,6,8(13)-tetraen-9-one (Rucaparib or AG014699), 11-methoxy-2-((4-methylpiperazin-1-yl)methyl)-4,5,6,7-tetrahydro-1H-cyclopenta[a]pyrrolo[3,4-c]carbazole-1,3(2H)-dione (CEP-9722), or 2-[4-[(3S)-piperidin-3-yl]phenyl]indazole-7-carboxamide (Niraparib or MK 4827), and wherein said disorder associated with mitochondrial dysfunction is a neurodegenerative disease.

2. The method according to claim 1, wherein the one or more compounds is a NAD booster.

3. The method of claim 2, wherein the NAD booster is tryptophan, nicotinamide riboside (NR), niacin, nicotinic acid (NA), nicotinamide (NAM), N-formylkynurenine, quinolinic acid, nicotinamide riboside kinase (NRK), or nicotinamide mononucleotide (NMN).

4. The method of claim 1, wherein the neurodegenerative disease is Dementia, Alzheimer's disease, Parkinson's disease, or Huntington's disease.

5. A method of increasing the concentration of NAD$^+$ within the mitochondria, the method comprising contacting mitochondria with a PARP inhibitor and a NAD$^+$ precursor selected from the group consisting of nicotinamide riboside (NR), nicotinic acid (NA), nicotinamide (NAM), nicotinamide mononucleotide (NMN), and tryptophan, wherein the PARP inhibitor is N-(6-Oxo-5,6-dihydrophenanthridin-2-yl)-(N,N-dimethylamino)acetamide hydrochloride (PJ34), Thieno[2,3-c]isoquinolin-5-one (TIQ), 4-iodo-3-nitrobenzamide (Iniparib or BSI-201), 4-[[3-[4-(cyclopropanecarbonyl)piperazine-1-carbonyl]-4-fluorophenyl]methyl]-2H-phthalazin-1-one (Olaparib or AXD2281), 2-[(2R)-2-methylpyrrolidin-2-yl]-1H-benzimidazole-4-carboxamide (Veliparib or ABT-888), 6-fluoro-2-[4-(methylaminomethyl)phenyl]-3,10-diazatricyclo[6.4.1.04,13]trideca-1,4,6,8(13)-tetraen-9-one (Rucaparib or AGO 14699), 11-methoxy-2-((4-methylpiperazin-1-yl)methyl)-4,5,6,7-tetrahydro-1H-cyclopenta[a]pyrrolo[3,4-c]carbazole-1,3(2H)-dione (CEP-9722), or 2-[4-[(3S)-piperidin-3-yl]phenyl]indazole-7-carboxamide (Niraparib or MK 4827).

6. A method of activating mitochondrial sirtuin, the method comprising contacting mitochondria with a PARP inhibitor and a NAD$^+$ precursor selected from the group consisting of nicotinamide riboside (NR), nicotinic acid (NA), nicotinamide (NAM), nicotinamide mononucleotide (NMN), and tryptophan, wherein the PARP inhibitor is N-(6-Oxo-5,6-dihydrophenanthridin-2-yl)-(N,N-dimethylamino)acetamide hydrochloride (PJ34), Thieno[2,3-c]isoquinolin-5-one (TIQ), 4-iodo-3-nitrobenzamide (Iniparib or BSI-201), 4-[[3-[4-(cyclopropanecarbonyl)piperazine-1-carbonyl]-4-fluorophenyl]methyl]-2H-phthalazin-1-one (Olaparib or AXD2281), 2-[(2R)-2-methylpyrrolidin-2-yl]-1H-benzimidazole-4-carboxamide (Veliparib or ABT-888), 6-fluoro-2-[4-(methylaminomethyl)phenyl]-3,10-diazatricyclo[6.4.1.04,13]trideca-1,4,6,8(13)-tetraen-9-one (Rucaparib or AG014699), 11-methoxy-2-((4-methylpiperazin-1-yl)methyl)-4,5,6,7-tetrahydro-1H-cyclopenta[a]pyrrolo[3,4-c]carbazole-1,3(2H)-dione (CEP-9722), or 2-[4-[(3S)-piperidin-3-yl]phenyl]indazole-7-carboxamide (Niraparib or MK 4827).

7. The method of claim 6, wherein the sirtuin is SIRT3, SIRT4 or SIRT5.

* * * * *